United States Patent
Bachovchin et al.

(10) Patent No.: US 11,583,516 B2
(45) Date of Patent: Feb. 21, 2023

(54) DASH INHIBITORS, AND USES RELATED THERETO

(71) Applicant: Trustees of Tufts College, Medford, MA (US)

(72) Inventors: William W. Bachovchin, Cambridge, MA (US); Hung-sen Lai, Andover, MA (US); Wengen Wu, Winchester, MA (US)

(73) Assignee: Trustees of Tufts College, Boston, MA (US)

( * ) Notice: Subject to any disclaimer, the term of this patent is extended or adjusted under 35 U.S.C. 154(b) by 344 days.

(21) Appl. No.: 16/331,181

(22) PCT Filed: Sep. 7, 2017

(86) PCT No.: PCT/US2017/050445
§ 371 (c)(1),
(2) Date: Mar. 7, 2019

(87) PCT Pub. No.: WO2018/049008
PCT Pub. Date: Mar. 15, 2018

(65) Prior Publication Data
US 2019/0209525 A1    Jul. 11, 2019

Related U.S. Application Data

(60) Provisional application No. 62/482,750, filed on Apr. 7, 2017, provisional application No. 62/384,403, filed on Sep. 7, 2016, provisional application No. 62/384,407, filed on Sep. 7, 2016.

(51) Int. Cl.
| | |
|---|---|
| *A61K 31/402* | (2006.01) |
| *A61K 31/69* | (2006.01) |
| *A61K 45/06* | (2006.01) |
| *A61K 39/39* | (2006.01) |
| *A61P 37/04* | (2006.01) |
| *A61P 35/00* | (2006.01) |
| *A61K 31/4025* | (2006.01) |
| *A61K 31/4035* | (2006.01) |
| *A61K 31/4439* | (2006.01) |
| *A61K 35/13* | (2015.01) |
| *A61K 39/00* | (2006.01) |

(52) U.S. Cl.
CPC ........ *A61K 31/402* (2013.01); *A61K 31/4025* (2013.01); *A61K 31/4035* (2013.01); *A61K 31/4439* (2013.01); *A61K 31/69* (2013.01); *A61K 35/13* (2013.01); *A61K 39/39* (2013.01); *A61K 45/06* (2013.01); *A61P 35/00* (2018.01); *A61P 37/04* (2018.01); *A61K 2039/505* (2013.01)

(58) Field of Classification Search
CPC combination set(s) only.
See application file for complete search history.

(56) References Cited

U.S. PATENT DOCUMENTS

| | | | |
|---|---|---|---|
| 7,115,650 B1 * | 10/2006 | Broqua | ................... A61P 15/00 514/423 |
| 9,839,646 B2 | 12/2017 | Bachovchin | |
| 11,096,924 B2 | 8/2021 | Bachovchin et al. | |
| 2001/0031275 A1 | 10/2001 | Forse et al. | |
| 2005/0228021 A1 | 10/2005 | Hamann et al. | |
| 2010/0009961 A1 | 1/2010 | Kroth et al. | |
| 2010/0256153 A1 | 10/2010 | Frederich et al. | |
| 2011/0082108 A1 * | 4/2011 | Bachovchin | ......... C07D 207/16 514/64 |
| 2011/0218142 A1 | 9/2011 | Bachovchin et al. | |
| 2011/0230462 A1 | 9/2011 | Hendricks et al. | |
| 2014/0271725 A1 | 9/2014 | Bachovchin | |
| 2015/0202218 A1 | 7/2015 | Bachovchin | |
| 2015/0210769 A1 | 7/2015 | Freeman et al. | |
| 2016/0310513 A1 | 10/2016 | Bachovchin | |
| 2017/0266280 A1 | 9/2017 | Rastelli et al. | |
| 2019/0209525 A1 | 7/2019 | Bachovchin et al. | |
| 2020/0022956 A1 | 1/2020 | Bachovchin et al. | |
| 2022/0040149 A1 | 2/2022 | Bachovchin et al. | |

FOREIGN PATENT DOCUMENTS

| | | | |
|---|---|---|---|
| WO | WO-00/28997 A1 | | 5/2000 |
| WO | WO2007100374 | * | 9/2007 |
| WO | WO-2007/127204 A2 | | 11/2007 |
| WO | WO-2013/078059 A1 | | 5/2013 |
| WO | WO2013078059 | * | 5/2013 |
| WO | WO-2018/049008 A1 | | 3/2018 |
| WO | WO-2018/049014 A1 | | 3/2018 |
| WO | WO-2018/049015 A1 | | 3/2018 |
| WO | WO-2018/049027 A1 | | 3/2018 |
| WO | WO-2018/187698 A2 | | 10/2018 |
| WO | WO-2019/236567 A2 | | 12/2019 |

OTHER PUBLICATIONS

Shukshith (Water for Pharmaceutical Use, Int. J. Pharm. Sci. Rev. Res., 36(1), Jan.-Feb. 2016; Article No. 35, pp. 199-204).*
Da Silva et al., "Dipeptidylpeptidase 4 inhibition enhances lymphocyte trafficking, improving both naturally occurring tumor immunity and immunotherapy," Nat Immunol, 16:850-858 (2015).
International Search Report and Written Opinion for International Application No. PCT/US18/26470 dated Sep. 21, 2018.
International Search Report and Written Opinion for International Application No. PCT/US2017/050445 dated Jan. 2, 2018.
International Search Report and Written Opinion for International Application No. PCT/US2017/050457 dated Feb. 5, 2018.

(Continued)

*Primary Examiner* — Kathrien A Cruz

(74) *Attorney, Agent, or Firm* — Foley Hoag LLP; Dana M. Gordon; Alexander J. Chatterley

(57) ABSTRACT

Disclosed are potent immuno-DASH inhibitors and their use in the treatment of cell proliferative diseases.

18 Claims, 34 Drawing Sheets

Specification includes a Sequence Listing.

(56) References Cited

OTHER PUBLICATIONS

International Search Report and Written Opinion for International Application No. PCT/US2017/050474 dated Dec. 28, 2017.
International Search Report and Written Opinion for International Application No. PCT/US2017/50455 dated Dec. 28, 2017.
Li et al., "Hydrogel dual delivered celecoxib and anti-PD-1 synergistically improve antitumor immunity," OncoImmunology, 5(2): e1074374 (12 pages) (2016).
Quach et al., "Secretory phospholipase A2 enzymes as pharmacological targets for treatment of disease," Biochem Pharmacol, 90(4):338-348 (2014).
Wagner et al., "Unravelling the immunological roles of dipeptidyl peptidase 4 (DPP4) activity and/or structure homologue (DASH) proteins," J Transl Immunol, 184(3):265-283 (2016).
Hadoke et al., "Therapeutic manipulation of glucocorticoid metabolism in cardiovascular disease: Therapeutic targeting of glucocorticoid metabolism," British Journal of Pharmacology, 156(5):689-712 (2009).
Partial European Search Report for EP Application No. 17849528.9 dated Apr. 28, 2020.
Van der Veken et al., "Inhibitors of dipeptidyl peptidase 8 and dipeptidyl peptidase 9. Part 1: Identification of dipeptide derived leads," Bioorganic & Medicinal Chemistry Letters, 18(14):4154-4158 (2008).
Extended European Search Report for EP Application No. 17849528.9 dated Jul. 29, 2020.
Giercksky et al., "COX-2 inhibition and prevention of cancer," CAS: 137:103189 (2001).
Göbel et al., "Functional expression cloning identifies COX-2 as a suppressor of antigen-specific cancer immunity," Cell Death Dis, 5: e1568 (8 pages) (2014).
Hua et al., "Cyclooxygenase02 Regulates NLRP3 Inflammasome-Derived IL-1β Production," J Cell Physiol, 230: 863-874 (2015).
Jansen et al., "Selective Inhibitors of Fibroblast Activation Protein (FAP) with a (4-Quinolinoyl)-glycyl-2-cyanopyrrolidine Scaffold," ACS Med Chem Lett, 4: 491-496 (2013).
Liu et al., "Cyclooxygenase-2 promotes tumor growth and suppresses tumor immunity," Cancer Cell Int, 15: 106 ( pages) (2015).
Okondo et al., "DPP8/9 inhibition induces pro-caspase-1-dependent monocyte and macrophage pyroptosis," Nat Chem Biol, 13(1): 45-53 (2017).

\* cited by examiner

5 μg IP ARI-5544
After 26 days

Val-boroPro (10μg, I.P., Q.D.)

Val-boroPro (20μg P.O., B.I.D.)

Vehicle (P.O., B.I.D.)

MTD Survival and Serum Drug Concentrations in Sprague-Dawley rats following Single Dose of Val-boroPro (+/- COX inhibitor) or ARI-4268

1/10 regressed

3/5 regressed

MTD Survival and Serum Drug Concentrations of PT-100 in Sprague-Dawley rats following Single Dose of PT-100 +/- cPLA2 inhibitor

DASH INHIBITORS, AND USES RELATED THERETO

RELATED APPLICATIONS

This application is the U.S. National Stage of PCT/US20171050445, filed Sep. 7, 2017; which claims the benefit of priority to U.S. Provisional Patent Application Ser. No. 62/384,403, filed Sep. 7, 2016; 62/384,407, filed Sep. 7, 2016; and 62/482,750, filed Apr. 7, 2017.

GOVERNMENT SUPPORT

This invention was made with government support under grant number CA174008 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 16, 2017, is named TUV-102_25_SL.txt and is 13,917 bytes in size.

BACKGROUND

Mammalian post-proline cleaving enzymes form a sub-family of serine proteases called the dipeptidyl peptidase (DPP)-4 and/or structural homologs ("DASH" enzymes). DASH comprise DPP4, DPP2, DPP8, DPP9, fibroblast activation protein (FAP) and prolyl endopeptidase. The DPPs selectively cleave after proline or alanine residues when either is located as the penultimate residue at the N-terminus of peptides. It has been proposed that conserved prolines act as regulatory elements in biologically active peptides, for which post-proline cleaving proteases in the DASH sub-family provide checkpoints. The mature forms of several chemokines frequently possess N-terminally penultimate proline or alanine, suggesting that their biological activity might be regulated by DPP activity. This has been shown to be the case for the chemokine stromal cell-derived factor-1 in vivo, and more recently, for GM-CSF, G-CSF, IL-3, and erythropoietin, in the homeostatic regulation of hematopoiesis.

DPP4 (EC 3.4.14.5) is a validated drug target for human type II diabetes, and the use of small molecule inhibitors of DPP4 represents a nearly ten billon US dollar class of drugs. However, during the identification and development of DPP4 inhibitors for treating diabetes, many research groups pointed to the lack of selectivity toward the related enzymes DPP8 and DPP9 as a possible source of drug-induced toxicity in compounds those groups were testing. For instance, Merck reported that in rats at all doses, DPP8/9 specific inhibitors produced profound toxicity, including alopecia, thrombocytopenia, anemia, enlarged spleen, multiple histological pathologies, and mortality. Lankas et al. Diabetes 2005; 54: 2988-2994. Likewise, it was reported that DPP8/9 specific inhibitors were found to produce mortality in both wild type and DPP4 deficient mice, which was the basis in the prior art for suggesting that observed toxicity in early DPP4 inhibitor candidates was not due to DPP4 inhibition, but rather "off-target" inhibition of DPP9 and DPP9. From the body of work relating to DPP4 inhibitors came the general notion that inhibition of DPP8/9 was associated with profound toxicities in preclinical species, and that selective inhibition of DPP4 was required for an acceptable safety and tolerability profile for this class of antihyperglycemic agents.

It has previously been reported preclinically that pharmacological inhibition of the enzymatic activity of DPP4 and/or other DASH enzymes with dipeptide boronic acids can mediate tumor regression in an immune-mediated manner. In the clinic a DASH inhibitor PT-100 (Talabostat) achieved some partial and complete responses but has since been discontinued due to dose-limiting toxicity. See Eager et al. Clin Oncol 2009; 21:464-472; and Eager et al. BMC Cancer. 2009; 9:263. A second generation pan-inhibitor of DASH, ARI-4175, has been reported to induce significant immune-dependent anti-tumor activity against established rhabdomyosarcoma preclinically. Duncan B, et al. Journal of Immunotherapy. 2013; 36:400-411 and Donahue et al. Vaccine 2014; 32:3223-3231.

However, continuing concern over the body of literature suggesting that inhibition of DPP8 and DPP9 results in severe toxicity, improvements to therapeutic index achieved with ARI-4175 relative to PT-100 have not resulted in subsequent development of I-DASH inhibitors as antitumor agents. Indeed, in 2015 and 2016, other groups have continued to publish articles referring to a need to avoid DPP8 and DPP9 inhibition as a challenge for drug selectivity to avoid unwanted side effects (see, for example Lim et al. Korean J Intern Med October 2015; 30: 759-770 "its high selectivity ensures targeted action on DPP4 and avoids unwanted secondary effects or potential toxicities resulting from cross-inhibition of other DPP peptides, such as DPP8 or DPP9"). And recently, a paper published suggesting that Sitagliptin, a highly selective DPP4 inhibitor relative to inhibition of DPP8 and DPP9 (at least 3 orders of magnitude greater potency for DPP4 inhibition than for DPP8 or DPP9), could be used in a triple combination with PD-1 and CTLA-4 inhibitors to cause regression of tumors, further teaching away from a desirability of inhibiting DPP8 and DPP9. Barreira da Silva "Dipeptidylpeptidase 4 inhibition enhances lymphocyte trafficking, improving both naturally occurring tumor immunity and immunotherapy", Nature Immunology, 2015; 16:791-792. Those authors speculated that inhibition of DPP4 increased the serum halflife of CXCL10, which enhanced lymphocyte trafficking to tumors. However, the effects reported by those authors were under circumstances in which sitagliptin was being administered at a supra-pharmaceutical dose (mice were fed chow containing 1.1% sitagliptin), with drug administration beginning prior to animals being injected with tumor.

The present invention is based on the finding that potent DPP8/DPP9 inhibitors, which are also multimediator inhibitors of DPP4, can be used alone or combination with other agents to treat tumors, and when tumor regression is achieved, the consequences also include induction of immunological memory selectively for the tumor. Moreover, improving the potency of these inhibitors with respect to inhibition of DPP8 and DPP9 in whole cells (i.e., appropriate enzymatic inhibitory potency and cell permeability to reach intracellular DPP8 and DPP9), particularly with respect to macrophage, resulted in improved therapeutic index—suggesting that at least some of the toxicity observed with PT-100 and with other DPP4 inhibitors was likely resulting from off target effects of the drug rather than due to DPP8 or DPP9 inhibition.

SUMMARY OF THE INVENTION

One aspect of the present invention relates to compositions-of-matter for enhancing a cell-mediated immune response against a cancer, and specifically to "immuno-DASH inhibitors" which are characterized as (a) the immuno-DASH inhibitor has a parmacokinetic profile of being an inhibitor of DPP8, DPP9 and DPP4 when administered at a therapeutically effective amount; and (b) the immuno-DASH inhibitor has: i) an in vivo $IC_{50}$ for DPP4 inhibition of less than 10 nM, and ii) an intracellular $IC_{50}$ for DPP8 and DPP9 inhibition less than 10 nM. In certain embodiments, the in vivo $IC_{50}$ for DPP4 inhibition is less than 1 nM, 0.1 nM, 0.01 nM or even 0.001 nM. In certain embodiments, the in vitro cell-free $IC_{50}$ for DPP4 inhibition is less than 1 nM, 0.1 nM, 0.01 nM or even 0.001 nM. In certain embodiments, the EnPlex $IC_{50}$ for DPP4 inhibition is less than 1 nM, 0.1 nM, 0.01 nM or even 0.001 nM.

In certain preferred embodiments of the subject method, the immuno-DASH-inhibitor possess an intracellular $IC_{50}$ for DPP8 and DPP9 inhibition less than 100 nM, an in vitro $IC_{50}$ of less than 100 nM for DPP4 inhibition, an $IC_{50}$ of less than 100 nM for inducing pyroptosis of macrophage in cell culture, and a $k_{off}$ rate for interaction with DPP4 less than $1\times10^{-4}$/sec.

Another aspect of the present invention relates to pharmaceutical preparations, such as medicaments, for enhancing a cell-mediated immune response against a cancer, and which preparations include an immuno-DASH inhibitor of the present invention and, as appropriate, pharmaceutically acceptable excipient(s). In this regard, the present invention also provides a method for manufacturing a medicament for the treatment of patients, particularly cancer patients and particularly human cancer patients, including the formulation of an immuno-DASH inhibitor of the present invention one or more pharmaceutically acceptable excipients. The formulation may be for oral, intravenous, intraperitoneal, subcutaneous, intratumoral or other local delivery, intramuscular, topical or transdermal delivery if the immuno-DASH inhibitor. In certain preferred embodiments, the pharmaceutical preparations of the present invention can be for oral deliver of the immuno-DASH inhibitor. In certain other embodiments, the formulation is an injectable and/or infusible solution including the immuno-DASH inhibitor.

Still another aspect of the present invention relates to a method of enhancing a cell-mediated immune response against a cancer, comprising administering to a mammal in need thereof a therapeutically effective amount of an immuno-DASH inhibitor; wherein: (a) at the therapeutically effective amount, the immuno-DASH inhibitor is characterized by a parmacokinetic profile of being an inhibitor of DPP8, DPP9 and DPP4; and (b) the immuno-DASH inhibitor has: i) an in vivo $IC_{50}$ for DPP4 inhibition of less than 10 nM, and ii) an intracellular $IC_{50}$ for DPP8 and DPP9 inhibition less than 10 nM. In certain embodiments, the in vivo $IC_{50}$ for DPP4 inhibition is less than 1 nM, 0.1 nM, 0.01 nM or even 0.001 nM. In certain embodiments, the in vitro cell-free $IC_{50}$ for DPP4 inhibition is less than 1 nM, 0.1 nM, 0.01 nM or even 0.001 nM. In certain embodiments, the EnPlex $IC_{50}$ for DPP4 inhibition is less than 1 nM, 0.1 nM, 0.01 nM or even 0.001 nM.

In certain embodiments, the in vivo $IC_{50}$ for DPP4 inhibition is less than 1 nM, 0.1 nM, 0.01 nM or even 0.001 nM. In certain embodiments, the in vitro cell-free $IC_{50}$ for DPP4 inhibition is less than 1.0 nM, 0.1 nM, 0.01 nM or even 0.001 nM. In certain embodiments, the EnPlex $IC_{50}$ for DPP4 inhibition is less than 1.0 nM, 0.1 nM, 0.01 nM, 0.001 nM (1 picomolar) or even 0.0001 nM (100 femtomolar). In certain embodiments, the Ki for DPP4 inhibition is less than 1.0 nM, 0.1 nM, 0.01 nM, 0.001 nM (1 picomolar) or even 0.0001 nM (100 femtomolar).

In certain embodiments, the in vitro cell-free $IC_{50}$ for DPP8 and/or DPP9 (and preferably for both DPP8 and DPP) inhibition is less than 1.0 nM, 0.1 nM, 0.01 nM or even 0.001 nM. In certain embodiments, the EnPlex $IC_{50}$ for DPP8 and/or DPP9 (and preferably for both DPP8 and DPP) inhibition is less than 1.0 nM, 0.1 nM, 0.01 nM, 0.001 nM (1 picomolar) or even 0.0001 nM (100 femtomolar). In certain embodiments, the Ki for DPP8 and/or DPP9 (and preferably for both DPP8 and DPP) inhibition is less than 1.0 nM, 0.1 nM, 0.01 nM, 0.001 nM (1 picomolar) or even 0.0001 nM (100 femtomolar).

In certain embodiments, the in vitro cell-free $IC_{50}$ for DPP8 and/or DPP9 (and preferably for both DPP8 and DPP) inhibition is within 100-fold of the $IC_{50}$ for DPP4 inhibition. In certain embodiments, the in vitro cell-free $IC_{50}$ for DPP8 and/or DPP9 (and preferably for both DPP8 and DPP) inhibition is at least 5-fold less (more potent) than the $IC_{50}$ for DPP4 inhibition, and even more preferably at least 10, 50, 100, 500 or even 1000-fold less (more potent) than the $IC_{50}$ for DPP4 inhibition.

In certain embodiments, the EnPlex $IC_{50}$ for DPP8 and/or DPP9 (and preferably for both DPP8 and DPP) inhibition is within 100-fold of the $IC_{50}$ for DPP4 inhibition. In certain embodiments, the EnPlex $IC_{50}$ for DPP8 and/or DPP9 (and preferably for both DPP8 and DPP) inhibition is at least 5-fold less (more potent) than the $IC_{50}$ for DPP4 inhibition, and even more preferably at least 10, 50, 100, 500 or even 1000-fold less (more potent) than the $IC_{50}$ for DPP4 inhibition.

In certain embodiments, the Ki for DPP8 and/or DPP9 (and preferably for both DPP8 and DPP) inhibition is within 100-fold of the Ki for DPP4 inhibition. In certain embodiments, the Ki for DPP8 and/or DPP9 (and preferably for both DPP8 and DPP) inhibition is at least 5-fold less (more potent) than the Ki for DPP4 inhibition, and even more preferably at least 10, 50, 100, 500 or even 1000-fold less (more potent) than the Ki for DPP4 inhibition.

In certain embodiments, the subject immuno-DASH inhibitors also inhibit Fibroblast Activating Protein (FAP) within the concentration range of the drug being an effective antitumor agent. For instance, the immuno-DASH inhibitor can have a Ki for inhibition FAP less than 1.0 nM, 0.1 nM, 0.01 nM, 0.001 nM (1 picomolar) or even 0.0001 nM (100 femtomolar).

In certain embodiments, the I-DASH inhibitor exhibits slow binding inhibition kinetics.

In certain embodiments, the I-DASH inhibitor has a $k_{off}$ rate for interaction with DPP4 less than $1\times10^{-4}$/sec, and preferably less than $5\times10^{-5}$/sec, $3\times10^{-5}$/sec or even less than $1\times10^{-5}$/sec.

In certain embodiments, the I-DASH inhibitor has a Cmax in human patients or mice, when administered in a single oral dose, that is less than 80% of the Cmax produced by oral administration of 10 millgrams of Val-boroPro, and even more preferably has a Cmax less than 70%, 60%, 50%, 40%, 30% or even 20% of the Cmax produced by oral administration of 10 millgrams of Val-boroPro.

In certain embodiments, the I-DASH inhibitor is administered to the patient in a sufficient amount to cause an increase in serum concentration of CXCL10.

In certain embodiments, the I-DASH inhibitor is administered to the patient in a sufficient amount to cause a decrease in the number of tumor-associated macrophages.

In certain embodiments, the I-DASH inhibitor is administered to the patient in a sufficient amount to reduces monocytic myeloid-derived suppressor cells in the tumor.

In certain embodiments, the I-DASH inhibitor is administered to the patient in a sufficient amount to reduces T-cell suppressive activity of granulocytic myeloid-derived suppressor cells in the tumor.

In certain embodiments, the I-DASH inhibitor produces full tumor regression at the therapeutically effective amount and the therapeutically effective amount is less than the immuno-DASH inhibitor's maximum tolerated dose.

In certain embodiments, the I-DASH inhibitor has a therapeutic index of at least 10, and more preferably at least 20, 40, 60, 80 or even at least 100.

In certain embodiments, the I-DASH inhibitor has a maximum tolerated dose of at least 50 mg in C57BL/6 mice, and even more preferably at least 100 mg, 150 mg, 200 mg, 250 mg or even at least 300 mg, and able to induce full tumor regression in the C57BL/6 mice at doses less than the maximum tolerated dose, preferably at a dose less than 75% of the maximum tolerated dose, and even more preferably at a dose less than 50%, 25%, 10% or even less than 5% of the maximum tolerated dose.

In certain embodiments, the I-DASH inhibitor has a maximum tolerated dose, alone or in combination with a PGE2 inhibitor, the produces a Cmax of at least 50 nM in Sprague Dawley rats, and even more preferably at least 100 nM, 500 nM, 1000 nM, 1500 nM, 2000 nM, 3000 nM, 5000 nM, 10,000 nM or even at least 20,000 nM, and able to induce full tumor regression in the C57BL/6 mice at serum concentrations less than the maximum tolerated dose in those mice, preferably at a dose producing a Cmax less than 75% of the maximum tolerated dose, and even more preferably at a dose producing a Cmax less than 50%, 25%, 10% or even less than 5% of the maximum tolerated dose.

Another aspect of the present invention relates to a method of treating a myeloproliferative neoplasms, such as myelodysplastic syndrome and acute myeloid leukemia (AML), comprising administering to a mammal in need thereof a therapeutically effective amount of an immuno-DASH inhibitor; wherein: (a) at the therapeutically effective amount, the immuno-DASH inhibitor is characterized by a pharmacokinetic profile of being an inhibitor of DPP8, DPP9 and DPP4; and (b) the immuno-DASH inhibitor has: i) an in vivo $IC_{50}$ for DPP4 inhibition of less than 10 nM, and ii) an intracellular $IC_{50}$ for DPP8 and DPP9 inhibition less than 10 nM. Certain preferred embodiments of the I-DASH inhibitor used in the treatment of a myeloproliferative disease, such as AML, are as described above.

Another aspect of the present invention relates to a method treating a relapse of a cancer, comprising administering to a mammal in need thereof a therapeutically effective amount of an immuno-DASH inhibitor; wherein: (a) at the therapeutically effective amount, the immuno-DASH inhibitor is characterized by a pharmacokinetic profile of being an inhibitor of DPP8, DPP9 and DPP4; and (b) the immuno-DASH inhibitor has: i) an in vivo $IC_{50}$ for DPP4 inhibition of less than 10 nM, and ii) an intracellular $IC_{50}$ for DPP8 and DPP9 inhibition less than 10 nM. Certain preferred embodiments of the I-DASH inhibitor used in the treatment of relapsed cancer patients are as described above.

Another aspect of the invention relates the immuno-DASH inhibitor represented by formula I, or a pharmaceutical salt thereof:

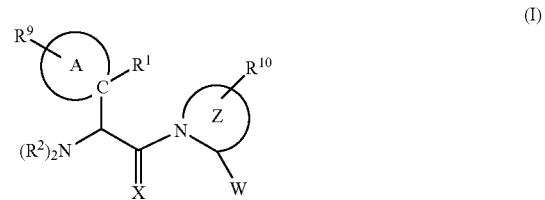

wherein
ring A represents a 3-10 membered ring structure;
ring Z represents a 4-10 membered heterocycle including the N and the Cα carbon;
W represents —CN, —CH=NR$^4$, a functional group which reacts with an active site residue of the target, or

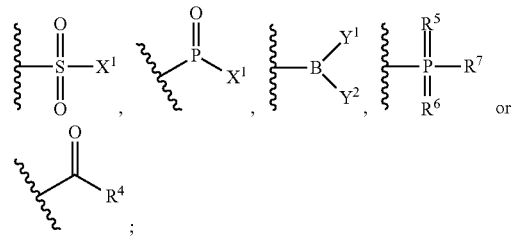

X is O or S;
X$^1$ represents a halogen;
Y$^1$ and Y$^2$ are independently OH, or together with the boron atom to which they are attached represent a group that is hydrolysable to a boronic acid, or together with the boron atom to which they are attached form a 5-8 membered ring that is hydrolysable to a boronic acid;
R$^1$ represents a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —CF$_3$, —(CH$_2$)$_m$—R$^3$, —(CH$_2$)$_m$OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)-lower alkenyl, or —(CH$_2$)$_n$—S—(CH$_2$)$_m$—R$^3$;
R$^2$ represents, for each occurrence, hydrogen, lower alkyl, lower alkynyl, —(CH$_2$)$_m$—R$^3$, —C(=O)-alkyl, —C(=O)-alkenyl, —C(=O)-alkynyl, or —C(=O)—(CH$_2$)$_m$—R$^3$;
R$^3$ represents, for each occurrence, hydrogen, or a substituted or unsubstituted lower alkyl, lower alkenyl, aryl, aralkyl, cycloalkyl, cycloalkenyl, or heterocycle;
R$^4$ represents a hydrogen, a lower alkyl, a lower alkenyl, a lower alkynyl, —(CH$_2$)$_m$—R$^3$, —(CH$_2$)$_n$—OH, —(CH$_2$)$_n$—O-lower alkyl, —(CH$_2$)$_n$—O-alkenyl, —(CH$_2$)$_n$—O-alkynyl, —(CH$_2$)$_n$—O—(CH$_2$)$_m$—R$_7$, —(CH$_2$)$_n$—SH, —(CH$_2$)$_n$—S-lower alkyl, —(CH$_2$)$_n$—S-lower alkenyl, —(CH$_2$)$_n$—S-lower alkynyl, —(CH$_2$)$_n$—S—(CH$_2$)$_m$—R$^3$, —C(O)C(O)NH$_2$, or —C(O)C(O)OR$^8$;
R$^5$ represents O or S;
R$^6$ represents N$_3$, SH, NH$_2$, NO$_2$ or OR$^8$;
R$^7$ represents hydrogen, a lower alkyl, an amine, OR$^8$, or a pharmaceutically acceptable salt, or R$^5$ and R$^6$ taken together with the phosphorous atom to which they are attached complete a heterocyclic ring having from 5 to 8 atoms in the ring structure;

R$^8$ represents, hydrogen, a substituted or unsubstituted alkyl, alkenyl, aryl, aralkyl, cycloalkyl, cycloalkenyl or heterocyclyl;

R$^9$ and R$^{10}$, each independently, are absent or represents one, two, or three substitutions to the ring A or to the ring Z to which they are appended, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, an isocyano, a thiocyanato, an isothiocyanato, a cyanato, a nitro, an azido, a sulfate, a sulfonate, a sulfonamido, lower alkyl-C(O)OH, —O-lower alkyl-C(O)OH, -guanidinyl; —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$^3$;

n is 0, 1, 2, or 3; and m is 0, 1, 2, or 3.

Another aspect of the invention relates the immuno-DASH inhibitor represented by formula II, or a pharmaceutical salt thereof:

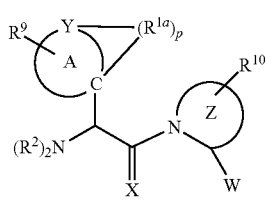

(II)

wherein ring A, along with each occurrence of R$^{1a}$, represents a 7-12 membered polycyclic ring structure;

ring Z represents a 4-10 membered heterocycle including the N and the Cα carbon;

W represents —CN, —CH=NR$^4$, a functional group which reacts with an active site residue of the target, or

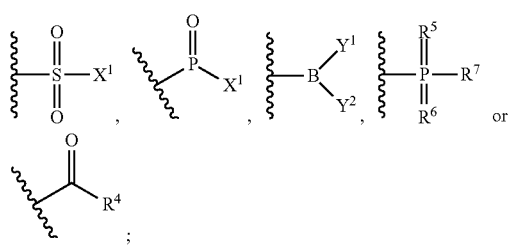

;

X is O or S;

X$^1$ represents a halogen;

Y is C or N;

Y$^1$ and Y$^2$ are independently OH, or together with the boron atom to which they are attached represent a group that is hydrolysable to a boronic acid, or together with the boron atom to which they are attached form a 5-8 membered ring that is hydrolysable to a boronic acid;

R$^{1a}$ represents a lower alkyl, —(CH$_2$)$_m$—, —(CH$_2$)$_m$—O—(CH$_2$)$_m$—; —(CH$_2$)$_m$—N—(CH$_2$)$_m$—; or —(CH$_2$)$_m$—S—(CH$_2$)$_m$—;

R$^2$ represents, for each occurrence, hydrogen, lower alkyl, lower alkynyl, —(CH$_2$)$_m$—R$^3$, —C(=O)-alkyl, —C(=O)-alkenyl, —C(=O)-alkynyl, or —C(=O)—(CH$_2$)$_m$—R$^3$;

R$^3$ represents, for each occurrence, hydrogen, or a substituted or unsubstituted lower alkyl, lower alkenyl, aryl, aralkyl, cycloalkyl, cycloalkenyl, or heterocycle;

R$^4$ represents a hydrogen, a lower alkyl, a lower alkenyl, a lower alkynyl, —(CH$_2$)$_m$—R$^3$, —(CH$_2$)$_n$—OH, —(CH$_2$)$_n$—O-lower alkyl, —(CH$_2$)$_n$—O-alkenyl, —(CH$_2$)$_n$—O-alkynyl, —(CH$_2$)—O—(CH$_2$)$_m$—R$_7$, —(CH$_2$)$_n$—SH, —(CH$_2$)$_n$—S-lower alkyl, —(CH$_2$)$_n$—S-lower alkenyl, —(CH$_2$)$_n$—S-lower alkynyl, —(CH$_2$)$_n$—S—(CH$_2$)$_m$—R$^3$, —C(O)C(O)NH$_2$, or —C(O)C(O)OR$^8$;

R$^5$ represents O or S;

R$^6$ represents N$_3$, SH, NH$_2$, NO$_2$ or OR$^8$;

R$^7$ represents hydrogen, a lower alkyl, an amine, OR$^8$, or a pharmaceutically acceptable salt, or R$^5$ and R$^6$ taken together with the phosphorous atom to which they are attached complete a heterocyclic ring having from 5 to 8 atoms in the ring structure;

R$^8$ represents, hydrogen, a substituted or unsubstituted alkyl, alkenyl, aryl, aralkyl, cycloalkyl, cycloalkenyl or heterocyclyl;

R$^9$ and R$^{10}$, each independently, are absent or represents one, two, or three substitutions to the ring A or to the ring Z to which they are appended, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, an isocyano, a thiocyanato, an isothiocyanato, a cyanato, a nitro, an azido, a sulfate, a sulfonate, a sulfonamido, lower alkyl-C(O)OH, —O-lower alkyl-C(O)OH, -guanidinyl; —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—(CH$_2$)$_m$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$^3$;

n is 0, 1, 2, or 3;

m is 0, 1, 2, or 3; and p is 1, 2, or 3.

Another aspect of the invention relates the immuno-DASH inhibitor represented by formula III, or a pharmaceutical salt thereof:

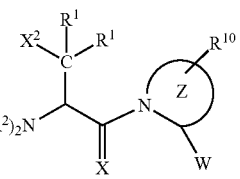

(III)

ring Z represents a 4-10 membered heterocycle including the N and the Cα carbon;

W represents —CN, —CH=NR$^4$, a functional group which reacts with an active site residue of the target, or

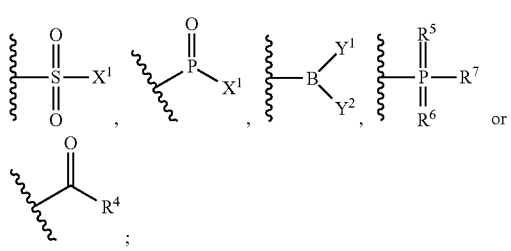

X is O or S;
X² represents, independently for each occurrence, a halogen;
Y¹ and Y² are independently OH, or together with the boron atom to which they are attached represent a group that is hydrolysable to a boronic acid, or together with the boron atom to which they are attached form a 5-8 membered ring that is hydrolysable to a boronic acid;
$R^1$ represents, independently for each occurrence, a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —CF₃, —(CH₂)$_m$—R³, —(CH₂)$_m$OH, —(CH₂)$_m$—O-lower alkyl, —(CH₂)$_m$—O-lower alkenyl, —(CH₂)$_n$—O—(CH₂)$_m$—R³, —(CH₂)$_m$—SH, —(CH₂)$_m$—S-lower alkyl, —(CH₂)$_m$—S-lower alkenyl, or —(CH₂)$_n$—S—(CH₂)$_m$—R³;
$R^2$ represents, for each occurrence, hydrogen, lower alkyl, lower alkynyl, —(CH₂)$_m$—R³, —C(═O)-alkyl, —C(═O)-alkenyl, —C(═O)-alkynyl, or —C(═O)—(CH₂)$_m$—R³;
$R^3$ represents, for each occurrence, hydrogen, or a substituted or unsubstituted lower alkyl, lower alkenyl, aryl, aralkyl, cycloalkyl, cycloalkenyl, or heterocycle;
$R^4$ represents a hydrogen, a lower alkyl, a lower alkenyl, a lower alkynyl, —(CH₂)$_m$—R³, —(CH₂)$_n$—OH, —(CH₂)$_n$—O-lower alkyl, —(CH₂)$_n$—O-alkenyl, —(CH₂)$_n$—O-alkynyl, —(CH₂)$_n$—O—(CH₂)$_m$—R₇, —(CH₂)$_n$—SH, —(CH₂)$_n$—S-lower alkyl, —(CH₂)$_n$—S-lower alkenyl, —(CH₂)$_n$—S-lower alkynyl, —(CH₂)$_n$—S—(CH₂)$_m$—R³, —C(O)C(O)NH₂, or —C(O)C(O)OR⁸;
$R^5$ represents O or S;
$R^6$ represents N₃, SH, NH₂, NO₂ or OR⁸;
$R^7$ represents hydrogen, a lower alkyl, an amine, OR⁸, or a pharmaceutically acceptable salt, or R⁵ and R⁶ taken together with the phosphorous atom to which they are attached complete a heterocyclic ring having from 5 to 8 atoms in the ring structure;
$R^8$ represents, hydrogen, a substituted or unsubstituted alkyl, alkenyl, aryl, aralkyl, cycloalkyl, cycloalkenyl or heterocyclyl;
$R^{10}$ is absent or represents one to three substitutions to the ring Z to which they are appended, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, an isocyano, a thiocyanato, an isothiocyanato, a cyanato, a nitro, an azido, a sulfate, a sulfonate, a sulfonamido, lower alkyl-C(O)OH, —O-lower alkyl-C(O)OH, -guanidinyl; —(CH₂)—R₇, —(CH₂)$_m$—OH, —(CH₂)$_m$—O-lower alkyl, —(CH₂)$_m$—O-lower alkenyl, —(CH₂)$_n$—O—(CH₂)$_m$—R³, —(CH₂)$_m$—SH, —(CH₂)$_m$—S-lower alkyl, —(CH₂)$_m$—S-lower alkenyl, —(CH₂)$_n$—S—(CH₂)$_m$—R³;
n is 0, 1, 2, or 3; and
m is 0, 1, 2, or 3.

Another aspect of the invention relates the immuno-DASH inhibitor represented by formula IV, or a pharmaceutical salt thereof:

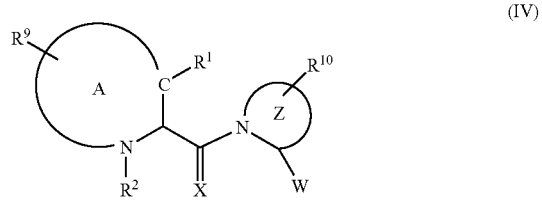

(IV)

wherein
ring A represents a 3-10 membered ring structure including the N;
ring Z represents a 4-10 membered heterocycle including the N and the Cα carbon;
W represents —CN, —CH═NR⁴, a functional group which reacts with an active site residue of the target, or

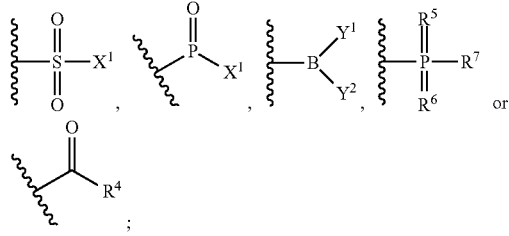

X is O or S;
$X^1$ represents a halogen;
Y¹ and Y² are independently OH, or together with the boron atom to which they are attached represent a group that is hydrolysable to a boronic acid, or together with the boron atom to which they are attached form a 5-8 membered ring that is hydrolysable to a boronic acid;
$R^1$ represents a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —CF₃, —(CH₂)$_m$—R³, —(CH₂)$_m$OH, —(CH₂)$_m$—O-lower alkyl, —(CH₂)$_m$—O-lower alkenyl, —(CH₂)$_n$—O—(CH₂)$_m$—R³, —(CH₂)$_m$—SH, —(CH₂)$_m$—S-lower alkyl, —(CH₂)$_m$—S-lower alkenyl, or —(CH₂)$_n$—S—(CH₂)$_m$—R³;
$R^2$ represents, for each occurrence, hydrogen, lower alkyl, lower alkynyl, —(CH₂)$_m$—R³, —C(═O)-alkyl, —C(═O)-alkenyl, —C(═O)-alkynyl, or —C(═O)—(CH₂)$_m$—R³;
$R^3$ represents, for each occurrence, hydrogen, or a substituted or unsubstituted lower alkyl, lower alkenyl, aryl, aralkyl, cycloalkyl, cycloalkenyl, or heterocycle;
$R^4$ represents a hydrogen, a lower alkyl, a lower alkenyl, a lower alkynyl, —(CH₂)$_m$—R³, —(CH₂)$_n$—OH, —(CH₂)$_n$—O-lower alkyl, —(CH₂)$_n$—O-alkenyl, —(CH₂)$_n$—O-alkynyl, —(CH₂)$_n$—O—(CH₂)$_m$—R₇, —(CH$_2$)$_n$—SH, —(CH$_2$)$_n$—S-lower alkyl, —(CH$_2$)$_n$—S-lower alkenyl, —(CH$_2$)$_n$—S-lower alkynyl, —(CH$_2$)$_n$—S—(CH$_2$)$_m$—R$^3$, —C(O)C(O)NH$_2$, or —C(O)C(O)OR$^8$;

R$^5$ represents O or S;

R$^6$ represents N$_3$, SH, NH$_2$, NO$_2$ or OR$^8$;

R$^7$ represents hydrogen, a lower alkyl, an amine, OR$^8$, or a pharmaceutically acceptable salt, or R$^5$ and R$^6$ taken together with the phosphorous atom to which they are attached complete a heterocyclic ring having from 5 to 8 atoms in the ring structure;

R$^8$ represents, hydrogen, a substituted or unsubstituted alkyl, alkenyl, aryl, aralkyl, cycloalkyl, cycloalkenyl or heterocyclyl;

R$^9$ and R$^{10}$, each independently, are absent or represents one to three substitutions to the ring A or to the ring Z to which they are appended, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, an isocyano, a thiocyanato, an isothiocyanato, a cyanato, a nitro, an azido, a sulfate, a sulfonate, a sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$^3$;

n is 0, 1, 2, or 3; and m is 0, 1, 2, or 3.

In certain embodiments of the present invention, the I-DASH inhibitor is administered conjointly with one or more PGE2 antagonist (i.e., a PGE2 pathway inhibitor). In certain preferred embodiments, the PGE2 antagonist increases the maximum tolerated dose of the I-DASH inhibitor by at least 30%, and more preferably at least 50%, 75%, 100%, or even at least 2, 5, 10, 20, 40 or even more than 50-fold compared to the MTD of the I-DASH inhibitor in the absence of the PGE2 antagonist.

In certain embodiments of the present invention, the PGE2 antagonist is a cyclooxygenase (COX) inhibitor, i.e., an inhibitor of COX-1, COX-2 or both. In certain preferred embodiments, the COX inhibitor is a COX-2 selective inhibitor. In certain preferred embodiments, the COX inhibitor is selected from the group consisting of celecoxib, deracoxib, parecoxib, valdecoxib, rofecoxib, lumiracoxib, etoricoxib, meloxicam, and mixtures and prodrugs thereof.

In certain embodiments of the present invention, the PGE2 antagonist does not bind PPARγ and modulate PPARγ activity at pharmacologically relevant concentrations in the combination with an I-DASH inhibitor. In certain embodiments of the present invention, the PGE2 antagonist is not indomethacin.

In other embodiments, the PGE2 antagonist is a phospholipases A2 inhibitor, and more preferably an inhibitor of cytosolic phospholipases A2 (cPLA2).

In certain embodiments, the subject immuno-DASH inhibitors and PGE2 antagonists are co-formulated. For example, the subject immuno-DASH inhibitors are co-formulated with a PGE2 antagonist such as a cyclo-oxygenase inhibitor. In preferred embodiments, the subject immuno-DASH inhibitors are co-formulated, i.e., into a single dosage formulation, for oral administration with a PGE2 antagonist such as a cyclo-oxygenase inhibitor. In preferred embodiments, the immuno-DASH inhibitor and PGE2 antagonist are co-formulated in a form suitable for once daily or twice daily dosages, such as tablets, capsules or the like.

In certain preferred embodiments, the PGE2 antagonist increases the maximum tolerated dose of the I-DASH inhibitor by at least 30%, and more preferably at least 50%, 75%, 100%, or even at least 2, 5, 10, 20, 40 or even more than 50-fold compared to the MTD of the I-DASH inhibitor in the absence of the PGE2 antagonist.

In certain preferred embodiments, the PGE2 antagonist improves the efficacy rate and/or complete response rate of the I-DASH inhibitor by at least 30%, and more preferably at least 50%, 75%, 100%, or even at least 2, 5, 10, 20, 40 or even more than 50-fold compared to the efficacy and/or complete response rate of the I-DASH inhibitor in the absence of the PGE2 antagonist.

In certain preferred embodiments, the PGE2 antagonist reduces the dose of immuno-DASH inhibitor required, compared to administration of the immuno-DASH inhibitor alone, to produce a given antitumor effect (such as average percentage reduction in tumor volume over time compared to placebo and/or average rate of survival compared to placebo). In certain embodiments, the PGE2 antagonist reduces the dose of immuno-DASH inhibitor required, compared to administration of the immuno-DASH inhibitor alone, to produce a given antitumor effect by 10%, and more preferably at least 15%, 20%, 30%, 40%, 50% or even 75%. In certain embodiments, the PGE2 antagonist reduces the effect dose (ED) of immuno-DASH inhibitor required, compared to administration of the immuno-DASH inhibitor alone, to produce a given antitumor effect by 10%, and more preferably at least 15%, 20%, 30%, 40%, 50% or even 75%. In certain embodiments, the PGE2 antagonist reduces the minimum effect dose of immuno-DASH inhibitor required, compared to administration of the immuno-DASH inhibitor alone, to produce a given antitumor effect by 10%, and more preferably at least 15%, 20%, 30%, 40%, 50% or even 75%. In certain embodiments, the PGE2 antagonist reduces the maximum effect dose of immuno-DASH inhibitor required, compared to administration of the immuno-DASH inhibitor alone, to produce a given antitumor effect by 10%, and more preferably at least 15%, 20%, 30%, 40%, 50% or even 75%.

In certain preferred embodiments, the PGE2 antagonist increases the therapeutic index for an immuno-DASH inhibitor, compared to administration of the immuno-DASH inhibitor alone, by at least a factor of 2, and more preferably at least 5, 10, 15, 20, 25, 30, 40, 50, 75 or even 100.

In certain embodiments, the subject immuno-DASH inhibitor can be administered as part of a therapy involving one or more other chemotherapeutic agents, immuno-oncology agents or radiation. The combination therapy can also include a PGE2 antagonist. It can also be used a part of therapy including tumor vaccines, adoptive cell therapy, gene therapy, oncolytic viral therapies and the like.

Merely to illustrate, the immuno-DASH inhibitor can be administered as part of a combination immuno-oncology treatment including a PD-1 antagonist (including anti-PD-1 antibodies such as Keytruda, Opdivo, PDR001, Pidilizumab and MEDI0680, and/or anti-PD-L1 antibodies such as Atezolizumab or Durvalumab), an anti-CTLA4 MAb (such as Yervoy), an anti-VEGF-2 MAb (such as Cyramza), an anti-EGFr MAb (such as Necitumumab), an IDO inhibitor (such as NLG919), an IDO1 inhibitor (such as Epacadostat), an anti-B7-H3 MAb (such as MGA271), an anti-GITR MAb (such a MK-4166), an HDAC inhibitor (such as entiostat), an anti-CD137 Mab (such as Urelumab or PF-05082566), an anti-CD20 MAb (such as Ublituximab or Gazyva), a PI3K delta inhibitor (such as TGR-1202), an IL-15 agonist (such as IL15Ra-Fc fusion protein ALT-803), a CXCR4 antagonist (such as Ulocuplumab, Plerixafor and BL-8040), a CXCL12 antagonist (such as the Spiegelmer NOX-A12), a DNMT inhibitor (such as azacitidine), an anti-LAG3 MAb (such as BMS-986016 or LAG525), interleukin-21, an anti-KIR MAb (such as Lirilumab), an anti-CD27 MAb (such as Varlilumab), an anti-CSF-1R MAb (such as FPA008 or RO5509554), an anti-CCR4 MAb (such as Mogamulizumab), GMCSF (such as sargamostim), an anti-PS MAb (such as Bavituximab), and anti-CD30 MAb-aurstatin E conjugate (such as Adcetris), an anti-CD19 MAb (such as MEDI-551), a CD40 agonist (such as RO7009789), and anti-CEA IL-2 MAb (such as RG7813), an anti-OX40 MAb (such as RG7888 or MEDI-6469), an OX40 agonist (such as MEDI6383), an anti-NY-ESO-1 MAb (such as CDX-1401), an anti-NKG2A MAb (such as IPH2201), a STING agonist, an NLRP3 or NLRP1 agonist, an anti-CD73 MAb (such as MEDI9447).

BRIEF DESCRIPTION OF THE DRAWINGS

FIG. 12 shows the average change in tumor volume for untreated versus ARI-5544 treated cohorts, as well as the average change in weight (rapid weight loss would be an indication of toxicity). FIG. 13: Top row of panels showing animals treated either with vehicle alone (simple line) or with drug (line with terminating asterisk). Bottom row of panels showing animals treated either with anti-PD-1 and anti-CTLA-4 antibody and vehicle (simple line) or with anti-PD-1 and anti-CTLA-4 antibody and drug (line with terminating asterisk). IP is intraperitoneal. IT is intratumoral injection. In each case, "vehicle" refers to the base treatment-isotype control in the case of the top panels, and anti-PD-1+anti-CTLA-4 antibodies in the case of the bottom panels. The asterisked lines are those animals treated with vehicle plus ARI-4175 or ARI-5544 as indicated.

FIGS. 18, 19 and 20 show the measured tumor volumes over time, while FIG. 21 shows the individual animal tumor growth curves for the Val-boroPro (+/−celecoxib) treated groups. Treatment with vehicle (control) or Val-boroPro began at Day 3 after tumor inoculation, and was administered on days 4-8, 11-15 and 18-22.

Of the animals indicated to have "regressed" in FIGS. 21, 25, 26, 30 and 32, more than 80 percent of those animals maintained immunity to the MB49 tumor and did not grow new tumors when rechallenged with the MB49 tumor cells 30 days after the last dose of I-DASH inhibitor had been administered, indicating a T-cell mediated immune response was invoked by the therapies including the I-DASH inhibitor.

DETAILED DESCRIPTION

I. Overview

The immuno-DASH (I-DASH) inhibitors of the present invention are multimediator immuo-oncology agents targeting a novel checkpoint pathway involving macrophages through DPP8 and DPP9 inhibition, and chemokine/cytokine signaling pathways (such as CXCL10) though DPP4 and (potentially) FAP inhibition.

Figure 2:
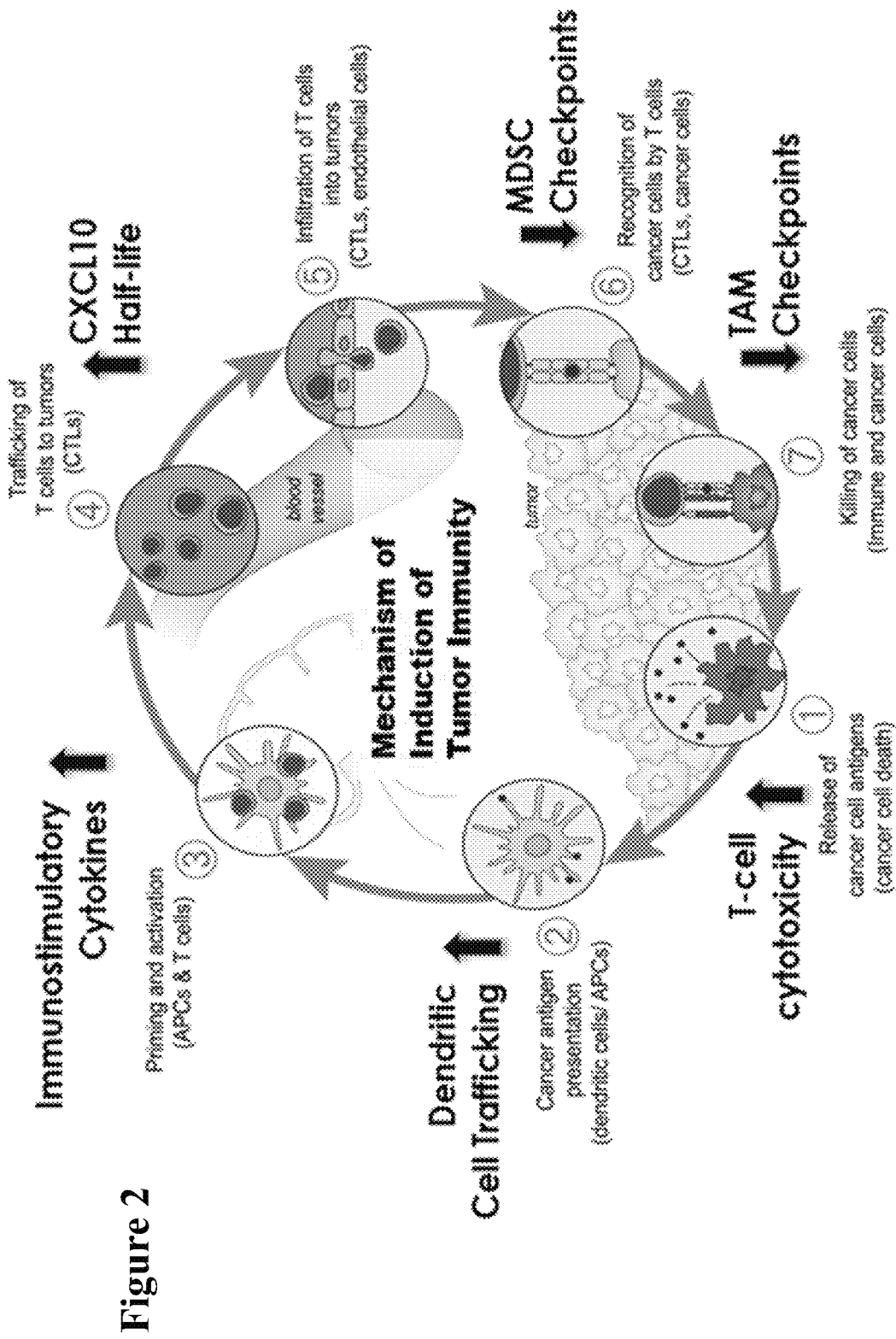
FIG. 2 is a graphical representation of the immune mechanism mediated by extracellular and intracellular targets of the subject immuno-DASH inhibitors, with the up- and down-arrows (and associated text) indicating the inhibition or stimulation/prolongation of a particular effect (direct or indirect). MDSC=Myeloid-derived Suppressor Cell. TAM=Tumor Associated Macrophage. Immune wheel adapted from Chen and Mellman 2013, Immunity 39(1):1-10.

FIG. 2 shows the direct and indirect effects on tumor-directed immune responses that are brought about by treatment with the immuno-DASH inhibitors of the present invention. For instance, merely to illustrate, the present immuno-DASH inhibitors are able to:

induce programmed cell death selectively in macrophages;
reduce monocytic MDSCs in tumor;
reduce T-cell suppressive activity of granulocytic MDSCs;
enhance trafficking of key effector immunocytes;
increase levels of NK and dendritic cells;
accelerate expansion of tumor specific T-cells;
sensitize carcinoma cells to CTL killing;
induces the expression of cell surface proteins on tumor cells increasing immune reactivity, such as increased expression of MHC class I proteins, calreticulin and/or tumor cell antigens;
induce immunostimulatory cytokines and chemokines; and
stabilizes biologically active forms of several key cytokines and chemokines—including CXCL10

Figure 3:
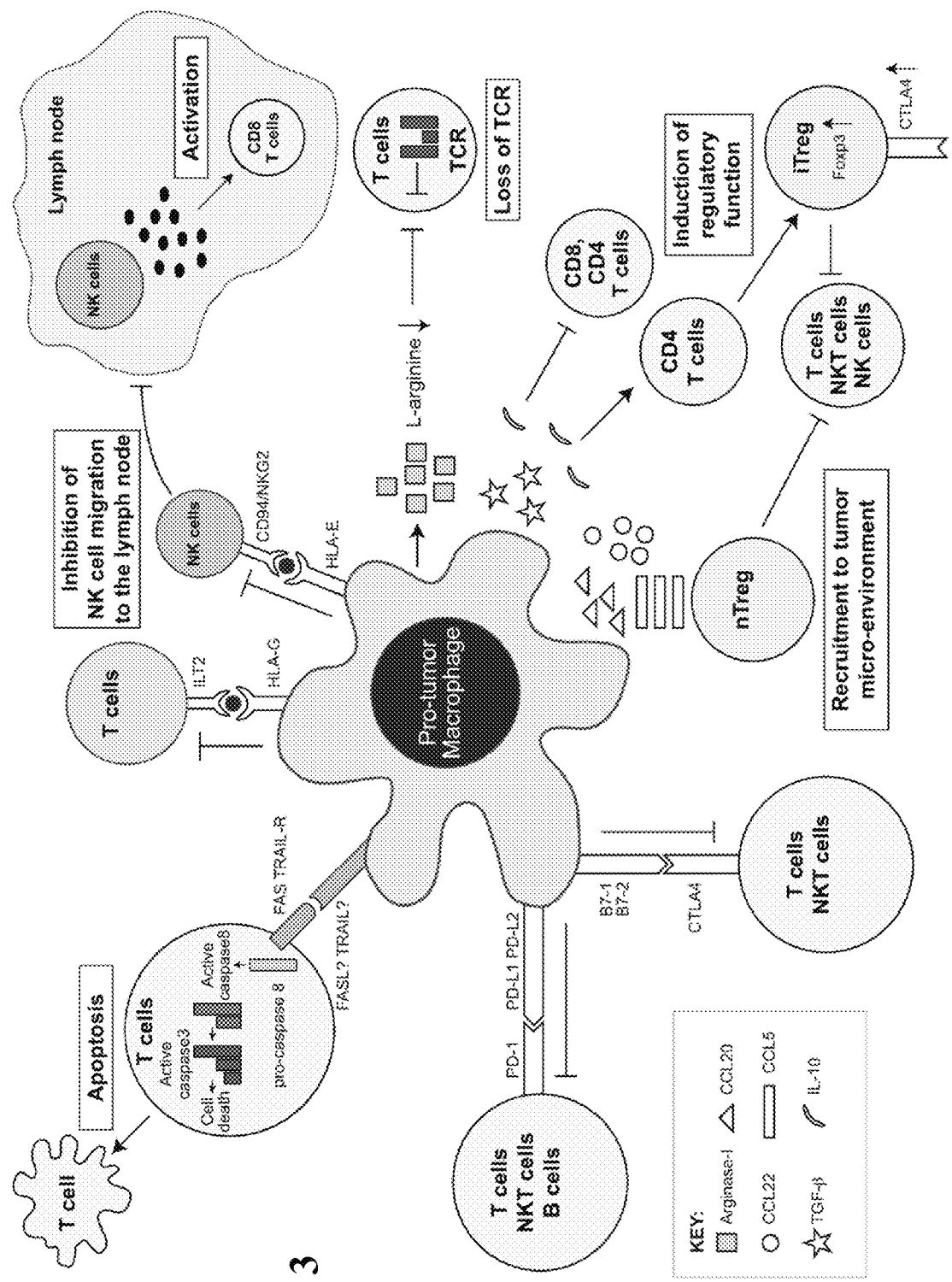
FIG. 3 depicts tumor-associated macrophages (TAMs) as central immune regulators of the tumor microenvironment. Adapted from Noy and Pollard. Immunity (2014) 41, 49-81.
Figure 4:
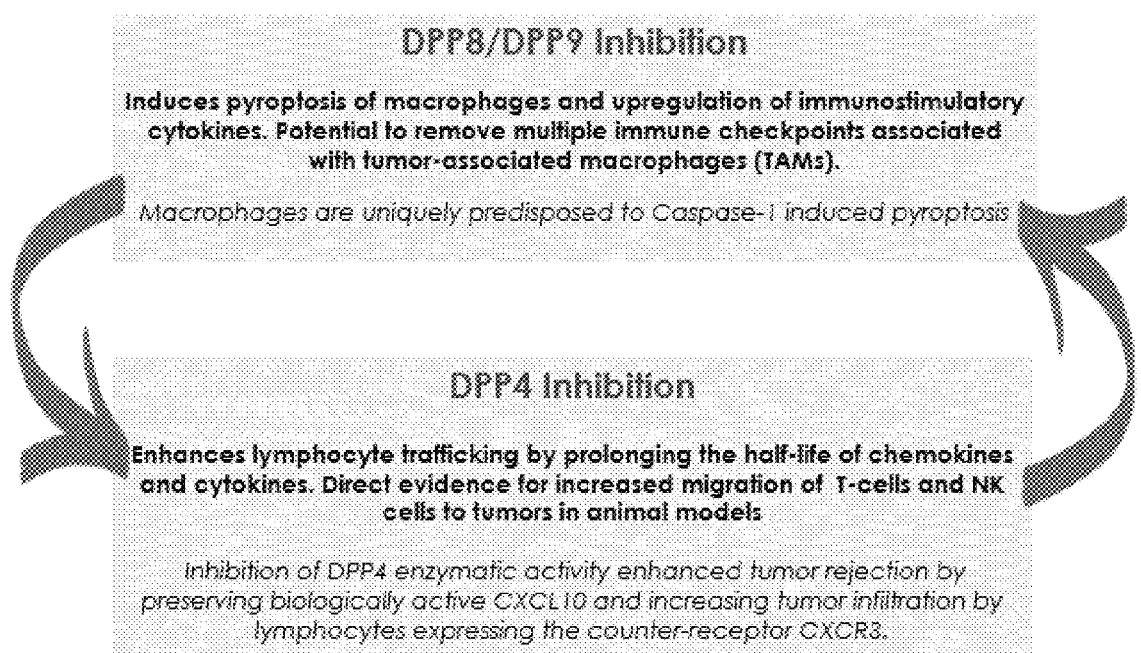
FIG. 4 is a simple graphical representation of the interplay between DPP8 and DPP9 inhibition as an induction event, and DPP4 inhibition as a prolongation event.

In cell culture, only macrophage (and macrophage derived cells such as AML cells) are killed by I-DASH inhibitors, and through a mechanism involving pyroptosis. I-DASH inhibitors are not directly toxic to non-macrophage normal or tumor cells. As shown in FIG. 3, tumor-associated macrophages (TAMs) express an array of effector molecules that inhibit the antitumor immune responses; this includes cell surface receptors, cytokines, chemokines, and enzymes. While not wishing to be bound by any particular theory, by selectively targeting tumor-associated macrophages to undergo pyroptosis by virtue of the selectivity of those cells to DPP8/DPP9 inhibition relative to other cells, immuno-DASH inhibitors can remove multiple immune checkpoint in the tumor microenvironment.

In the proposed mechanism-of-action, potent and prolonged (long $K_{off}$ rate) inhibition of DPP8 and DPP9 induces release of immunostimulatory cytokines such as IL-1beta, potentially involving programmed cell death of macrophage through pyroptosis, which leads to stimulation of immune responses and de-repression of immunosuppressive actions of the tumor-associated macrophages. While inhibition of DPP8 and DPP9 represent the induction of the response, inhibition of DPP4 and (potentially) FAP represent the prolongation mechanism, increasing the serum half-life of chemokines and cytokines, such as CXCL10, which enhance trafficking of immune cells to the tumor.

Figure 11:
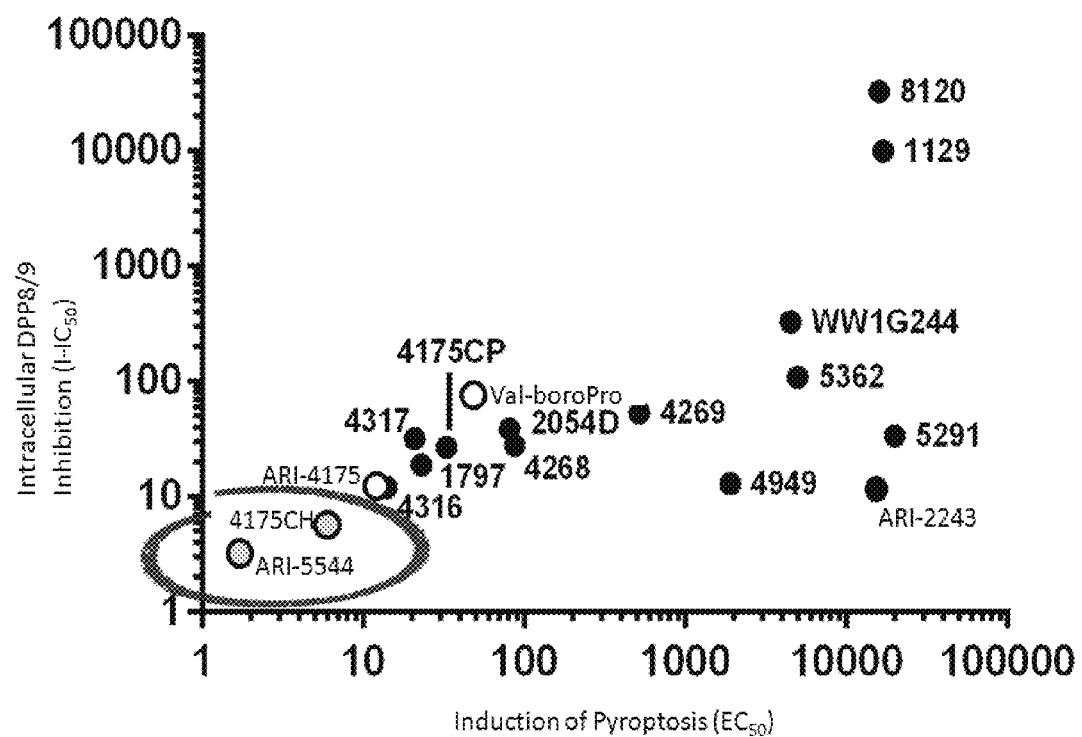
FIG. 11 shows the developing correlation between potency for inhibition of DPP8 and DPP9 when used to treat whole cells (intracellular $IC_{50}$ or $IIC_{50}$) and the $IC_{50}$ for inducing pyroptosis of macrophages in cell culture.

FIG. 11 illustrates that more effective and safer immuno-DASH inhibitors can be identified by optimizing inhibitors according to intracellular IC50 ("IIC50") for DPP8 and DPP9 inhibition, and that (again, not wishing to be bound by any particular theory), the potency of the agent being able to induce pyroptosis in macrophages in vitro.

ARI-4175 (t-butylglycine-boroProline) is one example of a compound that exhibits a more potent inhibition of intracellular DPP8 and DPP9, with an IIC50 that is 7-fold less than that of Valine-boroProline. ARI-4175CH and ARI-5544, which are described in greater detail in the Examples section below, illustrate that immuno-DASH compounds of the present invention have DPP8/DPP9 IIC50 values that are, respectively, −12- and −35-fold less than that of Valine-borProline. These compounds exemplify immuno-DASH inhibitors having improved in vivo potency and improved therapeutic index relative to both ARI-4175 and Valine-boroProline.

Figure 5:
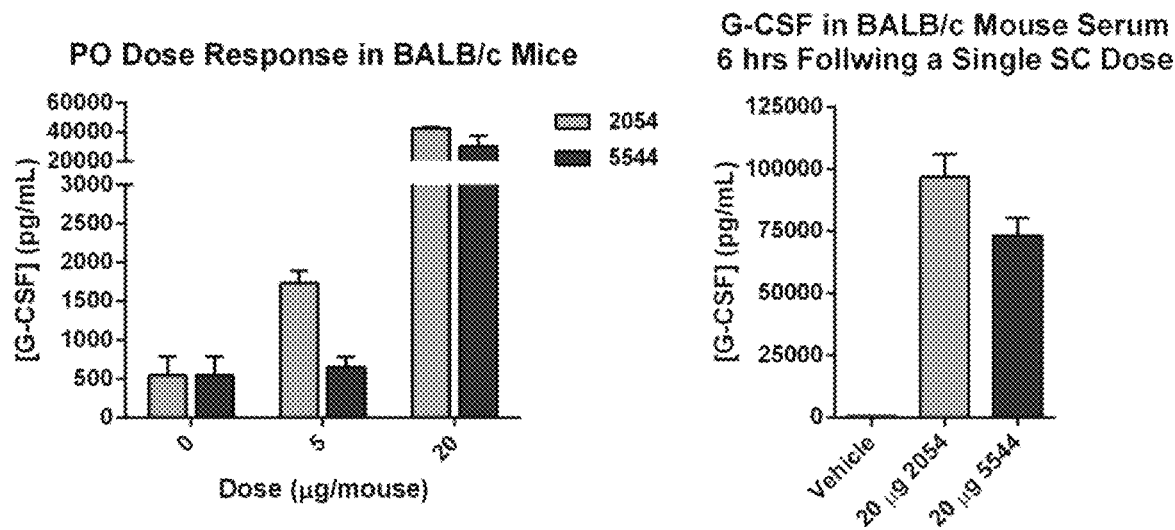
FIG. 5 is bar graphs showing cytokine induction by ARI-5544, with comparison to ARI-2054 (Val-boroPro).
Figure 12:
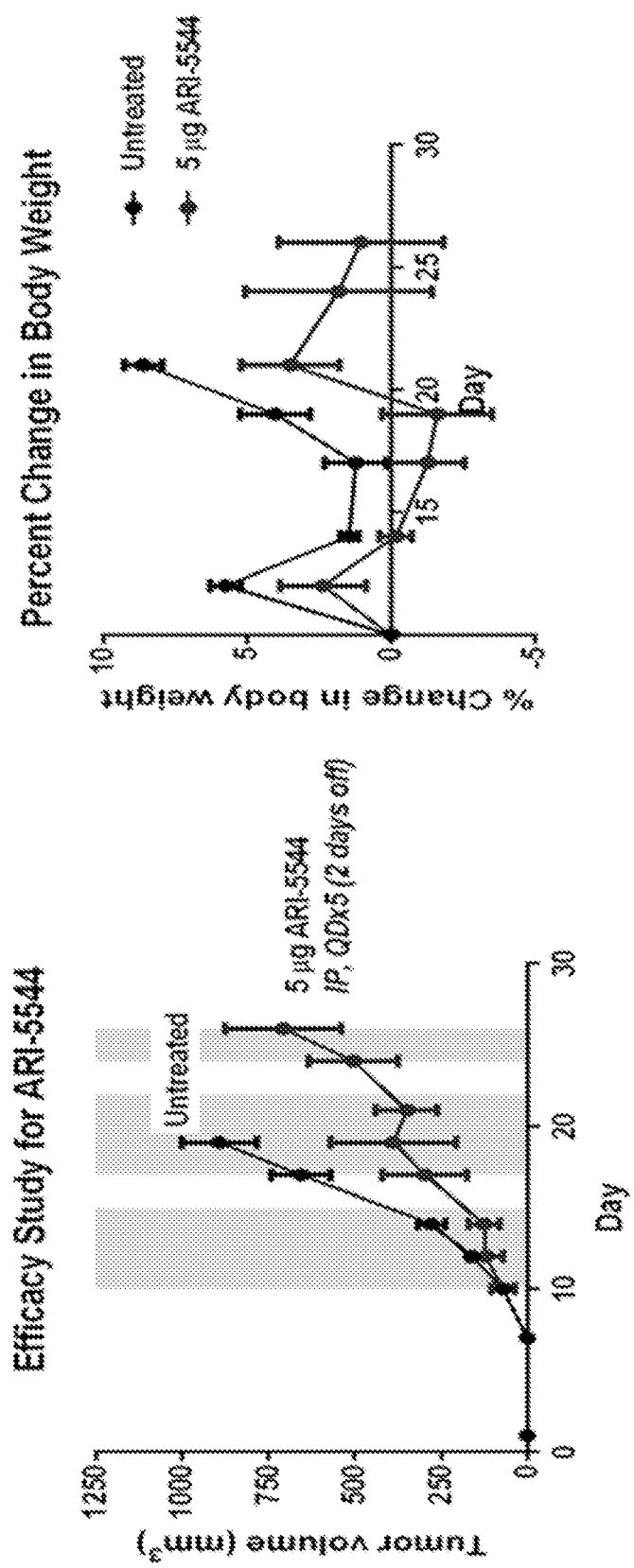
FIGS. 12 and 13 show the results of treating CT26 tumor bearing mice with ARI-5544 and ARI-4175 (t-butylglycine-boroProline) with and without combination with anti-PD-1 and anti-CTLA-4 antibody therapies.
Figure 13:
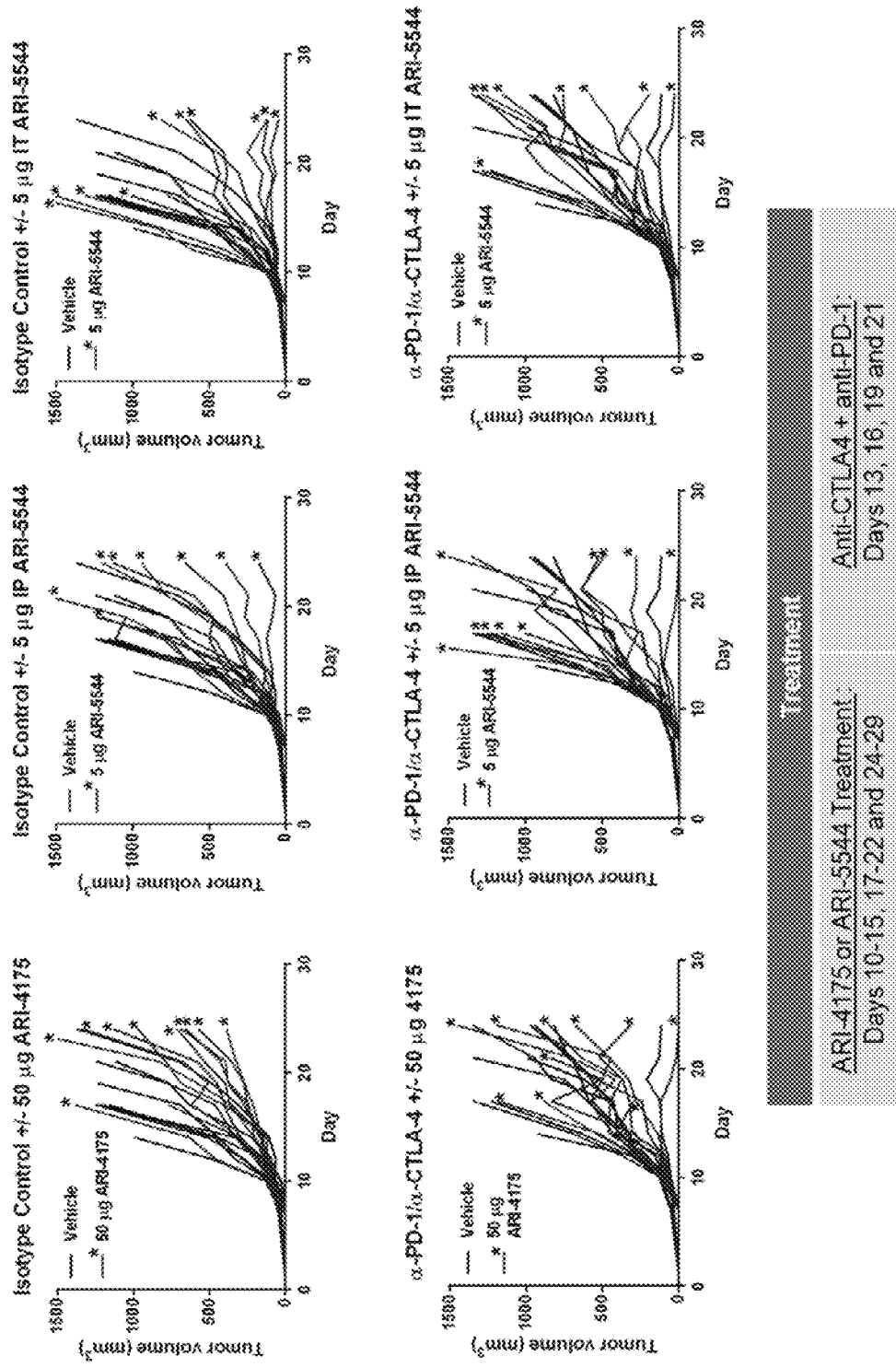

As shown in FIGS. 12 and 13, 5 micrograms of ARI-5544 alone (intraperitoneal injection shown in FIG. 13, top row, middle panel; intratumoral injection shown in FIG. 13, top row, right panel) outperforms 50 micrograms of ARI-4175 alone (intraperitoneal injection—FIG. 13, top row, left panel) in the established CT26 colon carcinoma model (animals treated 10 days after tumor inoculation and have developed sizable tumors before treatment). When combined in a triple therapy protocol with an anti-PD-1 antibody and an anti-CTLA-4 inhibitor, 5 micrograms of ARI-5544 produced complete regression of tumors in several of the treated animals. See FIG. 13, bottom row, middle and right panels.

Figure 14:
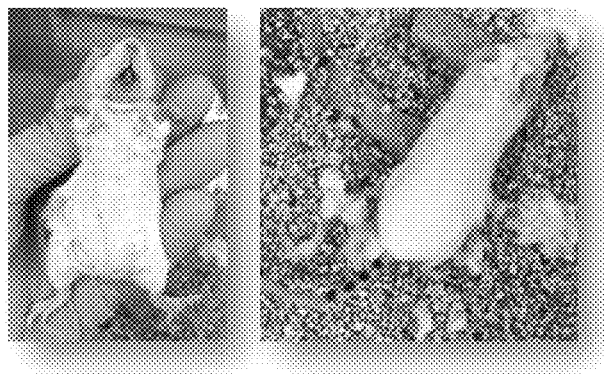
FIG. 14 shows pictures showing the overall health (as manifest in fur coat) of mice after treatment with 5 micrograms of ARI-5544 (sufficient to produce more than 50% inhibition of tumor growth) as compared to 10 and 20 micrograms of Valine-boroProline (sufficient to produce an average of about 30% and 80% inhibition, respectively, of tumor growth) and as compared to animals treating with vehicle (no drug) alone.
Figure 14:
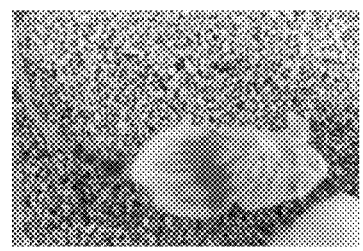
Figure 14:
Figure 14:
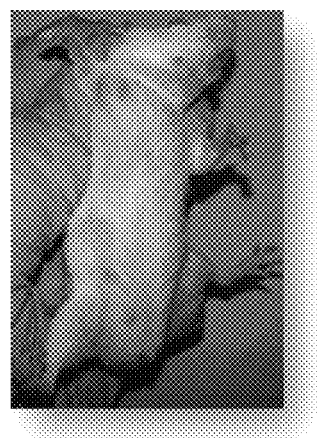

As shown in FIG. 14, animals to which 5 micrograms of ARI-5544 has been administered over a course of 26 days (an amount sufficient to produce more than an average of 50% inhibition of tumor growth in the CT26 model) are significantly healthier than the animals dosed with 10 micrograms or 20 micrograms Valine-boroProline (amounts sufficient to produce an average of about 30% and 80% inhibition, respectively, of tumor growth).

II. Definitions

For convenience, before further description of the present invention, certain terms employed in the specification, examples, and appended claims are collected here.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{30}$ for straight chain, $C_3$-$C_{30}$ for branched chain), for example 20 or fewer. Likewise, certain cycloalkyls have from 3-10 carbon atoms in their ring structure, for example, 5, 6 or 7 carbons in the ring structure. "Alkyl" (or "lower alkyl") as used throughout the specification and claims is intended to include both "unsubstituted alkyls" and "substituted alkyls".

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, for example, from one to four or one to six carbon atoms in its backbone structure. Likewise, "lower alkenyl" and "lower alkynyl" have similar chain lengths. In some embodiments, alkyl groups are lower alkyls. In some embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphionate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, for example, 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heteroaryl" refers to a monovalent aromatic monocyclic ring system wherein at least one ring atoms is a heteroatom independently selected from the group consisting of O, N and S. The term 5-membered heteroaryl refers to a heteroaryl wherein the number of ring atoms is 5. Examples of 5-membered heteroaryl groups include pyrrolyl, pyrazolyl, oxazolyl, isoxazolyl, thiazolyl, isothiazolyl, oxadiazolyl, thiadiazolyl, furazanyl, imidazolinyl, and triazolyl.

The term "heterocycloalkyl" refers to a monocyclic or bicyclic monovalent saturated or non-aromatic unsaturated ring system wherein from 1 to 4 ring atoms are heteroatoms independently selected from the group consisting of O, N and S. The term "3-10 membered heterocycloalkyl" refers to a heterocycloalkyl wherein the number of ring atoms is from 3 to 10. Examples of 3-10 membered heterocycloalkyl include 3 to 6-membered heterocycloalkyl. Bicyclic ring systems include fused, bridged, and spirocyclic ring systems. More particular examples of heterocycloalkyl groups include azepanyl, azetidinyl, aziridinyl, imidazolidinyl, morpholinyl, oxazolidinyl, oxazolidinyl, piperazinyl, piperidinyl, pyrazolidinyl, pyrrolidinyl, quinuclidinyl, and thiomorpholinyl.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Exemplary heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

"Halogen" or "halo" by themselves or as part of another substituent refers to fluorine, chlorine, bromine and iodine, or fluoro, chloro, bromo and iodo.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. Substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —$CH(NH_2)COOH$ portion, as defined by K. D. Kopple, "Peptides and Amino Acids", W. A. Benjamin Inc., New York and Amsterdam, 1966, pages 2 and 33.

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term amino acid residue further includes analogs, derivatives and congeners of any specific amino acid referred to herein, as for instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as, falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "$IC_{50}$" refers to the concentration of an inhibitor where the response (or binding) is reduced by half, and can be measured in whole cell, animals or in vitro cell-free (purified enzyme) systems. Inhibition of cell-free enzyme may also be reported as Ki values with some formal kinetics measurements.

The term "ICIC$_{50}$" or "IIC$_{50}$" is the measure of DPP8 and DPP9 inhibition in the context of a whole cell such that cell permeability becomes a factor (DPP8 and DPP9, which are cell permeable, the purified enzymes miss the cell permeable requirements for measuring IC50)

The term "DPP4" refers to the protein dipeptidyl peptidase 4, also known as adenosine deaminase complexing protein 2 or CD26 (cluster of differentiation 26).

The term "DPP8" refers to the protein dipeptidyl peptidase 8.

The term "DPP9" refers to the protein dipeptidyl peptidase 9.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The term "EnPlex" refers to a purified enzyme activity assay described in Bachovchin et al. Nature Chemical Biology 10, 656-663 (2014). Briefly, purified enzymes are coupled to Luminex microspheres, with a different bead color for each enzyme. Multiplexed bead complexes are incubated with a compound before being treated with a biotinylated activity-based probe and a streptavidin R-phycoerythrin conjugate (SAPE). The mixtures are scanned on a Luminex flow cytometer, where one laser detects the bead color (enzyme identity) and a second laser detects the R-phycoerythrin signal (enzyme activity). The enzyme concentration is calculated assuming 100% of the protein was coupled to the beads.

An "Enplex IC$_{50}$" is the IC % for enzyme inhibition as measured using EnPlex.

The terms "P1 position" and "P2 position", in the case of a dipeptide (or dipeptide analog), refer to the carboxy and amino terminal residues, respectively. In the case of the subject I-DASH inhibitors, the P1 position is the amino acid (or amino acid analog) in which the boronic acid replaces the carboxy terminus.

III. Exemplary Embodiments

One aspect of the present invention relates to a method of enhancing a cell-mediated immune response against a cancer, comprising administering to a mammal in need thereof a therapeutically effective amount of an immuno-DASH inhibitor, wherein: (a) at the therapeutically effective amount, the immuno-DASH inhibitor is characterized by a parmacokinetic profile of being an inhibitor of DPP8, DPP9 and DPP4; and (b) the immuno-DASH inhibitor has: i) an in vivo IC$_{50}$ for DPP4 inhibition of less than 50 nM, and ii) an intracellular IC$_{50}$ for DPP8 and DPP9 inhibition less than 50 nM.

Another aspect of the present invention relates to a method of treating a myeloproliferative disease, comprising administering to a mammal in need thereof a therapeutically effective amount of an immuno-DASH inhibitor; wherein: (a) at the therapeutically effective amount, the immuno-DASH inhibitor is characterized by a parmacokinetic profile of being an inhibitor of DPP8, DPP9 and DPP4; and (b) the immuno-DASH inhibitor has: i) an in vivo IC$_{50}$ for DPP4 inhibition of less than 50 nM, and ii) an intracellular IC$_{50}$ for DPP8 and DPP9 inhibition less than 50 nM.

Another aspect of the present invention relates to a method treating a relapse of a cancer, comprising administering to a mammal in need thereof a therapeutically effective amount of an immuno-DASH inhibitor; wherein: (a) at the therapeutically effective amount, the immuno-DASH inhibitor is characterized by a parmacokinetic profile of being an inhibitor of DPP8, DPP9 and DPP4; and (b) the immuno-DASH inhibitor has: i) an in vivo IC$_{50}$ for DPP4 inhibition of less than 50 nM, and ii) an intracellular IC$_{50}$ for DPP8 and DPP9 inhibition less than 50 nM.

In some embodiments of any one of the foregoing methods, said compound increases CXCL10 serum concentration.

In some embodiments of any one of the foregoing methods, the immuno-DASH-inhibitor decreases the number of cancer associated macrophages.

In some embodiments of any one of the foregoing methods, the immuno-DASH-inhibitor reduces monocytic myeloid-derived suppressor cells in the cancer.

In some embodiments of any one of the foregoing methods, wherein at the therapeutically effective amount, the immuno-DASH-inhibitor reduces T-cell suppressive activity of granulocytic myeloid-derived suppressor cells in the cancer In some embodiments of any one of the foregoing methods, the immuno-DASH-inhibitor produces full cancer regression, and the therapeutically effective amount is less than the immuno-DASH inhibitor's maximum tolerated dose.

In some embodiments of any one of the foregoing methods, the immuno-DASH-inhibitor possess an Ki for DPP8 and DPP9 inhibition less than 100 nM, and preferably less than 10 nM or even less than 1.0 nM. In some embodiments, the immuno-DASH-inhibitor possess an intracellular IC$_{50}$ for DPP8 and DPP9 inhibition less than 100 nM, and preferably less than 10 nM or even less than 1.0 nM.

In some embodiments, the immuno-DASH-inhibitor possess an IC$_{50}$ for DPP4 inhibition less than 100 nM, and preferably less than 10 nM or even less than 1.0 nM.

In some embodiments of any one of the foregoing methods, the immuno-DASH-inhibitor possess a k$_{off}$ rate for interaction with DPP4 less than $1\times10^4$/sec.

Another aspect of the present invention relates to any one of the foregoing methods, wherein the cancer is selected from the group consisting of basal cell carcinoma, biliary tract cancer, bladder cancer, bone cancer, brain cancer, breast cancer, cervical cancer, choriocarcinoma, CNS cancer, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, acute myeloid leukemia, acute lymphoid leukemia, chronic myeloid leukemia, chronic lymphoid leukemia, liver cancer, small cell lung cancer, non-small cell lung cancer, lymphoma, Hodgkin's lymphoma, Non-Hodgkin's lymphoma, melanoma, myeloma, myeloproliferative disease, neuroblastoma, oral cavity cancer, ovarian cancer, pancreatic cancer, prostate cancer, retinoblastoma, rhabdomyosarcoma, rectal cancer, renal cancer, cancer of the respiratory system, sarcoma, skin cancer, stomach cancer, testicular cancer, thyroid cancer, uterine cancer, and cancer of the urinary system.

In some embodiments, the cancer is selected from the group consisting of carcinoma, sarcoma, leukemia, lymphoma or myeloma.

In some embodiments, the cancer selected from the group consisting of lung cancer, lymphomas, breast cancer, colorectal cancer, thyroid cancer, uterine cancer, pancreatic cancer, prostate cancer, skin cancer, kidney cancer, liver cancer and brain cancer.

Another aspect of the present invention relates to any one of the foregoing methods, wherein the myeloproliferative disease is acute myeloid leukemia.

Another aspect of the present invention relates to any one of the foregoing methods, wherein the myeloproliferative disease is a chronic myeloproliferative disease.

Another aspect of the present invention relates to any one of the foregoing methods, wherein: the maximum tolerated dose of the immune-DASH inhibitor in C57BL/6 mice is at least 10 mg/kg; and the immune-DASH inhibitor induces fill cancer regression in C57BL/6 mice at a dose less than the maximum tolerated dose in C57BL/6 mice.

In some embodiments, the immuno-DASH inhibitor induces immunological memory.

In some embodiments, the immunological memory induces an immune response greater than a previous immune response.

In some embodiments, the patient has previously received or is currently receiving a cancer vaccine.

In some embodiments, the patient has previously received or is currently receiving an adoptive cell transfer, including T-cell therapy, NK cell therapy, CAR-T cell therapy, or ACTR cell therapy.

In some embodiments, the patient has previously received or is currently receiving and antibody therapy.

In some embodiments, the patient has previously received or is currently receiving at least one additional checkpoint inhibitor.

In some embodiments, the patient has previously received or is currently receiving a MAP kinase pathway inhibitor or a WNT pathway inhibitor.

In some embodiments, the immuno-DASH inhibitor is administered orally or parenterally.

In some embodiments, the immuno-DASH inhibitor is administered orally.

In some embodiments, the immuno-DASH inhibitor is administered parenterally.

In some embodiments, the immuno-DASH inhibitor is administered topically.

In some embodiments, the immuno-DASH inhibitor is administered in a solid dosage form.

In some embodiments, the solid dosage form is a tablet, capsule or pill.

In some embodiments, the solid dosage form is a tablet.

In some embodiments, the immune-DASH inhibitor is administered in an amount sufficient to stimulate the immune system without dose limiting toxicity.

Another aspect of the invention relates the immuno-DASH inhibitor represented by formula I, or a pharmaceutical salt thereof:

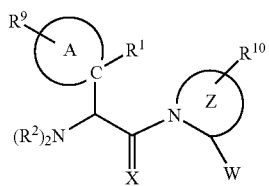

(I)

wherein
ring A represents a 3-10 membered ring structure;
ring Z represents a 4-10 membered heterocycle including the N and the Cα carbon;
W represents —CN, —CH=NR$^4$, a functional group which reacts with an active site residue of the target, or

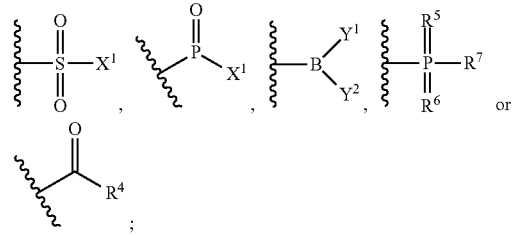

X is O or S;
X$^1$ represents a halogen;
Y$^1$ and Y$^2$ are independently OH, or together with the boron atom to which they are attached represent a group that is hydrolysable to a boronic acid, or together with the boron atom to which they are attached form a 5-8 membered ring that is hydrolysable to a boronic acid;
R$^1$ represents a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —CF$_3$, —(CH$_2$)$_m$—R$^3$, —(CH$_2$)$_m$OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$^3$;
R$^2$ represents, for each occurrence, hydrogen, lower alkyl, lower alkynyl, —(CH$_2$)$_m$—R$^3$, —C(=O)-alkyl, —C(=O)-alkenyl, —C(=O)-alkynyl, or —C(=O)—(CH$_2$)$_m$—R$^3$;
R$^3$ represents, for each occurrence, hydrogen, or a substituted or unsubstituted lower alkyl, lower alkenyl, aryl, aralkyl, cycloalkyl, cycloalkenyl, or heterocycle;
R$^4$ represents a hydrogen, a lower alkyl, a lower alkenyl, a lower alkynyl, —(CH$_2$)$_m$—R$^3$, —(CH$_2$)$_n$—OH, —(CH$_2$)$_n$—O-lower alkyl, —(CH$_2$)$_n$—O-alkenyl, —(CH$_2$)$_n$—O-alkynyl, —(CH$_2$)$_n$—O—(CH$_2$)$_m$—R$_7$, —(CH$_2$)$_n$—SH, —(CH$_2$)$_n$—S-lower alkyl, —(CH$_2$)$_n$—S-lower alkenyl, —(CH$_2$)$_n$—S-lower alkynyl, —(CH$_2$)$_n$—S—(CH$_2$)$_m$—R$^3$, —C(O)C(O)NH$_2$, or —C(O)C(O)OR$^8$;
R$^5$ represents O or S;
R$^6$ represents N$_3$, SH, NH$_2$, NO$_2$ or OR$^8$;
R$^7$ represents hydrogen, a lower alkyl, an amine, OR$^8$, or a pharmaceutically acceptable salt, or R$^5$ and R$^6$ taken together with the phosphorous atom to which they are attached complete a heterocyclic ring having from 5 to 8 atoms in the ring structure;
R$^8$ represents, hydrogen, a substituted or unsubstituted alkyl, alkenyl, aryl, aralkyl, cycloalkyl, cycloalkenyl or heterocyclyl;
R$^9$ and R$^{10}$, each independently, are absent or represents one, two, or three substitutions to the ring A or to the ring Z to which they are appended, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, an isocyano, a thiocyanato, an isothiocyanato, a cyanato, a nitro, an azido, a sulfate, a sulfonate, a sulfonamido, lower alkyl-C(O)OH, —O-lower alkyl-C(O)OH, -guanidinyl; —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$^3$;

n is 0, 1, 2, or 3; and m is 0, 1, 2, or 3.

In certain embodiments, the immuno-DASH inhibitor of Formula I is represented in Formula Ia, or is a pharmaceutical salt thereof:

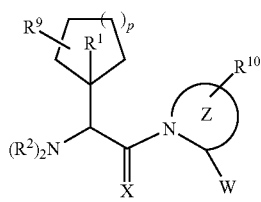

(Ia)

wherein X, W, Z, R$^1$, R$^2$, R$^9$ and R$^{10}$ are as defined above for Formula I, and p is 1, 2 or 3.

In certain preferred embodiments of Ia: R$^1$ is a lower alkyl; R$^9$ is absent, or independently for each occurrence, is a lower alkyl, —OH, —NH$_2$, —N$_3$, -lower alkyl-C(O)OH, —O-lower alkyl, —O-lower alkyl-C(O)OH, -guanidinyl; X is O; each R$^2$ is hydrogen, R$^{10}$ is absent, or represents a single substitution of —OH, —NH$_2$, —CN or —N$_3$; and W is —B(OH)$_2$ or —CN (and more preferably —B(OH)$_2$).

In certain embodiments, the immuno-DASH inhibitor of Formula I is represented in Formula Ib, or is a pharmaceutical salt thereof:

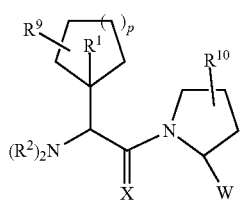

(Ib)

wherein X, W, R$^1$, R$^2$, R$^9$ and R$^{10}$ are as defined above for Formula I, and p is 1, 2 or 3.

In certain preferred embodiments of Ib: R$^1$ is a lower alkyl; R$^9$ is absent, or independently for each occurrence, is a lower alkyl, —OH, —NH$_2$, —N$_3$, -lower alkyl-C(O)OH, —O-lower alkyl, —O-lower alkyl-C(O)OH, -guanidinyl; X is O; each R$^2$ is hydrogen, R$^{10}$ is absent, or represents a single substitution of —OH, —NH$_2$, —CN or —N$_3$; and W is —B(OH)$_2$ or —CN (and more preferably —B(OH)$_2$).

In certain embodiments, the immuno-DASH inhibitor of Formula I is represented in Formula Ic, or is a pharmaceutical salt thereof:

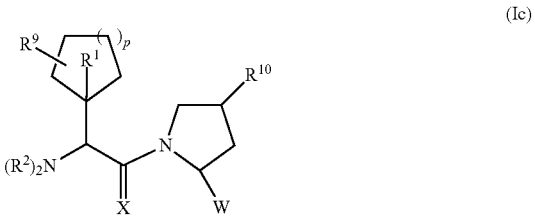

(Ic)

wherein X, W, R$^1$, R$^2$, R$^9$ and R$^{10}$ are as defined above for Formula I, and p is 1, 2 or 3.

In certain preferred embodiments of Ic: R$^1$ is a lower alkyl; R$^9$ is absent, or independently for each occurrence, is a lower alkyl, —OH, —NH$_2$, —N$_3$, -lower alkyl-C(O)OH, —O-lower alkyl, —O-lower alkyl-C(O)OH, -guanidinyl; X is O; each R$^2$ is hydrogen, R$^{10}$ is absent, or represents a single substitution of —OH, —NH$_2$, —CN or —N$_3$; and W is —B(OH)$_2$ or —CN (and more preferably —B(OH)$_2$).

In some embodiments, the immuno-DASH inhibitor is represented by:

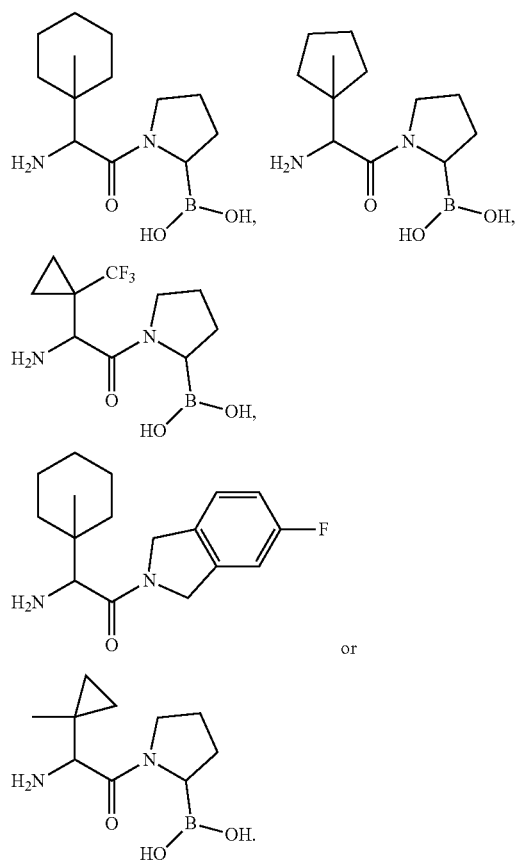

Another aspect of the invention relates the immuno-DASH inhibitor represented by formula II, or a pharmaceutical salt thereof:

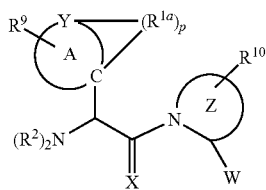

(II)

wherein
ring A, along with each occurrence of $R^{1a}$, represents a 7-12 membered polycyclic ring structure;
ring Z represents a 4-10 membered heterocycle including the N and the Cα carbon;
W represents —CN, —CH=NR$^4$, a functional group which reacts with an active site residue of the target, or

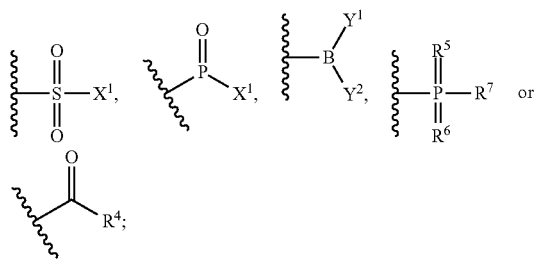

X is O or S;
$X^1$ represents a halogen;
Y is C or N;
$Y^1$ and $Y^2$ are independently OH, or together with the boron atom to which they are attached represent a group that is hydrolysable to a boronic acid, or together with the boron atom to which they are attached form a 5-8 membered ring that is hydrolysable to a boronic acid;
$R^{1a}$ represents a lower alkyl, —(CH$_2$)$_m$—, —(CH$_2$)$_m$—O—(CH$_2$)$_m$—; —(CH$_2$)$_m$—N—(CH$_2$)$_m$—; or —(CH$_2$)$_m$—S—(CH$_2$)$_m$—;
$R^2$ represents, for each occurrence, hydrogen, lower alkyl, lower alkynyl, —(CH$_2$)$_m$—R$^3$, —C(=O)-alkyl, —C(=O)-alkenyl, —C(=O)-alkynyl, or —C(=O)—(CH$_2$)$_m$—R$^3$;
$R^3$ represents, for each occurrence, hydrogen, or a substituted or unsubstituted lower alkyl, lower alkenyl, aryl, aralkyl, cycloalkyl, cycloalkenyl, or heterocycle;
$R^4$ represents a hydrogen, a lower alkyl, a lower alkenyl, a lower alkynyl, —(CH$_2$)$_m$—R$^3$, —(CH$_2$)$_n$—OH, —(CH$_2$)$_n$—O-lower alkyl, —(CH$_2$)$_n$—O-alkenyl, —(CH$_2$)$_n$—O-alkynyl, —(CH$_2$)$_n$—O—(CH$_2$)$_m$—R$_7$, —(CH$_2$)$_n$—SH, —(CH$_2$)$_n$—S-lower alkyl, —(CH$_2$)$_n$—S-lower alkenyl, —(CH$_2$)$_n$—S-lower alkynyl, —(CH$_2$)$_n$—S—(CH$_2$)$_m$—R$^3$, —C(O)C(O)NH$_2$, or —C(O)C(O)OR$^8$;
$R^5$ represents O or S;
$R^6$ represents N$_3$, SH, NH$_2$, NO$_2$ or OR$^1$;
$R^7$ represents hydrogen, a lower alkyl, an amine, OR$^8$, or a pharmaceutically acceptable salt, or $R^5$ and $R^6$ taken together with the phosphorous atom to which they are attached complete a heterocyclic ring having from 5 to 8 atoms in the ring structure;
$R^8$ represents, hydrogen, a substituted or unsubstituted alkyl, alkenyl, aryl, aralkyl, cycloalkyl, cycloalkenyl or heterocyclyl;

$R^9$ and $R^{10}$, each independently, are absent or represents one, two, or three substitutions to the ring A or to the ring Z to which they are appended, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, an isocyano, a thiocyanato, an isothiocyanato, a cyanato, a nitro, an azido, a sulfate, a sulfonate, a sulfonamido, lower alkyl-C(O)OH, —O-lower alkyl-C(O)OH, -guanidinyl; —(CH$_2$)$_m$—R$_7$, (CH$_2$)$_m$—OH, —(CH$_2$)$_m$—O-lower alkyl, —(CH$_2$)$_m$—O-lower alkenyl, —(CH$_2$)$_n$—O—(CH$_2$)$_n$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_n$—R$^3$;
n is 0, 1, 2, or 3;
m is 0, 1, 2, or 3; and
p is 1, 2, or 3.

In certain embodiments, the immuno-DASH inhibitor of Formula II is represented in Formula IIa, or is a pharmaceutical salt thereof:

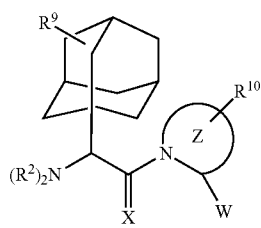

(IIa)

wherein X, W, Z, $R^2$, $R^9$ and $R^{10}$ are as defined above for Formula H.

In certain preferred embodiments of Ha: $R^9$, independently for each occurrence, is a lower alkyl, —OH, —NH$_2$, —N$_3$, -lower alkyl-C(O)OH, —O-lower alkyl, —O-lower alkyl-C(O)OH, -guanidinyl; X is O; each $R^2$ is hydrogen, $R^{10}$ is absent, or represents a single substitution of —OH, —NH$_2$, —CN or —N$_3$; and W is —B(OH)$_2$ or —CN (and more preferably —B(OH)$_2$).

In certain embodiments, the immuno-DASH inhibitor of Formula II is represented in Formula IIb, or is a pharmaceutical salt thereof:

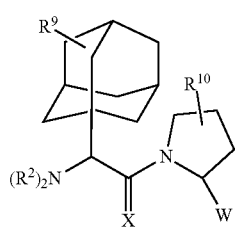

(IIb)

wherein X, W, $R^2$, $R^9$ and $R^{10}$ are as defined above for Formula H.

In certain preferred embodiments of Ib: $R^9$, independently for each occurrence, is a lower alkyl, —OH, —NH$_2$, —N$_3$, -lower alkyl-C(O)OH, —O-lower alkyl, —O-lower alkyl-C(O)OH, -guanidinyl; X is O; each $R^2$ is hydrogen, $R^{10}$ is absent, or represents a single substitution of —OH, —NH$_2$, —CN or —N$_3$; and W is —B(OH)$_2$ or —CN (and more preferably —B(OH)$_2$).

In certain embodiments, the immuno-DASH inhibitor of Formula II is represented in Formula IIc, or is a pharmaceutical salt thereof:

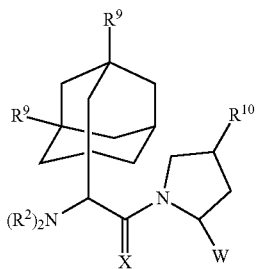
(IIc)

wherein X, W, R², R⁹ and R¹⁰ are as defined above for Formula II.

In certain preferred embodiments of IIc: R⁹, independently for each occurrence, is a lower alkyl, —OH, —NH₂, —N₃, -lower alkyl-C(O)OH, —O-lower alkyl, —O-lower alkyl-C(O)OH, -guanidinyl; X is O; each R² is hydrogen, R¹⁰ is absent, or represents a single substitution of —OH, —NH₂, —CN or —N₃; and W is —B(OH)₂ or —CN (and more preferably —B(OH)₂).

In certain embodiments, the immuno-DASH inhibitor of Formula II is represented in Formula IId, or is a pharmaceutical salt thereof:

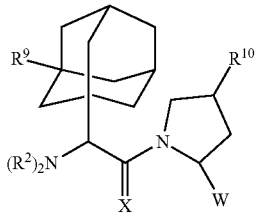
(IId)

wherein X, W, R², R⁹ and R¹⁰ are as defined above for Formula H.

In certain preferred embodiments of IId: R⁹, independently for each occurrence, is a lower alkyl, —OH, —NH₂, —N₃, -lower alkyl-C(O)OH, —O-lower alkyl, —O-lower alkyl-C(O)OH, -guanidinyl; X is O; each R² is hydrogen, R¹⁰ is absent, or represents a single substitution of —OH, —NH₂, —CN or —N₃; and W is —B(OH)₂ or —CN (and more preferably —B(OH)₂).

In certain embodiments, the immuno-DASH inhibitor of Formula H is represented in Formula IIe, or is a pharmaceutical salt thereof:

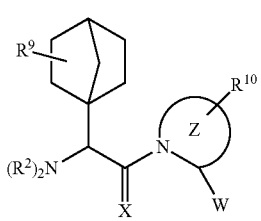
(IIe)

wherein X, W, Z, R², R⁹ and R¹⁰ are as defined above for Formula II.

In certain preferred embodiments of IIe: R⁹, independently for each occurrence, is a lower alkyl, —OH, —NH₂, —N₃, -lower alkyl-C(O)OH, —O-lower alkyl, —O-lower alkyl-C(O)OH, -guanidinyl; X is O; each R² is hydrogen, R¹⁰ is absent, or represents a single substitution of —OH, —NH₂, —CN or —N₃; Z is a pyrrolidine or piperidine ring (and more preferably a pyrrolidine ring); and W is —B(OH)₂ or —CN (and more preferably —B(OH)₂).

Figure 1:
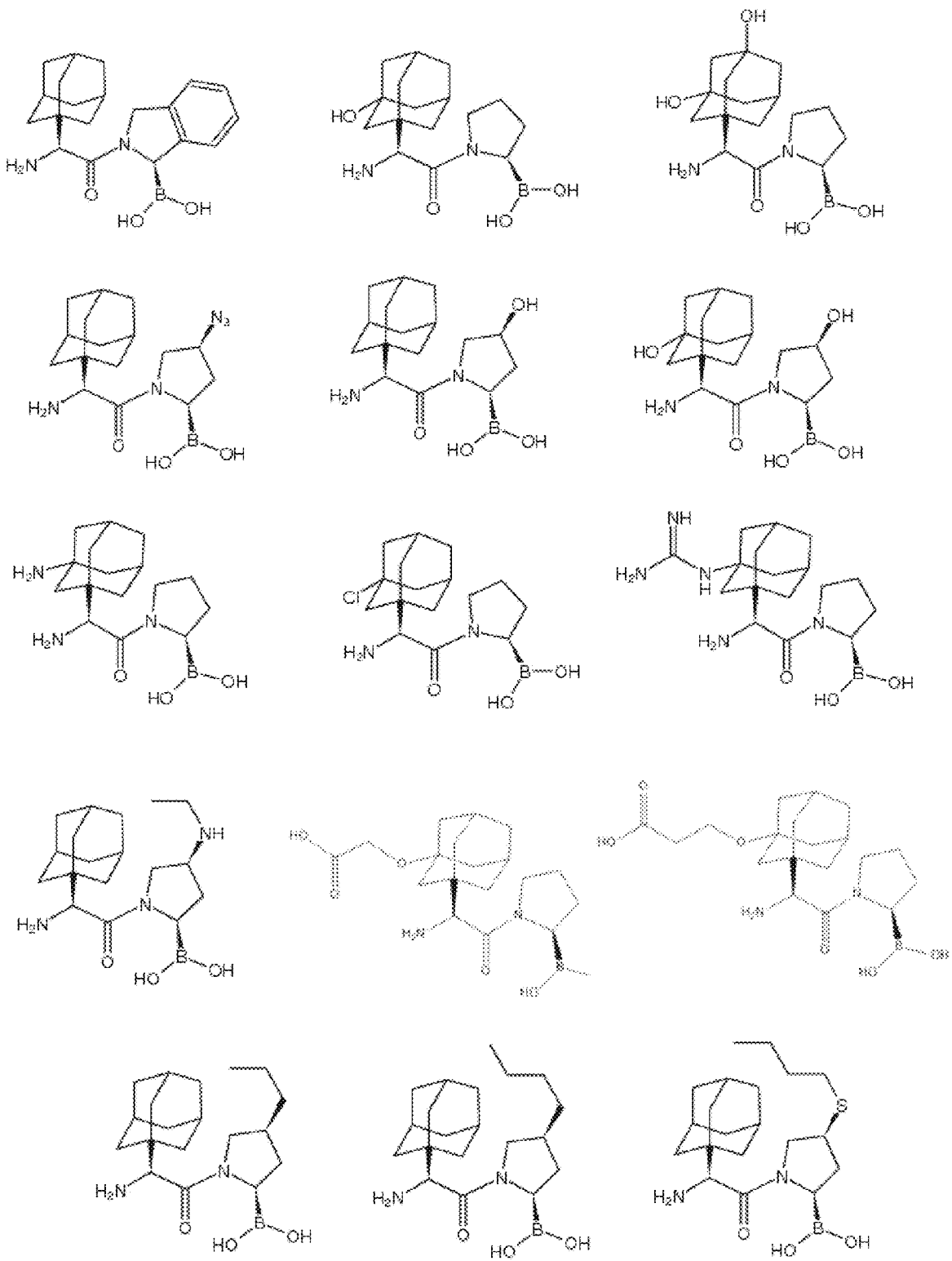
FIG. 1 shows the structures for a number of representative examples of I-DASH inhibitors.
Figure 1:
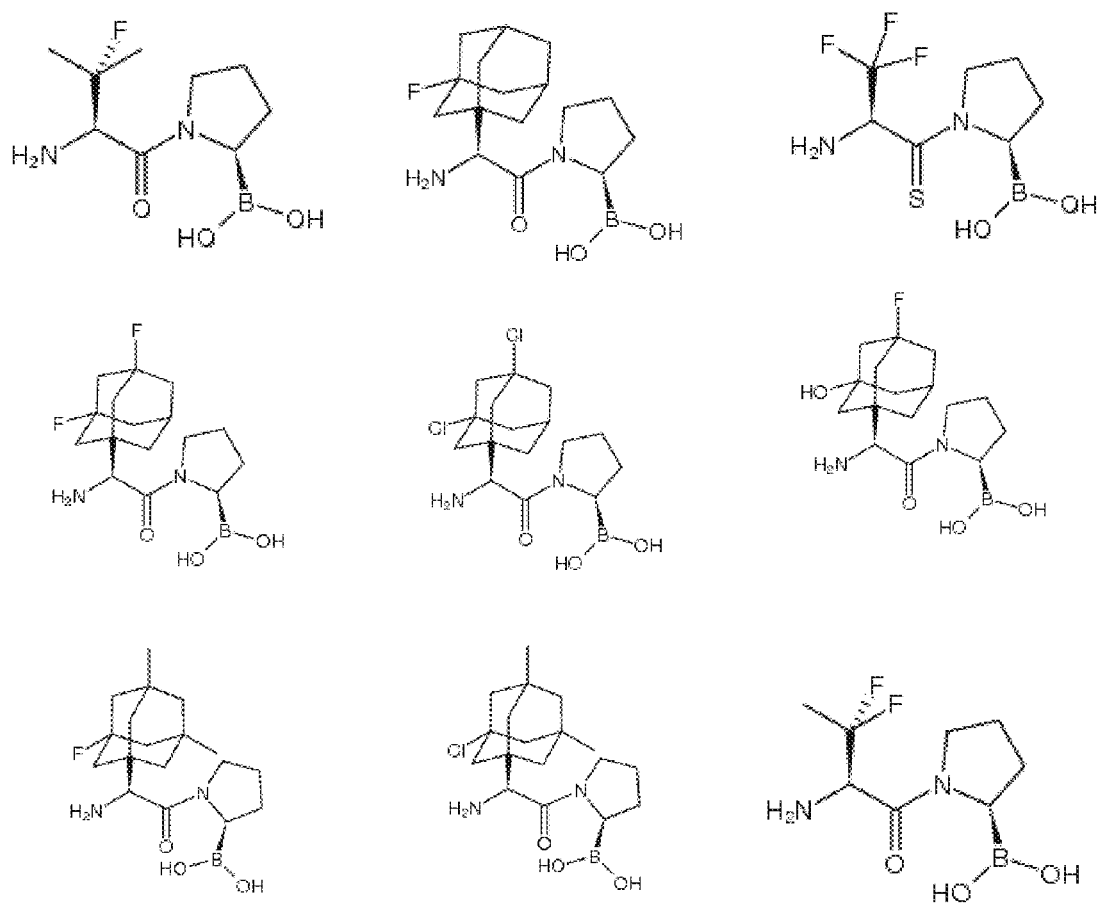

In some embodiments, the immuno-DASH inhibitor is represented in FIG. 1, and/or is one of the following:

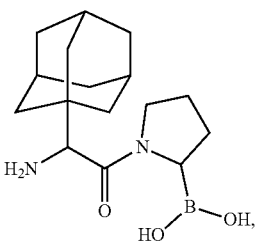

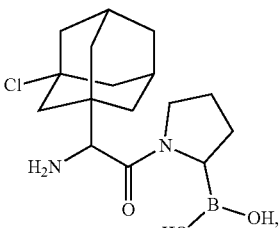

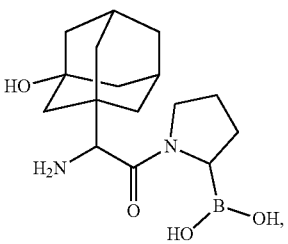

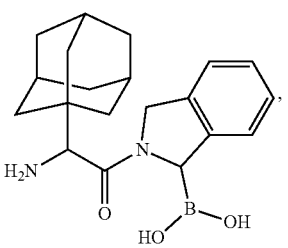

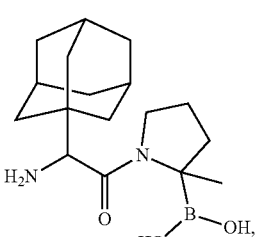

-continued

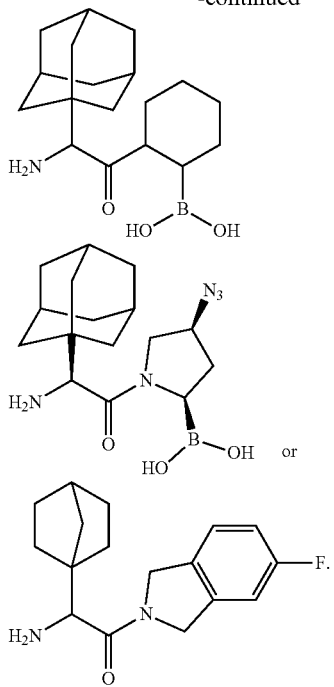

Another aspect of the invention relates the immuno-DASH inhibitor represented by formula III, or a pharmaceutical salt thereof:

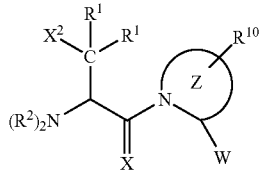

(III)

wherein ring Z represents a 4-10 membered heterocycle including the N and the Cα carbon;

W represents —CN, —CH=NR$^4$, a functional group which reacts with an active site residue of the target, or

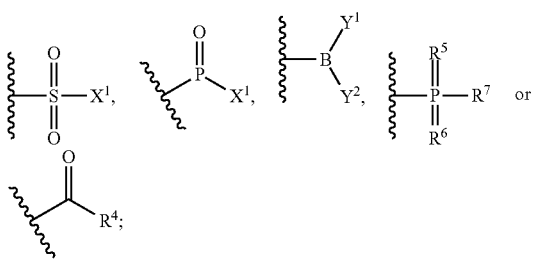

X is O or S;

X$^2$ represents, independently for each occurrence, a halogen;

Y$^1$ and Y$^2$ are independently OH, or together with the boron atom to which they are attached represent a group that is hydrolysable to a boronic acid, or together with the boron atom to which they are attached form a 5-8 membered ring that is hydrolysable to a boronic acid;

R$^1$ represents, independently for each occurrence, a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —CF$_3$, —(CH$_2$)$_m$—R$^3$, —(CH$_2$)$_m$OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$^3$;

R$^2$ represents, for each occurrence, hydrogen, lower alkyl, lower alkynyl, —(CH$_2$)$_m$—R$^3$, —C(=O)-alkyl, —C(=O)-alkenyl, —C(=O)-alkynyl, or —D(=O)—(CH$_2$)$_m$—R$^3$;

R$^3$ represents, for each occurrence, hydrogen, or a substituted or unsubstituted lower alkyl, lower alkenyl, aryl, aralkyl, cycloalkyl, cycloalkenyl, or heterocycle;

R$^4$ represents a hydrogen, a lower alkyl, a lower alkenyl, a lower alkynyl, —(CH$_2$)$_m$—R$^3$, —(CH$_2$)$_n$—OH, —(CH$_2$)$_n$—O-lower alkyl, —(CH$_2$)$_n$—O-alkenyl, —(CH$_2$)$_n$—O-alkynyl, —(CH$_2$)$_n$—O—(CH$_2$)$_m$—R$_7$, —(CH$_2$)$_n$—SH, —(CH$_2$)$_n$—S-lower alkyl, —(CH$_2$)$_n$—S-lower alkenyl, —(CH$_2$)$_n$—S-lower alkynyl, —(CH$_2$)$_n$—S—(CH$_2$)$_m$—R$^3$, —C(O)C(O)NH$_2$, or —C(O)C(O)OR$^8$;

R$^5$ represents O or S;

R$^6$ represents N$_3$, SH, NH$_2$, NO$_2$ or OR$^8$;

R$^7$ represents hydrogen, a lower alkyl, an amine, OR$^8$, or a pharmaceutically acceptable salt, or R$^5$ and R$^6$ taken together with the phosphorous atom to which they are attached complete a heterocyclic ring having from 5 to 8 atoms in the ring structure;

R$^8$ represents, hydrogen, a substituted or unsubstituted alkyl, alkenyl, aryl, aralkyl, cycloalkyl, cycloalkenyl or heterocyclyl;

R$^{10}$ is absent or represents one to three substitutions to the ring Z to which they are appended, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, an isocyano, a thiocyanato, an isothiocyanato, a cyanato, a nitro, an azido, a sulfate, a sulfonate, a sulfonamido, lower alkyl-C(O)OH, —O-lower alkyl-C(O)OH, -guanidinyl; —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$^3$;

n is 0, 1, 2, or 3; and m is 0, 1, 2, or 3.

In certain embodiments, the immuno-DASH inhibitor of Formula III is represented in Formula IIa, or is a pharmaceutical salt thereof:

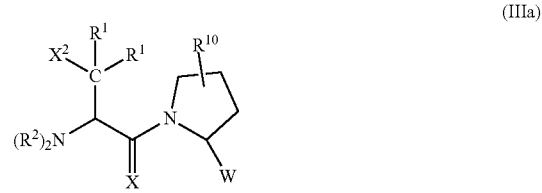

(IIIa)

wherein X, $X^2$, W, $R^1$, $R^2$ and $R^{10}$ are as defined above for Formula III.

In certain preferred embodiments of IIIa: $R^1$, independently for each occurrence, is a lower alkyl; X is O; each $R^2$ is hydrogen, $R^{10}$ is absent, or represents a single substitution of —OH, —$NH_2$, —CN or —$N_3$; and W is —$B(OH)_2$ or —CN (and more preferably —$B(OH)_2$).

In certain embodiments, the immuno-DASH inhibitor of Formula III is represented in Formula IIIb or IIIc, or is a pharmaceutical salt thereof:

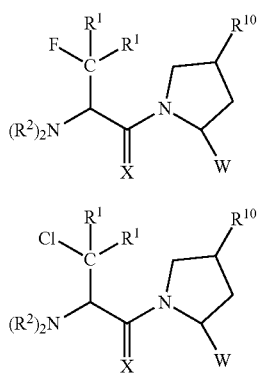

wherein X, W, $R^1$, $R^2$ and $R^{10}$ are as defined above for Formula III.

In certain preferred embodiments of IIIb and IIIc: $R^1$, independently for each occurrence, is a lower alkyl; X is O; each $R^2$ is hydrogen, $R^{10}$ is H, —OH, —$NH_2$, —CN or —$N_3$; and W is —$B(OH)_2$ or —CN (and more preferably —$B(OH)_2$).

With regard to the various immuno-DASH inhibitors above, e.g., represented in formulas I-III, and Ia-Ic, IIa-IIe and IIIa-IIc (as structure and valence permit), the following are exemplary embodiments of certain preferred substituents and sub-structures.

In some embodiments, $R^1$ is a halogen, a lower alkyl, —$(CH_2)_m$—$R^3$, —$(CH_2)_m OH$, or —$(CH_2)_m$—O-lower alkyl.

In some embodiments, $R^1$ is a halogen.

In some embodiments, $R^1$ is —$(CH_2)_m OH$, or —$(CH_2)_m$—O-lower alkyl.

In some embodiments, $R^1$ is —$CF_3$.

In some embodiments, $R^1$ is an unsubstituted lower alkyl.

In some embodiments, $R^1$ is a substituted lower alkyl.

In some embodiments, $R^1$ is methyl, ethyl, n-propyl, i-propyl, n-butyl, i-butyl, or t-butyl.

In some embodiments, $R^1$ is methyl.

In some embodiments, $R^{1a}$ is an unsubstituted lower alkyl.

In some embodiments, $R^{1a}$ is a substituted lower alkyl.

In some embodiments, $R^{1a}$ is methyl or ethyl.

In some embodiments, $R^2$ represents, for each occurrence, hydrogen, lower alkyl, —C(=O)-alkyl, or —C(=O)—$(CH_2)_m$—$R^3$.

In some embodiments, $R^2$ represents, for each occurrence, hydrogen or lower alkyl.

In some embodiments, $R^2$ represents, for each occurrence, hydrogen, methyl, or ethyl.

In some embodiments, $R^2$ represents, for each occurrence, hydrogen.

In some embodiments of Formula I, ring A represents a 3-10 membered ring structure. In some embodiments, the 3-10 membered ring structure is a saturated ring. In some embodiments, the 3-10 membered ring structure is an unsaturated ring. In some embodiments, the 3-10 membered ring structure is a 3-membered ring. In some embodiments, the 3-10 membered ring structure is a 4-membered ring. In some embodiments, the 3-10 membered ring structure is a 5-membered ring. In some embodiments, the 3-10 membered ring structure is a 6-membered ring.

In some embodiments, one $R^2$ is hydrogen and the second $R^2$ is methyl.

In some embodiments, ring Z represents a 4-10-membered heterocycle;

In some embodiments, ring Z represents a polycyclic heterocycle.

In some embodiments, ring Z represents a monocyclic heterocycle.

In some embodiments, ring Z represents a 4-10-membered heteroaryl.

In some embodiments, ring Z represents a 5-membered heterocycloalkyl.

In some embodiments, ring Z represents a 6-membered heterocycloalkyl.

In some embodiments, W represents —CN, or

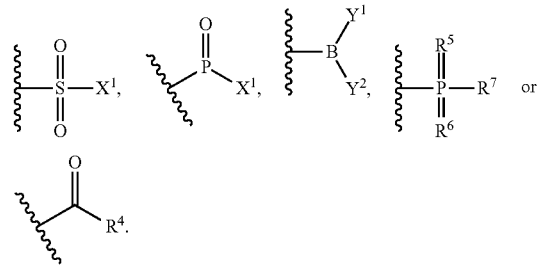

In some embodiments, W represents —CN, or

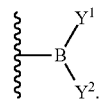

In some embodiments, W is CN.

In some embodiments, W is

In some embodiments, X is O.

In some embodiments, X is S.

In some embodiments, Y is C.

In some embodiments, Y is N.

In some embodiments, $Y^1$ and $Y^2$ are each OH.

In some embodiments, p is 1 or 2.

In some embodiments, the immuno-DASH inhibitor is represented by:

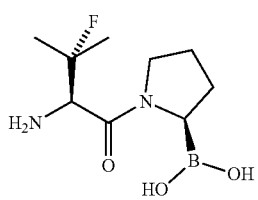

Another aspect of the invention relates the immuno-DASH inhibitor represented by formula IV, or a pharmaceutical salt thereof:

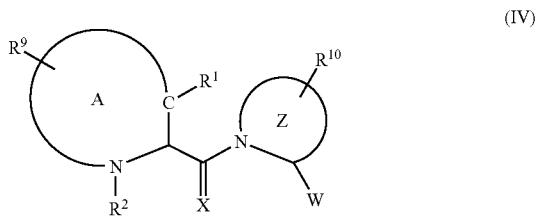

(IV)

wherein
ring A represents a 3-10 membered ring structure including the N;
ring Z represents a 4-10 membered heterocycle including the N and the Cα carbon;
W represents —CN, —CH=NR$^4$, a functional group which reacts with an active site residue of the target, or

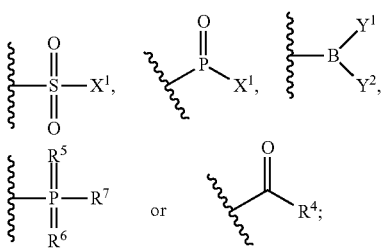

X is O or S;
X$^1$ represents a halogen;
Y$^1$ and Y$^2$ are independently OH, or together with the boron atom to which they are attached represent a group that is hydrolysable to a boronic acid, or together with the boron atom to which they are attached form a 5-8 membered ring that is hydrolysable to a boronic acid;
R$^1$ represents a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —CF$_3$, —(CH$_2$)$_m$—R$^3$, —(CH$_2$)$_m$OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$^3$;
R$^2$ represents, for each occurrence, hydrogen, lower alkyl, lower alkynyl, —(CH$_2$)$_m$—R$^3$, —C(=O)-alkyl, —C(=O)-alkenyl, —C(=O)-alkynyl, or —C(=O)—(CH$_2$)$_m$—R$^3$;

R$^3$ represents, for each occurrence, hydrogen, or a substituted or unsubstituted lower alkyl, lower alkenyl, aryl, aralkyl, cycloalkyl, cycloalkenyl, or heterocycle;
R$^4$ represents a hydrogen, a lower alkyl, a lower alkenyl, a lower alkynyl, —(CH$_2$)$_m$—R$^3$, —(CH$_2$)$_n$—OH, —(CH$_2$)$_n$—O-lower alkyl, —(CH$_2$)$_n$—O-alkenyl, —(CH$_2$)$_n$—O-alkynyl, —(CH$_2$)$_n$—O—(CH$_2$)$_m$—R$_7$, —(CH$_2$)$_n$—SH, —(CH$_2$)$_n$—S-lower alkyl, —(CH$_2$)$_n$—S-lower alkenyl, —(CH$_2$)$_n$—S-lower alkynyl, —(CH$_2$)$_n$—S—(CH$_2$)$_m$—R$^3$, —C(O)C(O)NH$_2$, or —C(O)C(O)OR$^8$;
R$^5$ represents O or S;
R$^6$ represents N$_3$, SH, NH$_2$, NO$_2$ or OR$^8$;
R$^7$ represents hydrogen, a lower alkyl, an amine, OR$^8$, or a pharmaceutically acceptable salt, or R$^5$ and R$^6$ taken together with the phosphorous atom to which they are attached complete a heterocyclic ring having from 5 to 8 atoms in the ring structure;
R$^8$ represents, hydrogen, a substituted or unsubstituted alkyl, alkenyl, aryl, aralkyl, cycloalkyl, cycloalkenyl or heterocyclyl;
R$^9$ and R$^{10}$, each independently, are absent or represents one to three substitutions to the ring A or to the ring Z to which they are appended, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, an isocyano, a thiocyanato, an isothiocyanato, a cyanato, a nitro, an azido, a sulfate, a sulfonate, a sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O —(CH$_2$)$_m$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$^3$;
n is 0, 1, 2, or 3; and
m is 0, 1, 2, or 3.

In certain embodiments, the immuno-DASH inhibitor of Formula IV is represented in Formula IVa, or is a pharmaceutical salt thereof:

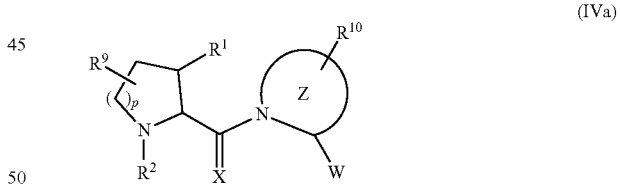

(IVa)

wherein X, W, Z, R$^1$, R$^2$, R$^9$ and R$^{10}$ are as defined above for Formula IV, and p is 1, 2 or 3.

In certain embodiments, the immuno-DASH inhibitor of Formula IV is represented in Formula IVb, or is a pharmaceutical salt thereof:

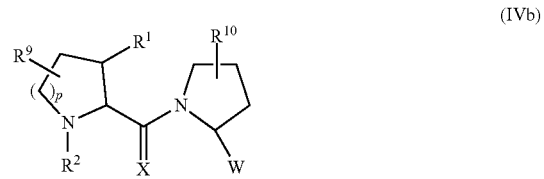

(IVb)

wherein X, W, R¹, R², R⁹ and R¹⁰ are as defined above for Formula IV, and p is 1, 2 or 3.

In certain embodiments, the immuno-DASH inhibitor of Formula IV is represented in Formula IVc, or is a pharmaceutical salt thereof:

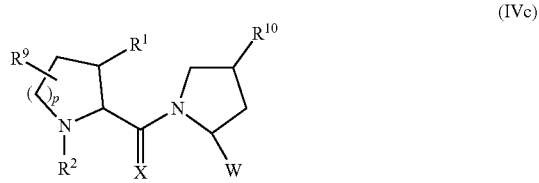

(IVc)

wherein X, W, R¹, R², R⁹ and R¹⁰ are as defined above for Formula IV, and p is 1, 2 or 3.

In some embodiments the immuno-DASH inhibitor is represented by:

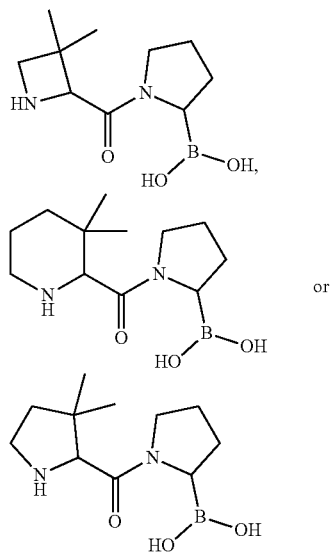

Another aspect of the present invention relates to a compound represented by formula I or, II or, III above, or a pharmaceutically acceptable salt thereof.

In some embodiments, the compound represented by formula I, or II, or III, or IV, or a pharmaceutically acceptable salt thereof is used in the treatment of a cancer.

Another aspect of the present invention relates to pharmaceutical composition comprising a compound represented by formula I, or II, or III, or IV, or a pharmaceutically acceptable salt thereof and a pharmaceutically acceptable excipient for use in the treatment of a cancer.

In some embodiments, the pharmaceutical composition comprising the compound represented by formula IV, or a pharmaceutically acceptable salt thereof, is for use in the treatment of a cancer.

IV. Exemplary Combination Therapies

In certain embodiments, therapy involving an I-DASH inhibitor can be further supplemented by treatment with one or more additional agents, such as other immuno-oncology agents (i.e., other checkpoint inhibitors), chemotherapeutic agents, adjuvants and/or agents which further sensitive the tumor cells to chemical or immunological killing. The present invention also contemplates the combination of the subject immuno-DASH inhibitors with cytokine antagonists (such as IL-6 antagonists) and inhibitors of prostaglandin biosynthesis and/or activity, preferably eicosanoid antagonists and more preferably PGE2 antagonists.

The various combination therapies contemplated by the subject invention include conjoint administration of the two or more different therapeutic compounds (drug agents) such that the second drug agents is administered while the previously administered drug agents is still effective in the body (e.g., the immuno-DASH inhibitors and one or more other drug agents are simultaneously effective in the patient, which may include synergistic effects of the immuno-DASH inhibitors with other drug agents). For example, the different drug agents can be administered either in the same formulation or in a separate formulation, either concomitantly or sequentially. In certain embodiments, the different drug agents can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, the subject immuno-DASH inhibitors are co-formulated with one or more other drug agents. For example, the subject immuno-DASH inhibitors are co-formulated with a PGE2 inhibitor such as a cyclo-oxygenase inhibitor. In preferred embodiments, the subject immuno-DASH inhibitors are co-formulated for oral administration with a PGE2 inhibitor such as a cyclo-oxygenase inhibitor.

A. Representative PGE2 Inhibitors

Figure 16:
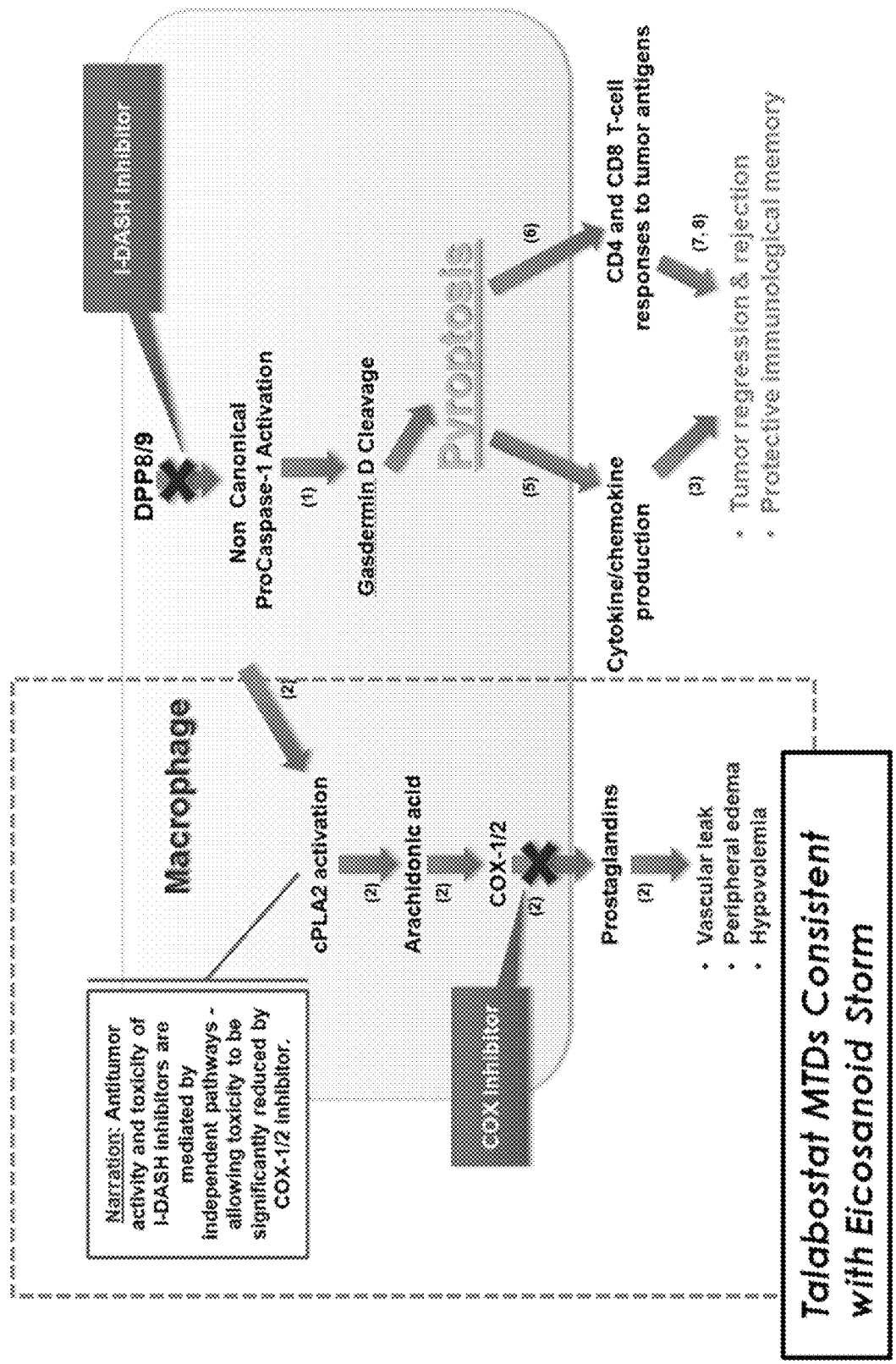
FIG. 16 is a schematic showing the caspase-1 dependent pyroptosis pathway, and IL-1β release, that I-DASH inhibitors are understood to trigger, as well as the induction of a prostaglandin pathway that is consistent with the dose limiting toxicities of Talabostat.

At the time of the Talabostat clinical trials, the underlying mechanism of action giving rise to the dose limiting toxicity was not known, nor was there any understanding of whether or not the toxicity was a consequence to on-target or off-target effects of the drug. Another aspect of the present invention derives from the discovery of the antitumor mechanism of action of I-DASH inhibitors involving selective pyroptosis of macrophages. As illustrated in FIG. 16, inhibition of DPP8/9 activities in macrophage leads selectively to the caspase-1 mediated immunogenic death phenomena known as pyroptosis, which leads to the release of a variety of antitumor cytokines that are understood to produce/enhance the T-cell mediated immunological response to tumors observed with I-DASH inhibitors. The present invention contemplates combination therapies utilizing immuno-DASH inhibitors with PGE2 inhibitors that is based on the additional observations that: (i) induction of pyroptosis in other contexts also results in the activation of eicosanoid production pathway(s) involving cyclooxygenase(s) and phospholipase enzymes with the production of such inflammatory eicosanoids as prostaglandin E2 (PGE2); (ii) retrospective analysis of the Talabostat clinical trial revealed two features—a dose limiting toxicity that was consistent with inflammatory eicosanoids release, particularly PGE2, and that in the one phase 2 study involving cohorts of two different drug doses there were signals of potential efficacy (albeit modest) amongst the secondary endpoints measured, indicating that could the dose limiting toxicity be mitigated and Talabostat be dosed at 2, 5 or even 10 times higher concentration that the primary and secondary endpoints of the study might have been met.

However, a priori, it would have been neither apparent nor predictable as to what effect the addition of a PGE2 antagonist, such as a COX inhibitor, would have on the antitumor activity of an I-DASH inhibitor. Until the observations made herein, one of skill in the art would not understand to what extent, if any, if prostaglandin release and/or the activities of enzymes such as cyclooxygenases and phospholipases were required for the antitumor activity of the I-DASH inhibitor, or if the PGE2 pathway could be successfully inhibited without mitigating the antitumor activity—particularly the ability of the I-DASH inhibitor to produce complete regression of tumors and T-cell dependent immunity to tumor rechallenge.

Figure 17:
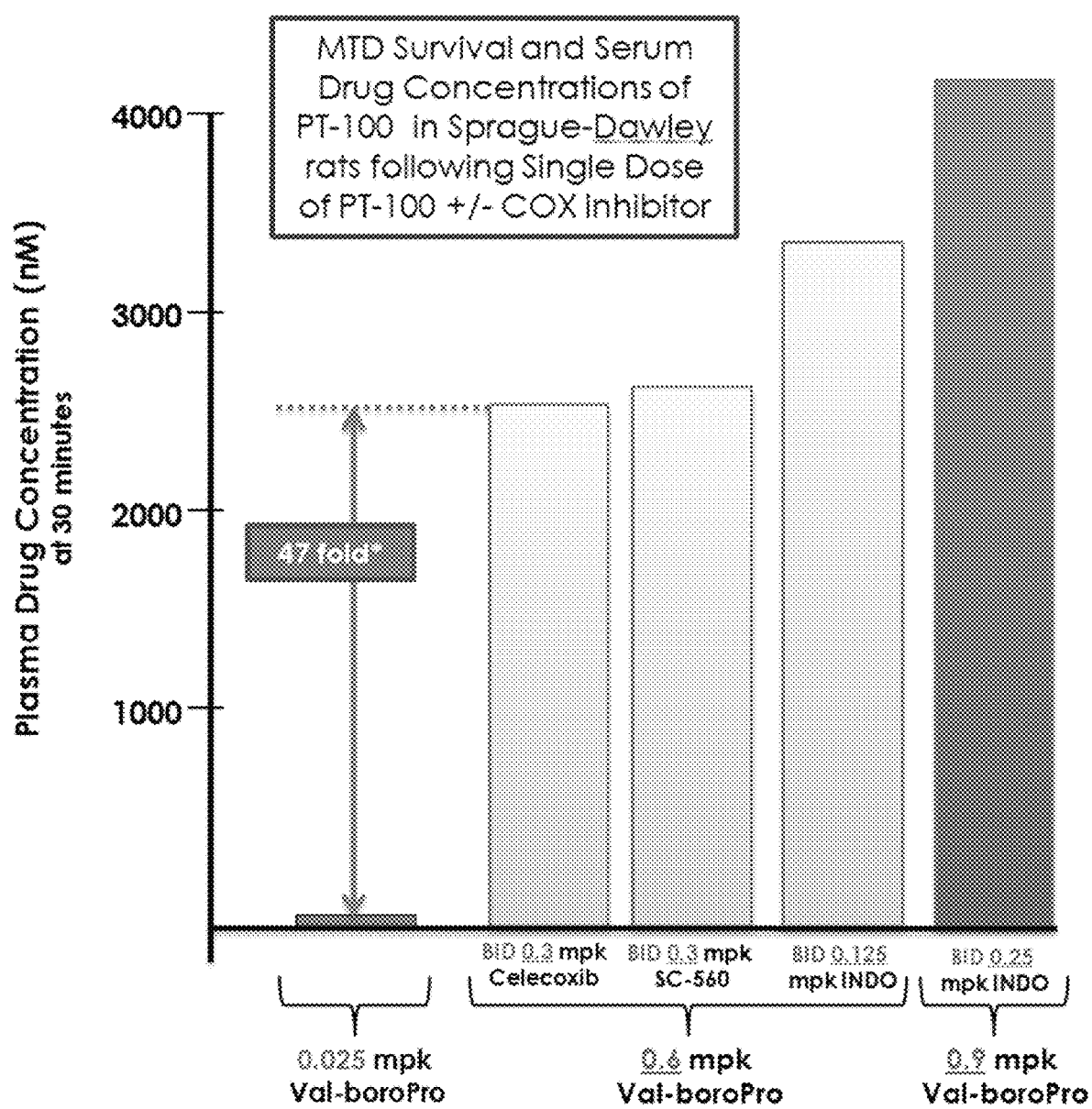
FIG. 17 shows the maximum tolerated dose study results (single dose) of treating Sprague Dawley rats with Val-boroPro (Valine-boroProline) with and without combination with the cyclooxygenase inhibitors celecoxib (a COX-2 selective nonsteroidal anti-inflammatory drug), indomethacin (a nonselective inhibitor of COX-1 and COX-2) and SC-560. Bars show the MTD single dose in SD rats prior to seeing animal death. Based on serum drug levels, the addition of a cyclooxygenase inhibitor to the I-DASH inhibitor increases that MTD dose from 47 to 75-fold. See also FIG. 33 for a similar comparison using cPLA2 inhibitors instead of COX inhibitors.
Figure 18:
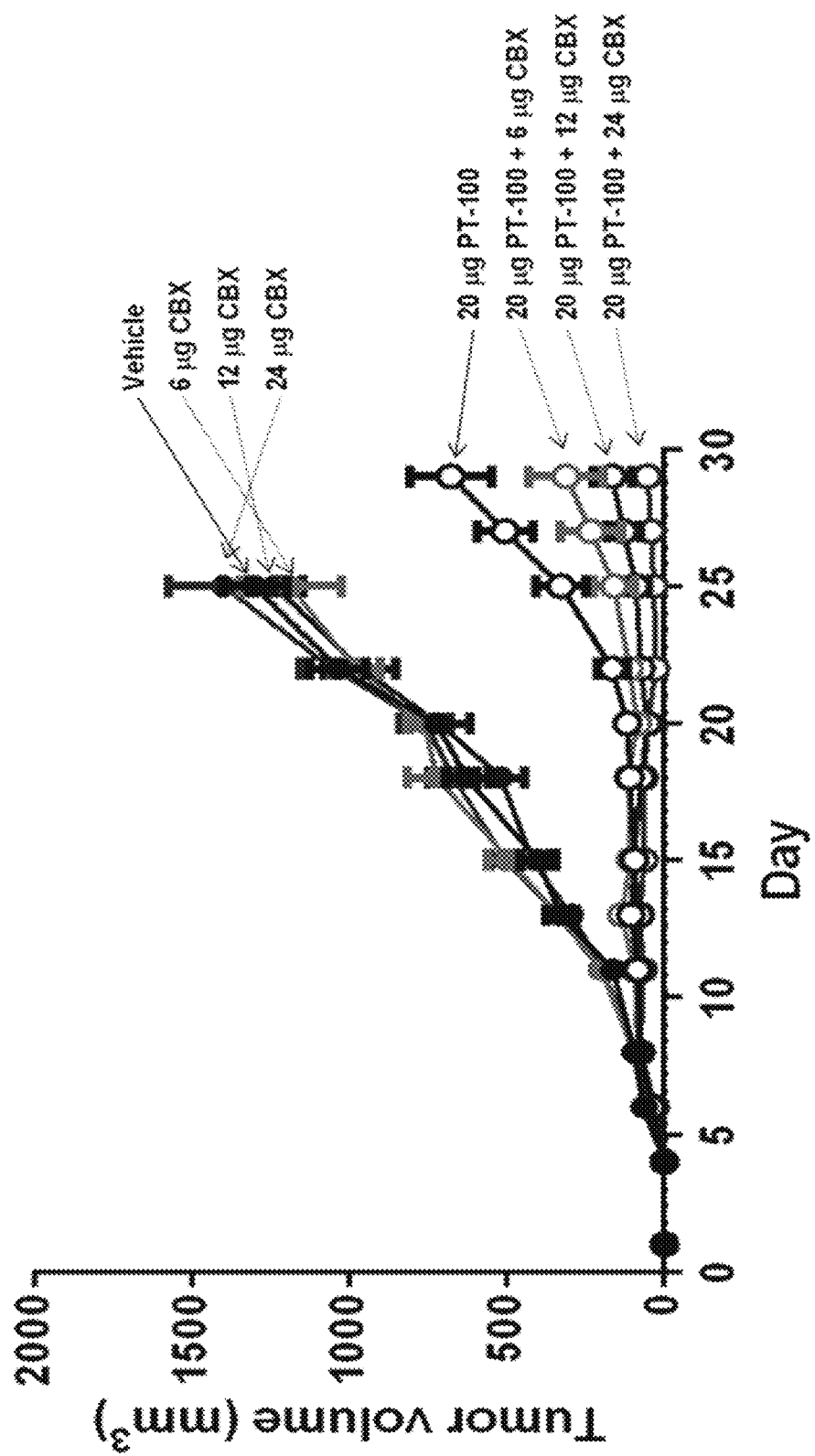
FIGS. 18-21 show the results of treating MB49 tumor bearing mice with Val-boroPro (Valine-boroProline) with and without celecoxib.
Figure 19:
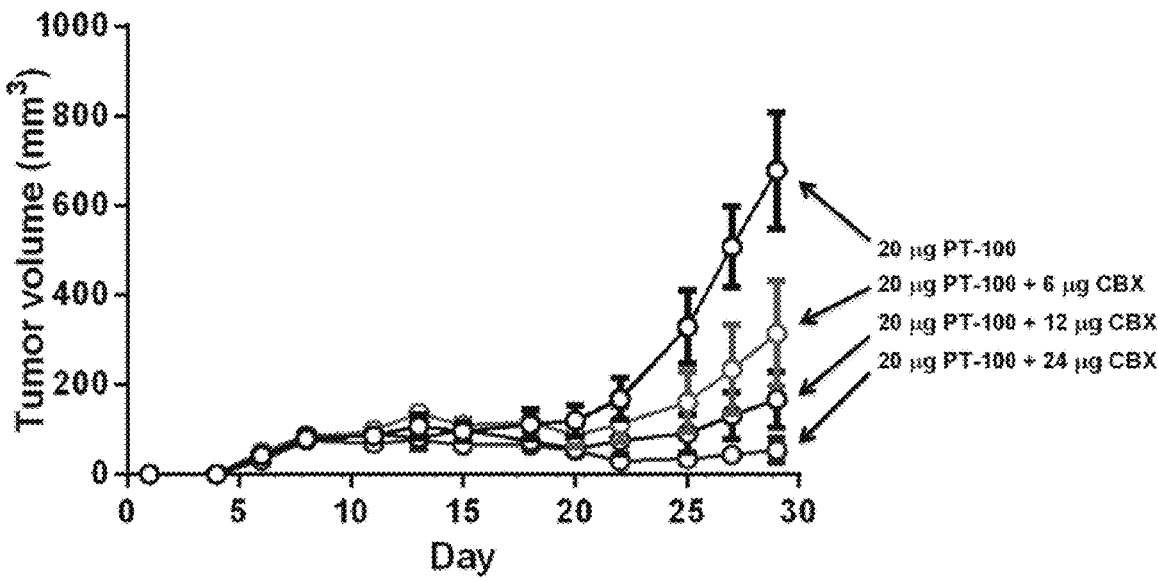
Figure 20:
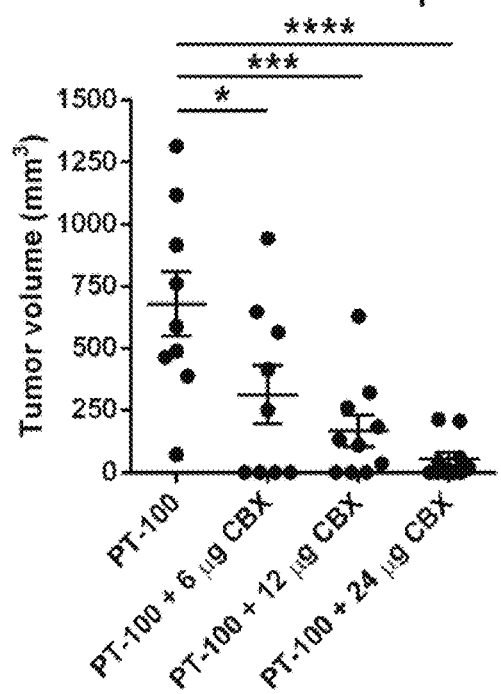
Figure 21:
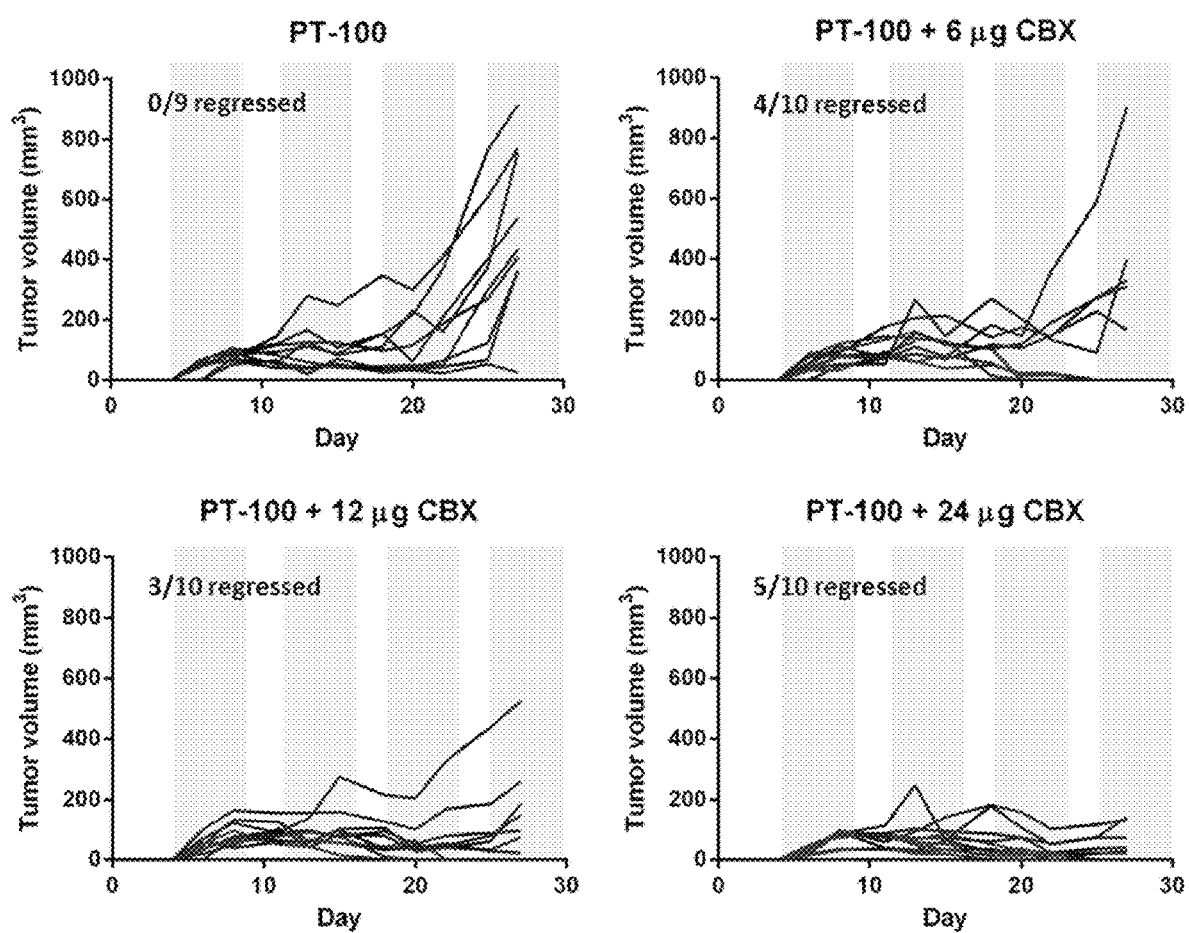
Figure 22:
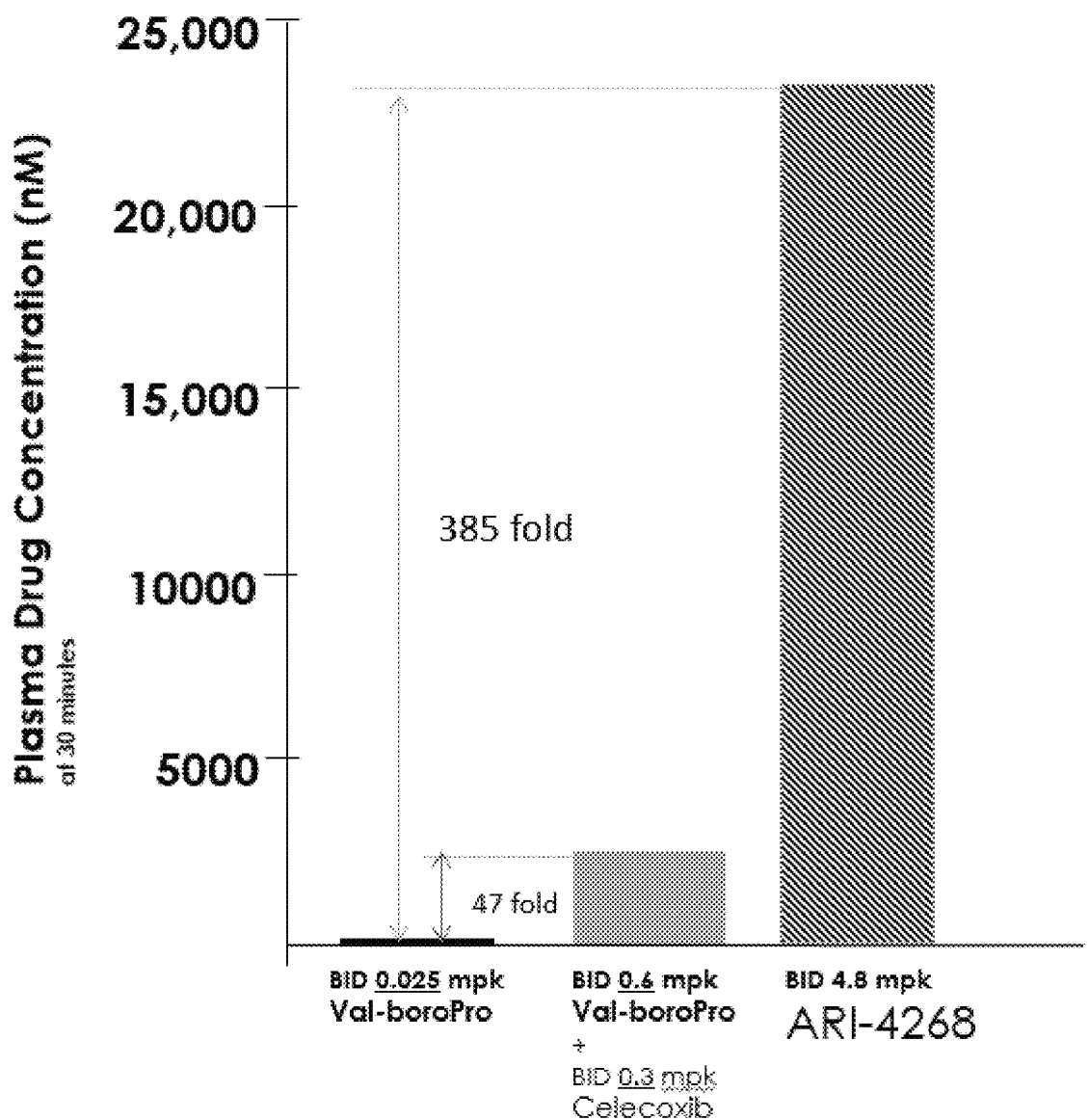
FIG. 22 shows the surprising feature to the halogenated immuno-DASH inhibitors, demonstrating that ARI-4268 has dramatically increased MTD (survival) without the need for a PGE2 inhibitor as required in the case of Val-boroPro, such as the COX inhibitors shown in FIG. 17.
Figure 23:
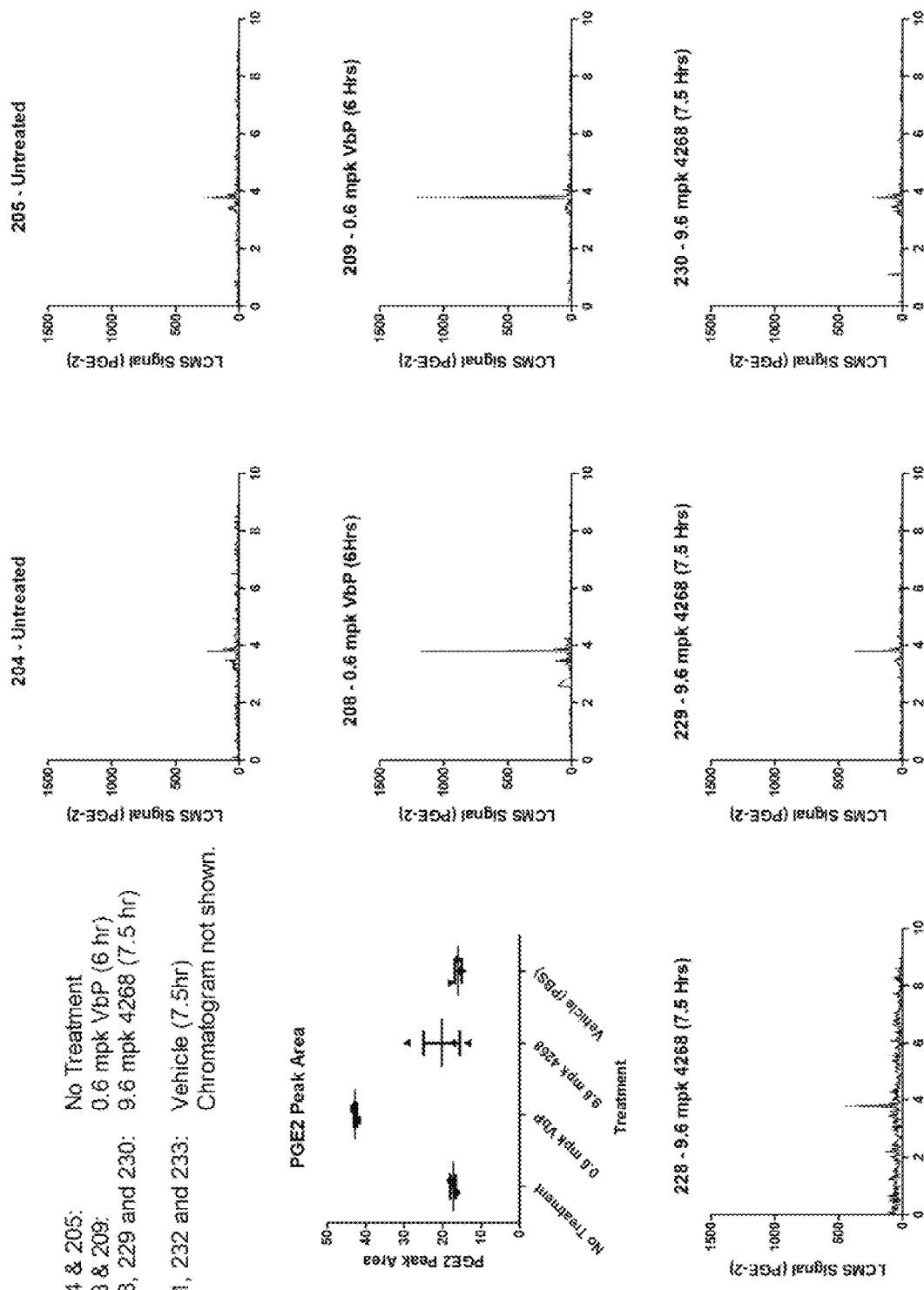
FIG. 23 shows that ARI-4268 dosing, even at substantially higher doses than Val-boroPro, does not induce peritoneal PGE2 levels to the same extent as Val-boroPro.
Figure 24A:
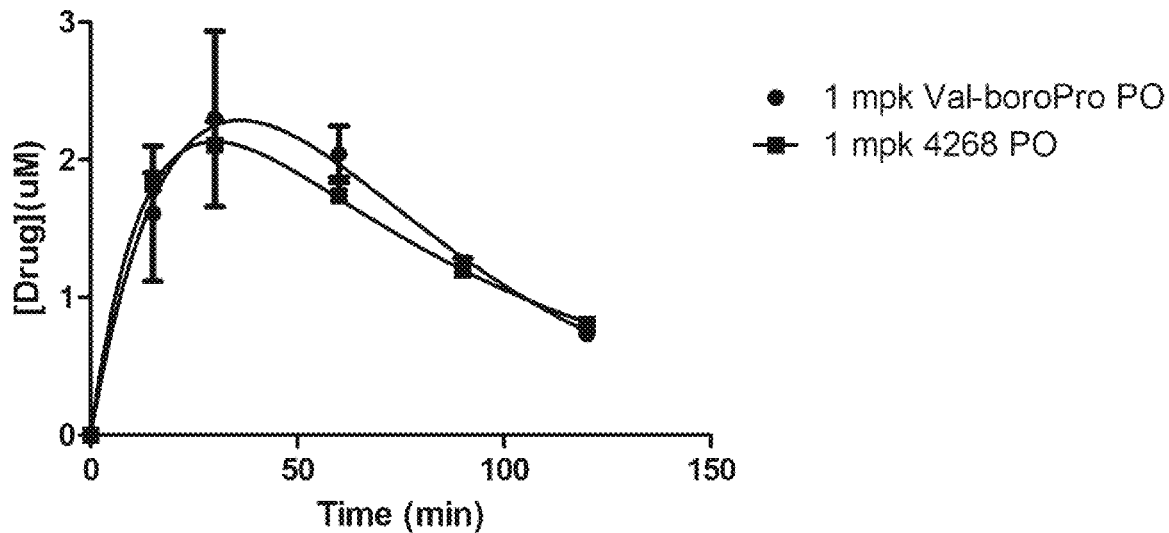
FIG. 24A shows oral PK of Val-boroPro (PT-100) and ARI-4268 in normal mice.
Figure 24B:
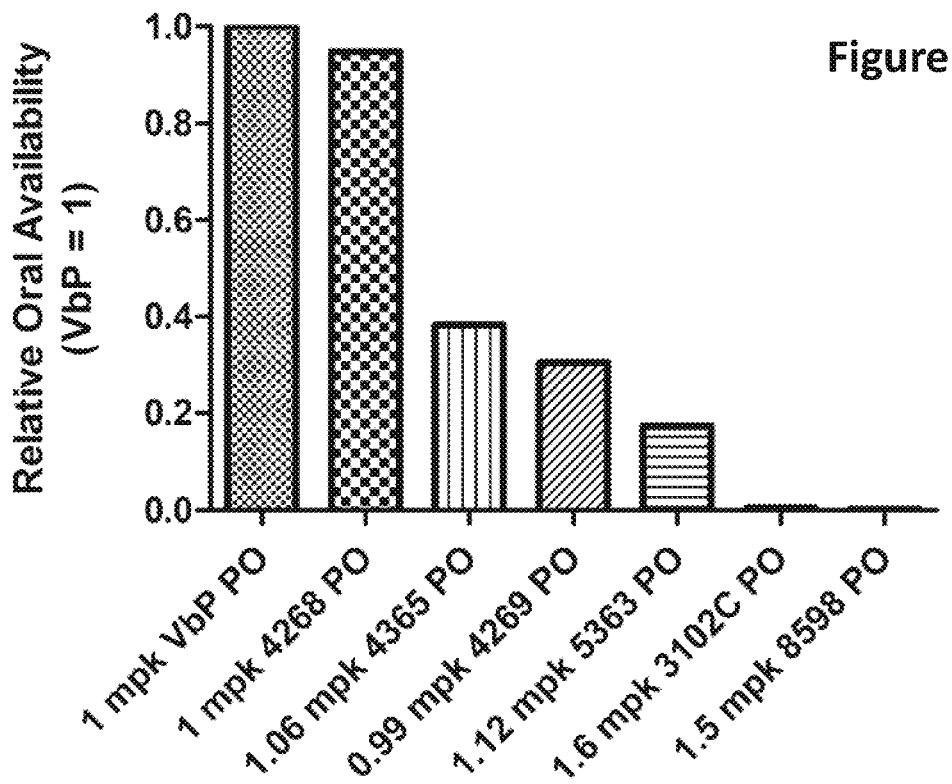
FIG. 24B shows oral activity screen of several drug in comparison to Val-boroPro, and indicates that ARI-4268 shows good oral activity—on par with highly orally active Val-boroPro.
Figure 25:
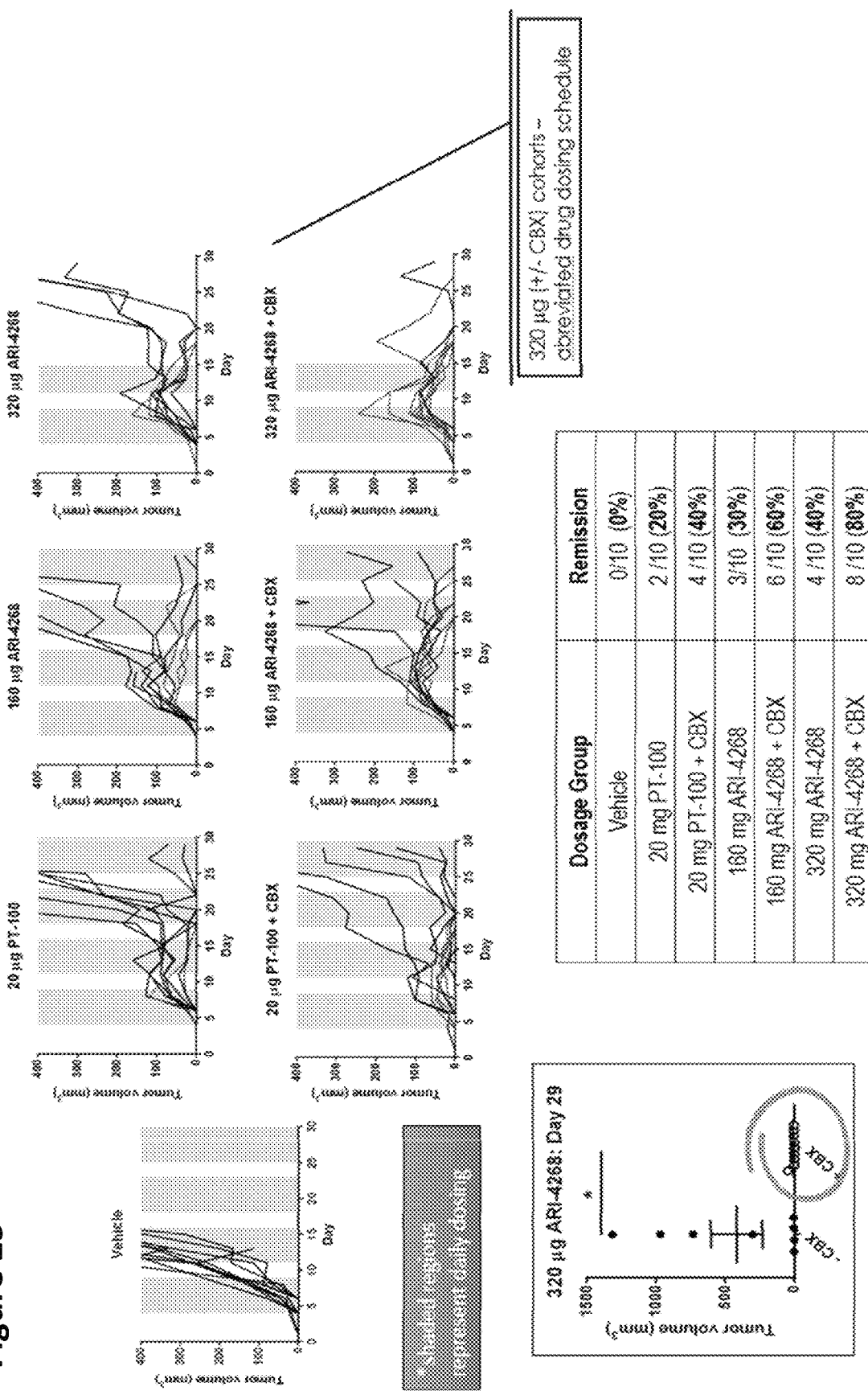
FIG. 25 indicates that ARI-4268 displays antitumor activity in the MB49 mouse tumor model at doses indicating improved therapeutic index—even with truncated dosing schedules.
Figure 26:
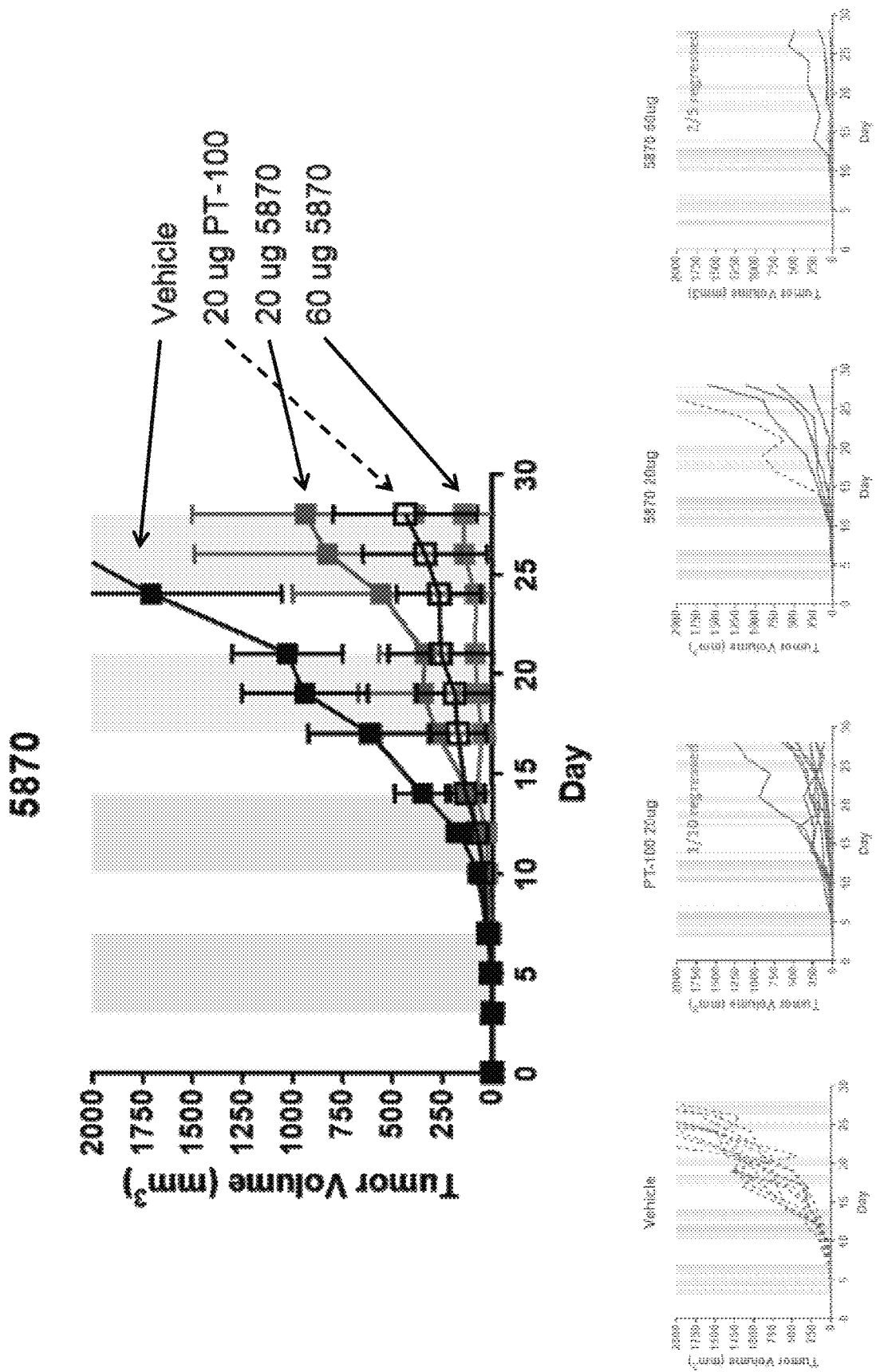
FIG. 26 shows the antitumor activity of ARI-5870 in the MB49 mouse tumor model.
Figure 27:
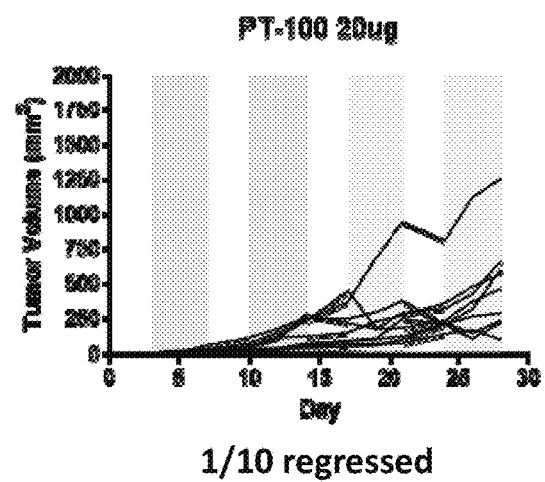
FIG. 27 shows the antitumor activity of ARI-5544 in the MB49 mouse tumor model.
Figure 27:
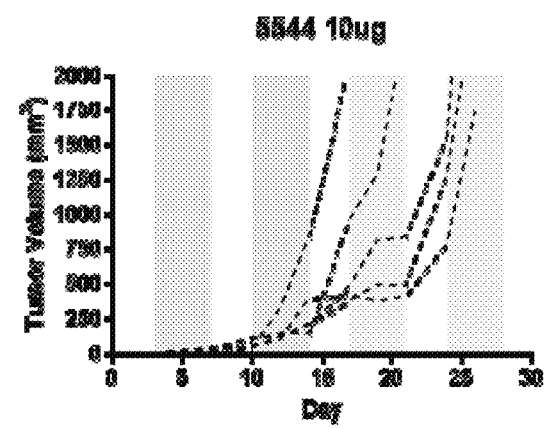
Figure 27:
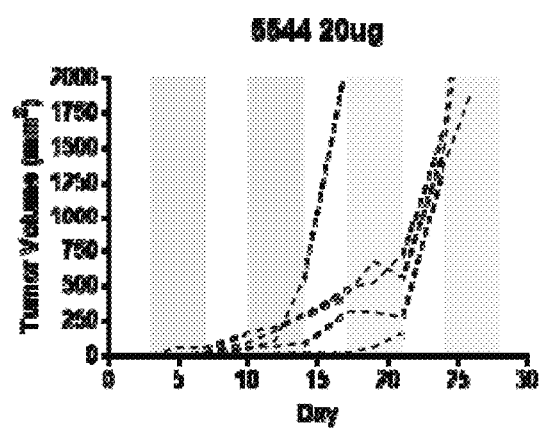
Figure 27:
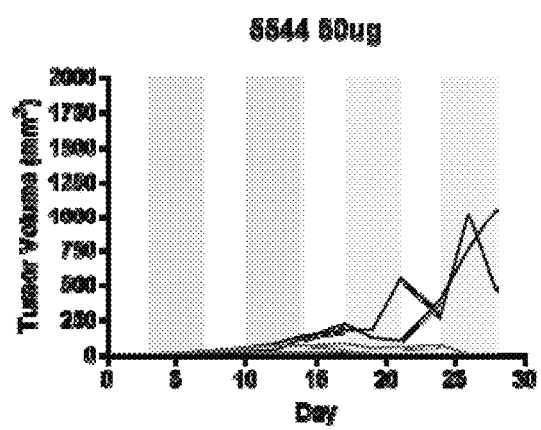
Figure 28:
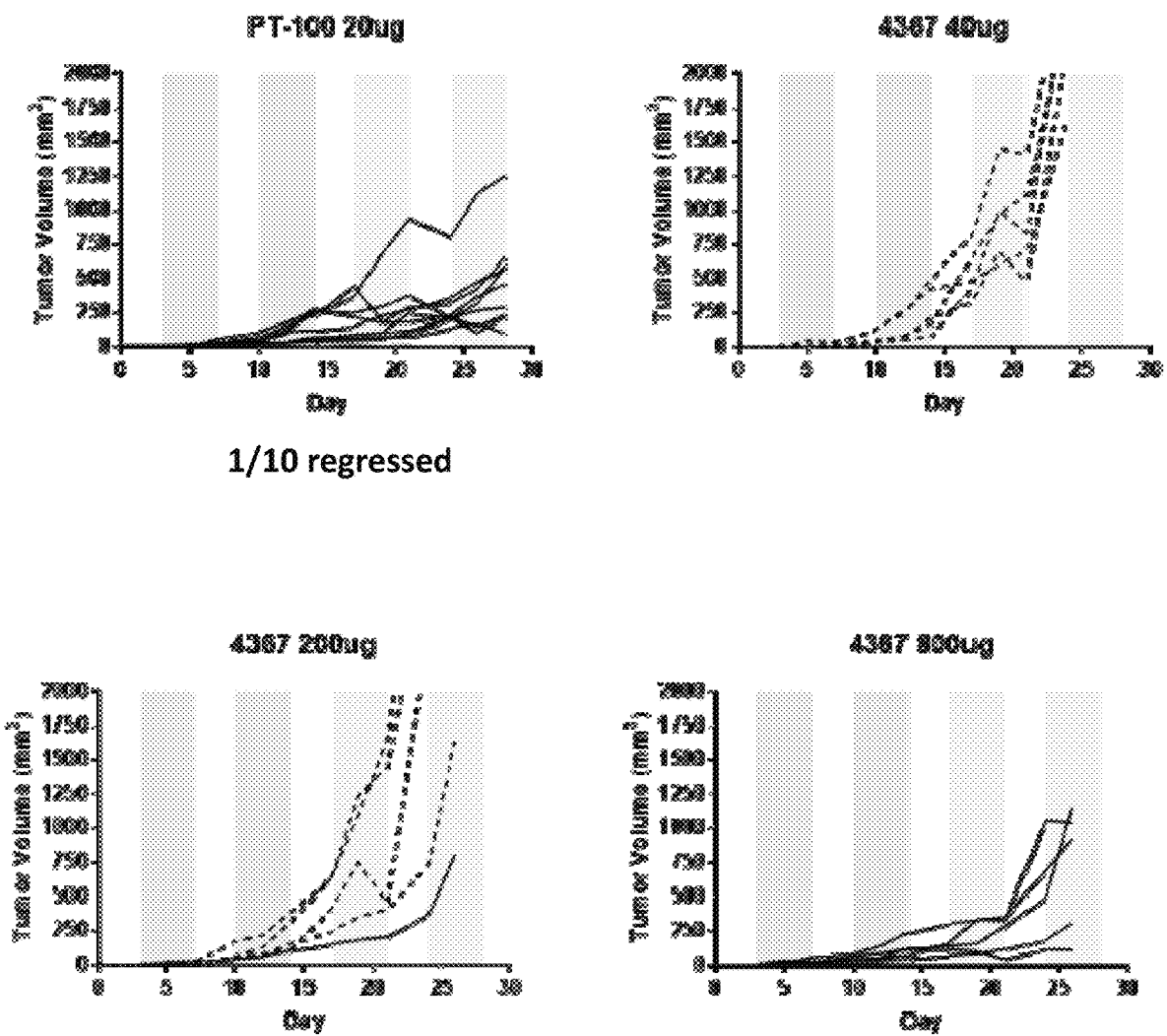
FIG. 28 shows the antitumor activity of ARI-4367 in the MB49 mouse tumor model.
Figure 29:
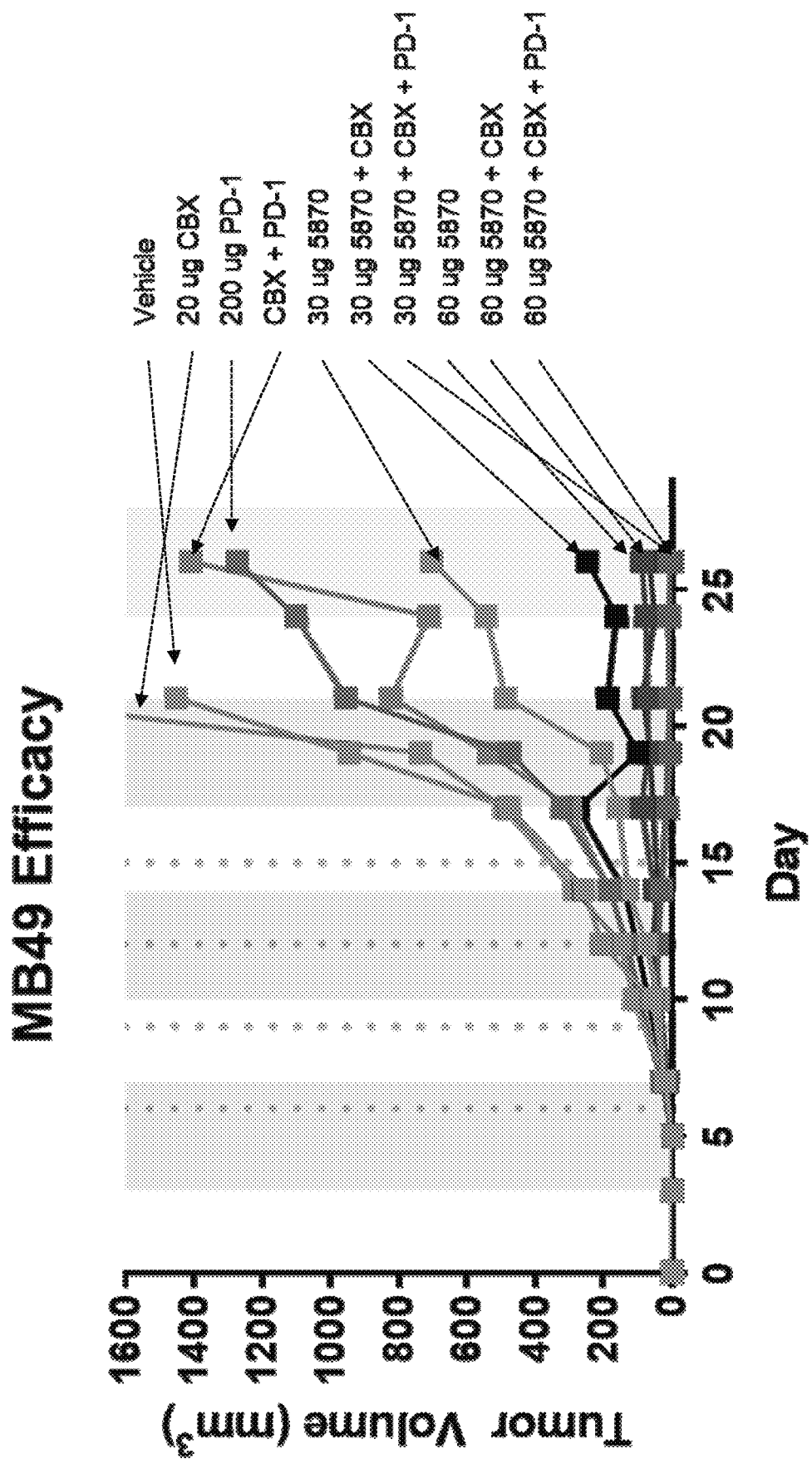
FIGS. 29 and 30 show the antitumor activity of ARI-5870 in the MB49 mouse tumor model, alone or when combined with Celebrex (COX inhibitor) or an anti-PD-1 antibody or both.
Figure 30:
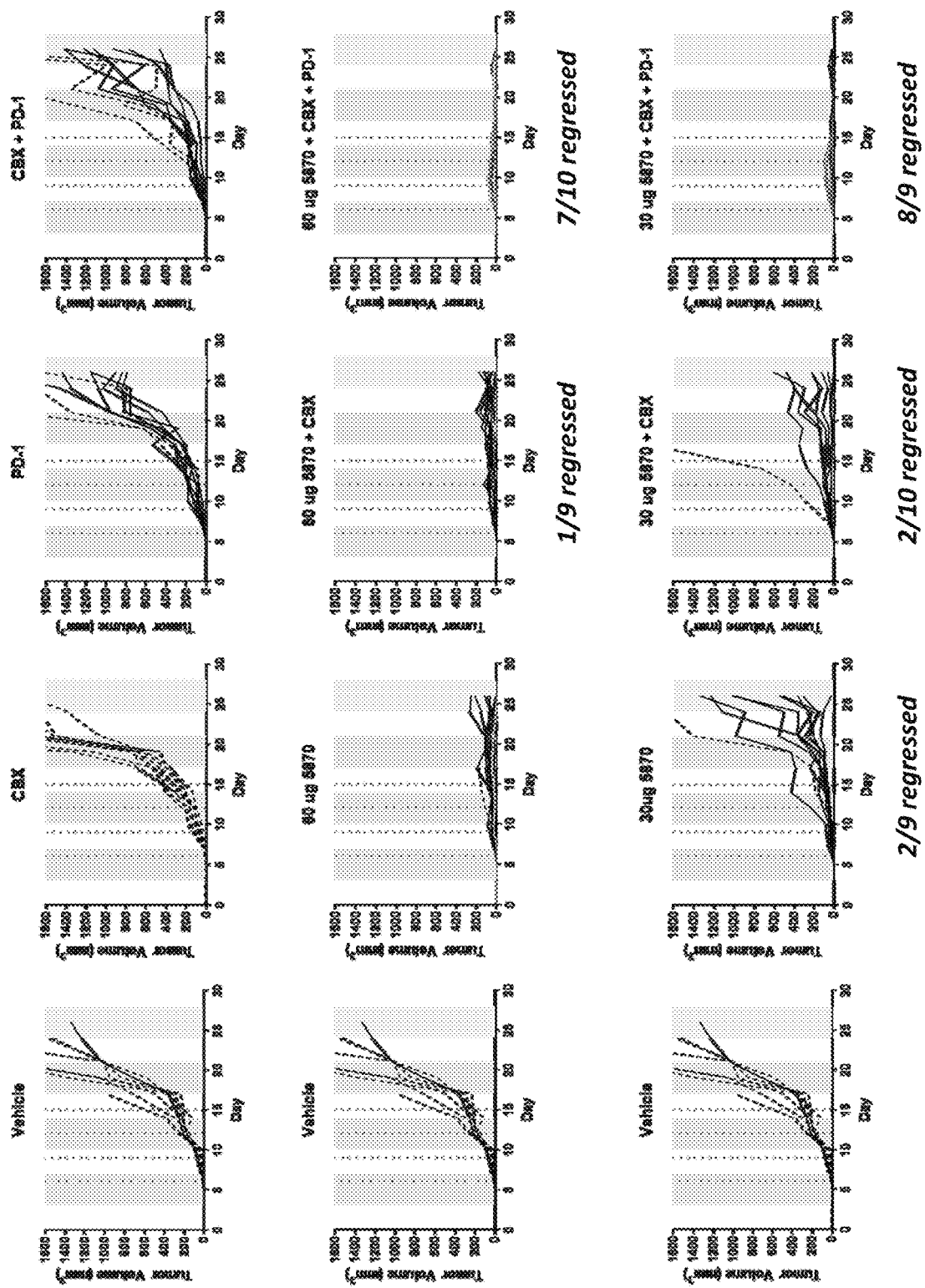
Figure 31:
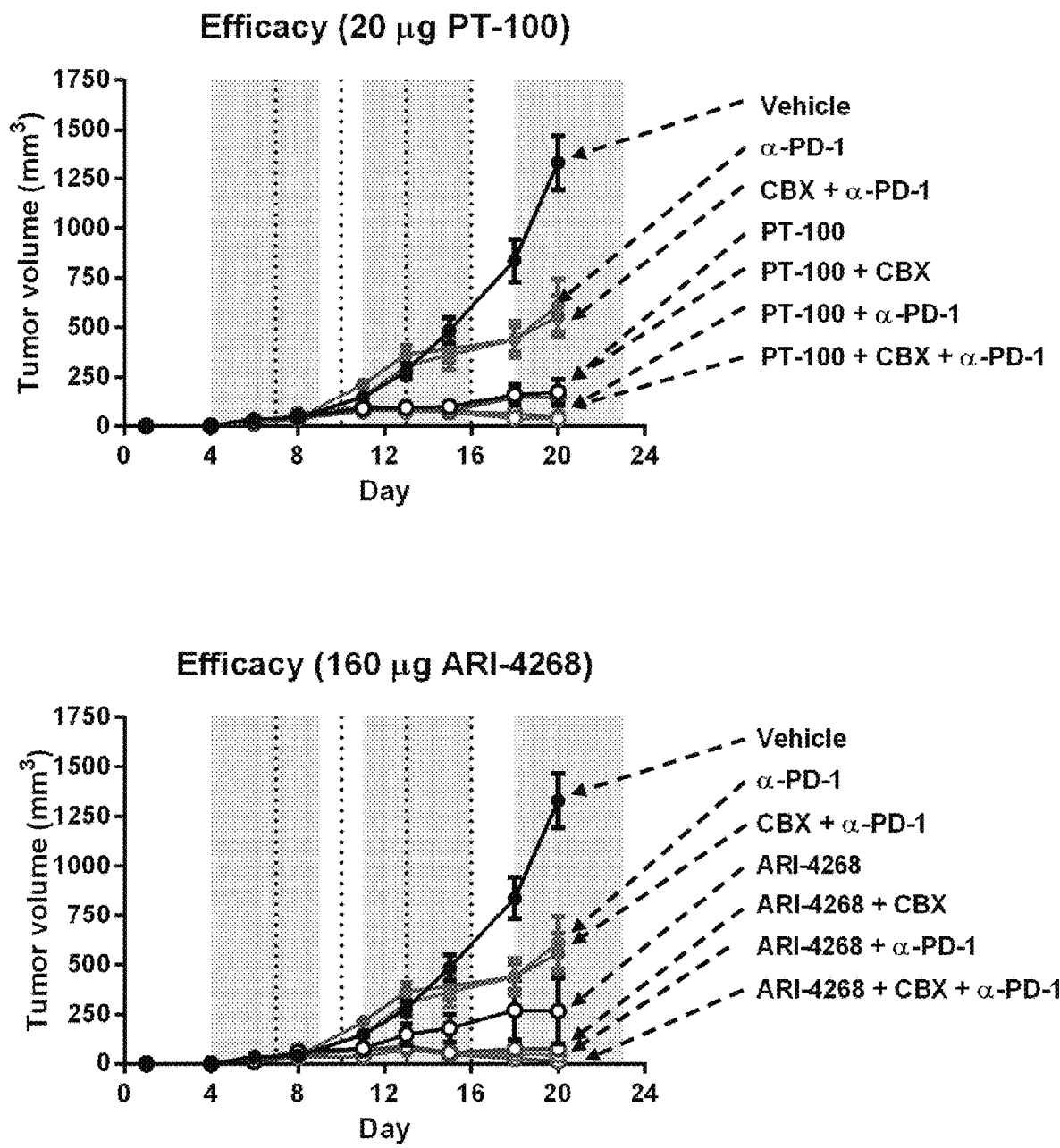
FIGS. 31 and 32 show the antitumor activity of ARI-4268 in the MB49 mouse tumor model, alone or when combined with Celebrex (COX inhibitor) or an anti-PD-1 antibody or both.
Figure 32:
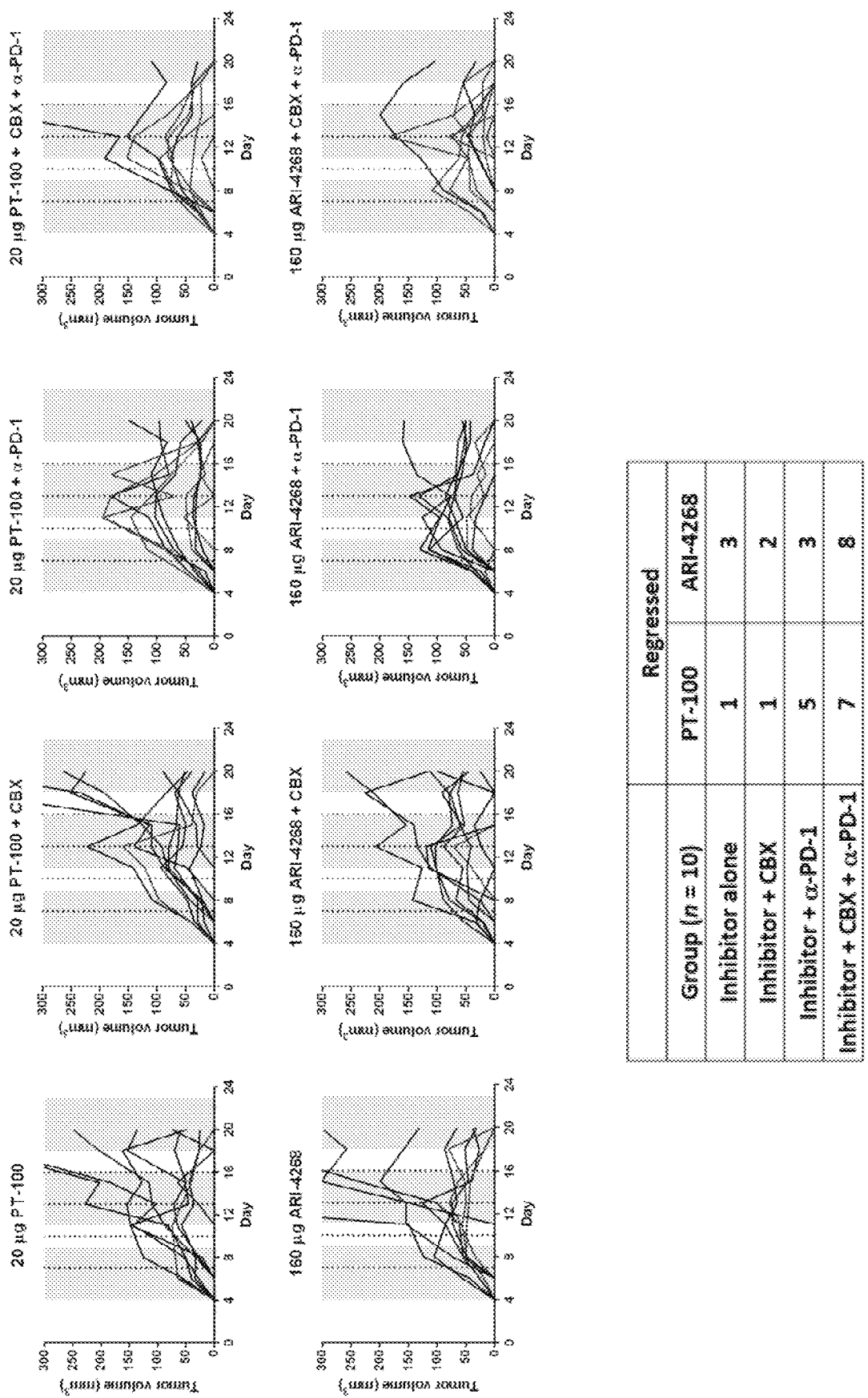
Figure 33:
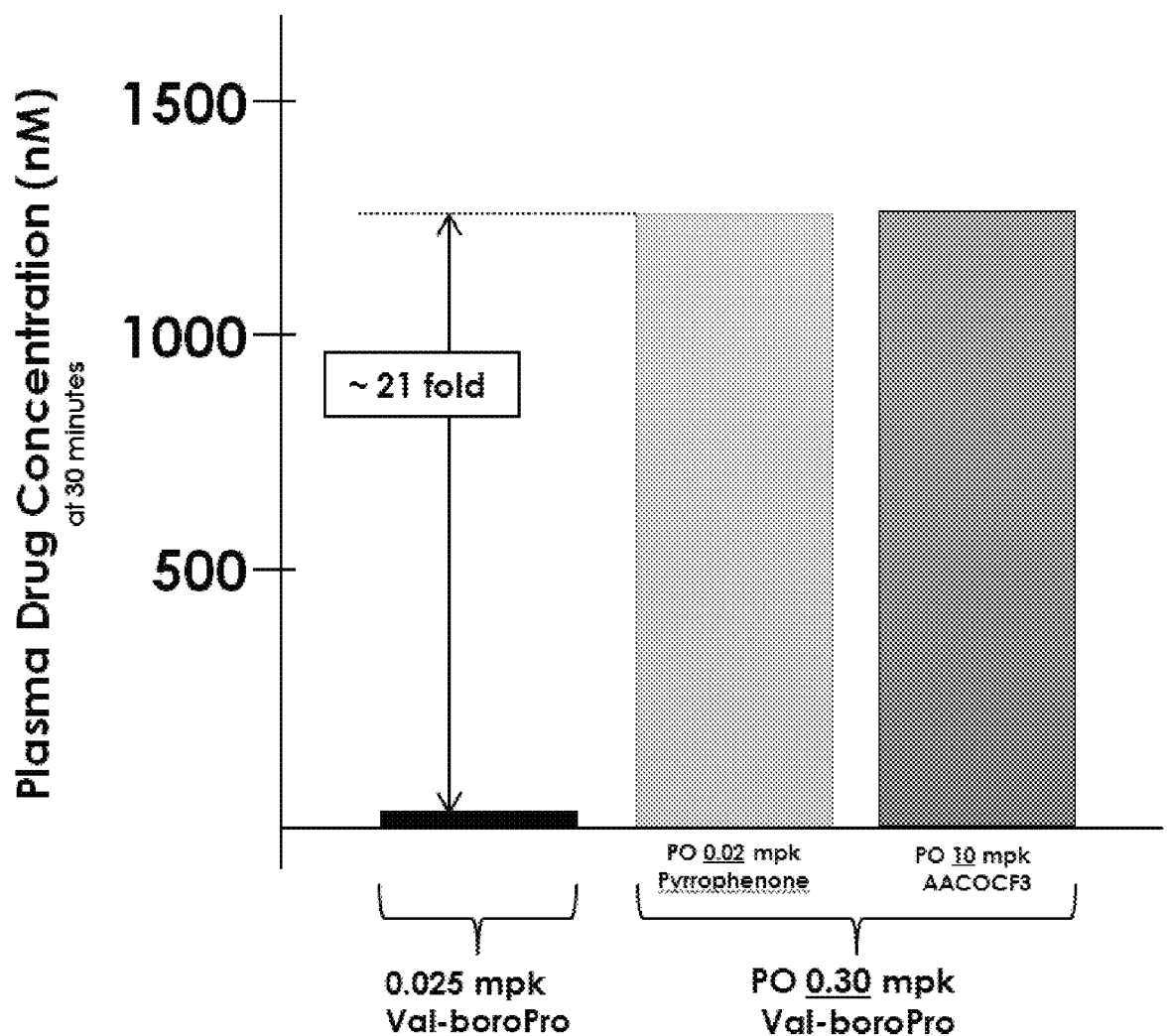
FIG. 33 shows the maximum tolerated dose study results (single dose) of treating Sprague Dawley rats with Val-boroPro (Valine-boroProline) with and without combination with cPLA2 inhibitors Pyrrophenone and AACOCF3. Bars show the MTD single dose in SD rats prior to seeing animal death. Based on serum drug levels, the addition of a cPLA2 inhibitors to the I-DASH inhibitor increases that MTD dose by at least 20-fold.

FIG. 17 shows the maximum tolerated dose study results (single dose) of treating Sprague Dawley rats with Val-boroPro (Valine-boroProline) with and without various cyclooxygenase inhibitors, such as celecoxib (a COX-2 selective nonsteroidal anti-inflammatory drug), indomethacin (a nonselective inhibitor of COX-1 and COX-2) and SC-560. Bars show the MTD single dose in SD rats prior to seeing animal death. Based on serum drug levels, the addition of a cyclooxygenase inhibitor to the I-DASH inhibitor increases that MTD dose from 47 to 75-fold. FIG. 33 is a similar experiment showing the maximum tolerated dose study results (single dose) of treating Sprague Dawley rats with Val-boroPro (Valine-boroProline) with and without various cPLA2 inhibitors indicating that addition of a cPLA2 inhibitor to the I-DASH inhibitor increases that MTD dose by at least 20-fold.

These findings indicated that that the combination of I-DASH inhibitors with PGE2 antagonists, particularly COX inhibitors, could provide an increased safety profile by increasing the maximum tolerated dose of I-DASH inhibitor that might be given to patients. FIGS. 18-21 demonstrate that not only does addition of celecoxib not mute the antitumor activity of Val-boroPro, but at celecoxib has a synergistic effect enhancing the antitumor activity of Val-boroPro. At various concentrations of celecoxib alone, there was no observed differences in tumor growth rates compared to control (vehicle). See FIG. 18. However, celecoxib increased the antitumor activity of Val-boroPro markedly (statistically significantly) and in a dose-dependent manner. See FIGS. 19 and 20. Considering the individual animal curves, see FIG. 21, the combination not only produced dramatic differences in tumor growth rates, but it also facilitated the achievement of tumor regression at the 20 microgram dose of Val-boroPro, which in this experiment did produce that effect by itself at that dose.

In certain embodiments, the immuno-DASH inhibitor is administered in combination with an agent that inhibits PGE2 production. The process of $PGE_2$ synthesis involves phospholipase A2 (PLA2) family members, that mobilize arachidonic acid from cellular membranes, cyclooxygenases (constitutively-active COX1 and inducible COX2) that convert arachidonic acid into prostaglandin H2 ($PGH_2$), and prostaglandin E synthase (PGES), needed for the final formulation of $PGE_2$. While the rate of $PGE_2$ synthesis and the resulting inflammatory process can be affected by additional factors, such as local availability of AA, in most physiologic conditions, the rate of $PGE_2$ synthesis is controlled by local expression and activity of COX2.

In other embodiments, the subject immuno-DASH inhibitor is administered in combination with agents which promote $PGE_2$ degradation. The rate of $PGE_2$ degradation is controlled by 15-hydroxyprostaglandin dehydrogenase (15-PGDH), suggesting that in addition to the rate of $PGE_2$ synthesis, also the rate of $PGE_2$ decay constitutes a target for therapeutic intervention in the subject immuno-DASH inhibitor combinations.

In still other embodiments, the subject immuno-DASH inhibitor is administered in combination with agents that reduce PGE2 responsiveness. Four different $PGE_2$ receptors are EP1, EP2, EP3 and EP4. The signaling through the two $G_s$-coupled receptors, EP2 and EP4, is mediated by the adenylate cyclase-triggered cAMP/PKA/CREB pathway, mediating the dominant aspects of the anti-inflammatory and suppressive activity of $PGE_2$. While EP2 is believed to signal in a largely cAMP-dependent fashion, EP4 also activates the PI3K-dependent ERK1/2 pathway. However, both EP2 and EP4 have been shown to activate the GSK3/β-catenin pathway. The expression of EP2 and the resulting responsiveness to PGE2 can be suppressed by hyper-methylation, as observed in patients with idiopathic lung fibrosis. These observations raise the possibility that, in addition to the regulation of PGE2 production and its degradation, the regulation of $PGE_2$ responsiveness at the level of expression of individual $PGE_2$ receptors can also contribute to the pathogenesis of human disease and be exploited in their therapy. In support, the use of synthetic inhibitors, preferentially affecting EP2, EP3, or EP4 signaling, allow for differential suppression of different aspects of $PGE_2$ activity.

Agents which reduce PGE2 responsiveness also include prostaglandin (PG) signaling inhibitors. Prostaglandins signal through numerous receptors, with the key immunosuppressive effects being mediated by the activation of adenylate cyclase, the resulting elevation of the intracellular cyclic (c)AMP, PKA and the downstream activation of the PKA/CREB pathway.

Another level of interference with the PG responsiveness includes the interference with their binging to PG receptors. In case of PGE2, the two key cAMP-activating receptors are EP2 and EP4, for which a number of specific inhibitors exist.

The increase of cAMP levels induced by prostaglandins or other factors can be prevented by phosphodiesterases (PDEs; currently known 6 types, PDE1-PDE5 and PDE10, which reduce the levels of intracellular cAMP). PDEs can be controlled by phosphodiesterase inhibitors, which include such substances as xanthines (caffeine, aminophylline, IBMX, pentoxyphylline, theobromine, theophylline, or paraxanthine), which all increase the levels of intracellular cAMP, and the more selective synthetic and natural factors, including vinpocetine, cilostazol, inaminone, cilostazol, mesembrine, rolipram, ibudilast, drotaverine, piclamilast, sildafenil, tadalafil, verdenafil, or papaverine.

Furthermore, interference with PGE2 signaling (or with the signaling of other cAMP-elevating factors, such as histamine, of beta-adrenergic agonists) can be achieved by the inhibition of downstream signals of cAMP, such as PKA or CREB.

Cyclooxygenase Inhibitors

In certain preferred embodiments, the subject immuno-DASH inhibitor is administered in combination with one or more prostaglandin (PG) synthesis inhibitors. Factor which inhibit the synthesis of PGs in general or the synthesis of a specific type of PGs. PG synthesis inhibitors include non-selective inhibitors of COX-1 and COX-2, the two key enzymes in the PG synthesis pathway, and selective inhibitors of COX-2, which are believed to be more specific to COX-2 and less toxic. The examples of non-selective PG inhibitors include aspirin, indomethacin, or ibuprofen (Advil, Motrin). The examples of COX-2-selective inhibitors include Celecoxib (Celebrex) and rofecoxib (Vioxx). The example of COX-1-specific inhibitor is sulindac (Clinoril). Other drugs that suppress prostaglandin synthesis include steroids (example: hydrocortisone, cortisol, prednisone, or dexamethasone) and acetaminophen (Tylenol, Panadol), commonly used as anti-inflammatory, antipyretic and analgesic drugs. Examples of the most commonly used selective COX2 inhibitors include celecoxib, alecoxib, valdecoxib, and rofecoxib.

Examples of the most commonly used non-selective COX 1 and COX2 inhibitors include: acetylsalicylic acid (aspirin) and other salicylates, acetaminophen (Tylenol), ibuprofen (Advil, Motrin, Nuprin, Rufen), naproxen (Naprosyn, Aleve), nabumetone (Relafen), or diclofenac (Cataflam).

A component of the present invention is a Cox-2 inhibitor. The terms "cyclooxygenase-2 inhibitor", or "Cox-2 inhibitor", which can be used interchangeably herein, embrace compounds which inhibit the Cox-2 enzyme regardless of the degree of inhibition of the Cox-1 enzyme, and include pharmaceutically acceptable salts of those compounds. Thus, for purposes of the present invention, a compound is considered a Cox-2 inhibitor irrespective of whether the compound inhibits the Cox-2 enzyme to an equal, greater, or lesser degree than the Cox-1 enzyme.

In one embodiment of the present invention, it is preferred that the Cox-2 inhibitor compound is a non-steroidal anti-inflammatory drug (NSAID). Therefore, preferred materials that can serve as the Cox-2 inhibitor of the present invention include non-steroidal anti-inflammatory drug compounds, a pharmaceutically acceptable salt thereof, or a pure (−) or (+) optical isomeric form thereof.

Examples of NSAID compounds that are useful in the present invention include acemetacin, acetyl salicylic acid, alclofenac, alminoprofen, azapropazone, benorylate, benoxaprofen, bucloxic acid, carprofen, choline magnesium trisalicylate, clidanac, clopinac, dapsone, diclofenac, diflunisal, droxicam, etodolac, fenoprofen, fenbufen, fenclofenec, fentiazac, floctafenine, flufenisal, flurbiprofen, (r)-flurbiprofen, (s)-flurbiprofen, furofenac, feprazone, flufenamic acid, fluprofen, ibufenac, ibuprofen, indometacin, indomethacin, indoprofen, isoxepac, isoxicam, ketoprofen, ketorolac, miroprofen, piroxicam, meloxicam, mefenamic, mefenamic acid, meclofenamic acid, meclofen, nabumetone, naproxen, niflumic acid, oxaprozin, oxipinac, oxyphenbutazone, phenylbutazone, podophyllotoxin derivatives, proglumetacin, piprofen, pirprofen, prapoprofen, salicylic acid, salicylate, sudoxicam, suprofen, sulindac, tenoxicam, tiaprofenic acid, tiopinac, tioxaprofen, tolfenamic acid, tolmetin, zidometacin, zomepirac, and 2-fluoro-a-methyl[1,1'-biphenyl]-4-acetic acid, 4-(nitrooxy)butyl ester.

In a preferred embodiment, the Cox-2 inhibitor is a Cox-2 selective inhibitor. The term "Cox-2 selective inhibitor" embraces compounds which selectively inhibit the Cox-2 enzyme over the Cox-1 enzyme, and also include pharmaceutically acceptable salts and prodrugs of those compounds.

In practice, the selectivity of a Cox-2 inhibitor varies depending upon the condition under which the test is performed and on the inhibitors being tested. However, for the purposes of this specification, the selectivity of a Cox-2 inhibitor can be measured as a ratio of the in vitro or in vivo $IC_{50}$ value for inhibition of Cox-1, divided by the $IC_{50}$ value for inhibition of Cox-2 (Cox-1 $IC_{50}$/Cox-2 $IC_{50}$). A Cox-2 selective inhibitor is any inhibitor for which the ratio of Cox-1 $IC_{50}$ to Cox-2 $IC_{50}$ is greater than 1. In preferred embodiments, this ratio is greater than 2, more preferably greater than 5, yet more preferably greater than 10, still more preferably greater than 50, and more preferably still greater than 100.

As used herein, the term "$IC_{50}$" refers to the concentration of a compound that is required to produce 50% inhibition of cyclooxygenase activity. Preferred Cox-2 selective inhibitors of the present invention have a Cox-2 $IC_{50}$ of less than about 1 µM, more preferred of less than about 0.5 µM, and even more preferred of less than about 0.2 µM.

Preferred Cox-2 selective inhibitors have a Cox-1 $IC_{50}$ of greater than about 1 µM, and more preferably of greater than 20 µM. Such preferred selectivity may indicate an ability to reduce the incidence of common NSAID-induced side effects.

Also included within the scope of the present invention are compounds that act as prodrugs of Cox-2-selective inhibitors. As used herein in reference to Cox-2 selective inhibitors, the term "prodrug" refers to a chemical compound that can be converted into an active Cox-2 selective inhibitor by metabolic or simple chemical processes within the body of the subject. One example of a prodrug for a Cox-2 selective inhibitor is parecoxib, which is a therapeutically effective prodrug of the tricyclic Cox-2 selective inhibitor valdecoxib. An example of a preferred Cox-2 selective inhibitor prodrug is sodium parecoxib. A class of prodrugs of Cox-2 inhibitors is described in U.S. Pat. No. 5,932,598.

The Cox-2 selective inhibitor of the present invention can be, for example, the Cox-2 selective inhibitor meloxicam, (CAS registry number 71125-38-7), or a pharmaceutically acceptable salt or prodrug thereof.

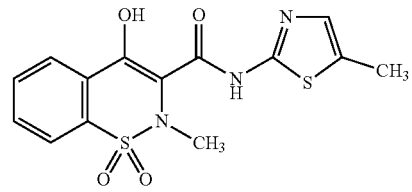 [SMILES: Cc1cnc(NC(=O)C2=C(O)c3ccccc3S(=O)(=O)N2C)s1]

In another embodiment of the invention the Cox-2 selective inhibitor can be the Cox-2 selective inhibitor RS 57067, 6-[[5-(4-chlorobenzoyl)-1,4-dimethyl-1H-pyrrol-2-yl] methyl]-3(2H)-pyridazinone, (CAS registry number 179382-91-3), or a pharmaceutically acceptable salt or prodrug thereof.

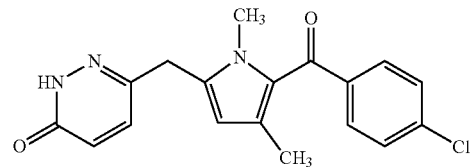 [SMILES: Cc1cc(Cc2ccc(=O)[nH]n2)n(C)c1C(=O)c1ccc(Cl)cc1]

As used herein, the term "alkyl", either alone or within other terms such as "haloalkyl" and "alkylsulfonyl"; embraces linear or branched radicals having one to about twenty carbon atoms. Lower alkyl radicals have one to about ten carbon atoms. The number of carbon atoms can also be expressed as "$C_1$-$C_5$", for example. Examples of lower alkyl radicals include methyl, ethyl, n-propyl, isopropyl, n-butyl, isobutyl, sec-butyl, tert-butyl, pentyl, isoamyl, hexyl, octyl and the, like.

The term "alkenyl" refers to an unsaturated, acyclic hydrocarbon radical, linear or branched, in so much as it contains at least one double bond. The alkenyl radicals may be optionally substituted with groups such as those defined below. Examples of suitable alkenyl radicals include propenyl, 2-chloropropylenyl, buten-1yl, isobutenyl, penten-1yl, 2-methylbuten-1-yl, 3-methylbuten-1-yl, hexen-1-yl, 3-hydroxyhexen-1-yl, hepten-1-yl, octen-1-yl, and the like.

The term "alkynyl" refers to an unsaturated, acyclic hydrocarbon radical, linear or branched, in so much as it contains one or more triple bonds, such radicals preferably containing 2 to about 6 carbon atoms, more preferably from 2 to about 3 carbon atoms. The alkynyl radicals may be optionally substituted with groups such as described below. Examples of suitable alkynyl radicals include ethynyl, proynyl, hydroxypropynyl, butyn-1-yl, butyn-2-yl, pentyn-1-yl, pentyn-2-yl, 4-methoxypentyn-2-yl, 3-methylbutyn-1-yl, hexyl-1-yl, hexyn-2-yl, hexyn-3-yl, 3,3-dimethylbutyn-1-yl radicals, and the like.

The term "oxo" means a single double-bonded oxygen.

The terms "hydrido", "—H", or "hydrogen", denote a single hydrogen atom (H). This hydrido radical may be attached, for example, to an oxygen atom to form a hydroxyl radical, or two hydrido radicals may be attached to a carbon atom to form a methylene (—CH$_2$—) radical.

The term "halo" means halogens such as fluorine, chlorine, and bromine or iodine atoms. The term "haloalkyl" embraces radicals wherein any one or more of the alkyl carbon atoms is substituted with halo as defined above. Specifically embraced are monohaloalkyl, dihaloalkyl, and polyhaloalkyl radicals. A monohaloalkyl radical, for one example, may have a bromo, chloro, or a fluoro atom within the radical. Dihalo alkyl radicals may have two or more of the same halo atoms or a combination of different halo radicals and polyhaloalkyl radicals may have more than two of the same halo atoms or a combination of different halo radicals.

The term "hydroxyalkyl" embraces linear or branched alkyl radicals having one to about ten carbon atoms any one of which may be substituted with one or more hydroxyl radicals.

The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro, or bromo, to provide "haloalkoxy" or "haloalkoxyalkyl" radicals. Examples of "alkoxy" radicals include methoxy, butoxy, and trifluoromethoxy.

The term "aryl", whether used alone or with other terms, means a carbocyclic aromatic system containing one, two, or three rings wherein such rings may be attached together in a pendent manner, or may be fused. The term "aryl" embraces aromatic radicals such as phenyl, naphthyl, tetrahydronaphthyl, indane, and biphenyl. The term "heterocyclyl" means a saturated or unsaturated mono- or multi-ring carbocycle wherein one or more carbon atoms are replaced by N, S, P, or O. This includes, for example, structures such as:

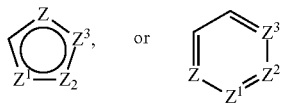

wherein Z, $Z^1$, $Z^2$, or $Z^3$ is C, S, P, O, or N, with the proviso that one of Z, $Z^1$, $Z^2$, or $Z^3$ is other than carbon, but is not O or S when attached to another Z atom by a double bond or when attached to another O or S atom. Furthermore, the optional substituents are understood to be attached to Z, $Z^1$, $Z^2$, or $Z^3$ only when each is C. The term "heterocycle" also includes fully saturated ring structures, such as piperazinyl, dioxanyl, tetrahydrofuranyl, oxiranyl, aziridinyl, morpholinyl, pyrrolidinyl, piperidinyl, thiazolidinyl, and others.

The term "heteroaryl" embraces unsaturated heterocyclic radicals. Examples of unsaturated heterocyclic radicals include thienyl, pyrryl, furyl, pyridyl, pyrimidyl, pyrazinyl, pyrazolyl, oxazolyl, isoxazolyl, imidazolyl, thiazolyl, pyranyl, and tetrazolyl. The term also embraces radicals where heterocyclic radicals are fused with aryl radicals. Examples of such fused bicyclic radicals include benzofuran, benzothiophene, and the like.

The term "sulfonyl", whether used alone or linked to other terms such as alkylsulfonyl, denotes respectively divalent radicals —SO$_2$—. "Alkylsulfonyl", embraces alkyl radicals attached to a sulfonyl radical, where alkyl is defined as above. The term "arylsulfonyl" embraces sulfonyl radicals substituted with an aryl radical. The term "aminosulfonyl" denotes a sulfonyl radical substituted with an amine radical, forming a sulfonamide (—SO$_2$—NH$_2$).

The terms "carboxy" or "carboxyl", whether used alone or with other terms, such as "carboxyalkyl", denotes —CO$_2$—H. The term "carboxyalkyl" embraces radicals having a carboxyradical as defined above, attached to an alkyl radical. The term "carbonyl", whether used alone or with other terms, such as "alkylcarbonyl", denotes —(C=O)—. The term "alkylcarbonyl" embraces radicals having a carbonyl radical substituted with an alkyl radical. An example of an "alkylcarbonyl" radical is CH$_3$—(CO)—. The term "alkoxycarbonyl" means a radical containing an alkoxy radical, as defined above, attached via an oxygen atom to a carbonyl (C=O) radical. Examples of such "alkoxycarbonyl" radicals include (CH$_3$)$_3$—C—O—C°O)— and —(O=)C—OCH$_3$. The term "amino", whether used alone or with other terms, such as "aminocarbonyl", denotes —NH$_2$.

The term "heterocycloalkyl" embraces heterocyclic-substituted alkyl radicals such as pyridylmethyl and thienylmethyl. The terms "aralkyl", or "arylalkyl" embrace arylsubstituted alkyl radicals such as benzyl, diphenylmethyl, triphenylmethyl, phenylethyl, and diphenylethyl. The terms benzyl and phenylmethyl are interchangeable. The term "cycloalkyl" embraces radicals having three to ten carbon atoms, such as cyclopropyl cyclobutyl, cyclopentyl, cyclohexyl, and cycloheptyl. The term "cycloalkenyl" embraces unsaturated radicals having three to ten carbon atoms, such as cylopropenyl, cyclobutenyl, cyclopentenyl, cyclohexenyl, and cycloheptenyl.

The term "alkylthio" embraces radicals containing a linear or branched alkyl radical, of one to ten carbon atoms, attached to a divalent sulfur atom. An example of "alkylthio" is methylthio, (CH$_3$—S—). The term "alkylsulfinyl" embraces radicals containing a linear or branched alkyl radical, of one to ten carbon atoms, attached to a divalent —S(—O)— atom. The term "acyl", whether used alone, or within a term such as "acylamino", denotes a radical provided by the residue after removal of hydroxyl from an organic acid.

The term "cyano", used either alone or with other terms, such as "cyanoalkyl", refers to C≡N. The term "nitro" denotes —NO$_2$.

In one embodiment of the invention the Cox-2 selective inhibitor is of the chromene/chroman structural class, which encompasses substituted benzopyrans or substituted benzopyran analogs, as well as substituted benzothiopyrans, dihydroquinolines, or dihydronaphthalenes having the structure of any one of the general Formulas shown below, and the diastereomers, enantiomers, racemates, tautomers, salts, esters, amides and prodrugs thereof.

Benzopyrans that can serve as a Cox-2 selective inhibitor of the present invention include substituted benzopyran derivatives that are described in U.S. Pat. Nos. 6,271,253 and 6,492,390. One such class of compounds is defined by the general formula shown below:

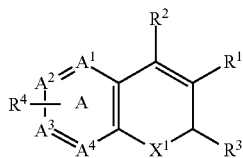

wherein $X^1$ is selected from O, S, $CR^cR^b$ and $NR^a$;
wherein $R^a$ is selected from hydrido, $C_1$-$C_3$-alkyl, (optionally substituted phenyl)-$C_1$-$C_3$-alkyl, acyl and carboxy-$C_1$-$C_6$-alkyl;
wherein each of $R^b$ and $R^c$ is independently selected from hydrido, $C_1$-$C_3$-alkyl, phenyl-$C_1$-$C_3$-alkyl, $C_1$-$C_3$-perfluoroalkyl, chloro, $C_1$-$C_6$-alkylthio, $C_1$-$C_6$-alkoxy, nitro, cyano and cyano-$C_1$-$C_3$-alkyl; or wherein $CR^bR^c$ forms a 3-6 membered cycloalkyl ring;
wherein $R^1$ is selected from carboxyl, aminocarbonyl, $C_1$-$C_6$-alkylsulfonylaminocarbonyl and $C_1$-$C_6$-alkoxycarbonyl;
wherein $R^2$ is selected from hydrido, phenyl, thienyl, $C_1$-$C_6$-alkyl and $C_2$-$C_6$-alkenyl;
wherein $R^3$ is selected from $C_1$-$C_3$-perfluoroalkyl, chloro, $C_1$-$C_6$-alkylthio, $C_1$-$C_6$-alkoxy, nitro, cyano and cyano-$C_1$-$C_3$-alkyl;
wherein $R^4$ is one or more radicals independently selected from hydrido, halo, $C_1$-$C_6$-alkyl, $C_2$-$C_6$-alkenyl, $C_2$-$C_6$-alkynyl, halo-$C_2$-$C_6$-alkynyl, aryl-$C_1$-$C_3$-alkyl, aryl-$C_2$-$C_6$-alkynyl, aryl-$C_2$-$C_6$-alkenyl, $C_1$-$C_6$-alkoxy, methylenedioxy, $C_1$-$C_6$-alkylthio, $C_1$-$C_6$-alkylsulfinyl, aryloxy, arylthio, arylsulfinyl, heteroaryloxy, $C_1$-$C_6$-alkoxy-$C_1$-$C_6$-alkyl, aryl-$C_1$-$C_6$-alkyloxy, heteroaryl-$C_1$-$C_6$-alkyloxy, aryl-$C_1$-$C_6$-alkoxy-$C_1$-$C_6$-alkyl, $C_1$-$C_6$-haloalkyl, $C_1$-$C_6$-haloalkoxy, $C_1$-$C_6$-haloalkylthio, $C_1$-$C_6$-haloalkylsulfinyl, $C_1$-$C_6$-haloalkylsulfonyl, $C_1$-$C_3$-(haloalkyl-$_1$-C3-hydroxyalkyl, $C_1$-$C_6$-hydroxyalkyl, hydroxyimino-$C_1$-$C_6$-alkyl, $C_1$-$C_6$-alkylamino, arylamino, aryl-$C_1$-$C_6$-alkylamino, heteroarylamino, heteroaryl-$C_1$-$C_6$-alkylamino, nitro, cyano, amino, aminosulfonyl, $C_1$-$C_6$-alkylaminosulfonyl, arylaminosulfonyl, heteroarylaminosulfonyl, aryl-$C_1$-$C_6$-alkylaminosulfonyl, heteroaryl-$C_1$-$C_6$-alkylaminosulfonyl, heterocyclylsulfonyl, $C_1$-$C_6$-alkylsulfonyl, aryl-$C_1$-$C_6$-alkylsulfonyl, optionally substituted aryl, optionally substituted heteroaryl, aryl-$C_1$-$C_6$-alkylcarbonyl, heteroaryl-$C_1$-$C_6$-alkylcarbonyl, heteroarylcarbonyl, arylcarbonyl, aminocarbonyl, $C_1$-$C_1$-alkoxycarbonyl, formyl, $C_1$-$C_6$-haloalkylcarbonyl and $C_1$-$C_6$-alkylcarbonyl; and
wherein the A ring atoms $A^1$, $A^2$, $A^3$ and $A^4$ are independently selected from carbon and nitrogen with the proviso that at least two of $A^1$, $A^2$, $A^3$ and $A^4$ are carbon;
or wherein $R^4$ together with ring A forms a radical selected from naphthyl, quinolyl, isoquinolyl, quinolizinyl, quinoxalinyl and dibenzofuryl; or an isomer or pharmaceutically acceptable salt thereof.

Another class of benzopyran derivatives that can serve as the Cox-2 selective inhibitor of the present invention includes compounds having the structure of:

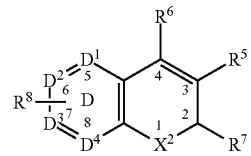

wherein $X^2$ is selected from O, S, $CR^cR^b$ and $NR^a$;
wherein $R^a$ is selected from hydrido, $C_1$-$C_3$-alkyl, (optionally substituted phenyl)-$C_1$-$C_3$-alkyl, alkylsulfonyl, phenylsulfonyl, benzylsulfonyl, acyl and carboxy-$C_1$-$C_6$-alkyl;
wherein each of $R^b$ and $R^c$ is independently selected from hydrido, $C_1$-$C_3$-alkyl, phenyl-$C_1$-$C_3$-alkyl, $C_1$-$C_3$-perfluoroalkyl, chloro, $C_1$-$C_6$-alkylthio, $C_1$-$C_6$-alkoxy, nitro, cyano and cyano-$C_1$-$C_3$-alkyl; or wherein $CR^cR^b$ form a cyclopropyl ring;
wherein $R^5$ is selected from carboxyl, aminocarbonyl, $C_1$-$C_6$-alkylsulfonylaminocarbonyl and $C_1$-$C_6$-alkoxycarbonyl;
wherein $R^6$ is selected from hydrido, phenyl, thienyl, $C_2$-$C_6$-alkynyl and $C_2$-$C_6$-alkenyl;
wherein $R^7$ is selected from $C_1$-$C_3$-perfluoroalkyl, chloro, $C_1$-$C_6$-alkylthio, $C_1$-$C_6$-alkoxy, nitro, cyano and cyano-$C_1$-$C_3$-alkyl;
wherein $R^8$ is one or more radicals independently selected from hydrido, halo, $C_1$-$C_6$-alkyl, $C_2$-$C_6$-alkenyl, $C_2$-$C_6$-alkynyl, halo-$C_2$-$C_6$-alkynyl, aryl-$C_1$-$C_3$-alkyl, aryl-$C_2$-$C_6$-alkynyl, aryl-$C_2$-$C_6$-alkenyl, $C_1$-$C_6$-alkoxy, methylenedioxy, $C_1$-$C_6$-alkylthio, $C_1$-$C_6$-alkylsulfinyl, —O(CF$_2$)$_2$O—, aryloxy, arylthio, arylsulfinyl, heteroaryloxy, $C_1$-$C_6$-alkoxy-$C_1$-$C_6$-alkyl, aryl-$C_1$-$C_6$-alkyloxy, heteroaryl-$C_1$-$C_6$-alkyloxy, aryl-$C_1$-$C_6$-alkoxy-$C_1$-$C_6$-alkyl, $C_1$-$C_6$-haloalkyl, $C_1$-$C_6$-haloalkoxy, $C_1$-$C_6$-haloalkylthio, $C_1$-$C_6$-haloalkylsulfinyl, $C_1$-$C_6$-haloalkylsulfonyl, $C_1$-$C_3$-(haloalkyl-$C_1$-$C_3$-hydroxyalkyl), $C_1$-$C_6$-hydroxyalkyl, hydroxyimino-$C_1$-$C_6$-alkyl, $C_1$-$C_6$-alkylamino, arylamino, aryl-$C_1$-$C_6$-alkylamino, heteroarylamino, heteroaryl-$C_1$-$C_6$-alkylamino, nitro, cyano, amino, aminosulfonyl, $C_1$-$C_6$-alkylaminosulfonyl, arylaminosulfonyl, heteroarylaminosulfonyl, aryl-$C_1$-$C_6$-alkylaminosulfonyl, heteroaryl-$C_1$-$C_6$-alkylaminosulfonyl, heterocyclylsulfonyl, $C_1$-$C_6$-alkylsulfonyl, aryl-$C_1$-$C_6$-alkylsulfonyl, optionally substituted aryl, optionally substituted heteroaryl, aryl-$C_1$-$C_6$-alkylcarbonyl, heteroaryl-$C_1$-$C_6$-alkylcarbonyl, heteroarylcarbonyl, arylcarbonyl, aminocarbonyl, $C_1$-$C_6$-alkoxycarbonyl, formyl, $C_1$-$C_6$-haloalkylcarbonyl and $C_1$-$C_6$-alkylcarbonyl; and
wherein the D ring atoms $D^1$, $D^2$, $D^3$ and $D^4$ are independently selected from carbon and nitrogen with the proviso that at least two of $D^1$, $D^2$, $D^3$ and $D^4$ are carbon; or
wherein $R^8$ together with ring D forms a radical selected from naphthyl, quinolyl, isoquinolyl, quinolizinyl, quinoxalinyl and dibenzofuryl; or an isomer or pharmaceutically acceptable salt thereof.

Other benzopyran Cox-2 selective inhibitors useful in the practice of the present invention are described in U.S. Pat. Nos. 6,034,256 and 6,077,850. The general formula for these compounds is:

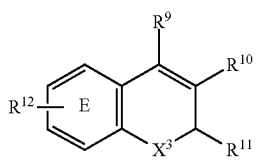

wherein $X^3$ is selected from the group consisting of O or S or $NR^a$;

wherein $R^a$ is alkyl;

wherein $R^9$ is selected from the group consisting of H and aryl;

wherein $R^{10}$ is selected from the group consisting of carboxyl, aminocarbonyl, alkylsulfonylaminocarbonyl and alkoxycarbonyl;

wherein $R^{11}$ is selected from the group consisting of haloalkyl, alkyl, aralkyl, cycloalkyl and aryl optionally substituted with one or more radicals selected from alkylthio, nitro and alkylsulfonyl; and wherein $R^{12}$ is selected from the group consisting of one or more radicals selected from H, halo, alkyl, aralkyl, alkoxy, aryloxy, heteroaryloxy, aralkyloxy, heteroaralkyloxy, haloalkyl, haloalkoxy, alkylamino, arylamino, aralkylamino, heteroarylamino, heteroarylalkylamino, nitro, amino, aminosulfonyl, alkylaminosulfonyl, arylaminosulfonyl, heteroarylaminosulfonyl, aralkylaminosulfonyl, heteroaralkylaminosulfonyl, heterocyclosulfonyl, alkylsulfonyl, hydroxyarylcarbonyl, nitroaryl, optionally substituted aryl, optionally substituted heteroaryl, aralkylcarbonyl, heteroarylcarbonyl, arylcarbonyl, aminocarbonyl, and alkylcarbonyl; or wherein $R^{12}$ together with ring E forms a naphthyl radical; or an isomer or pharmaceutically acceptable salt thereof; and including the diastereomers, enantiomers, racemates, tautomers, salts, esters, amides and prodrugs thereof.

A related class of compounds useful as Cox-2 selective inhibitors in the present invention is described by the structure below:

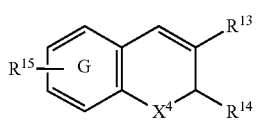

wherein $X^4$ is selected from O or S or $NR^a$;

wherein $R^a$ is alkyl;

wherein $R^{13}$ is selected from carboxyl, aminocarbonyl, alkylsulfonylaminocarbonyl and alkoxycarbonyl;

wherein $R^{14}$ is selected from haloalkyl, alkyl, aralkyl, cycloalkyl and aryl optionally substituted with one or more radicals selected from alkylthio, nitro and alkylsulfonyl; and wherein $R^{15}$ is one or more radicals selected from hydrido, halo, alkyl, aralkyl, alkoxy, aryloxy, heteroaryloxy, aralkyloxy, heteroaralkyloxy, haloalkyl, haloalkoxy, alkylamino, arylamino, aralkylamino, heteroarylamino, heteroarylalkylamino, nitro, amino, aminosulfonyl, alkylaminosulfonyl, arylaminosulfonyl, heteroarylaminosulfonyl, aralkylaminosulfonyl, heteroaralkylaminosulfonyl, heterocyclosulfonyl, alkylsulfonyl, optionally substituted aryl, optionally substituted heteroaryl, aralkylcarbonyl, heteroarylcarbonyl, arylcarbonyl, aminocarbonyl, and alkylcarbonyl;

or wherein $R^{15}$ together with ring G forms a naphthyl radical; or an isomer or pharmaceutically acceptable salt thereof.

Another related class of compounds useful as Cox-2 selective inhibitors in the present invention is described by the structure below:

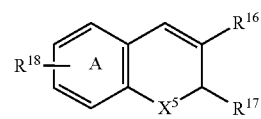

wherein:

$X^5$ is selected from the group consisting of O or S or $NR^b$;

$R^b$ is alkyl;

$R^{16}$ is selected from the group consisting of carboxyl, aminocarbonyl, alkylsulfonylaminocarbonyl and alkoxycarbonyl;

$R^{17}$ is selected from the group consisting of haloalkyl, alkyl, aralkyl, cycloalkyl and aryl, wherein haloalkyl, alkyl, aralkyl, cycloalkyl, and aryl each is independently optionally substituted with one or more radicals selected from the group consisting of alkylthio, nitro and alkylsulfonyl; and $R^{18}$ is one or more radicals selected from the group consisting of hydrido, halo, alkyl, aralkyl, alkoxy, aryloxy, heteroaryloxy, aralkyloxy, heteroaralkyloxy, haloalkyl, haloalkoxy, alkylamino, arylamino, aralkylamino, heteroarylamino, heteroarylalkylamino, nitro, amino, aminosulfonyl, alkylaminosulfonyl, arylaminosulfonyl, heteroarylaminosulfonyl, aralkylaminosulfonyl, heteroaralkylaminosulfonyl, heterocyclosulfonyl, alkylsulfonyl, optionally substituted aryl, optionally substituted heteroaryl, aralkylcarbonyl, heteroarylcarbonyl, arylcarbonyl, aminocarbonyl, and alkylcarbonyl; or wherein $R^{18}$ together with ring A forms a naphthyl radical;

or an isomer or pharmaceutically acceptable salt thereof.

The Cox-2 selective inhibitor may also be a compound of the above formula, wherein:

$X^5$ is selected from the group consisting of oxygen and sulfur;

$R^{16}$ is selected from the group consisting of carboxyl, lower alkyl, lower aralkyl and lower alkoxycarbonyl;

$R^{17}$ is selected from the group consisting of lower haloalkyl, lower cycloalkyl and phenyl; and $R^{18}$ is one or more radicals selected from the group of consisting of hydrido, halo, lower alkyl, lower alkoxy, lower haloalkyl, lower haloalkoxy, lower alkylamino, nitro, amino, aminosulfonyl, lower alkylaminosulfonyl, 5-membered heteroarylalkylaminosulfonyl, 6-membered heteroarylalkylaminosulfonyl, lower aralkylaminosulfonyl, 5-membered nitrogen-containing heterocyclosulfonyl, 6-membered nitrogen-containing heterocyclosulfonyl, lower alkylsulfonyl, optionally substituted phenyl, lower aralkylcarbonyl, and lower alkylcarbonyl; or wherein $R^{18}$ together with ring A forms a naphthyl radical; or an isomer or pharmaceutically acceptable salt thereof.

The Cox-2 selective inhibitor may also be a compound of the above formula, wherein:
$X^5$ is selected from the group consisting of oxygen and sulfur;
$R^{16}$ is carboxyl;
$R^{17}$ is lower haloalkyl; and
$R^{18}$ is one or more radicals selected from the group consisting of hydrido, halo, lower alkyl, lower haloalkyl, lower haloalkoxy, lower alkylamino, amino, aminosulfonyl, lower alkylaminosulfonyl, 5-membered heteroarylalkylaminosulfonyl, 6-membered heteroarylalkylaminosulfonyl, lower aralkylaminosulfonyl, lower alkylsulfonyl, 6-membered nitrogen-containing heterocyclosulfonyl, optionally substituted phenyl, lower aralkylcarbonyl, and lower alkylcarbonyl; or wherein $R^{18}$ together with ring A forms a naphthyl radical;
or an isomer or pharmaceutically acceptable salt thereof.

The Cox-2 selective inhibitor may also be a compound of the above formula, wherein:
$X^5$ is selected from the group consisting of oxygen and sulfur;
$R^{16}$ is selected from the group consisting of carboxyl, lower alkyl, lower aralkyl and lower alkoxycarbonyl;
$R^{17}$ is selected from the group consisting of fluoromethyl, chloromethyl, dichloromethyl, trichloromethyl, pentafluoroethyl, heptafluoropropyl, difluoroethyl, difluoropropyl, dichloroethyl, dichloropropyl, difluoromethyl, and trifluoromethyl; and
$R^{18}$ is one or more radicals selected from the group consisting of hydrido, chloro, fluoro, bromo, iodo, methyl, ethyl, isopropyl, tert-butyl, butyl, isobutyl, pentyl, hexyl, methoxy, ethoxy, isopropyloxy, tertbutyloxy, trifluoromethyl, difluoromethyl, trifluoromethoxy, amino, N,N-dimethylamino, N,N-diethylamino, N-phenylmethylaminosulfonyl, N-phenylethylaminosulfonyl, N-(2-furylmethyl)aminosulfonyl, nitro, N,N-dimethylaminosulfonyl, aminosulfonyl, N-methylaminosulfonyl, N-ethylsulfonyl, 2,2-dimethylethylaminosulfonyl, N,N-dimethylaminosulfonyl, N-(2-methylpropyl)aminosulfonyl, N-morpholinosulfonyl, methylsulfonyl, benzylcarbonyl, 2,2-dimethylpropylcarbonyl, phenylacetyl and phenyl; or wherein $R^2$ together with ring A forms a naphthyl radical; or an isomer or pharmaceutically acceptable salt thereof.

The Cox-2 selective inhibitor may also be a compound of the above formula, wherein:
$X^5$ is selected from the group consisting of oxygen and sulfur,
$R^{16}$ is selected from the group consisting of carboxyl, lower alkyl, lower aralkyl and lower alkoxycarbonyl;
$R^{17}$ is selected from the group consisting trifluoromethyl and pentafluoroethyl; and
$R^{18}$ is one or more radicals selected from the group consisting of hydrido, chloro, fluoro, bromo, iodo, methyl, ethyl, isopropyl, tert-butyl, methoxy, trifluoromethyl, trifluoromethoxy, N-phenylmethylaminosulfonyl, N-phenylethylaminosulfonyl, N-(2-furylmethyl)aminosulfonyl, N,N-dimethylaminosulfonyl, N-methylaminosulfonyl, N-(2,2-dimethylethyl)aminosulfonyl, dimethylaminosulfonyl, 2-methylpropylaminosulfonyl, N-morpholinosulfonyl, methylsulfonyl, benzylcarbonyl, and phenyl; or wherein $R^{18}$ together with ring A forms a naphthyl radical;
or an isomer or prodrug thereof.

The Cox-2 selective inhibitor of the present invention can also be a compound having the structure of:

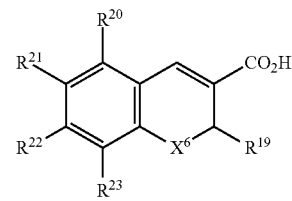

wherein:
$X^6$ is selected from the group consisting of O and S;
$R^{19}$ is lower haloalkyl;
$R^{20}$ is selected from the group consisting of hydrido, and halo;
$R^{21}$ is selected from the group consisting of hydrido, halo, lower alkyl; lower haloalkoxy, lower alkoxy, lower aralkylcarbonyl, lower dialkylaminosulfonyl, lower alkylaminosulfonyl, lower aralkylaminosulfonyl, lower heteroaralkylaminosulfonyl, 5-membered nitrogen-containing heterocyclosulfonyl, and 6-membered nitrogen-containing heterocyclosulfonyl;
$R^{22}$ is selected from the group consisting of hydrido, lower alkyl, halo, lower alkoxy, and aryl; and
$R^{23}$ is selected from the group consisting of the group consisting of hydrido, halo, lower alkyl, lower alkoxy, and aryl;
or an isomer or prodrug thereof.

The Cox-2 selective inhibitor can also be a compound of having the structure of the above formula, wherein:
$X^6$ is selected from the group consisting of O and S;
$R^{19}$ is selected from the group consisting of trifluoromethyl and pentafluoroethyl;
$R^{20}$ is selected from the group consisting of hydrido, chloro, and fluoro;
$R^{21}$ is selected from the group consisting of hydrido, chloro, bromo, fluoro, iodo, methyl, tert-butyl, trifluoromethoxy, methoxy, benzylcarbonyl, dimethylaminosulfonyl, isopropylaminosulfonyl, methylaminosulfonyl, benzylaminosulfonyl, phenylethylaminosulfonyl, methylpropylaminosulfonyl, methylsulfonyl, and morpholinosulfonyl;
$R^{22}$ is selected from the group consisting of hydrido, methyl, ethyl, isopropyl, tert-butyl, chloro, methoxy, diethylamino, and phenyl; and
$R^{23}$ is selected from the group consisting of hydrido, chloro, bromo, fluoro, methyl, ethyl, tert-butyl, methoxy, and phenyl;
or an isomer or prodrug thereof.

Examples include:

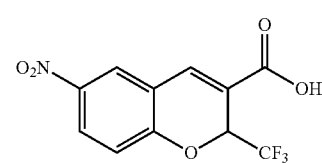

B-3

51

6-Nitro-2-trifluoromethyl-2H-1-benzopyran-3-carboxylic acid

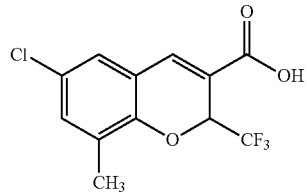
B-4

6-Chloro-8-methyl-2-trifluoromethyl-2H-1-benzopyran-3-carboxylic acid

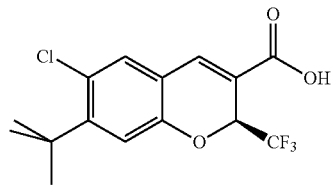
B-5

((S)-6-Chloro-7-(1,1-dimethylethyl)-2-(trifluoromethyl-2H-1-benzo-3-carboxylic acid

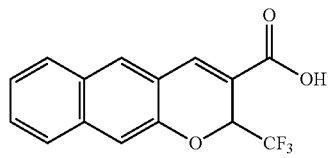
B-6

2-Trifluoromethyl-2H-naphtho[2,3-b]pyran-3-carboxylic acid

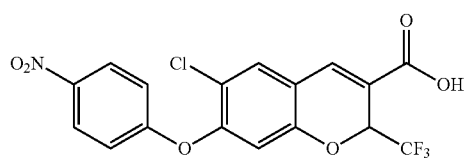
B-7

52

6-Chloro-7-(4-nitrophenoxy)-2-(trifluoromethyl)-2H-1-benzopyran-3-carboxylic acid

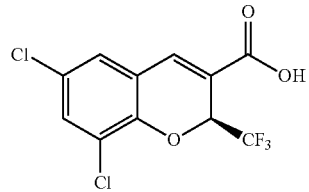
B-8

((S)-6,8-Dichloro-2-(trifluoromethyl)-2H-1-benzopyran-3-carboxylic acid

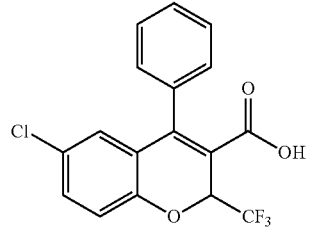
B-9

6-Chloro-2-(trifluoromethyl)-4-phenyl-2H-1-benzopyran-3-carboxylic acid

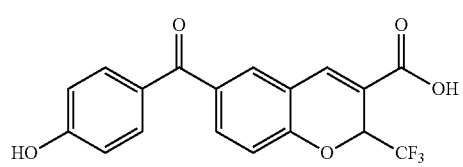
B-10

6-(4-Hydroxybenzoyl)-2-(trifluoromethyl)-2H-1-benzopyran-3-carboxylic acid

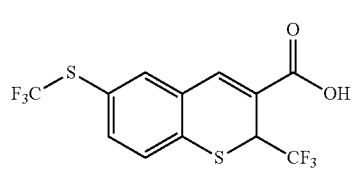
B-11

53

2-(Trifluoromethyl)-6-[(trifluoro-methyl)thio]-2H-1-benzothiopyran-3-carboxylic acid

54

6-Chloro-1,2-dihydro-1-methyl-2-(trifluoromethyl)-3-quinolinecarboxylic acid

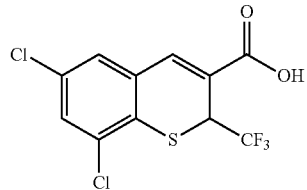

B-12

6,8-Dichloro-2-trifluoromethyl-2H-1-benzothiopyran-3-carboxylic acid

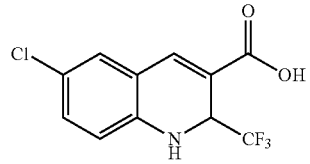

B-16

6-Chloro-2-(trifluoromethyl)-1,2-dihydro[1,8]naphthyridine-3-carboxylic acid

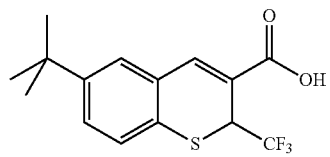

B-13

6-(1,1-Dimethylethyl)-2-(trifluoromethyl)-2H-1-benzothiopyran-3-carboxylic acid

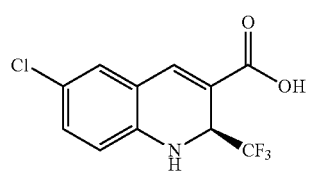

B-17

((S)-6-Chloro-1,2-dihydro-2-(trifluoromethyl)-3-quinolinecarboxylic acid

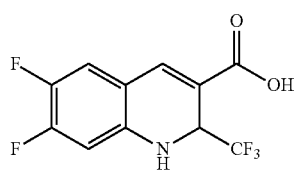

B-14

6,7-Difluoro-1,2-dihydro-2-(trifluoromethyl)-3-quinolinecarboxylic acid

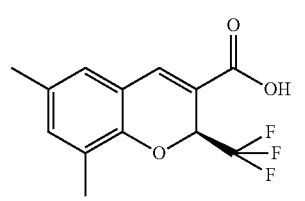

B-18

(2S)-6,8-dimethyl-2-(trifluoromethyl)-2H-chromene-3-carboxylic acid

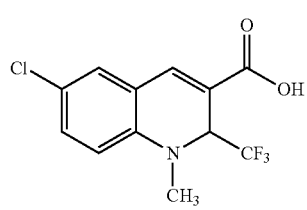

B-15

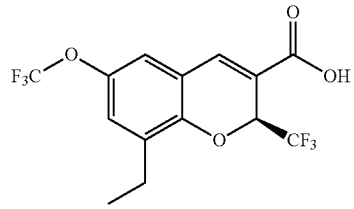

B-19

(2S)-8-ethyl-6-(trifluoromethoxy)-2-(trifluoromethyl)-2H-chromene-3-carboxylic acid

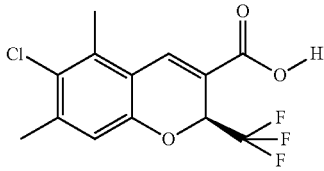

B-20

(2S)-6-chloro-5,7-dimethyl-2-(trifluoromethyl)-2H-chromene-3-carboxylic acid

In preferred embodiments the chromene Cox-2 inhibitor is selected from (S)-6-chloro-7-(1,1-dimethylethyl)-2-(trifluoromethyl)-2H-1-benzopyran-3-carboxylic acid, (2S)-6,8-dimethyl-2-(trifluoromethyl)-2H-chromene-3-carboxylic acid, (2S)-6-chloro-8-methyl-2-(trifluoromethyl)-2H-chromene-3-carboxylic acid, (2S)-8-ethyl-6-(trifluoromethoxy)-2-(trifluoromethyl)-2H-chromene-3-carboxylic acid, (S)-6,8-dichloro-2-(trifluoromethyl)-2H-1-benzopyran-3-carboxylic acid, (2S)-6-chloro-5,7-dimethyl-2-(trifluoromethyl)-2H-chromene-3-carboxylic acid, and mixtures thereof.

In a preferred embodiment of the invention the Cox-2 inhibitor can be selected from the class of tricyclic Cox-2 selective inhibitors represented by the general structure of:

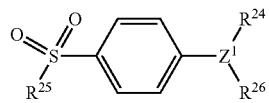

wherein:
$Z^1$ is selected from the group consisting of partially unsaturated or unsaturated heterocyclyl and partially unsaturated or unsaturated carbocyclic rings;
$R^{24}$ is selected from the group consisting of heterocyclyl, cycloalkyl, cycloalkenyl and aryl, wherein $R^{24}$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;
$R^{25}$ is selected from the group consisting of methyl or amino; and
$R^{26}$ is selected from the group consisting of a radical selected from H, halo, alkyl, alkenyl, alkynyl, oxo, cyano, carboxyl, cyanoalkyl, heterocyclyloxy, alkyloxy, alkylthio, alkylcarbonyl, cycloalkyl, aryl, haloalkyl, heterocyclyl, cycloalkenyl, aralkyl, heterocyclylalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl;

or a prodrug thereof.

In a preferred embodiment of the invention the Cox-2 selective inhibitor represented by the above formula is selected from the group of compounds which includes celecoxib (B-21), valdecoxib (B-22), deracoxib (B-23), rofecoxib (B-24), etoricoxib (MK-663; B-25), JTE-522 (B-26), or prodrugs thereof.

Additional information about selected examples of the Cox-2 selective inhibitors discussed above can be found as follows: celecoxib (CAS RN 169590-42-5, C-2779, SC-58653, and in U.S. Pat. No. 5,466,823 (incorporated by reference)); deracoxib (CAS RN 169590-41-4); rofecoxib (CAS RN 162011-90-7); compound B-24 (U.S. Pat. No. 5,840,924); compound B-26 (WO 00/25779 (incorporated by reference)); and etoricoxib (CAS RN 202409-33-4, MK-663, SC-86218, and in WO 98/03484 (incorporated by reference)).

Structural Formula

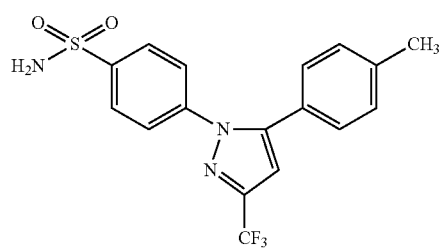

B-21

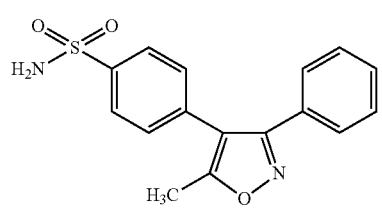

B-22

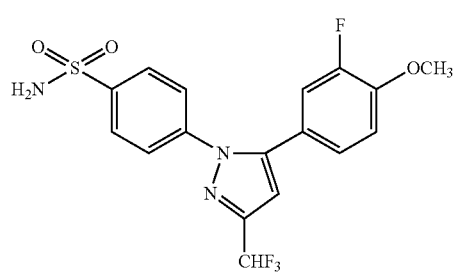

B-23

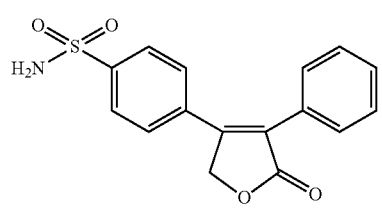

B-24

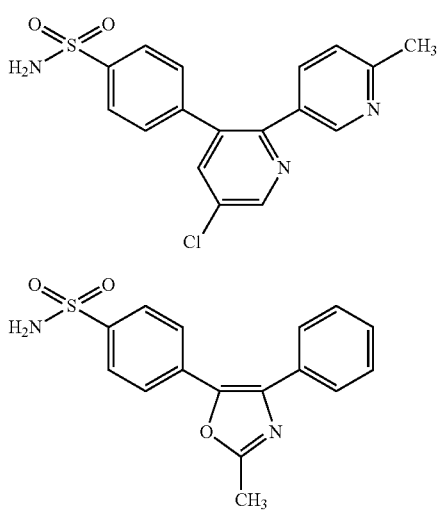

B-25

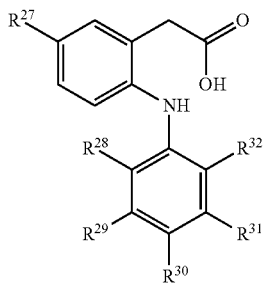

B-26

In a more preferred embodiment of the invention, the Cox-2 selective inhibitor is selected from the group consisting of celecoxib, rofecoxib and etoricoxib.

In a preferred embodiment, parecoxib (See, U.S. Pat. No. 5,932,598 (incorporated by reference)), having the structure shown in B-27, and which is a therapeutically effective prodrug of the tricyclic Cox-2 selective inhibitor valdecoxib, B-22, (See, U.S. Pat. No. 5,633,272 (incorporated by reference)), may be advantageously employed as the Cox-2 inhibitor of the present invention.

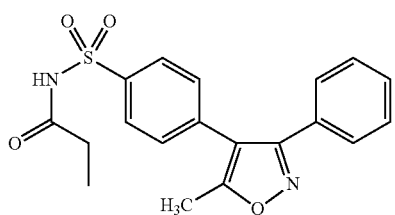

B-27

A preferred form of parecoxib is sodium parecoxib.

Another tricyclic Cox-2 selective inhibitor useful in the present invention is the compound ABT-%3, having the formula B-28 shown below, that has been previously described in International Publication Number WO 00/24719.

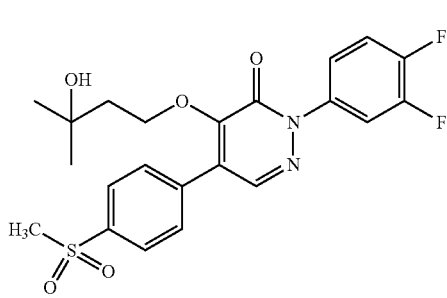

B-28

In a further embodiment of the invention, the Cox-2 inhibitor can be selected from the class of phenylacetic acid derivative Cox-2 selective inhibitors represented by the general structure of:

wherein:
$R^{27}$ is methyl, ethyl, or propyl;
$R^{28}$ is chloro or fluoro;
$R^{29}$ is hydrogen, fluoro, or methyl;
$R^{30}$ is hydrogen, fluoro, chloro, methyl, ethyl, methoxy, ethoxy or hydroxyl;
$R^{31}$ is hydrogen, fluoro, or methyl; and
$R^{32}$ is chloro, fluoro, trifluoromethyl, methyl, or ethyl,
provided that R28, R29, R30 and R31 are not all fluoro when R27 is ethyl and R30 is H.

An exemplary phenylacetic acid derivative Cox-2 selective inhibitor that is described in WO 99/11605 (incorporated by reference) is a compound that has the structure shown in the above formula,
wherein:
$R^{27}$ is ethyl;
$R^{28}$ and $R^{30}$ are chloro;
$R^{29}$ and $R^{31}$ are hydrogen; and
$R^{32}$ is methyl.

Another phenylacetic acid derivative Cox-2 selective inhibitor is a compound that has the structure shown in the above formula,
wherein:
$R^{27}$ is propyl;
$R^{28}$ and $R^{30}$ are chloro;
$R^{29}$ and $R^{31}$ are methyl; and
$R^{32}$ is ethyl.

Another phenylacetic acid derivative Cox-2 selective inhibitor that is disclosed in WO 02/20090 is a compound that is referred to as COX-189 (also termed lumiracoxib; CAS Reg. No. 220991-20-8), having the structure shown in the above formula,
wherein:
$R^{27}$ is methyl;
$R^{28}$ is fluoro;
$R^{32}$ is chloro; and
$R^{29}$, $R^{30}$, and $R^{31}$ are hydrogen.

Compounds having a structure similar to that shown in in the above formula, that can serve as the Cox-2 selective inhibitor of the present invention, are described in U.S. Pat. Nos. 6,451,858, 6,310,099, 6,291,523, and 5,958,978 (all incorporated by reference).

Other Cox-2 selective inhibitors that can be used in the present invention have the general structure shown in below, where the J group is a carbocycle or a heterocycle. Preferred embodiments have the structure:

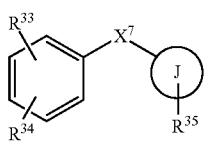

wherein:
$X^7$ is O; J is 1-phenyl; $R^{33}$ is 2-NHSO$_2$CH$_3$; $R^{34}$ is 4-NO$_2$; and there is no $R^{35}$ group, (nimesulide), or $X^7$ is O; J is 1-oxo-inden-5-yl; $R^{33}$ is 2-F; $R^{34}$ is 4-F; and $R^{35}$ is 6-NHSO$_2$CH$_3$, (flosulide); or $X^7$ is O; J is cyclohexyl; $R^{33}$ is 2-NHSO$_2$CH$_3$; $R^{34}$ is 5-NO$_2$; and there is no $R^{35}$ group, (NS-398); or $X^7$ is S; J is 1-oxo-inden-5-yl; $R^{33}$ is 2-F; $R^{34}$ is 4-F; and $R^{35}$ is 6-N$^-$SO$_2$CH$_3$.Na$^+$, (L-745337); or $X^7$ is S; J is thiophen-2-yl; $R^{33}$ is 4-F; there is no $R^{34}$ group; and $R^{35}$ is 5-NHSO$_2$CH$_3$, (RWJ-63556); or $X^7$ is O; J is 2-oxo-5(R)-methyl-5-(2,2,2-trifluoroethyl) furan-(5H)-3-yl; $R^{33}$ is 3-F; $R^{34}$ is 4-F; and $R^{35}$ is 4-(p-SO$_2$CH$_3$)C$_6$H$_4$, (L-784512).

The Cox-2 selective inhibitor NS-398, also known as N-(2-cyclohexyloxynitrophenyl)methane sulfonamide (CAS RN 123653-11-2), having a structure as shown below in formula B-29, has been described in, for example, Yoshimi, N. et al., in *Japanese J. Cancer Res.*, 90(4):406-412 (1999).

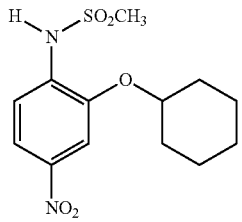

B-29

An evaluation of the anti-inflammatory activity of the Cox-2 selective inhibitor, RWJ 63556, in a canine model of inflammation, was described by Kirchner et al., in *J Pharmacol Exp Ther* 282, 1094-1101 (1997).

Materials that can serve as the Cox-2 selective inhibitor of the present invention include diarylmethylidenefuran derivatives that are described in U.S. Pat. No. 6,180,651 (incorporated by reference). Such diarylmethylidenefuran derivatives have the general formula shown below in:

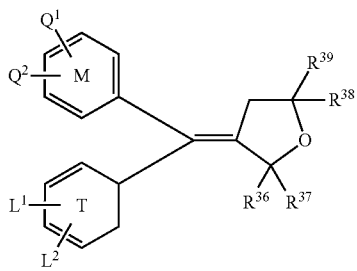

wherein:
the rings T and M independently are a phenyl radical, a naphthyl radical, a radical derived from a heterocycle comprising 5 to 6 members and possessing from 1 to 4 heteroatoms, or a radical derived from a saturated hydrocarbon ring having from 3 to 7 carbon atoms;

at least one of the substituents $Q^1$, $Q^2$, $L^1$ or $L^2$ is an —S(O)$_n$—R group, in which n is an integer equal to 0, 1 or 2 and R is a lower alkyl radical having 1 to 6 carbon atoms, a lower haloalkyl radical having 1 to 6 carbon atoms, or an —SO$_2$NH$_2$ group;

and is located in the para position, the others independently being a hydrogen atom, a halogen atom, a lower alkyl radical having 1 to 6 carbon atoms, a trifluoromethyl radical, or a lower O-alkyl radical having 1 to 6 carbon atoms, or $Q^1$ and $Q^2$ or $L^1$ and $L^2$ are a methylenedioxy group; and $R^{36}$, $R^{37}$, $R^{38}$ and $R^{39}$ independently are a hydrogen atom, a halogen atom, a lower alkyl radical having 1 to 6 carbon atoms, a lower haloalkyl radical having 1 to 6 carbon atoms, or an aromatic radical selected from the group consisting of phenyl, naphthyl, thienyl, furyl and pyridyl; or, $R^{36}$, $R^{37}$ or $R^{38}$, $R^{39}$ are an oxygen atom; or $R^{36}$, $R^{37}$ or $R^{38}$, $R^{39}$, together with the carbon atom to which they are attached, form a saturated hydrocarbon ring having from 3 to 7 carbon atoms;

or an isomer or prodrug thereof.

Particular diarylmethylidenefuran derivatives that can serve as the Cox-2 selective inhibitor of the present invention include, for example, N-(2-cyclohexyloxynitrophenyl) methane sulfonamide, and (E)-4-[(4-methylphenyl)(tetrahydro-2-oxo-3-furanylidene) methyl]benzenesulfonamide.

Other Cox-2 selective inhibitors that are useful in the present invention include darbufelone (Pfizer), CS-502 (Sankyo), LAS 34475 (Almirall Profesfarma), LAS 34555 (Almirall Profesfarma), S-33516 (Servier), SD 8381 (Pharmacia, described in U.S. Pat. No. 6,034,256), BMS-347070 (Bristol Myers Squibb, described in U.S. Pat. No. 6,180,651), MK-966 (Merck), L-783003 (Merck), T-614 (Toyama), D-1367 (Chiroscience), L-748731 (Merck), CT3 (Atlantic Pharmaceutical), CGP-28238 (Novartis), BF-389 (Biofor/Scherer), GR-253035 (Glaxo Wellcome), 6-dioxo-9H-purin-8-yl-cinnamic acid (Glaxo Wellcome), and S-2474 (Shionogi).

Compounds that may act as Cox-2 selective inhibitors of the present invention include multibinding compounds containing from 2 to 10 ligands covalently attached to one or more linkers, as described in U.S. Pat. No. 6,395,724 (incorporated by reference).

Conjugated linoleic, as described in U.S. Pat. No. 6,077,868 (incorporated by reference), is useful as a Cox-2 selective inhibitor in the present invention.

Compounds that can serve as a Cox-2 selective inhibitor of the present invention include heterocyclic aromatic oxazole compounds that are described in U.S. Pat. No. 5,994,381 (incorporated by reference) and U.S. Pat. No. 6,362,209 (incorporated by reference). Such heterocyclic aromatic oxazole compounds have the formula shown below in:

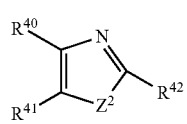

wherein:

$Z^2$ is an oxygen atom;

one of $R^{40}$ and $R^{41}$ is a group of the formula

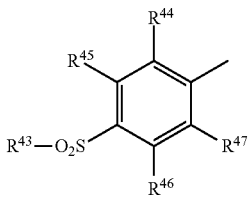

wherein:

$R^{43}$ is lower alkyl, amino or lower alkylamino; and $R^{44}$, $R^{45}$, $R^{46}$ and $R^{47}$ are the same or different and each is hydrogen atom, halogen atom, lower alkyl, lower alkoxy, trifluoromethyl, hydroxyl or amino, provided that at least one of $R^{44}$, $R^{45}$, $R^{46}$ and $R^{47}$ is not hydrogen atom, and the other is an optionally substituted cycloalkyl, an optionally substituted heterocyclic group or an optionally substituted aryl; and $R^{30}$ is a lower alkyl or a halogenated lower alkyl, and a pharmaceutically acceptable salt thereof.

Cox-2 selective inhibitors that are useful in the method and compositions of the present invention include compounds that are described in U.S. Pat. No. 6,080,876 (incorporated by reference) and U.S. Pat. No. 6,133,292 (incorporated by reference), and described by:

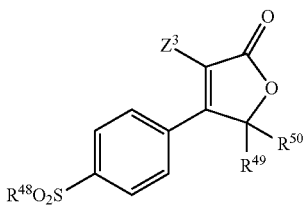

wherein:

$Z^3$ is selected from the group consisting of linear or branched $C_1$-$C_6$ alkyl, linear or branched $C_1$-$C_6$ alkoxy, unsubstituted, mono-, di- or tri-substituted phenyl or naphthyl wherein the substituents are selected from the group consisting of hydrogen, halo, $C_1$-$C_3$ alkoxy, CN, $C_1$-$C_3$ fluoroalkyl $C_1$-$C_3$ alkyl, and —$CO_2H$;

$R^{48}$ is selected from the group consisting of $NH_2$ and $CH_3$, $R^{49}$ is selected from the group consisting of $C_1$-$C_6$ alkyl unsubstituted or substituted with $C_3$-$C_6$ cycloalkyl, and $C_3$-$C_6$ cycloalkyl;

$R^{50}$ is selected from the group consisting of: $C_1$-$C_6$ alkyl unsubstituted or substituted with one, two or three fluoro atoms, and $C_3$-$C_6$ cycloalkyl;

with the proviso that $R^{49}$ and $R^{50}$ are not the same.

Pyridines that are described in U.S. Pat. Nos. 6,596,736, 6,369,275, 6,127,545, 6,130,334, 6,204,387, 6,071,936, 6,001,843 and 6,040,450 (all incorporated by reference), and can serve as Cox-2 selective inhibitors of the present invention, have the general formula described by formula:

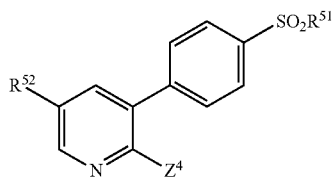

wherein:

$R^{51}$ is selected from the group consisting of $CH_3$, $NH_2$, $NHC(O)CF_3$, and $NHCH_3$;

$Z^4$ is a mono-, di-, or trisubstituted phenyl or pyridinyl (or the N-oxide thereof), wherein the substituents are chosen from the group consisting of hydrogen, halo, $C_1$-$C_6$ alkoxy, $C_1$-$C_6$ alkylthio, CN, $C_1$-$C_6$ alkyl, $C_1$-$C_6$ fluoroalkyl, $N_3$, —$CO_2R^{53}$, hydroxyl, —$C(R^{54})(R^{55})$—OH, —$C_1$-$C_6$ alkyl-$CO_2$—$R^{56}$, $C_1$-$C_6$fluoroalkoxy;

$R^{52}$ is chosen from the group consisting of: halo, $C_1$-$C_6$ alkoxy, $C_1$-$C_6$alkylthio, CN, $C_1$-$C_6$ alkyl, $C_1$-$C_6$ fluoroalkyl, $N_3$, —$CO_2R^{57}$, hydroxyl, —$C(R^{58})(R^{59})$—OH, —$C_1$-$C_6$ alkyl-$CO_2$—$R^{60}$, $C_1$-$C_6$fluoroalkoxy, $NO_2$, $NR^{61}R^{62}$, and $NHCOR^{63}$;

$R^{53}$, $R^{54}$, $R^{55}$, $R^{56}$, $R^{57}$, $R^{58}$, $R^{59}$, $R^{60}$, $R^{61}$, $R^{62}$, and $R^{63}$, are each independently chosen from the group consisting of hydrogen and $C_1$-$C_6$ alkyl;

or $R^{54}$ and $R^{55}$, $R^{58}$ and $R^{59}$, or $R^{61}$ and $R^{62}$ together with the atom to which they are attached form a saturated monocyclic ring of 3, 4, 5, 6, or 7 atoms.

Materials that can serve as the Cox-2 selective inhibitor of the present invention include diarylbenzopyran derivatives that are described in U.S. Pat. No. 6,340,694 (incorporated by reference). Such diarylbenzopyran derivatives have the general formula shown below:

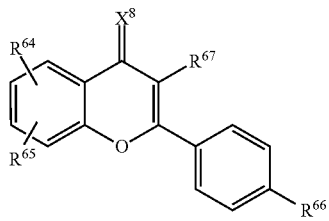

wherein:

$X^8$ is an oxygen atom or a sulfur atom;

$R^{64}$ and $R^{65}$, identical to or different from each other, are independently a hydrogen atom, a halogen atom, a $C_1$-$C_6$ lower alkyl group, a trifluoromethyl group, an alkoxy group, a hydroxyl group, a nitro group, a nitrile group, or a carboxyl group;

$R^{66}$ is a group of a formula: $S(O)_nR$ wherein n is an integer of 0~2, $R^{68}$ is a hydrogen atom, a $C_1$-$C_6$ lower alkyl group, or a group of a formula: $NR^{69}R^{70}$ wherein $R^{69}$ and $R^{70}$, identical to or different from each other, are independently a hydrogen atom, or a $C_1$-$C_6$ lower alkyl group; and $R^{67}$ is oxazolyl, benzo[b]thienyl, furanyl, thienyl, naphthyl, thiazolyl, indolyl, pyrolyl, benzofuranyl, pyrazolyl, pyrazolyl substituted with a $C_1$-$C_6$ lower alkyl group, indanyl, pyrazinyl, or a substituted group represented by the following structures:

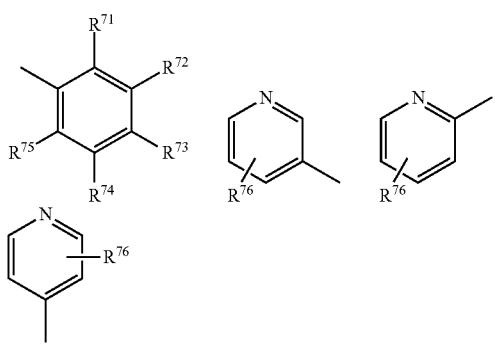

wherein:
R$^{71}$ through R$^{75}$, identical to or different from one another, are independently a hydrogen atom, a halogen atom, a C$_1$-C$_6$ lower alkyl group, a trifluoromethyl group, an alkoxy group, a hydroxyl group, a hydroxyalkyl group, a nitro group, a group of a formula: S(O)$_n$R$^{68}$, a group of a formula: NR$^{69}$R$^{70}$, a trifluoromethoxy group, a nitrile group a carboxyl group, an acetyl group, or a formyl group,
wherein n, R$^{68}$, R$^{69}$ and R$^{70}$ have the same meaning as defined by R$^{66}$ above; and
R$^{76}$ is a hydrogen atom, a halogen atom, a C$_1$-C$_6$ lower alkyl group, a trifluoromethyl group, an alkoxy group, a hydroxyl group, a trifluoromethoxy group, a carboxyl group, or an acetyl group.

Materials that can serve as the Cox-2 selective inhibitor of the present invention include 1-(4-sulfamylaryl)-3-substituted-5-aryl-2-pyrazolines that are described in U.S. Pat. No. 6,376,519 (incorporated by reference). Such 1-(4-sulfamylaryl)-3-substituted-5-aryl-2-pyrazolines have the formula shown below:

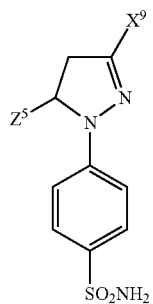

wherein:
X$^9$ is selected from the group consisting of C$_1$-C$_6$ trihalomethyl, preferably trifluoromethyl; C$_1$-C$_6$ alkyl; and an optionally substituted or di-substituted phenyl group of formula:

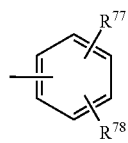

wherein:
R$^{77}$ and R$^{78}$ are independently selected from the group consisting of hydrogen, halogen, preferably chlorine, fluorine and bromine; hydroxyl; nitro; C$_1$-C$_6$ alkyl, preferably C$_1$-C$_3$ alkyl; C$_1$-C$_6$ alkoxy, preferably C$_1$-C$_3$ alkoxy; carboxy; C$_1$-C$_6$ trihaloalkyl, preferably trihalomethyl, most preferably trifluoromethyl; and cyano;
Z$^5$ is selected from the group consisting of substituted and unsubstituted aryl.

Compounds useful as Cox-2 selective inhibitors of the present invention include heterocycles that are described in U.S. Pat. No. 6,153,787 (incorporated by reference). Such heterocycles have the general formulas shown below:

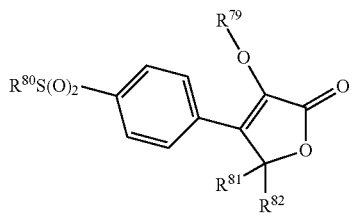

wherein:
R$^{79}$ is a mono-, di-, or tri-substituted C$_1$-C$_{12}$alkyl, or a mono-, or an unsubstituted or mono-, di- or tri-substituted linear or branched C$_2$-C$_{10}$alkenyl, or an unsubstituted or mono-, di- or tri-substituted linear or branched C$_2$-C$_{10}$ alkynyl, or an unsubstituted or mono-, di- or tri-substituted C$_3$-C$_{12}$cycloalkenyl, or an unsubstituted or mono-, di- or tri-substituted C$_5$-C$_{12}$cycloalkynyl, wherein the substituents are chosen from the group consisting of halo selected from F, Cl, Br, and 1, OH, CF$_3$, C$_3$-C$_6$ cycloalkyl, =O, dioxolane, CN;

R$^{80}$ is selected from the group consisting of CH$_3$, NH$_2$, NHC(O)CF$_3$, and NHCH$_3$;

R$^{81}$ and R$^{82}$ are independently chosen from the group consisting of hydrogen and C$_1$-C$_{10}$ alkyl;

or R$^{81}$ and R$^{82}$ together with the carbon to which they are attached form a saturated monocyclic carbon ring of 3, 4, 5, 6 or 7 atoms.

Another example is the structure:

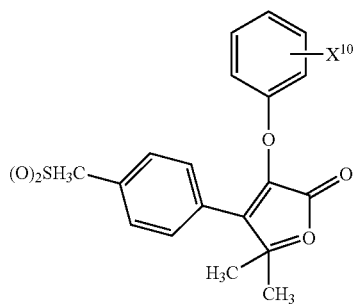

wherein X$^{10}$ is fluoro or chloro.

Materials that can serve as the Cox-2 selective inhibitor of the present invention include 2,3,5-trisubstituted pyridines that are described in U.S. Pat. No. 6,046,217 (incorporated by reference). Such pyridines have the general formula shown below:

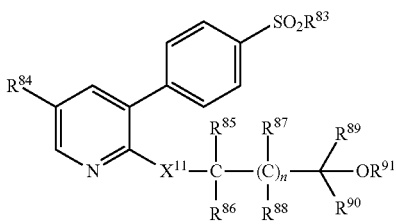

or a pharmaceutically acceptable salt thereof,
wherein:
$X^{11}$ is selected from the group consisting of O, S, and a bond;
n is 0 or 1;
$R^{83}$ is selected from the group consisting of $CH_3$, $NH_2$, and $NHC(O)CF_3$;
$R^{84}$ is chosen from the group consisting of halo, $C_1$-$C_6$ alkoxy, $C_1$-$C_6$ alkylthio, CN, $C_1$-$C_6$ alkyl, $C_1$-$C_6$ fluoroalkyl, $N_3$, —$CO_2R^{92}$, hydroxyl, —$C(R^{93})(R^{94})$—OH, —$C_1$-$C_6$ alkyl-$CO_2$—$R^{95}$, $C_1$-$C_6$ fluoroalkoxy, $NO_2$, $NR^{96}R^{97}$, and $NHCOR^{98}$;
$R^{85}$ to $R^{89}$ are independently chosen from the group consisting of hydrogen and $C_1$-$C_6$ alkyl;
or $R^{85}$ and $R^{89}$, or $R^{89}$ and $R^{90}$ together with the atoms to which they are attached form a carbocyclic ring of 3, 4, 5, 6 or 7 atoms, or $R^{85}$ and $R^{87}$ are joined to form a bond.

Compounds that are useful as the Cox-2 selective inhibitor of the present invention include diaryl bicyclic heterocycles that are described in U.S. Pat. No. 6,329,421 (incorporated by reference). Such diaryl bicyclic heterocycles have the general formula shown below:

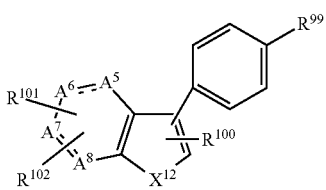

or pharmaceutically acceptable salts thereof wherein:
-$A^5$=$A^6$-$A^7$=$A^8$- is selected from the group consisting of:
(a) —CH=CH—CH=CH—,
(b) —$CH_2$—$CH_2$—$CH_2$—C(O)—, —$CH_2$—$CH_2$—C(O)—$CH_2$—, —$CH_2$—C(O)—$CH_2$—$CH_2$—, —C(O)—$CH_2$—$CH_2$—$CH_2$,
(c) —$CH_2$—$CH_2$—C(O)—, —$CH_2$—C(O)—$CH_2$—, —C(O)—$CH_2$—$CH_2$—
(d) —$CH_2$—$CH_2$—O—C(O)—, $CH_2$—O—C(O)—$CH_2$—, —O—C(O)—$CH_2$—$CH_2$—,
(e) —$CH_2$—$CH_2$—C(O)—O—, —$CH_2$—C(O)—$OCH_2$—, —C(O)—O—$CH_2$—$CH_2$—,
(f) —$C(R^{105})_2$—O—C(O)—, —C(O)—O—$C(R^{105})_2$, —O—C(O)—$C(R^{105})_2$—, —$C(R^{105})_2$—C(O)—O—,
(g) —N=CH—CH=CH—,
(h) —CH=N—CH=H—,
(i) —CH=CH—N=CH—,
(j) —CH=CH—CH=N—,
(k) —N=CH—CH=N—,
(l) —N=CH—N=CH—,
(m) —CH=N—CH=N—,
(n) —S—CH=N—,
(o) —S—N=CH—,
(p) —N=N—NH—,
(q) —CH=N—S—, and
(r) —N=CH—S—;
$R^{99}$ is selected from the group consisting of $S(O)_2CH_3$, $S(O)_2NH_2$, $S(O)_2NHCOCF_3$, $S(O)(NH)CH_3$, $S(O)(NH)NH_2$, $S(O)(NH)NHCOCF_3$, $P(O)(CH_3)OH$, and $P(O)(CH_3)NH_2$;
$R^{100}$ is selected from the group consisting of:
(a) $C_1$-$C_6$ alkyl,
(b) $C_3$-$C_7$ cycloalkyl,
(c) mono- or di-substituted phenyl or naphthyl wherein the substituent is selected from the group consisting of:
(1) hydrogen,
(2) halo, including F, Cl, Br, I,
(3) $C_1$-$C_6$ alkoxy,
(4) $C_1$-$C_6$ alkylthio,
(5) CN,
(6) $CF_3$,
(7) $C_1$-$C_6$ alkyl,
(8) $N_3$,
(9) —$CO_2H$,
(10) —CO—$C_1$-$C_4$ alkyl,
(11) —$C(R^{103})(R^{104})$—H,
(12) —$C(R^{103})(R^{104})$—O—$C_1$-$C_4$ alkyl, and
(13) —$C_1$-$C_6$ alkyl-$CO_2$—$R^{106}$;
(d) mono- or di-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2, 3, or 4 additional N atoms; said substituents are selected from the group consisting of:
(1) hydrogen,
(2) halo, including fluoro, chloro, bromo and iodo,
(3) $C_1$-$C_6$ alkyl,
(4) $C_1$-$C_6$ alkoxy,
(5) $C_1$-$C_6$ alkylthio,
(6) CN,
(7) $CF_3$,
(8) $N_3$,
(9) —$C(R^{103})(R^{104})$—OH, and
(10) —$C(R^{103})(R^{104})$—O—$C_1$-$C_4$ alkyl;
(e) benzoheteroaryl which includes the benzo fused analogs of (d);
$R^{101}$ and $R^{102}$ are the substituents residing on any position of -$A^3$=$A^6$-$A^7$=A- and are selected independently from the group consisting of:
(a) hydrogen,
(b) $CF_3$,
(c) CN,
(d) $C_1$-$C_6$ alkyl,
(e) -$Q^3$ wherein $Q^3$ is $Q^4$, $CO_2H$, $C(R^{103})(R^{104})OH$,
(f) —O-$Q^4$,
(g) —S-$Q^4$, and
(h) optionally substituted:
(1) —$C_1$-$C_5$ alkyl-$Q^3$,
(2) —O—$C_1$-$C_5$ alkyl-$Q^3$,
(3) —S—$C_1$-$C_5$ alkyl-$Q^3$,
(4) —$C_1$-$C_3$ alkyl-O—$C_{1-3}$ alkyl-$Q^3$,
(5) —$C_1$-$C_3$ alkyl-S—$C_{1-3}$ alkyl-$Q^3$,
(6) —$C_1$-$C_5$ alkyl-O-$Q^4$,
(7) —$C_1$-$C_5$ alkyl-S-$Q^4$,
wherein the substituent resides on the alkyl chain and the substituent is $C_1$-$C_3$ alkyl, and $Q^3$ is $Q^4$, $CO_2H$, $C(R^{103})$ ($R^{104}$)OH $Q^4$ is $CO_2$—$C_1$-$C_4$ alkyl, tetrazolyl-5-yl, or C($R^{103}$)($R^{104}$)O—$C_1$-$C_4$ alkyl;

$R^{103}$, $R^{104}$ and $R^{105}$ are each independently selected from the group consisting of hydrogen and $C_1$-$C_6$ alkyl; or $R^{103}$ and $R^{104}$ together with the carbon to which they are attached form a saturated monocyclic carbon ring of 3, 4, 5, 6 or 7 atoms, or two $R^{105}$ groups on the same carbon form a saturated monocyclic carbon ring of 3, 4, 5, 6 or 7 atoms;

$R^{106}$ is hydrogen or $C_1$-$C_6$ alkyl;

$R^{107}$ is hydrogen, $C_1$-$C_6$ alkyl or aryl;

$X^7$ is O, S, $NR^{107}$, CO, $C(R^{107})_2$, $C(R^{107})(OH)$, —$C(R^{107})$=$C(R^{107})$—; —$C(R^{107})$=N—; or —N=C($R^{107}$)—.

Compounds that may act as Cox-2 selective inhibitors include salts of 5-amino or a substituted amino 1,2,3-triazole compound that are described in U.S. Pat. No. 6,239,137 (incorporated by reference). The salts are of a class of compounds of formula:

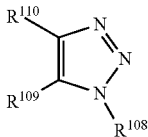

wherein:

$R^{106}$ is:

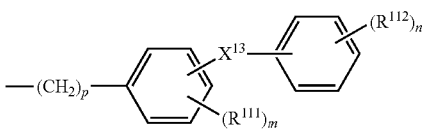

wherein:

p is 0 to 2; m is 0 to 4; and n is 0 to 5;

$X^{13}$ is O, S, SO, $SO_2$, CO, CHCN, $CH_2$ or C=$NR^{113}$ wherein $R^{113}$ is hydrogen, loweralkyl, hydroxyl, loweralkoxy, amino, loweralkylamino, diloweralkylamino or cyano;

$R^{111}$ and $R^{112}$ are independently halogen, cyano, trifluoromethyl, loweralkanoyl, nitro, loweralkyl, loweralkoxy, carboxy, lowercarbalkoxy, trifuloromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl;

$R^{109}$ is amino, mono or diloweralkyl amino, acetamido, acetimido, ureido, formamido, or guanidino; and $R^{110}$ is carbamoyl, cyano, carbazoyl, amidino or N-hydroxycarbamoyl;

wherein the loweralkyl, loweralkyl containing, loweralkoxy and loweralkanoyl groups contain from 1 to 3 carbon atoms.

Pyrazole derivatives such as those described in U.S. Pat. No. 6,136,831 (incorporated by reference) can serve as a Cox-2 selective inhibitor of the present invention. Such pyrazole derivatives have the formula shown below:

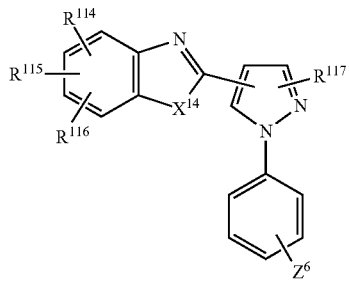

wherein:

$R^{114}$ is hydrogen or halogen;

$R^{115}$ and $R^{116}$ are each independently hydrogen, halogen, lower alkyl, lower alkoxy, hydroxyl or lower alkanoyloxy;

$R^{117}$ is lower haloalkyl or lower alkyl;

$X^{14}$ is sulfur, oxygen or NH; and $Z^6$ is lower alkylthio, lower alkylsulfonyl or sulfamoyl; or a pharmaceutically acceptable salt thereof.

Materials that can serve as a Cox-2 selective inhibitor of the present invention include substituted derivatives of benzosulphonamides that are described in U.S. Pat. No. 6,297,282. Such benzosulphonamide derivatives have the formula shown below:

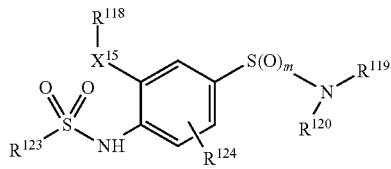

wherein:

$X^{15}$ denotes oxygen, sulphur or NH;

$R^{118}$ is an optionally unsaturated alkyl or alkyloxyalkyl group, optionally mono- or polysubstituted or mixed substituted by halogen, alkoxy, oxo or cyano, a cycloalkyl, aryl or heteroaryl group optionally mono- or polysubstituted or mixed substituted by halogen, alkyl, $CF_3$, cyano or alkoxy;

$R^{119}$ and $R^{120}$, independently from one another, denote hydrogen, an optionally polyfluorised alkyl group, an aralkyl, aryl or heteroaryl group or a group $(CH_2)_n$—$X^{16}$; or $R^{119}$ and $R^{210}$, together with the N— atom, denote a 3 to 7-membered, saturated, partially or completely unsaturated heterocycle with one or more heteroatoms N, O or S, which can optionally be substituted by oxo, an alkyl, alkylaryl or aryl group, or a group $(CH_2)_n$—$X^{16}$;

$X^{16}$ denotes halogen, $NO_2$, —$OR^{121}$, —$COR^{121}$, —$CO_2R^{21}$, —$OCO_2R^{121}$, —CN, —$CONR^{121}R^{122}$, —$CONR^{121}R^{122}$, —$SR^{121}$, —$S(O)R^{121}$, —$S(O)_2R^{121}$, —$NR^{121}R^{122}$, —$NHC(O)R^{121}$, —$NHS(O)_2R^{121}$;

n denotes a whole number from 0 to 6;

$R^{123}$ denotes a straight-chained or branched alkyl group with 1-10 C-atoms, a cycloalkyl group, an alkylcarboxyl group, an aryl group, aralkyl group, a heteroaryl or heteroaralkyl group which can optionally be mono- or polysubstituted or mixed substituted by halogen or alkoxy;

$R^{124}$ denotes halogen, hydroxyl, a straight-chained or branched alkyl, alkoxy, acyloxy or alkyloxycarbonyl group with 1-6 C-atoms, which can optionally be mono- or polysubstituted by halogen, $NO_2$, —$OR^{21}$, —$COR^{121}$, —$CO_2R^{121}$, —$OCO_2R^{121}$, —CN, —$CONR^{121}R^{122}$, —$CONR^{121}R^{122}$, —$SR^{121}$, —$S(O)R^{121}$, —$S(O)_2R^{121}$, —$NR^{121}R^{122}$, —$NHC(O)R^{121}$, —$NHS(O)_2R^{121}$, or a polyfluoroalkyl group;

$R^{121}$ and $R^{122}$, independently from one another, denote hydrogen, alkyl, aralkyl or aryl; and m denotes a whole number from 0 to 2;

and the pharmaceutically-acceptable salts thereof.

Compounds that are useful as Cox-2 selective inhibitors of the present invention include phenyl heterocycles that are described in U.S. Pat. No. 5,474,995 (incorporated by reference) and U.S. Pat. No. 6,239,173 (incorporated by reference). Such phenyl heterocyclic compounds have the formula shown below:

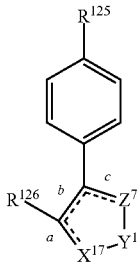

or pharmaceutically acceptable salts thereof wherein:

$X^{17}$—$Y^1$—$Z^7$— is selected from the group consisting of:
(a) —$CH_2CH_2CH_2$—,
(b) —$C(O)CH_2CH_2$—,
(c) —$CH_2CH_2C(O)$—,
(d) —$CR^{129}(R^{129'})$—O—$C(O)$—,
(e) —$C(O)$—O—$CR^{129}(R^{129'})$—,
(f) —$CH_2$—$NR^{127}$—$CH_2$—,
(g) —$CR^{129}(R^{129'})$—$NR^{127}$—$C(O)$—,
(h) —$CR^{128}$=$CR^{128'}$—S—,
(i) —S—$CR^{128}$=$CR^{128'}$—,
(j) —S—N=CH—,
(k) —CH=N—S—,
(l) —N=$CR^{128}$—O—,
(m) —O—$CR^{128}$=N—,
(n) —N=$CR^{128}$—NH—,
(o) —$NCR^{128}$—S—, and
(p) —S—$CR^{128}$=N—,
(q) —$C(O)$—$NR^{127}$—$CR^{129}(R^{129'})$—,
(r) —$R^{127}$N—CH=CH— provided $R^{122}$ is not —$S(O)_2CH_3$,
(s) —CH=CH—$NR^{127}$— provided $R^{125}$ is not —$S(O)_2CH_3$;

when side b is a double bond, and sides a and c are single bonds; and $X^{17}$—$Y^1$—$Z^7$— is selected from the group consisting of:
(a) =CHO—CH=, and
(b) =CH—$NR^{127}$—CH=,
(c) =N—S—CH=,
(d) =CH—S—N=,
(e) =N—O—CH=,
(f) =CH—O—N=,
(g) =N—S—N=,
(h) =N—O—N=, when sides a and c are double bonds and side b is a single bond;

$R^{125}$ is selected from the group consisting of:
(a) $S(O)_2CH_3$,
(b) $S(O)_2NH_2$,
(c) $S(O)_2NHC(O)CF_3$,
(d) $S(O)(NH)CH_3$,
(e) $S(O)(NH)NH_2$,
(f) $S(O)(NH)NHC(O)CF_3$,
(g) $P(O)(CH_3)OH$, and
(h) $P(O)(CH_3)NH_2$;

$R^{126}$ is selected from the group consisting of
(a) $C_1$-$C_6$ alkyl,
(b) $C_3$, $C_4$, $C_5$, $C_6$, and $C_7$, cycloalkyl,
(c) mono-, di- or tri-substituted phenyl or naphthyl, wherein the substituent is selected from the group consisting of:
(1) hydrogen,
(2) halo,
(3) $C_1$-$C_6$ alkoxy,
(4) $C_1$-$C_6$ alkylthio,
(5) CN,
(6) $CF_3$,
(7) $C_1$-$C_6$ alkyl,
(8) $N_3$,
(9) —$CO_2H$,
(10) —$CO_2$—$C_1$-$C_4$ alkyl,
(11) —$C(R^{129})(R^{130})$—OH,
(12) —$C(R^{129})(R^{130})$—O—$C_1$-$C_4$ alkyl, and
(13) —$C_1$-$C_6$ alkyl-$CO_2$—$R^{129}$;
(d) mono-, di- or tri-substituted heteroaryl wherein the heteroaryl is a monocyclic aromatic ring of 5 atoms, said ring having one hetero atom which is S, O, or N, and optionally 1, 2, or 3 additionally N atoms; or the heteroaryl is a monocyclic ring of 6 atoms, said ring having one hetero atom which is N, and optionally 1, 2, 3, or 4 additional N atoms; said substituents are selected from the group consisting of:
(1) hydrogen,
(2) halo, including fluoro, chloro, bromo and iodo,
(3) $C_1$-$C_6$ alkyl,
(4) $C_1$-$C_6$ alkoxy,
(5) $C_1$-$C_6$ alkylthio,
(6) CN,
(7) $CF_3$,
(8) $N_3$,
(9) —$C(R^{129})(R^{130})$—OH, and
(10) —$C(R^{129})(R^{130})$—O—$C_1$-$C_4$ alkyl;
(e) benzoheteroaryl which includes the benzo fused analogs of (d);

$R^{127}$ is selected from the group consisting of:
(a) hydrogen,
(b) $CF_3$,
(c) CN,
(d) $C_1$-$C_6$ alkyl,
(e) hydroxyl $C_1$-$C_6$ alkyl,
(f) —$C(O)$—$C_1$-$C_6$ alkyl,
(g) optionally substituted:
(1) —$C_1$-$C_5$ alkyl-$Q^5$,
(2) —$C_1$-$C_5$ alkyl-O—$C_1$-$C_3$ alkyl-$Q^5$,
(3) —$C_1$-$C_3$ alkyl-S—$C_1$-$C_3$ alkyl-$Q^5$,
(4) —$C_1$-$C_5$ alkyl-O-$Q^5$, or
(5) —$C_1$-$C_5$ alkyl-S-$Q^5$,
wherein the substituent resides on the alkyl and the substituent is $C_1$-$C_3$ alkyl;
(h) -$Q^5$;

$R^{128}$ and $R^{128'}$ are each independently selected from the group consisting of:
(a) hydrogen,
(b) $CF_3$, (c) CN,
(d) $C_1$-$C_6$ alkyl,
(e) -$Q^5$,
(f) —O-$Q^5$;
(g) —S-$Q^5$, and
(h) optionally substituted:
  (1) —$C_1$-$C_5$ alkyl-$Q^5$,
  (2) —O—$C_1$-$C_5$ alkyl-$Q^5$,
  (3) —S—$C_1$-$C_5$ alkyl-$Q^5$,
  (4) —$C_1$-$C_3$ alkyl-O—$C_1$-$C_3$ alkyl-$Q^5$,
  (5) —$C_1$-$C_3$ alkyl-S—$C_1$-$C_3$ alkyl-$Q^5$,
  (6) —$C_1$-$C_5$ alkyl-O-$Q^5$,
  (7) —$C_1$-$C_5$ alkyl-S-$Q^5$,
wherein the substituent resides on the alkyl and the substituent is $C_1$-$C_3$ alkyl, and
$R^{29}$, $R^{29}$, $R^{30}$, $R^3$ and $R^{132}$ are each independently selected from the group consisting of:
(a) hydrogen,
(b) $C_1$-$C_6$ alkyl;
or $R^{129}$ and $R^{130}$ or $R^{131}$ and $R^{132}$ together with the carbon to which they are attached form a saturated monocyclic carbon ring of 3, 4, 5, 6 or 7 atoms;
$Q^5$ is $CO_2H$, $CO_2$—$C_1$-$C_4$ alkyl, tetrazolyl-5-yl, $C(R^{131})(R^{132})(OH)$, or $C(R^{131})(R^{132})(O$—$C_1$-$C_4$ alkyl);
provided that when X—Y—Z is —S—$CR^{128}$=$CR^{128'}$ then $R^{128}$ and $R^{128'}$ are other than $CF_3$.

An exemplary phenyl heterocycle that is disclosed in U.S. Pat. No. 6,239,173 is 3-phenyl-4-(4-(methylsulfonyl)phenyl)-2-(2H)-furanone.

Bicycliccarbonyl indole compounds such as those described in U.S. Pat. No. 6,303,628 (incorporated by reference) are useful as Cox-2 selective inhibitors of the present invention. Such bicycliccarbonyl indole compounds have the formula shown below:

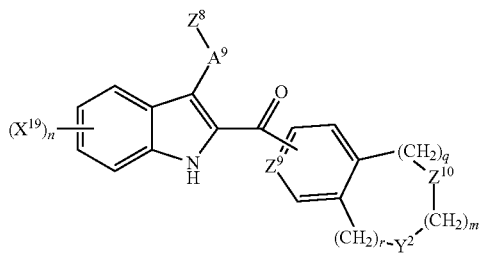

or the pharmaceutically acceptable salts thereof wherein:
$A^9$ is $C_1$-$C_6$ alkylene or —$NR^{133}$—;
$Z^8$ is $C(=L^3)R^{134}$, or $SO_2R^{135}$;
$Z^9$ is CH or N;
$Z^{10}$ and $Y^2$ are independently selected from —$CH_2$—, O, S and —N—$R^{133}$;
m is 1, 2 or 3;
q and r are independently 0, 1 or 2;
$X^{18}$ is independently selected from halogen, $C_1$-$C_4$ alkyl, halo-substituted $C_1$-$C_4$ alkyl, hydroxyl, $C_1$-$C_4$ alkoxy, halo-substituted $C_1$-$C_4$ alkoxy, $C_1$-$C_4$ alkylthio, nitro, amino, mono- or di-($C_1$-$C_4$alkyl)amino and cyano;
n is 0, 1, 2, 3 or 4;
$L^3$ is oxygen or sulfur;
$R^{133}$ is hydrogen or $C_1$-$C_4$ alkyl;
$R^{134}$ is hydroxyl, $C_1$-$C_6$ alkyl, halo-substituted $C_1$-$C_6$ alkyl, $C_1$-$C_6$ alkoxy, halo-substituted $C_1$-$C_6$ alkoxy, $C_3$-$C_7$ cycloalkoxy, $C_1$-$C_4$ alkyl($C_3$-$C_7$ cycloalkoxy), —$NR^{136}R^{137}$, $C_1$-$C_4$alkylphenyl-O— or phenyl-O—, said phenyl being optionally substituted with one to five substituents independently selected from halogen, $C_1$-$C_4$alkyl, hydroxyl, $C_1$-$C_4$ alkoxy and nitro;
$R^{135}$ is $C_1$-$C_6$ alkyl or halo-substituted $C_1$-$C_6$ alkyl; and
$R^{136}$ and $R^{137}$ are independently selected from hydrogen, $C_{1-6}$ alkyl and halo-substituted $C_1$-$C_6$ alkyl.

Materials that can serve as a Cox-2 selective inhibitor of the present invention include benzimidazole compounds that are described in U.S. Pat. No. 6,310,079 (incorporated by reference). Such benzimidazole compounds have the formula shown below:

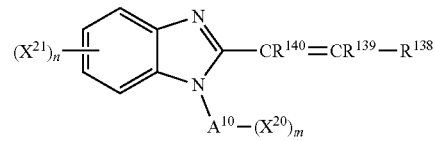

or a pharmaceutically acceptable salt thereof, wherein:
$A^{10}$ is heteroaryl selected from
a 5-membered monocyclic aromatic ring having one hetero atom selected from O, S and N and optionally containing one to three N atom(s) in addition to said hetero atom, or
a 6-membered monocyclic aromatic ring having one N atom and optionally containing one to four N atom(s) in addition to said N atom; and said heteroaryl being connected to the nitrogen atom on the benzimidazole through a carbon atom on the heteroaryl ring;
$X^{20}$ is independently selected from halo, $C_1$-$C_4$ alkyl, hydroxyl, $C_1$-$C_4$ alkoxy, halo-substituted $C_1$-$C_4$alkyl, hydroxyl-substituted $C_1$-$C_4$alkyl, ($C_1$-$C_4$alkoxy)$C_1$-$C_4$alkyl, halo-substituted $C_1$-$C_4$ alkoxy, amino, N—($C_1$-$C_4$alkyl)amino, N,N-di($C_1$-$C_4$ alkyl)amino, [N—($C_1$-$C_4$ alkyl)amino]$C_1$-$C_4$ alkyl, [N,N-di($C_1$-$C_4$ alkyl)amino]$C_1$-$C_4$ alkyl, N—($C_1$-$C_4$ alkanoyl)amino, N—($C_1$-$C_4$ alkyl)($C_1$-$C_4$ alkanoyl)amino, N—[($C_1$-$C_4$ alkyl)sulfonyl]amino, N-[(halo-substituted $C_1$-$C_4$ alkyl)sulfonyl]amino, $C_2$-$C_4$ alkanoyl, carboxy, ($C_1$-$C_4$ alkoxy)carbonyl, carbamoyl, [N—($C_1$-$C_4$alkyl)amino]carbonyl, [N,N-di($C_1$-$C_4$alkyl)amino]carbonyl, cyano, nitro, mercapto, ($C_1$-$C_4$ alkyl)thio, ($C_1$-$C_4$alkyl)sulfinyl, ($C_1$-$C_4$ alkyl)sulfonyl, aminosulfonyl, [N—($C_1$-$C_4$alkyl)amino]sulfonyl and [N,N-di($C_1$-$C_4$ alkyl)amino]sulfonyl;
$X^{21}$ is independently selected from halo, $C_1$-$C_4$ alkyl, hydroxyl, $C_1$-$C_4$ alkoxy, halo-substituted $C_1$-$C_4$ alkyl, hydroxyl-substituted $C_1$-$C_4$ alkyl, ($C_1$-$C_4$alkoxy)$C_1$-$C_4$ alkyl, halo-substituted $C_1$-$C_4$ alkoxy, amino, N—($C_1$-$C_4$alkyl)amino, N,N-di($C_1$-$C_4$ alkyl)amino, [N—($C_1$-$C_4$ alkyl)amino]$C_1$-$C_4$ alkyl, [N,N-di($C_1$-$C_4$ alkyl)amino]$C_1$-$C_4$ alkyl, N—($C_1$-$C_4$ alkanoyl)amino, N—($C_1$-$C_4$ alkyl)-N—($C_1$-$C_4$ alkanoyl)amino, N—[($C_1$-$C_4$ alkyl)sulfonyl]amino, N-[(halo-substituted $C_1$-$C_4$ alkyl)sulfonyl]amino, $C_1$-$C_4$ alkanoyl, carboxy, ($C_1$-$C_4$ alkoxy)hydroxyl, carbamoyl, [N—($C_1$-$C_4$alkyl)amino]carbonyl, [N,N-di($C_1$-$C_4$alkyl)amino]carbonyl, N-carbamoylamino, cyano, nitro, mercapto, ($C_1$-$C_4$alkyl)thio, ($C_1$-$C_4$ alkyl)sulfinyl, ($C_1$-$C_4$alkyl)sulfonyl, aminosulfonyl, [N—($C_1$-$C_4$alkyl)amino]sulfonyl and [N,N-di($C_1$-$C_4$ alkyl)amino]sulfonyl;
$R^{138}$ is selected from:
hydrogen;
straight or branched $C_1$-$C_4$ alkyl optionally substituted with one to three substituent(s) wherein said substituents are independently selected from halo, hydroxyl, $C_1$-$C_4$ alkoxy, amino, N—($C_1$-$C_4$ alkyl)amino and N,N-di($C_1$-$C_4$alkyl)amino;

$C_3$-$C_8$ cycloalkyl optionally substituted with one to three substituent(s) wherein said substituents are independently selected from halo, $C_1$-$C_4$ alkyl, hydroxyl, $C_1$-$C_4$ alkoxy, amino, N—($C_1$-$C_4$alkyl)amino and N,N-di($C_1$-$C_4$alkyl)amino;

$C_4$-$C_8$ cycloalkenyl optionally substituted with one to three substituent(s) wherein said substituents are independently selected from halo, $C_1$-$C_4$ alkyl, hydroxyl, $C_1$-$C_4$ alkoxy, amino, N—($C_1$-$C_4$ alkyl)amino and N,N-di($C_1$-$C_4$alkyl)amino;

phenyl optionally substituted with one to three substituent(s) wherein said substituents are independently selected from halo, $C_1$-$C_4$ alkyl, hydroxyl, $C_1$-$C_4$ alkoxy, halo-substituted $C_1$-$C_4$ alkyl, hydroxyl-substituted $C_1$-$C_4$ alkyl, ($C_1$-$C_4$ alkoxy)$C_1$-$C_4$ alkyl, halosubstituted $C_1$-$C_4$ alkoxy, amino, N—($C_1$-$C_4$alkyl)amino, N,N-di($C_1$-$C_4$alkyl)amino, [N—($C_1$-$C_4$alkyl)amino]$C_1$-$C_4$ alkyl, [N,N-di($C_1$-$C_4$ alkyl)amino]$C_1$-$C_4$ alkyl, N—($C_1$-$C_4$ alkanoyl)amino, N—[($C_1$-$C_4$ alkyl)($C_1$-$C_4$ alkanoyl)]amino, N—[($C_1$-$C_4$ alkyl)sulfony] amino, N-[(halo-substituted $C_1$-$C_4$alkyl)sulfonyl] amino, $C_1$-$C_4$ alkanoyl, carboxy, ($C_1$-$C_4$ alkoxy) carbonyl, carbamoyl, [N—($C_1$-$C_4$ alky)amino] carbonyl, [N,N-di($C_1$-$C_4$alkyl)amino]carbonyl, cyano, nitro, mercapto, ($C_1$-$C_4$alkyl)thio, ($C_1$-$C_4$alkyl)sulfinyl, ($C_1$-$C_4$alkyl)sulfonyl, aminosulfonyl, [N—($C_1$-$C_4$alkyl)amino]sulfonyl and [N,N-di($C_1$-$C_4$ alkyl)amino]sulfonyl; and heteroaryl selected from: a 5-membered monocyclic aromatic ring having one hetero atom selected from O, S and N and optionally containing one to three N atom(s) in addition to said hetero atom; or a 6-membered monocyclic aromatic ring having one N atom and optionally containing one to four N atom(s) in addition to said N atom; and said heteroaryl being optionally substituted with one to three substituent(s) selected from $X^{20}$;

$R^{139}$ and $R^{140}$ are independently selected from: hydrogen; halo; $C_1$-$C_4$ alkyl; phenyl optionally substituted with one to three substituent(s) wherein said substituents are independently selected from halo, $C_1$-$C_4$ alkyl, hydroxyl, $C_1$-$C_4$ alkoxy, amino, N—($C_1$-$C_4$ alkyl) amino and N,N-di($C_1$-$C_4$ alkyl)amino;

or $R^{138}$ and $R^{139}$ can form, together with the carbon atom to which they are attached, a $C_3$-$C_7$cycloalkyl ring;

m is 0, 1, 2, 3, 4 or 5; and n is 0, 1, 2, 3 or 4.

Compounds that may be employed as a Cox-2 selective inhibitor of the present invention include indole compounds that are described in U.S. Pat. No. 6,300,363 (incorporated by reference). Such indole compounds have the formula shown below:

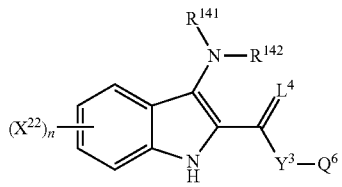

and the pharmaceutically acceptable salts thereof, wherein:

$L^4$ is oxygen or sulfur;

$Y^3$ is a direct bond or $C_1$-$C_4$ alkylidene;

$Q^6$ is:
(a) $C_1$-$C_6$ alkyl or halosubstituted $C_1$-$C_6$ alkyl, said alkyl being optionally substituted with up to three substituents independently selected from hydroxyl, $C_1$-$C_4$ alkoxy, amino and mono- or di-($C_1$-$C_4$ alkyl)amino,
(b) $C_3$-$C_7$ cycloalkyl optionally substituted with up to three substituents independently selected from hydroxyl, $C_1$-$C_4$ alkyl and $C_1$-$C_4$ alkoxy,
(c) phenyl or naphthyl, said phenyl or naphthyl being optionally substituted with up to four substituents independently selected from:
(c-1) halo, $C_1$-$C_4$alkyl, halosubstituted $C_1$-$C_4$alkyl, hydroxyl, $C_1$-$C_4$ alkoxy, halosubstituted $C_1$-$C_4$ alkoxy, $S(O)_2R^{143}$, $SO_2NH_2$, $SO_2N(C_1$-$C_4$ alkyl)$_2$, amino, mono- or di-($C_1$-$C_4$ alkyl)amino, $NHSO_2R^{143}$, NHC(O)$R^{143}$, CN, $CO_2H$, $CO_2(C_1$-$C_4$ alkyl), $C_1$-$C_4$ alkyl-OH, $C_1$-$C_4$alkyl-OR$^{143}$, $CONH_2$, CONH($C_1$-$C_4$alkyl), CON($C_1$-$C_4$alkyl)$_2$ and —O—Y-phenyl, said phenyl being optionally substituted with one or two substituents independently selected from halo, $C_1$-$C_4$ alkyl, $CF_3$, hydroxyl, $OR^{143}$, $S(O)_mR^{143}$, amino, mono- or di-($C_1$-$C_4$ alkyl)amino and CN;
(d) a monocyclic aromatic group of 5 atoms, said aromatic group having one heteroatom selected from O, S and N and optionally containing up to three N atoms in addition to said heteroatom, and said aromatic group being substituted with up to three substitutents independently selected from:
(d-1) halo, $C_1$-$C_4$ alkyl, halosubstituted $C_1$-$C_4$ alkyl, hydroxyl, $C_1$-$C_4$ alkoxy, halosubstituted $C_1$-$C_4$ alkoxy, $C_1$-$C_4$ alkyl-OH, $S(O)_mR^{143}$, $SO_2NH_2$, $SO_2N(C_1$-$C_4$ alkyl)$_2$, amino, mono- or di-($C_1$-$C_4$ alkyl)amino, $NHSO_2R^{143}$, NHC(O)$R^{143}$, CN, $CO_2H$, $CO_2(C_1$-$C_4$ alkyl), $C_1$-$C_4$ alkyl-OR$^{143}$, $CONH_2$, CONH($C_1$-$C_4$ alkyl), CON($C_1$-$C_4$ alkyl)$_2$, phenyl, and mono-, di- or tri-substituted phenyl wherein the substituent is independently selected from halo, $CF_3$, $C_1$-$C_4$ alkyl, hydroxyl, $C_1$-$C_4$ alkoxy, $OCF_3$, $SR^{143}$, $SO_2CH_3$, $SO_2NH_2$, amino, $C_{1-4}$ alkylamino and $NHSO_2R^{143}$;
(e) a monocyclic aromatic group of 6 atoms, said aromatic group having one heteroatom which is N and optionally containing up to three atoms in addition to said heteroatom, and said aromatic group being substituted with up to three substituents independently selected from the above group (d-1);

$R^{141}$ is hydrogen or $C_1$-$C_6$ alkyl optionally substituted with a substituent selected independently from hydroxyl, $OR^{143}$, nitro, amino, mono- or di-($C_1$-$C_4$alkyl)amino, $CO_2H$, $CO_2(C_1$-$C_4$ alkyl), $CONH_2$, CONH($C_1$-$C_4$ alkyl) and CON($C_1$-$C_4$ alkyl)$_2$;

$R^{142}$ is:
(a) hydrogen,
(b) $C_1$-$C_4$ alkyl,
(c) C(O)$R^{145}$,
wherein $R^{145}$ is selected from:
(c-1) $C_1$-$C_{22}$ alkyl or $C_2$-$C_{22}$ alkenyl, said alkyl or alkenyl being optionally substituted with up to four substituents independently selected from:
(c-1-1) halo, hydroxyl, $OR^{143}$, $S(O)_mR^{143}$, nitro, amino, mono- or di-($C_1$-$C_4$alkyl)amino, $NHSO_2R^{143}$, $CO_2H$, $CO_2(C_1$-$C_4$ alkyl), $CONH_2$, CONH($C_1$-$C_4$alkyl), CON($C_1$-$C_4$ alkyl)$_2$, $OC(O)R^{143}$, thienyl, naphthyl and groups of the following formulas:

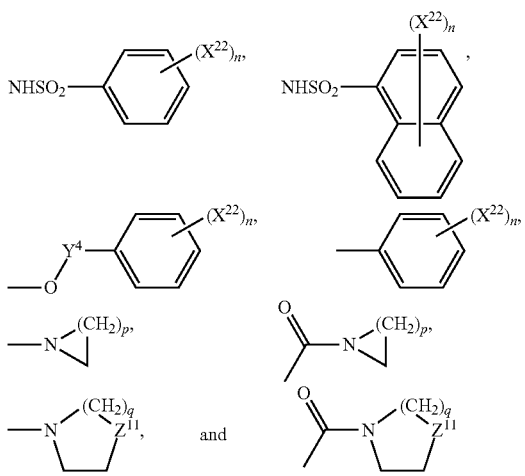

(c-2) $C_1$-$C_{22}$ alkyl or $C_2$-$C_{22}$ alkenyl, said alkyl or alkenyl being optionally substituted with five to forty-five halogen atoms, (c-3) —$Y^3$—$C_3$-$C_7$ cycloalkyl or —$Y^5$—$C_3$-$C_7$ cycloalkenyl, said cycloalkyl or cycloalkenyl being optionally substituted with up to three substituent independently selected from:

(c-3-1) $C_1$-$C_4$ alkyl, hydroxyl, $OR^{143}S(O)_mR^{143}$, amino, mono or di-($C_1$-$C_4$alkyl)amino, $CONH_2$, $CONH(C_1$-$C_4$ alkyl) and $CON(C_1$-$C_4$ alkyl)$_2$, (c-4) phenyl or naphthyl, said phenyl or naphthyl being optionally substituted with up to seven (preferably up to seven) substituents independently selected from:

(c-4-1) halo, $C_1$-$C_8$ alkyl, $C_1$-$C_4$ alkyl-OH, hydroxyl, $C_1$-$C_5$ alkoxy, halosubstituted $C_1$-$C_8$ alkyl, halosubstituted $C_1$-$C_5$ alkoxy, CN, nitro, $S(O)_mR^{143}$, $SO_2$ $NH_2$, $SO_2NH(C_1$-$C_4$ alkyl), $SO_2N(C_1$-$C_4$ alkyl)$_2$, amino, $C_1$-$C_4$alkylamino, di-($C_1$-$C_4$ alkyl)amino, $CONH_2$, $CONH(C_1$-$C_4$ alkyl), $CON(C_1$-$C_4$alkyl)$_2$, $OC(O)R^{143}$, and phenyl optionally substituted with up to three substituents independently selected from halo, $C_1$-$C_4$ alkyl, hydroxyl, $OCH_3$, $CF_3$, $OCF_3$, CN, nitro, amino, mono- or di-($C_1$-$C_4$ alkyl)amino, $CO_2H$, $CO_2(C_1$-$C_4$ alkyl) and $CONH_2$, (c-5) a monocyclic aromatic group as defined in (d) and (e) above, said aromatic group being optionally substituted with up to three substituents independently selected from:

(c-5-1) halo, $C_1$-$C_8$alkyl, $C_1$-$C_4$alkyl-OH, hydroxyl, $C_1$-$C_8$ alkoxy, $CF_3$, $OCF_3$, CN, nitro, $S(O)_mR^{43}$, amino, mono- or di-($C_1$-$C_4$ alkyl)amino, $CONH_2$, $CONH(C_1$-$C_4$alkyl), $CON(C_1$-$C_4$ alkyl)$_2$, $CO_2H$ and $CO_2(C_1$-$C_4$ alkyl), and —Y-phenyl, said phenyl being optionally substituted with up to three substituents independently selected halogen, $C_1$-$C_4$alkyl, hydroxyl, $C_1$-$C_4$ alkoxy, $CF_3$, $OCF_3$, CN, nitro, $S(O)_mR^{143}$ amino, mono- or di-($C_1$-$C_4$ alkyl)amino, $CO_2H$, $CO_2(C_1$-$C_4$ alkyl), $CONH_2$, $CONH(C_1$-$C_4$ alkyl) and $CON(C_1$-$C_4$ alkyl)$_2$, (c-6) a group of the following formula:

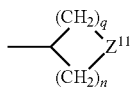

$X^{22}$ is halo, $C_1$-$C_4$ alkyl, hydroxyl, $C_1$-$C_4$ alkoxy, halo-substitutued $C_1$-$C_4$alkoxy, $S(O)_mR^{143}$, amino, mono- or di-($C_1$-$C_4$ alkyl)amino, $NHSO_2R^{143}$, nitro, halosubstitutued $C_1$-$C_4$alkyl, CN, $CO_2H$, $CO_2(C_1$-$C_4$ alkyl), $C_1$-$C_4$ alkyl-OH, $C_1$-$C_4$ alkyl$OR^{143}$, $CONH_2$, CONH ($C_1$-$C_4$ alkyl) or $CON(C_1$-$C_4$ alkyl)$_2$;

$R^{143}$ is $C_1$-$C_4$ alkyl or halosubstituted $C_1$-$C_4$ alkyl;

m is 0, 1 or 2; n is 0, 1, 2 or 3; p is 1, 2, 3, 4 or 5; q is 2 or 3;

$Z^{11}$ is oxygen, sulfur or $NR^{164}$; and $R_{144}$ is hydrogen, $C_1$-$C_6$ alkyl, halosubstitutued $C_1$-$C_4$ alkyl or —$Y^5$-phenyl, said phenyl being optionally substituted with up to two substituents independently selected from halo, $C_1$-$C_4$ alkyl, hydroxyl, $C_1$-$C_4$ alkoxy, $S(O)_mR^{143}$, amino, mono- or di-($C_1$-$C_4$ alkyl) amino, $CF_3$, $OCF_3$, CN and nitro;

with the proviso that a group of formula —$Y^5$-Q is not methyl or ethyl when $X^2$ is hydrogen;

$L^4$ is oxygen;

$R^{141}$ is hydrogen; and $R^{142}$ is acetyl.

Aryl phenylhydrazides that are described in U.S. Pat. No. 6,077,869 (incorporated by reference) can serve as Cox-2 selective inhibitors of the present invention. Such aryl phenylhydrazides have the formula shown:

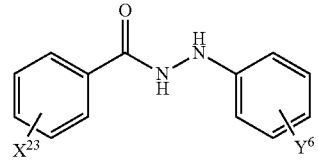

wherein:

$X^{23}$ and $Y^6$ are selected from hydrogen, halogen, alkyl, nitro, amino, hydroxy, methoxy and methylsulfonyl;

or a pharmaceutically acceptable salt thereof.

Materials that can serve as a Cox-2 selective inhibitor of the present invention include 2-aryloxy, 4-aryl furan-2-ones that are described in U.S. Pat. No. 6,140,515 (incorporated by reference). Such 2-aryloxy, 4-aryl furan-2-ones have the formula shown below:

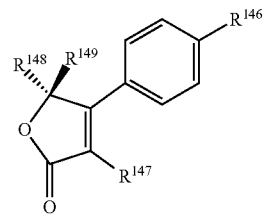

or a pharmaceutical salt thereof, wherein:

$R^{146}$ is selected from the group consisting of $SCH_3$, —$S(O)_2$ $CH_3$ and —$S(O)_2NH_2$;

$R^{147}$ is selected from the group consisting of $OR^{150}$, mono or di-substituted phenyl or pyridyl wherein the substituents are selected from the group consisting of methyl, chloro and F;

$R^{150}$ is unsubstituted or mono or di-substituted phenyl or pyridyl wherein the substituents are selected from the group consisting of methyl, chloro and F;

$R^{148}$ is H, $C_1$-$C_4$ alkyl optionally substituted with 1 to 3 groups of F, Cl or Br; and $R^{149}$ is H, $C_1$-$C_4$ alkyl optionally substituted with 1 to 3 groups of F, Cl or Br, with the proviso that $R^{148}$ and $R^{149}$ are not the same.

Materials that can serve as a Cox-2 selective inhibitor of the present invention include bisaryl compounds that are described in U.S. Pat. No. 5,994,379 (incorporated by reference). Such bisaryl compounds have the formula shown below:

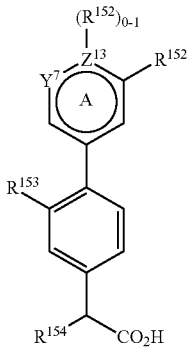

or a pharmaceutically acceptable salt, ester or tautomer thereof, wherein:

$Z^{13}$ is C or N;

when $Z^{13}$ is N, $R^{151}$ represents H or is absent, or is taken in conjunction with $R^{152}$ as described below:

when $Z^{13}$ is C, $R^{151}$ represents H and $R^{152}$ is a moiety which has the following characteristics:
 (a) it is a linear chain of 3-4 atoms containing 0-2 double bonds, which can adopt an energetically stable transoid configuration and if a double bond is present, the bond is in the trans configuration,
 (b) it is lipophilic except for the atom bonded directly to ring A, which is either lipophilic or non-lipophilic, and
 (c) there exists an energetically stable configuration planar with ring A to within about 15 degrees;

or $R^{151}$ and $R^{152}$ are taken in combination and represent a 5- or 6-membered aromatic or non-aromatic ring D fused to ring A, said ring D containing 0-3 heteroatoms selected from O, S and N;

said ring D being lipophilic except for the atoms attached directly to ring A, which are lipophilic or non-lipophilic, and said ring D having available an energetically stable configuration planar with ring A to within about 15 degrees;

said ring D further being substituted with 1 $R^a$ group selected from the group consisting of: $C_1$-$C_2$alkyl, —$OC_1$-$C_2$ alkyl, —NHC, —$C_2$alkyl, —N($C_1$-$C_2$ alkyl)$_2$, —C(O)$C_1$-$C_2$ alkyl, —S—$C_1$-$C_2$ alkyl and —C(S)$C_1$-$C_2$alkyl;

$Y^7$ represents N, CH or C—$OC_1$-$C_3$ alkyl, and when $Z^3$ is N, $Y^7$ can also represent a carbonyl group;

$R^{153}$ represents H, Br, Cl or F; and $R^{154}$ represents H or $CH_3$.

Compounds useful as Cox-2 selective inhibitors of the present invention include 1,5-diarylpyrazoles that are described in U.S. Pat. No. 6,028,202 (incorporated by reference). Such 1,5-diarylpyrazoles have the formula shown below:

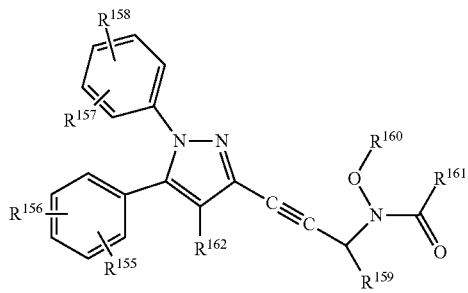

wherein:

$R^{155}$, $R^{156}$, $R^{157}$, and $R^{158}$ are independently selected from the groups consisting of hydrogen, $C_1$-$C_5$ alkyl, $C_1$-$C_5$ alkoxy, phenyl, halo, hydroxyl, $C_1$-$C_5$alkylsulfonyl, $C_1$-$C_5$ alkylthio, trihalo$C_1$-$C_5$ alkyl, amino, nitro and 2-quinolinylmethoxy;

$R^{159}$ is hydrogen, $C_1$-$C_5$ alkyl, trihalo$C_1$-$C_5$ alkyl, phenyl, substituted phenyl where the phenyl substituents are halogen, $C_1$-$C_5$ alkoxy, trihalo$C_1$-$C_5$ alkyl or nitro or $R^{159}$ is heteroaryl of 5-7 ring members where at least one of the ring members is nitrogen, sulfur or oxygen;

$R^{160}$ is hydrogen, $C_1$-$C_5$ alkyl, phenyl $C_1$-$C_5$ alkyl, substituted phenyl $C_1$-$C_5$alkyl where the phenyl substitutents are halogen, $C_1$-$C_5$ alkoxy, trihalo$C_1$-$C_5$alkyl or nitro, or $R^{160}$ is $C_1$-$C_5$ alkoxycarbonyl, phenoxycarbonyl, substituted phenoxycarbonyl where the phenyl substitutents are halogen, $C_1$-$C_5$ alkoxy, trihalo$C_1$-$C_5$ alkyl or nitro;

$R^{161}$ is $C_1$-$C_{10}$ alkyl, substituted $C_1$-$C_{10}$ alkyl where the substituents are halogen, trihalo$C_1$-$C_5$ alkyl, $C_1$-$C_5$ alkoxy, carboxy, $C_1$-$C_5$ alkoxycarbonyl, amino, $C_1$-$C_5$ alkylamino, di$C_1$-$C_5$ alkylamino, di$C_1$-$C_5$ alkylamino$C_1$-$C_5$alkylamino, $C_1$-$C_5$ alkylamino$C_1$-$C_5$ alkylamino or a heterocycle containing 4-8 ring atoms where one more of the ring atoms is nitrogen, oxygen or sulfur, where said heterocycle may be optionally substituted with $C_1$-$C_5$ alkyl; or $R^{161}$ is phenyl, substituted phenyl (where the phenyl substitutents are one or more of $C_1$-$C_5$ alkyl, halogen, $C_1$-$C_5$ alkoxy, trihalo$C_1$-$C_5$ alkyl or nitro), or $R^{161}$ is heteroaryl having 5-7 ring atoms where one or more atoms are nitrogen, oxygen or sulfur, fused heteroaryl where one or more 5-7 membered aromatic rings are fused to the heteroaryl; or $R^{161}$ is $NR^{163}R^{164}$ where $R^{163}$ and $R^{164}$ are independently selected from hydrogen and $C_{1-5}$ alkyl or $R^{163}$ and $R^{164}$ may be taken together with the depicted nitrogen to form a heteroaryl ring of 5-7 ring members where one or more of the ring members is nitrogen, sulfur or oxygen where said heteroaryl ring may be optionally substituted with $C_1$-$C_5$ alkyl; $R^{162}$ is hydrogen, $C_1$-$C_5$alkyl, nitro, amino, and halogen;

or pharmaceutically acceptable salts thereof.

Materials that can serve as a Cox-2 selective inhibitor of the present invention include 2-substituted imidazoles that are described in U.S. Pat. No. 6,040,320 (incorporated by reference). Such 2-substituted imidazoles have the formula shown below:

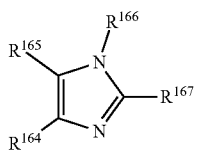

wherein:
R$^{154}$ is phenyl, heteroaryl wherein the heteroaryl contains 5 to 6 ring atoms, or substituted phenyl;
wherein the substituents are independently selected from one or members of the group consisting of C$_{1-5}$ alkyl, halogen, nitro, trifluoromethyl and nitrile;
R$^{165}$ is phenyl, heteroaryl wherein the heteroaryl contains 5 to 6 ring atoms, substituted heteroaryl;
wherein the substituents are independently selected from one or more members of the group consisting of C$_1$-C$_5$ alkyl and halogen, or
substituted phenyl,
wherein the substituents are independently selected from one or members of the group consisting of C$_1$-C$_5$ alkyl, halogen, nitro, trifluoromethyl and nitrile;
R$^{166}$ is hydrogen, 2-(trimethylsilyl)ethoxymethyl), C$_1$-C$_5$ alkoxycarbonyl, aryloxycarbonyl, arylC$_1$-C$_5$ alkyloxycarbonyl, arylC$_1$-C$_5$ alkyl, phthalimidoC$_1$-C$_5$alkyl, aminoC$_1$-C$_5$ alkyl, diaminoC$_1$-C$_5$ alkyl, succinimidoC$_1$-C$_5$ alkyl, C$_1$-C$_5$alkylcarbonyl, arylcarbonyl, C$_1$-C$_5$ alkylcarbonylC$_1$-C$_5$ alkyl, aryloxycarbonylC$_1$-C$_5$ alkyl, heteroarylC$_1$-C$_5$ alkyl where the heteroaryl contains 5 to 6 ring atoms, or substituted arylC$_1$-C$_5$ alkyl, wherein the aryl substituents are independently selected from one or more members of the group consisting of C$_1$-C$_5$ alkyl, C$_1$-C$_5$ alkoxy, halogen, amino, C$_1$-C$_5$ alkylamino, and diC$_1$-C$_5$alkylamino;
R$^{167}$ is (A$^{11}$)$_n$-(CH$^{165}$)$_q$—X$^{24}$ wherein:
A$^{11}$ is sulfur or carbonyl;
n is 0 or 1;
q is 0-9;
X$^{24}$ is selected from the group consisting of hydrogen, hydroxyl, halogen, vinyl, ethynyl, C$_1$-C$_5$ alkyl, C$_3$-C$_7$ cycloalkyl, C$_1$-C$_5$ alkoxy, phenoxy, phenyl, arylC$_1$-C$_5$ alkyl, amino, C$_1$-C$_5$ alkylamino, nitrile, phthalimido, amido, phenylcarbonyl, C$_1$-C$_5$ alkylaminocarbonyl, phenylaminocarbonyl, arylC$_1$-C$_5$alkylaminocarbonyl, C$_1$-C$_5$ alkylthio, C$_1$-C$_5$ alkylsulfonyl, phenylsulfonyl,
substituted sulfonamido,
wherein the sulfonyl substituent is selected from the group consisting of C$_1$-C$_5$ alkyl, phenyl, araC$_1$-C$_5$ alkyl, thienyl, furanyl, and naphthyl; substituted vinyl,
wherein the substituents are independently selected from one or members of the group consisting of fluorine, bromine, chlorine and iodine, substituted ethynyl,
wherein the substituents are independently selected from one or more members of the group consisting of fluorine, bromine chlorine and iodine,
substituted C$_1$-C$_5$ alkyl,
wherein the substituents are selected from the group consisting of one or more C$_1$-C$_5$ alkoxy, trihaloalkyl, phthalimido and amino,
substituted phenyl,
wherein the phenyl substituents are independently selected from one or more members of the group consisting of C$_1$-C$_5$ alkyl, halogen and C$_1$-C$_5$ alkoxy,
substituted phenoxy,
wherein the phenyl substituents are independently selected from one or more members of the group consisting of C$_1$-C$_5$ alkyl, halogen and C$_1$-C$_5$ alkoxy,
substituted C$_1$-C$_5$ alkoxy,
wherein the alkyl substituent is selected from the group consisting of phthalimido and amino,
substituted arylC$_1$-C$_5$ alkyl,
wherein the alkyl substituent is hydroxyl,
substituted arylC$_1$-C$_5$ alkyl,
wherein the phenyl substituents are independently selected from one or more members of the group consisting of C$_1$-C$_5$ alkyl, halogen and C$_1$-C$_5$ alkoxy,
substituted amido,
wherein the carbonyl substituent is selected from the group consisting of C$_1$-C$_5$ alkyl, phenyl, arylC$_1$-C$_5$ alkyl, thienyl, furanyl, and naphthyl,
substituted phenylcarbonyl,
wherein the phenyl substituents are independently selected from one or members of the group consisting of C$_1$-C$_5$ alkyl, halogen and C$_1$-C$_5$ alkoxy,
substituted C$_1$-C$_5$ alkylthio,
wherein the alkyl substituent is selected from the group consisting of hydroxyl and phthalimido,
substituted C$_1$-C$_5$ alkylsulfonyl,
wherein the alkyl substituent is selected from the group consisting of hydroxyl and phthalimido,
substituted phenylsulfonyl,
wherein the phenyl substituents are independently selected from one or members of the group consisting of bromine, fluorine, chlorine, C$_1$-C$_5$ alkoxy and trifluoromethyl,
with the proviso:
if A$^{11}$ is sulfur and X$^{24}$ is other than hydrogen, C$_1$-C$_5$ alkylaminocarbonyl, phenylaminocarbonyl, arylC$_1$-C$_5$ alkylaminocarbonyl, C$_1$-C$_5$ alkylsulfonyl or phenylsulfonyl, then q must be equal to or greater than 1;
if A$^{11}$ is sulfur and q is 1, then X$^{24}$ cannot be C$_1$-C$_2$alkyl;
if A$^{11}$ is carbonyl and q is 0, then X$^{24}$ cannot be vinyl, ethynyl, C$_1$-C$_5$alkylaminocarbonyl, phenylaminocarbonyl, arylC$_1$-C$_5$ alkylaminocarbonyl, C$_1$-C$_5$ alkylsulfonyl or phenylsulfonyl;
if A$^{11}$ is carbonyl, q is 0 and X$^{24}$ is H, then R$^{166}$ is not 2-(trimethylsilyl)ethoxymethyl;
if n is 0 and q is 0, then X$^{24}$ cannot be hydrogen;
or pharmaceutically acceptable salts thereof.

Materials that can serve as a Cox-2 selective inhibitor of the present invention include 1,3- and 2,3-diarylcycloalkano and cycloalkeno pyrazoles that are described in U.S. Pat. No. 6,083,969 (incorporated by reference). Such 1,3- and 2,3-diarylpyrazole compounds have the general formulas shown in the two formulas below:

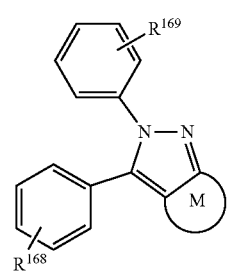

-continued

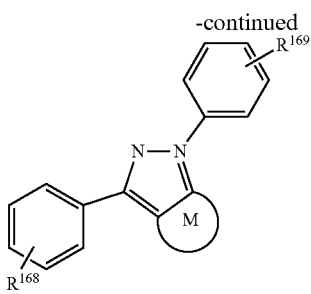

wherein:

$R^{168}$ and $R^{169}$ are independently selected from the group consisting of hydrogen, halogen, ($C_1$-$C_6$)alkyl, ($C_1$-$C_6$)alkoxy, nitro, amino, hydroxyl, trifluoro, —S($C_1$-$C_6$)alkyl, —SO($C_1$-$C_6$)alkyl and —SO$_2$($C_1$-$C_6$)alkyl; and the fused moiety M is a group selected from the group consisting of an optionally substituted cyclohexyl and cycloheptyl group having the formulae:

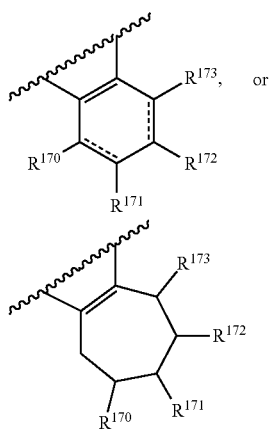

wherein:

$R^{170}$ is selected from the group consisting of hydrogen, halogen, hydroxyl and carbonyl;

or $R^{170}$ and $R^{171}$ taken together form a moiety selected from the group consisting of —OCOCH$_2$—, —ONH(CH$_3$)COCH$_2$—, —OCOCH= and —O—;

$R^{171}$ and $R^{172}$ are independently selected from the group consisting of hydrogen, halogen, hydroxyl, carbonyl, amino, ($C_1$-$C_6$)alkyl, ($C_1$-$C_6$)alkoxy, =NOH, —NR$^{174}$R$^{175}$, —OCH$_3$, —OCH$_2$CH$_3$, —OSO$_2$NHCO$_2$CH$_3$, =CHCO$_2$CH$_2$CH$_3$, —CH$_2$CO$_2$H, —CH$_2$CO$_2$CH$_3$, —CH$_2$CO$_2$CH$_2$CH$_3$, —CH$_2$CON(CH$_3$)$_2$, —CH$_2$CO$_2$NHCH$_3$, —CHCHCO$_2$CH$_2$CH$_3$, —OCON(CH$_3$)OH, —C(COCH$_3$)$_2$, di($C_1$-$C_6$)alkyl and di($C_1$-$C_6$)alkoxy;

$R^{173}$ is selected from the group consisting of hydrogen, halogen, hydroxyl, carbonyl, amino, ($C_1$-$C_6$)alkyl, ($C_1$-$C_6$)alkoxy and optionally substituted carboxyphenyl, wherein substituents on the carboxyphenyl group are selected from the group consisting of halogen, hydroxyl, amino, ($C_1$-$C_6$)alkyl and ($C_1$-$C_6$)alkoxy;

or $R^{172}$ and $R^{173}$ taken together form a moiety selected from the group consisting of —O— and

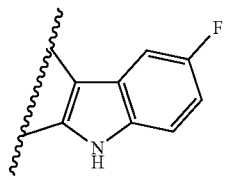

$R^{174}$ is selected from the group consisting of hydrogen, OH, —OCOCH$_3$, —CCH$_3$ and ($C_1$-$C_6$)alkyl; and $R^{175}$ is selected from the group consisting of hydrogen, OH, —OCOCH$_3$, —COCH$_3$, ($C_1$-$C_6$)alkyl, —CONH$_2$ and —SO$_2$CH$_3$;

with the proviso that if M is a cyclohexyl group, then $R^{170}$ through $R^{173}$ may not all be hydrogen; and pharmaceutically acceptable salts, esters and pro-drug forms thereof.

Esters derived from indolealkanols and novel amides derived from indoleakylamides that are described in U.S. Pat. No. 6,306,890 (incorporated by reference) can serve as Cox-2 selective inhibitors of the present invention. Such compounds have the general formula shown below:

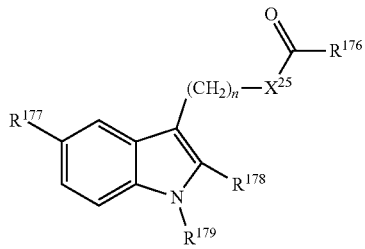

wherein:

$R^{176}$ is $C_1$-$C_6$ alkyl, $C_1$-$C_6$ branched alkyl, $C_4$-$C_8$ cycloalkyl, $C_1$-$C_6$ hydroxyalkyl, branched $C_1$-$C_6$ hydroxyalkyl, hydroxyl substituted $C_4$-$C_8$ aryl, primary, secondary or tertiary $C_1$-$C_6$ alkylamino, primary, secondary or tertiary branched $C_1$-$C_6$ alkylamino, primary, secondary or tertiary $C_4$-$C_8$ arylamino, $C_1$-$C_6$ alkylcarboxylic acid, branched $C_1$-$C_6$ alkylcarboxylic acid, $C_1$-$C_6$alkylester, branched $C_1$-$C_6$ alkylester, $C_4$-$C_8$ aryl, $C_4$-$C_8$ arylcarboxylic acid, $C_4$-$C_8$ arylester, $C_4$-$C_5$ aryl substituted $C_1$-$C_6$ alkyl, $C_4$-$C_8$ heterocyclic alkyl or aryl with O, N or S in the ring, alkyl-substituted or aryl-substituted $C_4$-$C_8$heterocyclic alkyl or aryl with O, N or S in the ring, or halo-substituted versions thereof, where halo is chloro, bromo, fluoro or iodo;

$R^{177}$ is $C_1$-$C_6$ alkyl, $C_1$-$C_6$ branched alkyl, $C_4$-$C_8$ cycloalkyl, $C_4$-$C_8$ aryl, $C_4$-$C_8$aryl-substituted $C_1$-$C_6$ alkyl, $C_1$-$C_6$ alkoxy, $C_1$-$C_6$ branched alkoxy, $C_4$-$C_8$aryloxy, or halo-substituted versions thereof or $R^{177}$ is halo where halo is chloro, fluoro, bromo, or iodo;

$R^{178}$ is hydrogen, $C_1$-$C_6$ alkyl or $C_1$-$C_6$ branched alkyl;

$R^{179}$ is $C_1$-$C_6$ alkyl, $C_4$-$C_8$ aroyl, $C_4$-$C_8$ aryl, $C_4$-$C_8$ heterocyclic alkyl or aryl with O, N or S in the ring, $C_4$-$C_8$ aryl-substituted $C_1$-$C_6$ alkyl, alkyl-substituted or aryl-substituted $C_4$-$C_8$ heterocyclic alkyl or aryl with O, N or S in the ring, alkyl-substituted $C_4$-$C_5$ aroyl, or alkyl-substituted $C_4$-$C_8$ aryl, or halo-substituted versions thereof where halo is chloro, bromo, or iodo;

n is 1, 2, 3, or 4; and $X^{25}$ is O, NH, or N—$R^{180}$, where $R^{180}$ is $C_1$-$C_6$ or $C_1$-$C_6$ branched alkyl.

Materials that can serve as a Cox-2 selective inhibitor of the present invention include pyridazinone compounds that are described in U.S. Pat. No. 6,307,047 (incorporated by reference). Such pyridazinone compounds have the formula shown below:

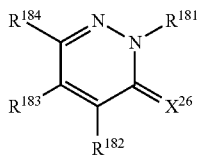

or a pharmaceutically acceptable salt, ester, or prodrug thereof, wherein:

$X^{26}$ is selected from the group consisting of O, S, —$NR^{185}$, —$NOR^a$, and —$NNR^bR^c$;

$R^{185}$ is selected from the group consisting of alkenyl, alkyl, aryl, arylalkyl, cycloalkenyl, cycloalkenylalkyl, cycloalkyl, cycloalkylalkyl, heterocyclic, and heterocyclic alkyl;

$R^a$, $R^b$, and $R^c$ are independently selected from the group consisting of alkyl, aryl, arylalkyl, cycloalkyl, and cycloalkylalkyl;

$R^{181}$ is selected from the group consisting of alkenyl, alkoxy, alkoxyalkyl, alkoxyiminoalkoxy, alkyl, alkylcarbonylalkyl, alkylsulfonylalkyl, alkynyl, aryl, arylalkenyl, arylalkoxy, arylalkyl, arylalkynyl, arylhaloalkyl, arylhydroxyalkyl, aryloxy, aryloxyhaloalkyl, aryloxyhydroxyalkyl, arylcarbonylalkyl, carboxyalkyl, cyanoalkyl, cycloalkenyl, cycloalkenylalkyl, cycloalkyl, cycloalkylalkyl, cycloalkylidenealkyl, haloalkenyl, haloalkoxyhydroxyalkyl, haloalkyl, haloalkynyl, heterocyclic, heterocyclic alkoxy, heterocyclic alkyl, heterocyclic oxy, hydroxyalkyl, hydroxyiminoalkoxy, —$(CH_2)C(O)R^{186}$, —$(CH_2)_nCH(OH)R^{186}$, —$(CH_2)_nC(NOR^d)R^{186}$, —$(CH_2)_nCH(NOR^d)R^{186}$, —$(CH_2)_nCH(NR^dR^e)R^{186}$, $R^{187}R^{188}$, —$(CH_2)_nC\equiv CR^{188}$, —$(CH_2)_n[CH(CX^{26'}_3)]_m(CH_2)_pR^{188}$, —$(CH_2)_n(CX^{26'}_2)_n(CH_2)_pR^{188}$, and —$(CH_2)_n(CHX^{26'})_m(CH_2)_mR^{188}$;

$R^{186}$ is selected from the group consisting of hydrogen, alkenyl, alkyl, alkynyl, aryl, arylalkyl, cycloalkenyl, cycloalkyl, haloalkenyl, haloalkyl, haloalkynyl, heterocyclic, and heterocyclic alkyl;

$R^{187}$ is selected from the group consisting of alkenylene, alkylene, halo-substituted alkenylene, and halo-substituted alkylene;

$R^{188}$ is selected from the group consisting of hydrogen, alkenyl, alkyl, alkynyl, aryl, arylalkyl, cycloalkyl, cycloalkenyl, haloalkyl, heterocyclic, and heterocyclic alkyl;

$R^d$ and $R^e$ are independently selected from the group consisting of hydrogen, alkenyl, alkyl, alkynyl, aryl, arylalkyl, cycloalkenyl, cycloalkyl, haloalkyl, heterocyclic, and heterocyclic alkyl;

$X^{26'}$ is halogen;

m is an integer from 0-5;

n is an integer from 0-10;

p is an integer from 0-10;

$R^{182}$, $R^{183}$, and $R^{184}$ are independently selected from the group consisting of hydrogen, alkenyl, alkoxyalkyl, alkoxyiminoalkoxy, alkoxyiminoalkyl, alkyl, alkynyl, alkylcarbonylalkoxy, alkylcarbonylamino, alkylcarbonylaminoalkyl, aminoalkoxy, aminoalkylcarbonyloxyalkoxy aminocarbonylalkyl, aryl, arylalkenyl, arylalkyl, arylalkynyl, carboxyalkylcarbonyloxyalkoxy, cyano, cycloalkenyl, cycloalkyl, cycloalkylidenealkyl, haloalkenyloxy, haloalkoxy, haloalkyl, halogen, heterocyclic, hydroxyalkoxy, hydroxyiminoalkoxy, hydroxyiminoalkyl, mercaptoalkoxy, nitro, phosphonatoalkoxy, $Y^8$, and $Z^{14}$; provided that one of $R^{182}$, $R^{183}$, or $R^{184}$ must be $Z^{14}$, and further provided that only one of $R^{182}$, $R^{183}$, or $R^{184}$ is $Z^{14}$;

$Z^{14}$ is selected from the group consisting of:

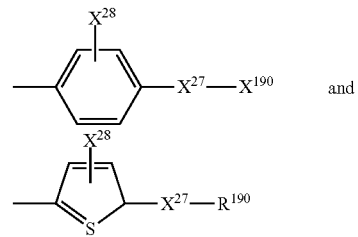

and $X^{27}$ is selected from the group consisting of $S(O)_2$, $S(O)(NR^{191})$, $S(O)$, $Se(O)_2$, $P(O)(OR^{192})$, and $P(O)(NR^{193}R^{194})$;

$X^{28}$ is selected from the group consisting of hydrogen, alkenyl, alkyl, alkynyl and halogen;

$R^{190}$ is selected from the group consisting of alkenyl, alkoxy, alkyl, alkylamino, alkylcarbonylamino, alkynyl, amino, cycloalkenyl, cycloalkyl, dialkylamino, —$NHNH_2$, and —$NCHN(R^{191})R^{192}$;

$R^{191}$, $R^{192}$, $R^{193}$, and $R^{194}$ are independently selected from the group consisting of hydrogen, alkyl, and cycloalkyl, or $R^{193}$ and $R^{194}$ can be taken together, with the nitrogen to which they are attached, to form a 3-6 membered ring containing 1 or 2 heteroatoms selected from the group consisting of O, S, and $NR^{188}$;

$Y^8$ is selected from the group consisting of —$OR^{195}$, —$SR^{195}$, —$C(R^{197})(R^{198})R^{195}$, —$C(O)R^{195}$, —$C(O)OR^{195}$, —$N(R^{197})C(O)R^{195}$, —$NC(R^{197})R^{195}$, and —$N(R^{197})R^{195}$;

$R^{195}$ is selected from the group consisting of hydrogen, alkenyl, alkoxyalkyl, alkyl, alkylthioalkyl, alkynyl, cycloalkenyl, cycloalkenylalkyl, cycloalkyl, cycloalkylalkyl, aryl, arylalkyl, heterocyclic, heterocyclic alkyl, hydroxyalkyl, and $NR^{199}R^{200}$; and $R^{97}$, $R^{198}$, $R^{199}$, and $R^{200}$ are independently selected from the group consisting of hydrogen, alkenyl, alkoxy, alkyl, cycloalkenyl, cycloalkyl, aryl, arylalkyl, heterocyclic, and heterocyclic alkyl.

Benzosulphonamide derivatives that are described in U.S. Pat. No. 6,004,948 (incorporated by reference) are useful as Cox-2 selective inhibitors of the present invention. Such benzosulphonamide derivatives have the formula shown below:

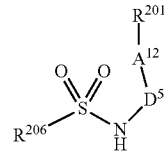

wherein:

$A^{12}$ denotes oxygen, sulphur or NH;

$R^{201}$ denotes a cycloalkyl, aryl or heteroaryl group optionally mono- or polysubstituted by halogen, alkyl, $CF_3$ or alkoxy;

$D^5$ denotes a group of one of the two formula:

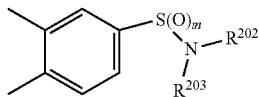

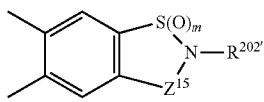

$R^{202}$ and $R^{203}$ independently of each other denote hydrogen, an optionally polyfluorinated alkyl radical, an aralkyl, aryl or heteroaryl radical or a radical $(CH_2)_n$—$X^{29}$; or $R^{202}$ and $R^{203}$ together with the N-atom denote a three- to seven-membered, saturated, partially or totally unsaturated heterocycle with one or more heteroatoms N, O, or S, which may optionally be substituted by oxo, an alkyl, alkylaryl or aryl group or a group $(CH_2)_n$—$X^{29}$, $R^{202'}$ denotes hydrogen, an optionally polyfluorinated alkyl group, an aralkyl, aryl or heteroaryl group or a group $(CH_2)_n$—$X^{29}$, wherein:

$X^{29}$ denotes halogen, $NO_2$, —$OR^{204}$, —$COR^{204}$, —$CO_2R^{204}$, —$OCO_2R^{204}$, —CN, —$CONR^{204}OR^{205}$, —$CONR^{204}R^{205}$, —$SR^{204}$, —$S(O)R^{204}$, —$S(O)_2R^{204}$, —$NR^{204}R^{205}$. —$NHC(O)R^{204}$, —$NHS(O)_2R^{204}$;

$Z^{15}$ denotes —$CH_2$—, —$CH_2$—$CH_2$—, —$CH_2$—$CH_2$—$CH_2$—, —$CH_2$—CH=CH—, —CH=CH—$CH_2$—, —$CH_2$—CO—, —CO—$CH_2$—, —NHCO—, —CONH—, —$NHCH_2$—, —$CH_2$ NH—, —N=CH—, —NHCH—, —$CH_2$—$CH_2$—NH—, —CH=CH—, >N—$R^{203}$, >C=O, >$S(O)_m$;

$R^{204}$ and $R^{205}$ independently of each other denote hydrogen, alkyl, aralkyl or aryl;

n is an integer from 0 to 6;

$R^{206}$ is a straight-chained or branched $C_1$-$C_4$ alkyl group which may optionally be mono- or polysubstituted by halogen or alkoxy, or $R^{206}$ denotes $CF_3$; and m denotes an integer from 0 to 2;

with the proviso that $A^{12}$ does not represent 0 if $R^{206}$ denotes $CF_3$;

and the pharmaceutically acceptable salts thereof.

Materials that can serve as Cox-2 selective inhibitors of the present invention include methanesulfonyl-biphenyl derivatives that are described in U.S. Pat. No. 6,583,321 (incorporated by reference). Such methanesulfonyl-biphenyl derivatives have the formula shown below:

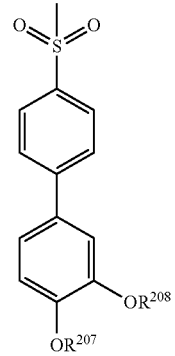

wherein:

$R^{207}$ and $R^{208}$ are respectively a hydrogen;

$C_1$-$C_4$-alkyl substituted or not substituted by halogens;

$C_3$-$C_7$-cycloalkyl;

$C_1$-$C_5$-alkyl containing 1-3 ether bonds and/or an aryl substitute;

substituted or not substituted phenyl;

or substituted or not substituted five or six ring-cycled heteroaryl containing more than one hetero atoms selected from a group consisting of nitrogen, sulfur, and oxygen (wherein phenyl or heteroaryl can be one- or multi-substituted by a substituent selected from a group consisting of hydrogen, methyl, ethyl, and isopropyl).

Cox-2 selective inhibitors such as 1H-indole derivatives described in U.S. Pat. No. 6,599,929 (incorporated by reference) are useful in the present invention. Such 1H-indole derivatives have the formula shown below:

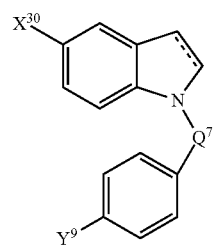

wherein:

$X^{30}$ is —$NHSO_2R^{209}$ wherein $R^{209}$ represents hydrogen or $C_1$-$C_3$-alkyl;

$Y^9$ is hydrogen, halogen, $C_1$-$C_3$-alkyl substituted or not substituted by halogen, $NO_2$, $NH_2$, OH, OMe, $CO_2H$, or CN; and $Q^7$ is C=O, C=S, or $CH_2$.

Compounds that are useful as Cox-2 selective inhibitors of the present invention include prodrugs of Cox-2 inhibitors that are described in U.S. Pat. No. 6,436,967 (incorporated by reference) and U.S. Pat. No. 6,613,790 (incorporated by reference). Such prodrugs of Cox-2 inhibitors have the formula shown below:

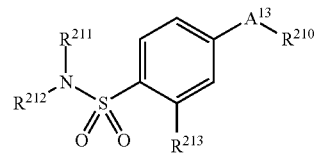

wherein:

A$^{13}$ is a ring substituent selected from partially unsaturated heterocyclic, heteroaryl, cycloalkenyl and aryl, wherein A$^{13}$ is unsubstituted or substituted with one or more radicals selected from alkylcarbonyl, formyl, halo, alkyl, haloalkyl, oxo, cyano, nitro, carboxyl, alkoxy, aminocarbonyl, alkoxycarbonyl, carboxyalkyl, cyanoalkyl, hydroxyalkyl, haloalkylsulfonyloxy, alkoxyalkyloxyalkyl, carboxyalkoxyalkyl, cycloalkylalkyl, alkenyl, alkynyl, heterocycloxy, alkylthio, cycloalkyl, aryl, heterocyclyl, cycloalkenyl, aralkyl, heterocyclylalkyl, alkylthioalkyl, arylcarbonyl, aralkylcarbonyl, aralkenyl, alkoxyalkyl, arylthioalkyl, aryloxyalkyl, aralkylthioalkyl, araalkoxyalkyl, alkoxycarbonylalkyl, aminocarbonylalkyl, alkylaminocarbonyl, N-arylaminocarbonyl, N-alkyl-N-arylaminocarbonyl, alkylaminocarbonylalkyl, alkylamino, -arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, and N-alkyl-N-arylaminosulfonyl;

R$^{210}$ is selected from heterocyclyl, cycloalkyl, cycloalkenyl, and aryl, wherein R$^{210}$ is unsubstituted or substituted with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy, and alkylthio;

R$^{211}$ is selected from hydrido and alkoxycarbonylalkyl;

R$^{212}$ is selected from alkyl, carboxyalkyl, acyl, alkoxycarbonyl, heteroarylcarbonyl, alkoxycarbonylalkylcarbonyl, alkoxycarbonylcarbonyl, amino acid residue, and alkylcarbonylaminoalkylcarbonyl; provided A$^{13}$ is not tetrazolium, or pyridinium; and further provided A$^{13}$ is not indanone when R$^{212}$ is alkyl or carboxyalkyl; further provided A$^{13}$ is not thienyl, when R$^{210}$ is 4-fluorophenyl, when R$^{211}$ is hydrido, and when R$^{212}$ is methyl or acyl; and R$^{213}$ is hydrido;

or a pharmaceutically-acceptable salt thereof.

Specific non-limiting examples of substituted sulfonamide prodrugs of Cox-2 inhibitors disclosed in U.S. Pat. No. 6,436,967 that are useful in the present invention include:

N-[[4-[3-(difluoromethyl)-5-(3-fluoro-4-methoxyphenyl)-1H-pyrazol-1-yl]phenyl]sulfonyl]propanamide;
N-[[4-[3-(difluoromethyl)-5-(3-fluoro-4-methoxyphenyl)-1H-pyrazol-1-yl]phenyl]sulfonyl]butanamide;
N-[[4-[1,5-dimethyl)-3-phenyl-1H-pyrazol-4-yl]phenyl]sulfonyl]acetamide;
N-[[4-(2-(3-pyridinyl)-4-(trifluoromethyl)-1H-imidazol-1-yl)phenyl]sulfonyl]acetamide;
N-[[4-[2-(5-methylpyridin-3-yl)-4-(trifluoromethyl)-1H-imidazol-1-yl]phenyl]sulfonyl]acetamide;
N-[[4-[2-(2-methylpyridin-3-yl)-4-(trifluoromethyl)-1H-imidazol-1-yl]phenyl]sulfonyl]acetamide;
N-[[4-[2-(5-methylpyridin-3-yl)-4-(trifluoromethyl)-1H-imidazol-1-yl]phenyl]sulfonyl]butanamide;
N-[[4-[2-(2-methylpyridin-3-yl)-4-(trifluoromethyl)-1H-imidazol-1-yl]phenyl]sulfonyl]butanamide;
N-[[4-[2-(3-chloro-5-methylphenyl)-4-(trifluoromethyl)-1H-imidazol-1-yl]phenyl]sulfonyl]acetamide;
N-[[4-[3-(3-fluorophenyl)-5-methylisoxazol-4-yl]phenyl]sulfonyl]acetamide;
2-methyl-N-[[4-(5-methyl-3-phenylisoxazol-4-yl)phenyl]sulfonyl]propanamide;
N-[[4-(5-methyl-3-phenylisoxazol-4-yl)phenyl]sulfonyl]propanamide;
N-[[4-(5-methyl-3-phenylisoxazol-4-yl)phenyl]sulfonyl]benzamide;
2,2-dimethyl-N-[[4-(5-methyl-3-phenylisoxazol-4-yl)phenyl]sulfonyl]propanamide;
N-[[4-5-methyl-3-phenylisoxazol-4-yl)phenyl]sulfonyl]butanamide;
N-[[4-(5-methyl-3-phenylisoxazol-4-yl)phenyl]sulfonyl]pentanamide;
N-[[4-(5-methyl-3-phenylisoxazol-4-yl)phenyl]sulfonyl]hexanamide;
3-methoxy-N-[[4-(5-methyl-3-phenylisoxazol-4-yl)phenyl]sulfonyl]propanamide;
2-ethoxy-N-[[4-(5-methyl-3-phenylisoxazol-4-yl)phenyl]sulfonyl]acetamide;
N-[[4-[5-methyl-3-phenylisoxazol-4-yl)phenyl]sulfonyl]acetamide;
N-[[4-[5-(4-chlorophenyl)-3-(trifluoromethyl)-1H pyrazol-1-yl]phenyl]sulfonyl]propanamide;
N-[[4-[5-(4-chlorophenyl)-3-(trifluoromethyl)-1H-pyrazol-1-yl]phenyl]sulfonyl]butanamide;
N-[[4-[5-(4-chlorophenyl)-3-(trifluoromethyl)-1H-pyrazol-1-yl]phenyl]sulfonyl]acetamide;
N-[[4-[3-(difluoromethyl)-6-fluoro-1,5-dihydro-7-methoxy-[2]benzothiopyrano[4,3-c]pyrazol-1-yl]phenyl]sulfonyl]acetamide;
N-[[4-[6-fluoro-1,5-dihydro-7-methoxy-3-(trifluoromethyl)-[2]benzothiopyrano[4,3-c]pyrazol-1-yl]phenyl]sulfonyl]acetamide;
N-[[4-[3-(difluoromethyl)-5-(3-fluoro-4-methoxyphenyl)-1H-pyrazol-1-yl]phenyl]sulfonyl]acetamide;
N-[[4-(2-methyl-4-phenyloxazol-5-yl)phenyl]sulfonyl]acetamide; methyl[[[4-(5-methyl-3-phenylisoxazol-4-yl)phenyl]sulfonyl]amino]oxoacetate;
2-methoxy-N-[[4-(5-methyl-3-phenylisoxazol-4-yl)phenyl]sulfonyl]acetamide;
N-[[4-[5-(difluoromethyl)-3-phenylisoxazol-4-yl]phenyl]sulfonyl]propanamide;
N-[[4-[5-(difluoromethyl)-3-phenylisoxazol-4-yl]phenyl]sulfonyl]butanamide;
N-[[4-(5-methyl-3-phenylisoxazol-4-yl)phenyl]sulfonyl]formamide;
1,1-dimethylethyl-N-[[4-(5-methyl-3-phenylisoxazol-4-yl)phenyl]sulfonyl]carbamate;
N-[[4-(5-methyl-3-phenylisoxazol-4-yl)phenyl]sulfonyl]glycine;
2-amino-N-[[4-(5-methyl-3-phenylisoxazol-4-yl)phenyl]sulfonyl]acetamide;
2-(acetylamino)-N-[[4-(5-methyl-3-phenylisoxazol-4-yl)phenyl]sulfonyl]acetamide;
methyl 4-[[[4-(5-methyl-3-phenylisoxazol-4-yl)phenyl]sulfonyl]amino]-4-oxobutanoate;
methyl N-[[4-(5-methyl-3-phenylisoxazol-4-yl)phenyl]sulfonyl]carbamate;
N-acetyl-N-[[4-(5-methyl-3-phenylisoxazol-4-yl)phenyl]sulfonyl]glycine, ethyl ester;
N-[[4-(5-(4-methylphenyl)-3-(trifluoromethyl)-1H-pyrazol-1-yl]phenyl]sulfonyl]acetamide;
methyl 3-[[[4-(5-methyl-3-phenylisoxazol-4-yl)phenyl]sulfonyl]amino]-3-oxopropanoate;
4-[5-(3-bromo-5-fluoro-4-methoxyphenyl)-2-(trifluoromethyl)oxazol-4-yl]-N-methylbenzenesulfonamide;
N-(11,1-dimethylethyl)-4-(5-methyl-3-phenylisoxazol-4-yl)benzenesulfonamide;

4-[5-(4-fluorophenyl)-3-(trifluoromethyl)-1H-pyrazol-1-yl]-N-methylbenzenesulfonamide;

N-methyl-4-(5-methyl-3-phenylisoxazol-4-yl)benezene-sulfonamide;

N-[[4-[5-(hydroxymethyl)-3-phenylisoxazol-4-yl]phenyl]sulfonyl]acetamide:

N-[[4-[5-(acetoxymethyl)-3-phenylisoxazol-4-yl]phenyl]sulfonyl]acetamide;

N-[[4-[2-(3-chloro-4-fluorophenyl)cyclopenten-1-yl)phenyl]sulfonyl]acetamide;

4-[2-(4-fluorophenyl)-1H-pyrrol-1-yl]-N-methylbenzenesulfonamide;

N-[[4-(3,4-dimethyl-1-phenyl-1H-pyrazol-5-yl]phenyl]sulfonyl]propanamide;

N-[[4-[2-(2-methylpyridin-3-yl)-4-trifluoromethylimidazol-1-yl]phenyl]sulfonyl]propanamide;

4-[2-(4-fluorophenyl)cyclopenten-1-yl]-N-methylbenzenesulfonamide; and

N-[[4-(3-phenyl-2,3-dihydro-2-oxofuran-4-yl)phenyl]sulfonyl]propanamide.

Those prodrugs disclosed in U.S. Pat. No. 6,613,790 (incorporated by reference) have the general formula shown in the above formula wherein:

$A^{13}$ is a pyrazole group optionally substituted at a substitutable position with one or more radicals independently selected at each occurrence from the group consisting of alkylcarbonyl, formyl, halo, alkyl, haloalkyl, oxo, cyano, intro, carboxyl, alkoxy, aminocarbonyl, alkoxycarbonyl, carboxyalkyl, cyanoalkyl, hydroxyalkyl, haloalkylsulonyloxy, alkoxyalkyloxyalkyl, carboxyalkoxyalkyl, alkenyl, alkynyl, alkylthio, alkylthioalkyl, alkoxyalkyl, alkoxycarbonylalkyl, aminocarbonylalkyl, alkylaminocarbonyl, alkylaminocarbonylalkyl, alkylamino, aminoalkyl, alkylaminoalkyl, alkylsulfinyl, alkylsulfonyl, aminosulfonyl, and alkylaminosulfonyl;

$R^{210}$ is a phenyl group optionally substituted at a substitutable position with one or more radicals independently selected at each occurrence from the group consisting of alkyl, haloalkyl, cyano, carboxyl, alkoxycarbonyl, hydroxyl, hydroxyalkyl, haloalkoxy, amino, alkylamino, nitro, alkoxyalkyl, alkylsulfinyl, halo, alkoxy, and alkylthio;

$R^{211}$ and $R^{212}$ are independently selected from the group consisting of hydroxyalkyl and hydrido but at least one of $R^{211}$ and $R^{212}$ is other than hydrido; and $R^{213}$ is selected from the group consisting of hydrido and fluoro.

Examples of prodrug compounds disclosed in U.S. Pat. No. 6,613,790 (incorporated by reference) that are useful as Cox-2 inhibitors of the present invention include, but are not limited to, N-(2-hydroxyethyl)-4-[5-(4-methylphenyl)-3-(trifluoromethyl)-1H-pyrazol-1-yl]benzenesulfonamide, N,N-bis(2-hydroxyethyl)-4-[5-(4-methylphenyl)-3-(trifluoromethyl)-1H-pyrazol-1-yl]benzenesulfonamide, or pharmaceutically-acceptable salts thereof.

Cox-2 selective inhibitors such as sulfamoylheleroaryl pyrazole compounds that are described in U.S. Pat. No. 6,583,321 (incorporated by reference) may serve as Cox-2 inhibitors of the present invention. Such sulfamoylheleroaryl pyrazole compounds have the formula shown below:

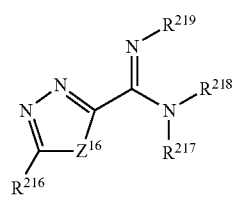

wherein:
$R^{214}$ is furyl, thiazolyl or oxazolyl;
$R^{215}$ is hydrogen, fluoro or ethyl; and
$X^{31}$ and $X^{32}$ are independently hydrogen or chloro.

Heteroaryl substituted amidinyl and imidazolyl compounds such as those described in U.S. Pat. No. 6,555,563 (incorporated by reference) are useful as Cox-2 selective inhibitors of the present invention. Such heteroaryl substituted amidinyl and imidazolyl compounds have the formula shown below:

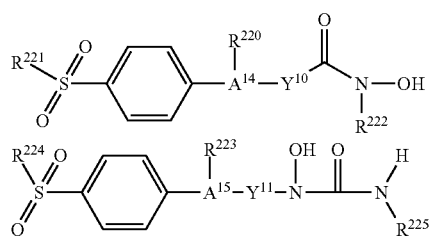

wherein:
$Z^{16}$ is O or S,
$R^{216}$ is optionally substituted aryl,
$R^{217}$ is aryl optionally substituted with aminosulfonyl, and
$R^{218}$ and $R^{219}$ cooperate to form an optionally substituted 5-membered ring.

Materials that can serve as Cox-2 selective inhibitors of the present invention include substituted hydroxamic acid derivatives that are described in U.S. Pat. No. 6,432,999 (incorporated by reference), U.S. Pat. No. 6,512,121 (incorporated by reference), and U.S. Pat. No. 6,515,014 (incorporated by reference). These compounds also act as inhibitors of the lipoxygenase-5 enzyme. Such substituted hydroxamic acid derivatives have the general formulas shown below in one of the following formulas:

Pyrazole substituted hydroxamic acid derivatives described in U.S. Pat. No. 6,432,999 have the formula shown above, wherein:

$A^{14}$ is pyrazolyl optionally substituted with a substituent selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl;

$Y^{10}$ is selected from lower alkenylene and lower alkynylene;

$R^{220}$ is a substituent selected from 5- and 6-membered heterocyclo, lower cycloalkyl, lower cycloalkenyl and aryl selected from phenyl, biphenyl and naphthyl, wherein $R^{220}$ is optionally substituted at a substitutable position with one or more substituents selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio;

$R^{221}$ is selected from lower alkyl and amino; and $R^{222}$ is selected from hydrido, lower alkyl, phenyl, 5- and 6-membered heterocyclo and lower cycloalkyl; or a pharmaceutically-acceptable salt thereof.

Pyrazole substituted hydroxamic acid derivatives described in U.S. Pat. No. 6,432,999 (incorporated by reference) may also have the formula shown in the above formula, wherein:

$A^{15}$ is pyrazolyl optionally substituted with a substituent selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl;

$Y^{11}$ is selected from lower alkylene, lower alkenylene and lower alkynylene;

$R^{223}$ is a substituent selected from 5- and 6-membered heterocyclo, lower cycloalkyl, lower cycloalkenyl and aryl selected from phenyl, biphenyl and naphthyl, wherein $R^{223}$ is optionally substituted at a substitutable position with one or more substituents selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio;

$R^{224}$ is selected from lower alkyl and amino; and $R^{225}$ is selected from hydrido, lower alkyl;

or a pharmaceutically-acceptable salt thereof.

Heterocyclo substituted hydroxamic acid derivatives described in U.S. Pat. No. 6,512,121 (incorporated by reference) have the formula shown in the above formula, wherein:

$A^{14}$ is a ring substituent selected from oxazolyl, furyl, pyrrolyl, thiazolyl, imidazolyl, isothiazolyl, isoxazolyl, cyclopentenyl, phenyl, and pyridyl; wherein $A^{14}$ is optionally substituted with a substituent selected from acyl, halo, hydroxy, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl;

$Y^{10}$ is lower alkylene, lower alkenylene, and lower alkynylene;

$R^{220}$ is a substituent selected from 5- and 6-membered heterocyclo, lower cycloalkyl, lower cycloalkenyl and aryl selected from phenyl, biphenyl and naphthyl, wherein $R^{220}$ is optionally substituted at a substitutable position with one or more substituents selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio;

$R^{221}$ is selected from lower alkyl and amino; and $R^{222}$ is selected from hydrido, lower alkyl, phenyl, 5- and 6-membered heterocyclo and lower cycloalkyl; or a pharmaceutically-acceptable salt thereof.

Heterocyclo substituted hydroxamic acid derivatives described in U.S. Pat. No. 6,512,121 (incorporated by reference) may also have the formula shown in the above formula, wherein:

$A^5$ is a ring substituent selected from oxazolyl, furyl, pyrrolyl, thiazolyl, imidazolyl, isothiazolyl, isoxazolyl, cyclopentenyl, phenyl, and pyridyl; wherein A is optionally substituted with a substituent selected from acyl, halo, hydroxy, lower alkyl, lower haloalkyl, oxo, cyano, nitro, carboxyl, lower alkoxy, aminocarbonyl, lower alkoxycarboryl, lower carboxyalkyl, lower cyanoalkyl, and lower hydroxyalkyl;

$Y^{11}$ is selected from lower alkyl, lower alkenyl and lower alkynyl;

$R^{223}$ is a substituent selected from 5- and 6-membered heterocyclo, lower cycloalkyl, lower cycloalkenyl and aryl selected from phenyl, biphenyl and naphthyl, wherein $R^{223}$ is optionally substituted at a substitutable position with one or more substituents selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitto, lower alkoxyalkyl, lower alkylsulfinyl, halo, lower alkoxy and lower alkylthio;

$R^{224}$ is selected from lower alkyl and amino; and $R^{225}$ is selected from hydrido and alkyl; or a pharmaceutically-acceptable salt thereof.

Thiophene substituted hydroxamic acid derivatives described in U.S. Pat. No. 6,515,014 (incorporated by reference) have the formula shown in the above formula, wherein:

$A^{14}$ is thienyl optionally substituted with a substituent selected from acyl, halo, hydroxy, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl;

$Y^{10}$ is ethylene, isopropylene, propylene, butylene, lower alkenylene, and lower alkynylene;

$R^{220}$ is a substituent selected from 5- and 6-membered heterocyclo, lower cycloalkyl, lower cycloalkenyl and aryl selected from phenyl, biphenyl and naphthyl, wherein $R^{220}$ is optionally substituted at a substitutable position with one or more substituents selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio;

$R^{221}$ is selected from lower alkyl and amino; and $R^{222}$ is selected from hydrido, lower alkyl, phenyl, 5- and 6-membered heterocyclo and lower cycloalkyl; or a pharmaceutically-acceptable salt thereof.

Thiophene substituted hydroxamic acid derivatives described in U.S. Pat. No. 6,515,014 (incorporated by reference) may also have the formula shown in the above formula, wherein:

$A^{15}$ is thienyl optionally substituted with a substituent selected from acyl, halo, hydroxy, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl;

$Y^{11}$ is selected from lower alkyl, lower alkenyl and lower alkynyl;

$R^{223}$ is a substituent selected from 5- and 6-membered heterocyclo, lower cycloalkyl, lower cycloalkenyl and aryl selected from phenyl, biphenyl and naphthyl, wherein $R^{223}$ is optionally substituted at a substitutable position with one or more substituents selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio;

$R^{224}$ is selected from lower alkyl and amino; and $R^{225}$ is selected from hydrido and alkyl; or a pharmaceutically-acceptable salt thereof.

Compounds that are useful as Cox-2 selective inhibitors of the present invention include pyrazolopyridine compounds that are described in U.S. Pat. No. 6,498,166 (incorporated by reference). Such pyrazolopyridine compounds have the formula shown below:

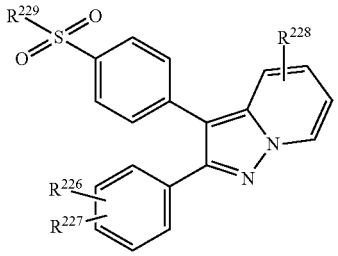

wherein:

$R^{226}$ and $R^{227}$ are independently selected from the group consisting of H, halogen, $C_1$-$C_6$ alkyl, $C_1$-$C_6$ alkoxy, and $C_1$-$C_6$ alkoxy substituted by one or more fluorine atoms;

$R^{228}$ is halogen, CN, $CONR^{230}R^{231}$, $CO_2H$, $CO_2C_1$-$C_6$ alkyl or $NHSO_2R^{230}$;

$R^{229}$ is $C_1$-$C_6$ alkyl or $NH_2$; and $R^{225}$ and $R^{225}$ are independently selected from the group consisting of H, $C_1$-$C_6$ alkyl, phenyl, phenyl substituted by one or more atoms or groups selected from the group consisting of halogen, $C_1$-$C_6$ alkyl, $C_1$-$C_6$ alkoxy, and $C_1$-$C_6$alkoxy substituted by one or more fluorine atoms, or a pharmaceutically acceptable salt, solvate, ester, or salt or solvate of such ester thereof.

Materials that are useful as Cox-2 selective inhibitors of the present invention include 4,5-diaryl-3(2H)-furanone derivatives that are described in U.S. Pat. No. 6,492,416 (incorporated by reference). Such 4,5-diaryl-3(2H)-furanone derivatives have the formula shown below:

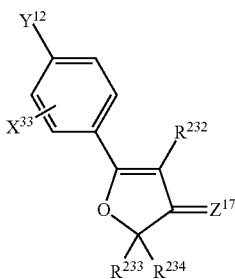

wherein:

$X^{33}$ represents halo, hydrido, or alkyl;

$Y^{12}$ represents alkylsulfonyl, aminosulfonyl, alkylsulfinyl, (N-acylamino)-sulfonyl, (N-alkylamino)sulfonyl, or alkylthio;

$Z^{17}$ represents oxygen or sulfur atom; $R^{223}$ and $R^{234}$ are selected independently from lower alkyl radicals; and $R^{232}$ represents a substituted or non-substituted aromatic group of 5 to 10 atoms;

or a pharmaceutically-acceptable salt thereof.

Cox-2 selective inhibitors that can be used in the present invention include 2-phenyl-1,2-benzisoselenazol-3(2H)-one derivatives and 2-phenylcarbomyl-phenylselenyl derivatives that are described in U.S. Pat. No. 6,492,416 (incorporated by reference). Such 2-phenyl-1,2-benzisoselenazol-3(2H)-one derivatives and 2-phenylcarbomyl-phenylselenyl derivatives have the formulas shown below in one of the following formulas:

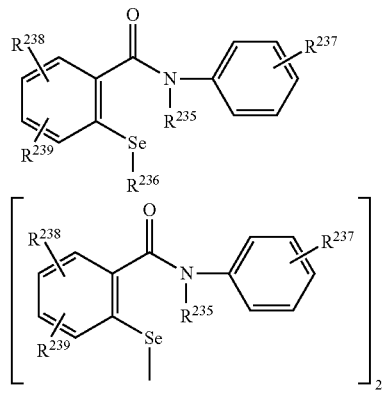

wherein:

$R^{235}$ is a hydrogen atom or an alkyl group having 1-3 carbon atoms;

$R^{236}$ is a hydrogen atom, a hydroxyl group, an organothiol group that is bound to the selenium atom by its sulfur atom, or $R^{235}$ and $R^{236}$ are joined to each other by a single bond;

$R^{237}$ is a hydrogen atom, a halogen atom, an alkyl group having 1-3 carbon atoms, an alkoxyl group having 1-3 carbon atoms, a trifluoromethyl group, or a nitro group;

$R^{238}$ and $R^{239}$ are identical to or different from each other, and each is a hydrogen atom, a halogen atom, an alkoxyl group having 1-4 carbon atoms, a trifluoromethyl group, or $R^{238}$ and $R^{239}$ are joined to each other to form a methylenedioxy group, a salt thereof, or a hydrate thereof.

Pyrones such as those disclosed in U.S. Pat. No. 6,465,509 (incorporated by reference) are also useful as Cox-2 inhibitors of the present invention. These pyrone compounds have the general formula shown below:

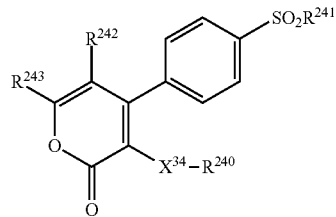

wherein:

$X^{34}$ is selected from the group consisting of:
(a) a bond,
(b) —(CH$_2$)$_m$—, wherein m 1 or 2,
(c) —C(O)—,
(d) —O—,
(e) —S—, and
(f) —N(R$^{244}$)—;

$R^{240}$ is selected from the group consisting of:
(a) C$_1$-C$_{10}$ alkyl, optionally substituted with 1-3 substituents independently selected from the group consisting of: hydroxy, halo, C$_1$-C$_{10}$ alkoxy, C$_1$-C$_{10}$alkylthio, and CN,
(b) phenyl or naphthyl, and
(c) heteroaryl, which is comprised of a monocyclic aromatic ring of 5 atoms having one hetero atom which is S, O or N, and optionally 1, 2, or 3 additional N atoms; or
a monocyclic ring of 6 atoms having one hetero atom which is N, and optionally 1, 2, or 3 additional N atoms, wherein groups (b) and (c) above are each optionally substituted with 1-3 substituents independently selected from the group consisting of: halo, C$_1$-C$_{10}$alkoxy, C$_1$-C$_{10}$alkylthio, CN, C$_1$-C$_{10}$alkyl, optionally substituted to its maximum with halo, and N$_3$;

$R^{241}$ is selected from the group consisting of
(a) C$_1$-C$_6$ alkyl, optionally substituted to its maximum with halo,
(b) NH$_2$, and
(c) NHC(O)C$_1$-C$_{10}$alkyl, optionally substituted to its maximum with halo;

$R^{242}$ and $R^{243}$ are each independently selected from the group consisting of: hydrogen, halo, and C$_1$-C$_6$ alkyl, optionally substituted to its maximum with halo; and $R^{244}$ is selected from the group consisting of: hydrogen and C$_1$-C$_6$ alkyl, optionally substituted to its maximum with halo.

Examples of pyrone compounds that are useful as Cox-2 selective inhibitors of the present invention include, but are not limited to:
4-(4-Methylsulfonyl)phenyl-3-phenyl-pyran-2-one,
3-(4-Fluorophenyl)-6-methyl-4-(4-methylsulfonyl)phenyl-pyran-2-one,
3-(3-Fluorophenyl)-6-methyl-4-(4-methylsulfonyl)phenyl-pyran-2-one,
6-Methyl-4-(4-methylsulfonyl)phenyl-3-phenyl-pyran-2-one,
6-Difluoromethyl-4-(4-methylsulfonyl)phenyl-3-phenyl-pyran-2-one,
6-Fluoromethyl-4-(4-methylsulfonyl)phenyl-3-phenyl-pyran-2-one,
6-Methyl-4-(4-methylsulfonyl)phenyl-3-phenylthio-pyran-2-one,
6-Methyl-4-(4-methylsulfonyl)phenyl-3-phenoxy-pyran-2-one,
6-Methyl-4-(4-methylsulfonyl)phenyl-3-pyridin-3-yl-pyran-2-one,
3-Isopropylthio-6-methyl-4-(4-methylsulfonyl)phenyl-pyran-2-one,
4-(4-Methylsulfonyl)phenyl)-3-phenylthio-6-trifluoromethyl-pyran-2-one,
3-Isopropylthio-4-(4-methylsulfonyl)phenyl-6-trifluoromethyl-pyran-2-one,
4-(4-Methylsulfonyl)phenyl-3-phenyl-6-(2,2,2-trifluoroethyl)-pyran-2-one, and
3-(3-Hydroxy-3-methylbutyl)-6-methyl-4-(4-methylsulfonyl)phenyl-pyran-2-one.

Organically synthesized or purified from plant sources, free-B-ring flavonoids such as those described in U.S. Published Application No. 2003/0165588 (incorporated by reference), are useful as Cox-2 selective inhibitors of the present invention. Such free-B-ring flavonoids have the general structure:

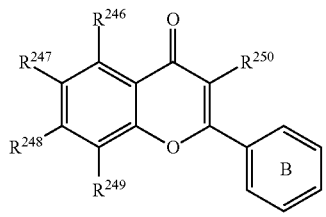

wherein:

$R^{246}$, $R^{247}$, $R^{248}$, $R^{249}$, and $R^{250}$ are independently selected from the group consisting of: —H, —OH, —SH, —OR, —SR, —NH$_2$, —NHR$^{245}$, —N(R$^{245}$)$_2$, —N(R$^{245}$)$_3$ $^+$X$^{35-}$, a carbon, oxygen, nitrogen or sulfur, glycoside of a single or a combination of multiple sugars including, aldopentoses, methyl-aldopentose, aldohexoses, ketohexose and their chemical derivatives thereof; wherein $R^{245}$ is an alkyl group having between 1-10 carbon atoms; and $X^{35}$ is selected from the group of pharmaceutically acceptable counter anions including, hydroxyl, chloride, iodide, sulfate, phosphate, acetate, fluoride and carbonate.

Heterocyclo-alkylsulfonyl pyrazoles such as those described in European Patent Application No. EP 1312367 are useful as Cox-2 selective inhibitors of the present invention. Such heterocyclo-alkylsulfonyl pyrazoles have the general formula shown below:

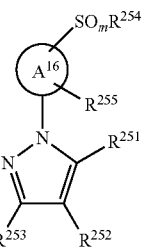

or a pharmaceutically acceptable salt thereof, wherein: the ring of the formula (R$^{255}$)-A-(SO$_m$R$^{254}$) is selected from the group consisting of:

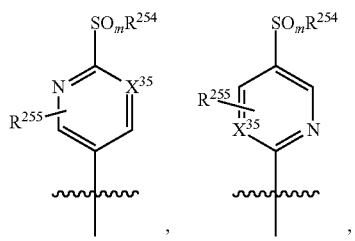

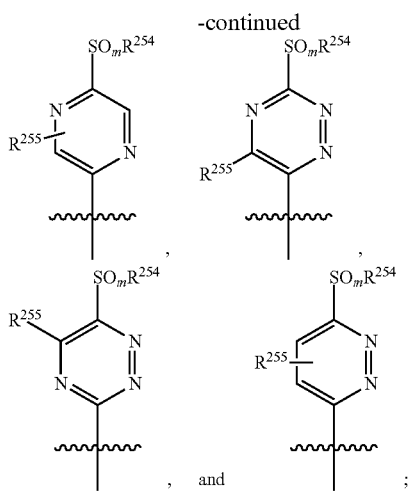

m is 0, 1 or 2;

$X^{35}$ is >$CR^{255}$ or >N; $R^{251}$ is a radical selected from the group consisting of H, $NO_2$, CN, ($C_1$-$C_6$)alkyl, ($C_1$-$C_6$)alkyl-$SO_2$—, ($C_6$-$C_{10}$)aryl-$SO_2$—, H—(C=O)—, ($C_1$-$C_6$)alkyl-(C=O)—, ($C_1$-$C_6$)alkyl-)-(C=O)—, ($C_1$-$C_9$)heteroaryl-(C=O)—, ($C_1$-$C_9$)heterocyclyl-(C=O)—, $H_2N$—(C=O)—, ($C_1$-$C_6$)alkyl-NH—(C=O)—, [($C_1$-$C_6$)alkyl]$_2$-N—(C=O)—, [($C_6$-$C_{10}$)aryl]$_2$-NH—(C=O)—, [($C_1$-$C_6$)alkyl]-[(($C_6$-$C_{10}$)aryl-N]—(C=O)—, HO—NH—(C=O)—, and ($C_1$-$C_6$)alkyl-O—NH—(C=O)—;

$R^{252}$ is a radical selected from the group consisting of H, —$NO_2$, —CN, ($C_2$-$C_6$)alkenyl, ($C_2$-$C_6$)alkynyl, ($C_3$-$C_7$)cycloalkyl, ($C_6$-$C_{10}$)aryl, ($C_1$-$C_9$)heteroaryl, ($C_1$-$C_9$)heterocyclyl, ($C_1$-$C_6$)alkyl-O—, ($C_3$-$C_7$)cycloalkyl-O—, ($C_6$-$C_{10}$)aryl-O—, ($C_1$-$C_9$)heteroaryl-O—, ($C_6$-$C_9$)heterocyclyl-O—, H—(C=O)—, ($C_1$-$C_6$)alkyl-(C=O)—, ($C_3$-$C_7$)cycloalkyl-(C=O)—, ($C_6$-$C_{10}$)aryl-(C=O)—, ($C_1$-$C_9$)heteroaryl-(C=O)—, ($C_1$-$C_9$)heterocyclyl-(C=O)—, ($C_1$-$C_6$)alkyl-O—(C=O)—, ($C_3$-$C_7$)cycloalkyl-O—(C=O)—, ($C_6$-$C_{10}$)aryl-O—(C=O)—, ($C_1$-$C_9$)heteroaryl-O—(C=O)—, ($C_1$-$C_9$)heterocyclyl-O—(C=O)—, ($C_1$-$C_6$)alkyl-(C=O)—O—, (C3-$C_7$)cycloalkyl-(C=O)—O—, ($C_6$-$C_{10}$)aryl-(C=O)—O—, ($C_1$-$C_9$)heteroaryl-(C=O)—O—, ($C_1$-$C_9$)heterocyclyl-(C=O)—O—, ($C_1$-$C_6$)alkyl-(C=O)—NH—, ($C_3$-$C_7$)cycloalkyl-(C=O)—NH—, ($C_6$-$C_{10}$aryl-(C=O)—NH—, ($C_1$-$C_9$)heteroaryl-(C=O)—NH—, ($C_1$-$C_9$)heterocyclyl-(C=O)—NH—, ($C_1$-$C_6$)alkyl-O—(C=O)—NH—, ($C_1$-$C_6$)alkyl-NH—, [($C_1$-$C_6$)alkyl]$_2$-N—, ($C_3$-$C_7$)cycloalkyl-NH—. [($C_3$-$C_7$)cycloalkyl]$_2$-N—, [($C_6$-$C_{10}$)aryl]-NH—, [($C_6$-$C_{10}$)aryl]$_2$-N—, [($C_1$-$C_6$)alkyl]-[(($C_6$-$C_{10}$)aryl)-N]—, [($C_1$-$C_9$)heteroaryl]-NH—, [($C_1$-$C_9$)heteroaryl]$_2$-N—, [($C_1$-$C_9$)heterocycly]-NH—, [($C_1$-$C_9$)heterocyclyl]$_2$-N—, $H_2N$—(C=O)—, HO—NH—(C=O)—, ($C_1$-$C_6$)alkyl-O—NH—(C=O)—, [($C_1$-$C_6$)alkyl]-NH—(C=O)—, [($C_1$-$C_6$)alkyl]$_2$-N—(C=O)—, [($C_3$-$C_7$)cycloalkyl]-NH—(C=O)—, [($C_3$-$C_7$)cycloalkyl]$_2$-N—(C=O)—, [($C_6$-$C_{10}$)aryl]-NH—(C=O)—, [($C_6$-$C_{10}$aryl]$_2$-N—(C=O)—, [($C_1$-$C_6$)alkyl]-[(($C_6$-$C_{10}$)aryl)-N]—(C=O)—, [($C_1$-$C_9$)heteroaryl]-NH—(C=O)—, [($C_1$-$C_9$)heteroaryl]$_2$-N—(O=O)—, [($C_1$-$C_9$)heterocyclyl]-NH—(C=O)—, ($C_1$-$C_6$)alkyl-S— and ($C_1$-$C_6$)alkyl optionally substituted by one —OH substituent or by one to four fluoro substituents;

$R^{253}$ is a saturated (3- to 4-membered)-heterocyclyl ring radical; or a saturated, partially saturated or aromatic (7- to 9-membered)-heterocyclyl ring radical;

wherein said saturated (3- to 4-membered)-heterocyclyl ring radical or said saturated, partially saturated or aromatic (7- to 9-membered)-heterocyclyl ring radical; may optionally contain one to four ring heteroatoms independently selected from the groups consisting of —N=, —NH—, —O—, and —S—;

wherein said saturated (3- to 4-membered)-heterocyclyl ring radical; or said saturated, partially saturated or aromatic (7- to 9-membered)-heterocyclyl ring radical; may optionally be substituted on any ring carbon atom by one to three substituents per ring independently selected from the group consisting of halo, —OH, —CN, —$NO_2$, ($C_2$-$C_6$)alkenyl, ($C_2$-$C_6$)alkynyl, ($C_3$-$C_7$)cycloalkyl, ($C_6$-$C_{10}$)aryl, ($C_2$-$C_9$)heterocyclyl, ($C_1$-$C_6$)alkyl-O—, H—(C=O)—, ($C_1$-$C_6$)alkyl-(C=O)—, HO—(C=O)—, ($C_1$-$C_6$)alkyl-O—(C=O)—, —$NH_2$, ($C_1$-$C_6$)alkyl-NH—, [($C_1$-$C_6$)alkyl]$_2$-N—, ($C_3$-$C_7$)cycloalkyl-NH—, ($C_6$-$C_{10}$)aryl-NH—, [($C_1$-$C_6$)alkyl]-[(($C_6$-$C_{10}$)aryl)-N]—, ($C_1$-$C_9$)heteroaryl-NH—, $H_2N$—(C=O)—[($C_1$-$C_6$)alkyl]-NH—(C=O)—, [($C_1$-$C_6$)alkyl]$_2$-N—(C=O)—, [($C_6$-$C_{10}$)aryl]-NH—(C=O)—, [($C_1$-$C_6$)alkyl]-[(($C_6$-$C_{10}$)aryl)-N]—(C=O)—, ($C_1$-$C_6$)alkyl-O—NH—(C=O)—, ($C_1$-$C_6$)alkyl-(C=O)—HN—, ($C_1$-$C_6$)alkyl-(C=O)—[($C_1$-$C_6$)alkyl-N]—, —SH, ($C_1$-$C_6$)alkyl-S—, ($C_1$-$C_6$)alkyl-(S=O)—, ($C_1$-$C_6$)alkyl-$SO_2$— and ($C_1$-$C_6$)alkyl optionally substituted with one to fourfluoro moieties;

wherein said saturated (3- to 4-membered)-heterocyclyl ring radical; or said saturated, partially saturated or aromatic (7- to 9-membered)-heterocyclyl ring radical; may also optionally be substituted on any ring nitrogen atom by one to three substituents per ring independently selected from the group consisting of ($C_3$-$C_7$)cycloalkyl, ($C_6$-$C_{10}$)aryl, ($C_2$-$C_9$)heterocyclyl, H—(C=O)—, ($C_1$-$C_6$)alkyl-(C=O)—, ($C_1$-$C_6$)alkyl-O—(C=O)—, $H_2N$—(C=O)—, [($C_1$-$C_6$)alkyl]-NH—(C=O)—, [($C_1$-$C_6$)alkyl]$_2$-N—(C=O)—, [($C_6$-$C_{10}$)aryl]-NH—(C=O)—, [($C_1$-$C_6$)alkyl]-[(($C_6$-$C_{10}$)aryl)-N]—(C=O)—, ($C_1$-$C_6$)alkyl-O—NH—(C=O)—, and ($C_1$-$C_6$)alkyl optionally substituted with one to four fluoro moieties;

$R^{254}$ is an ($C_1$-$C_6$)alkyl radical optionally substituted by one to four fluoro substituents; and $R^{255}$ is a radical selected from the group consisting of H, halo, —OH, ($C_1$-$C_6$)alkyl-O—, ($C_2$-$C_6$)alkenyl, ($C_2$-$C_6$)alkynyl, ($C_3$-$C_7$)cycloalkyl, —CN, H—(C=O)—, ($C_1$-$C_6$)alkyl-(C=O)—, ($C_1$-$C_6$)alkyl-(C=O)—O—, HO—(C=O)—, ($C_1$-$C_6$)alkyl-O—(C=O)—, ($C_1$-$C_6$)alkyl-NH—. [($C_1$-$C_6$)alkyl]$_2$-N—, ($C_3$-$C_7$)cycloalkyl-NH—, ($C_6$-$C_{10}$)aryl-NH—, [($C_1$-$C_6$)alkyl]-[(($C_6$-$C_{10}$)aryl)-N]—, ($C_1$-$C_9$)heteroaryl-NH—, $H_2N$—(C=O)—, ($C_1$-$C_6$)alkyl-NH—(C=O)—. [($C_1$-$C_6$)alkyl]$_2$-N—(C=O)—, ($C_6$-$C_{10}$)aryl-(C=O)—, [($C_1$-$C_6$)alkyl]-[(($C_6$-$C_{10}$)aryl)-N]—(C=O)—, ($C_1$-$C_6$)alkyl-O—NH—(C=O)—, ($C_1$-$C_6$)alkyl-S—, and ($C_1$-$C_6$)alkyl optionally substituted by one to four fluoro substituents.

2-phenylpyran-4-one derivatives such as those described in U.S. Pat. No. 6,518,303 (incorporated by reference) are also useful as Cox-2 selective inhibitors of the present invention. Such 2-phenylpyran-4-one derivatives have the general formula shown below:

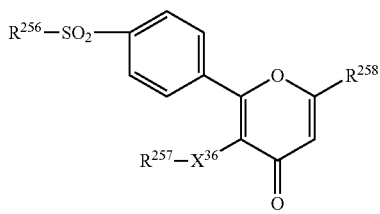

wherein:

$R^{256}$ represents an alkyl or —$NR^{259}R^{260}$ group, wherein $R^{259}$ and $R^{260}$ each independently represents a hydrogen atom or an alkyl group;

$R^{257}$ represents an alkyl, $C_3$-$C_7$ cycloalkyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^{258}$ represents a methyl, hydroxymethyl, alkoxymethyl, C3-$C_7$cycloalkoxymethyl, benzyloxymethyl, hydroxycarbonyl, nitrile, trifluoromethyl or difluoromethyl group or a $CH_2$—$R^{26}1$ group wherein $R^{26}1$ represents an alkyl group; and $X^{36}$ represents a single bond, an oxygen atom, a sulfur atom or a methylene group;

or a pharmaceutically acceptable salt thereof.

Examples of 2-phenylpyran-4-one derivatives useful in the present invention include, but are not limited to:

3-(4-fluorophenyl)-2-(4-methanesulfonylphenyl)-6-methylpyran-4-one, 3-(2-fluorophenyl)-2-(4-methanesulfonylphenyl)-6-methylpyran-4-one, 3-(4-chlorophenyl)-2-(4-methanesulfonylphenyl)-6-methylpyran-4-one, 3-(4-bromophenyl)-2-(4-methylsulfonylphenyl)-6-methylpyran-4-one, 3-(2,4-difluorophenyl)-2-(4-methanesulfonylphenyl)-6-methylpyran-4-one, 3-(3,4-dichlorophenyl)-2-(4-methanesulfonylphenyl)-6-methylpyran-4-one, 3-(3-chloro-4-methylphenyl)-2-(4-methanesulfonylphenyl)-6-methylpyran-4-one, 2-(4-methanesulfonylphenyl)-6-methyl-3-phenoxypyran-4-one, 3-(4-fluorophenoxy)-2-(4-methanesulfonylphenyl)-6-methylpyran-4-one, 3-(2-fluorophenoxy)-2-(methanesulfonylphenyl)-6-methylpyran-4-one, 3-(4-chlorophenoxy)-2-(methanesulfonylphenyl)-6-methylpyran-4-one, 3-(2-chlorophenoxy)-2-(methanesulfonylphenyl)-6-methylpyran-4-one, 3-(4-bromophenoxy)-2-(4-methanesulfonylphenyl)-6-methylpyran-4-one, 2-(4-methanesulfonylphenyl)-6-methyl-3-(4-methylphenoxy)pyran-4-one, 3-(2,4-difluorophenoxy)-2-(4-methanesulfonylphenyl)-6-methylpyran-4-one, 3-(2,5-difluorophenoxy)-2-(methanesulfonylphenyl)-6-methylpyran-4-one, 3-(4-chlorophenyl)-2-(4-methanesulfonylphenyl)-6-methoxymethylpyran-4-one, 3-(4-chlorophenyl)-6-difluoromethyl-2-(4-methanesulfonylphenyl)pyran-4-one, or pharmaceutically acceptable salts thereof.

Cox-2 selective inhibitors that are useful in the subject method and compositions can include the compounds that are described in U.S. Pat. No. 6,472,416 (sulfonylphenylpyrazoles); U.S. Pat. No. 6,451,794 (2,3-diaryl-pyrazolo [l1,5-b]pyridazines); U.S. Pat. Nos. 6,169,188, 6,020,343, and 5,981,576 ((methylsulfonyl)phenyl furanones); U.S. Pat. No. 6,222,048 (diaryl-2-(5H)-furanones); U.S. Pat. No. 6,057,319 (3,4-diaryl-2-hydroxy-2,5-dihydrofurans); U.S. Pat. No. 6,046,236 (carbocyclic sulfonamides); U.S. Pat. Nos. 6,002,014 and 5,945,539 (oxazole derivatives); and U.S. Pat. Nos. 6,359,182 and 6,538,116 (C-nitroso compounds) (all of which are incorporated by reference).

Examples of specific compounds that are useful as Cox-2 selective inhibitors include, without limitation:

a1) 8-acetyl-3-(4-fluorophenyl)-2-(4-methylsulfonyl)phenyl-imidazo(1,2-a)pyridine;

a2) 5,5-dimethyl-4-(4-methylsulfonyl)phenyl-3-phenyl-2-(5H)-furanone;

a3) 5-(4-fluorophenyl)-1-[4-(methylsulfonyl)phenyl]-3-(trifluoromethyl)pyrazole;

a4) 4-(4-fluorophenyl)-5-[4-(methylsulfonyl)phenyl]-1-phenyl-3-(trifluoromethyl)pyrazole;

a5) 4-(5-(4-chlorophenyl)-3-(4-methoxyphenyl)-1H-pyrazol-1-yl)benzenesulfonamide a6) 4-(3,5-bis(4-methylphenyl)-1H-pyrazol-1-yl)benzenesulfonamide;

a7) 4-(5-(4-chlorophenyl)-3-phenyl-1H-pyrazol-1-yl)benzenesulfonamide;

a8) 4-(3,5-bis(4-methoxyphenyl)-1H-pyrazol-1-yl)benzenesulfonamide;

a9) 4-(5-(4-chlorophenyl)-3-(4-methylphenyl)-1H-pyrazol-1-yl)benzenesulfonamide;

a10) 4-(5-(4-chlorophenyl)-3-(4-nitrophenyl)-1H-pyrazol-1-yl)benzenesulfonamide;

b1) 4-(5-(4-chlorophenyl)-3-(5-chloro-2-thienyl)-1H-pyrazol-1-yl)benzenesulfonamide;

b2) 4-(4-chloro-3,5-diphenyl-1H-pyrazol-1-yl)benzenesulfonamide b3) 4-[5-(4-chlorophenyl)-3-(trifluoromethyl)-1H-pyrazol-1-yl]benzenesulfonamide;

b4) 4-[5-phenyl-3-(trifluoromethyl)-1H-pyrazol-1-yl]benzenesulfonamide;

b5) 4-[5-(4-fluorophenyl)-3-(trifluoromethyl)-1H-pyrazol-1-yl]benzenesulfonamide;

b6) 4-[5-(4-methoxyphenyl)-3-(trifluoromethyl)-1H-pyrazol-1-yl]benzenesulfonamide;

b7) 4-[5-(4-chlorophenyl)-3-(difluoromethyl)-1H-pyrazol-1-yl]benzenesulfonamide;

b8) 4-[5-(4-methylphenyl)-3-(trifluoromethyl)-1H-pyrazol-1-yl]benzenesulfonamide;

b9) 4-[4-chloro-5-(4-chlorophenyl)-3-(trifluoromethyl)-1H-pyrazol-1-yl]benzenesulfonamide;

b10) 4-[3-(difluoromethyl)-5-(4-methylphenyl)-1H-pyrazol-1-yl]benzenesulfonamide;

c1) 4-[3-(difluoromethyl)-5-phenyl-1H-pyrazol-1-yl]benzenesulfonamide;

c2) 4-[3-(difluoromethyl)-5-(4-methoxyphenyl)-1H-pyrazol-1-yl]benzenesulfonamide;

c3) 4-[3-cyano-5-(4-fluorophenyl)-1H-pyrazol-1-yl]benzenesulfonamide;

c4) 4-[3-(difluoromethyl)-5-(3-fluoro-4-methoxyphenyl)-1H-pyrazol-1-yl]benzenesulfonamide;

c5) 4-[5-(3-fluoro-4-methoxyphenyl)-3-(trifluoromethyl)-1H-pyrazol-1-yl]benzenesulfonamide;

c6) 4-[4-chloro-5-phenyl-1H-pyrazol-1-yl]benzenesulfonamide;
c7) 4-[5-(4-chlorophenyl)-3-(hydroxymethyl)-1H-pyrazol-1-yl]benzenesulfonamide;
c8) 4-[5-(4-(N,N-dimethylamino)phenyl)-3-(trifluoromethyl)-1H-pyrazol-1-yl]benzenesulfonamide;
c9) 5-(4-fluorophenyl)-6-[4-(methylsulfonyl)phenyl]spiro[2.4]hept-5-ene;
c10) 4-[6-(4-fluorophenyl)spiro[2.4]hept-5-en-5-yl]benzenesulfonamide;
d1) 6-(4-fluorophenyl)-7-[4-(methylsulfonyl)phenyl]spiro[3.4]oct-6-ene;
d2) 5-(3-chloro-4-methoxyphenyl)-6-[4-(methylsulfonyl)phenyl]spiro[2.4]hept-5-ene;
d3) 4-[6-(3-chloro-4-methoxyphenyl)spiro[2.4]hept-5-en-5-yl]benzenesulfonamide;
d4) 5-(3,5-dichloro-4-methoxyphenyl)-6-[4-(methylsulfonyl)phenyl]spiro[2.4]hept-5-ene;
d5) 5-(3-chloro-4-fluorophenyl)-6-[4-(methylsulfonyl)phenyl]spiro[2.4]hept-5-ene;
d6) 4-[6-(3,4-dichlorophenyl)spiro[2.4]hept-5-en-5-yl]benzenesulfonamide;
d7) 2-(3-chloro-4-fluorophenyl)-4-(4-fluorophenyl)-5-(4-methylsulfonylphenyl)thiazole;
d8) 2-(2-chlorophenyl)-4-(4-fluorophenyl)-5-(4-methylsulfonylphenyl)thiazole;
d9) 5-(4-fluorophenyl)-4-(4-methylsulfonylphenyl)-2-methylthiazole;
d10) 4-(4-fluorophenyl)-5-(4-methylsulfonylphenyl)-2-trifluoromethylthiazole;
e1) 4-(4-fluorophenyl)-5-(4-methylsulfonylphenyl)-2-(2-thienyl)thiazole;
e2) 4-(4-fluorophenyl)-5-(4-methylsulfonylphenyl)-2-benzylaminothiazole;
e3) 4-(4-fluorophenyl)-5-(4-methylsulfonylphenyl)-2-(1-propylamino)thiazole;
e4) 2-[(3,5-dichlorophenoxy)methyl]-4-(4-fluorophenyl)-5-[4-(methylsulfonyl)phenyl]thiazole;
e5) 5-(4-fluorophenyl)-4-(4-methylsulfonylphenyl)-2-trifluoromethylthiazole;
e6) 1-methylsulfonyl-4-[1,1-dimethyl-4-(4-fluorophenyl)cyclopenta-2,4-dien-3-yl]benzene;
e7) 4-[4-(4-fluorophenyl)-1,1-dimethylcyclopenta-2,4-dien-3-yl]benzenesulfonamide;
e8) 5-(4-fluorophenyl)-6-[4-(methylsulfonyl)phenyl]spiro[2.4]hepta-4,6-diene;
e9) 4-[6-(4-fluorophenyl)spiro[2.4]hepta-4,6-dien-5-yl]benzenesulfonamide;
e10) 6-(4-fluorophenyl)-2-methoxy-5-[(4-methylsulfonyl)phenyl]-pyridine-3-carbonitrile;
f1) 2-bromo-6-(4-fluorophenyl)-5-[4-(methylsulfonyl)phenyl]-pyridine-3-carbonitrile;
f2) 6-(4-fluorophenyl)-5-[4-(methylsulfonyl)phenyl]-2-phenyl-pyridine-3-carbonitrile;
f3) 4-[2-(4-methylpyridin-2-yl)-4-(trifluoromethyl)-1H-imidazol-1-yl]benzenesulfonamide;
f4) 4-[2-(5-methylpyridin-3-yl)-4-(trifluoromethyl)-1H-imidazol-1-yl]benzenesulfonamide;
f5) 4-[2-(2-methylpyridin-3-yl)-4-(trifluoromethyl)-1H-imidazol-1-yl]benzenesulfonamide;
f6) 3-[1-[4-(methylsulfonyl)phenyl]-4-(trifluoromethyl)-1H-imidazol-2-yl]pyridine;
f7) 2-[1-[4-(methylsulfonyl)phenyl-4-(trifluoromethyl)-1H-imidazol-2-yl]pyridine;
f8) 2-methyl-4-[1-[4-(methylsulfonyl)phenyl-4-(trifluoromethyl)-1H-imidazol-2-yl]pyridine;
f9) 2-methyl-6-[1-[4-(methylsulfonyl)phenyl-4-(trifluoromethyl)-1H-imidazol-2-yl]pyridine;
f10) 4-[2-(6-methylpyridin-3-yl)-4-(trifluoromethyl)-1H-imidazol-1-yl]benzenesulfonamide;
g1) 2-(3,4-difluorophenyl)-1-[4-(methylsulfonyl)phenyl]-4-(trifluoromethyl)-1H-imidazole;
g2) 4-[2-(4-methylphenyl)-4-(trifluoromethyl)-1H-imidazol-1-yl]benzenesulfonamide;
g3) 2-(4-chlorophenyl)-1-[4-(methylsulfonyl)phenyl]-4-methyl-1H-imidazole;
g4) 2-(4-chlorophenyl)-1-[4-(methylsulfonyl)phenyl]-4-phenyl-1H-imidazole;
g5) 2-(4-chlorophenyl)-4-(4-fluorophenyl)-1-[4-(methylsulfonyl)phenyl]-1H-imidazole;
g6) 2-(3-fluoro-4-methoxyphenyl)-1-[4-(methylsulfonyl)phenyl-4-(trifluoromethyl)-1H-imidazole;
g7) 1-[4-(methylsulfonyl)phenyl]-2-phenyl-4-trifluoromethyl-1H-imidazole;
g8) 2-(4-methylphenyl)-1-[4-(methylsulfonyl)phenyl]-4-trifluoromethyl-1H-imidazole;
g9) 4-[2-(3-chloro-4-methylphenyl)-4-(trifluoromethyl)-1H-imidazol-1-yl]benzenesulfonamide;
g10) 2-(3-fluoro-5-methylphenyl)-1-[4-(methylsulfonyl)phenyl]-4-(trifluoromethyl)-1H-imidazole;
h1) 4-[2-(3-fluoro-5-methylphenyl)-4-(trifluoromethyl)-1H-imidazol-1-yl]benzenesulfonamide;
h2) 2-(3-methylphenyl)-1-[4-(methylsulfonyl)phenyl]-4-trifluoromethyl-1H-imidazole;
h3) 4-[2-(3-methylphenyl)-4-trifluoromethyl-1H-imidazol-1-yl]benzenesulfonamide;
h4) 1-[4-(methylsulfonyl)phenyl]-2-(3-chlorophenyl)-4-trifluoromethyl-1H-imidazole;
h5) 4-[2-(3-chlorophenyl)-4-trifluoromethyl-1H-imidazol-1-yl]benzenesulfonamide;
h6) 4-[2-phenyl-4-trifluoromethyl-1H-imidazol-1-yl]benzenesulfonamide;
h7) 4-[2-(4-methoxy-3-chlorophenyl)-4-trifluoromethyl-1H-imidazol-1-yl]benzenesulfonamide;
h8) 1-allyl-4-(4-fluorophenyl)-3-[4-(methylsulfonyl)phenyl]-5-(trifluoromethyl)-1H-pyrazole;
h9) 4-[1-ethyl-4-(4-fluorophenyl)-5-(trifluoromethyl)-1H-pyrazol-3-yl]benzenesulfonamide;
i1) N-phenyl-[4-(4-fluorophenyl)-3-[4-(methylsulfonyl)phenyl]-5-(trifluoromethyl)-1H-pyrazol-1-yl]acetamide;
i2) ethyl [4-(4-fluorophenyl)-3-[4-(methylsulfonyl)phenyl]-5-(trifluoromethyl)-1H-pyrazol-1-yl]acetate;
i3) 4-(4-fluorophenyl)-3-[4-(methylsulfonyl)phenyl]-1-(2-phenylethyl)-1H-pyrazole;
i4) 4-(4-fluorophenyl)-3-[4-(methylsulfonyl)phenyl]-1-(2-phenylethyl)-5-(trifluoromethyl)pyrazole;
i5) 1-ethyl-4-(4-fluorophenyl)-3-[4-(methylsulfonyl)phenyl]-5-(trifluoromethyl)-1H-pyrazole;
i6) 5-(4-fluorophenyl)-4-(4-methylsulfonylphenyl)-2-trifluoromethyl-1H-imidazole;
i7) 4-[(methylsulfonyl)phenyl]-5-(2-thiophenyl)-2-(trifluoromethyl)-1H-imidazole;
i8) 5-(4-fluorophenyl)-2-methoxy-4-[4-(methylsulfonyl)phenyl]-6-(trifluoromethyl)pyridine;
i9) 2-ethoxy-5-(4-fluorophenyl)-4-[4-(methylsulfonyl)phenyl]-6-(trifluoromethyl)pyridine;
i10) 5-(4-fluorophenyl)-4-[4-(methylsulfonyl)phenyl]-2-(2-propynyloxy)-6-(trifluoromethyl)pyridine;
j1) 2-bromo-5-(4-fluorophenyl)-4-[4-(methylsulfonyl)phenyl]-6-(trifluoromethyl)pyridine;
j2) 4-[2-(3-chloro-4-methoxyphenyl)-4,5-difluorophenyl]benzenesulfonamide;

j3) 1-(4-fluorophenyl)-2-[4-(methylsulfonyl)phenyl]benzene;
j4) 5-difluoromethyl-4-(4-methylsulfonylphenyl)-3-phenylisoxazole;
j5) 4-[3-ethyl-5-phenylisoxazol-4-yl]benzenesulfonamide;
j6) 4-[5-difluoromethyl-3-phenylisoxazol-4-yl]benzenesulfonamide;
j7) 4-[5-hydroxymethyl-3-phenylisoxazol-4-yl]benzenesulfonamide;
j8) 4-[5-methyl-3-phenyl-isoxazol-4-yl]benzenesulfonamide;
j9) 1-[2-(4-fluorophenyl)cyclopenten-1-yl]-4-(methylsulfonyl)benzene;
j10) 1-[2-(4-fluoro-2-methylphenyl)cyclopenten-1-yl]-4-(methylsulfonyl)benzene;
k1) 1-[2-(4-chlorophenyl)cyclopenten-1-yl]-4-(methylsulfonyl)benzene;
k2) 1-[2-(2,4-dichlorophenyl)cyclopenten-1-yl]-4-(methylsulfonyl)benzene;
k3) 1-[2-(4-trifluoromethylphenyl)cyclopenten-1-yl]-4-(methylsulfonyl)benzene;
k4) 1-[2-(4-methylthiophenyl)cyclopenten-1-yl]-4-(methylsulfonyl)benzene;
k5) 1-[2-(4-fluorophenyl)-4,4-dimethylcyclopenten-1-yl]-4-(methylsulfonyl)benzene;
k6) 4-[2-(4-fluorophenyl)-4,4-dimethylcyclopenten-1-yl]benzenesulfonamide;
k7) 1-[2-(4-chlorophenyl)-4,4-dimethylcyclopenten-1-yl]-4-(methylsulfonyl)benzene;
k8) 4-[2-(4-chlorophenyl)-4,4-dimethylcyclopenten-1-yl]benzenesulfonamide;
k9) 4-[2-(4-fluorophenyl)cyclopenten-1-yl]benzenesulfonamide;
k10) 4-[2-(4-chlorophenyl)cyclopenten-1-yl]benzenesulfonamide;
l1) 1-[2-(4-methoxyphenyl)cyclopenten-1-yl]-4-(methylsulfonyl)benzene;
l2) 1-[2-(2,3-difluorophenyl)cyclopenten-1-yl]-4-(methylsulfonyl)benzene;
l3) 4-[2-(3-fluoro-4-methoxyphenyl)cyclopenten-1-yl]benzenesulfonamide;
l4) 1-[2-(3-chloro-4-methoxyphenyl)cyclopenten-1-yl]-4-(methylsulfonyl)benzene;
l5) 4-[2-(3-chloro-4-fluorophenyl)cyclopenten-1-yl]benzenesulfonamide;
l6) 4-[2-(2-methylpyridin-5-yl)cyclopenten-1-yl]benzenesulfonamide;
l7) ethyl 2-[4-(4-fluorophenyl)-5-[4-(methylsulfonyl)phenyl]oxazol-2-yl]-2-benzyl-acetate;
l8) 2-[4-(4-fluorophenyl)-5-[4-(methylsulfonyl)phenyl]oxazol-2-yl]acetic acid;
l9) 2-(tert-butyl)-4-(4-fluorophenyl)-5-[4-(methylsulfonyl)phenyl]oxazole;
l10) 4-(4-fluorophenyl)-5-[4-(methylsulfonyl)phenyl]-2-phenyloxazole;
m1) 4-(4-fluorophenyl)-2-methyl-5-[4-(methylsulfonyl)phenyl]oxazole; and
m2) 4-[5-(3-fluoro-4-methoxyphenyl)-2-trifluoromethyl-4-oxazolyl]benzenesulfonamide.
m3) 6-chloro-2-trifluoromethyl-2H-1-benzopyran-3-carboxylic acid;
m4) 6-chloro-7-methyl-2-trifluoromethyl-2H-1-benzopyran-3-carboxylic acid;
m5) 8-(1-methylethyl)-2-trifluoromethyl-2H-1-benzopyran-3-carboxylic acid;
m6) 6-chloro-7-(1,1-dimethylethyl)-2-trifluoromethyl-2H-1-benzopyran-3-carboxylic acid;
m7) 6-chloro-8-(1-methylethyl)-2-trifluoromethyl-2H-1-benzopyran-3-carboxylic acid;
m8) 2-trifluoromethyl-3H-naphthopyran-3-carboxylic acid;
m9) 7-(1,1-dimethylethyl)-2-trifluoromethyl-2H-1-benzopyran-3-carboxylic acid;
m10) 6-bromo-2-trifluoromethyl-2H-1-benzopyran-3-carboxylic acid;
n1) 8-chloro-2-trifluoromethyl-2H-1-benzopyran-3-carboxylic acid;
n2) 6-trifluoromethoxy-2-trifluoromethyl-2H-1-benzopyran-3-carboxylic acid;
n3) 5,7-dichloro-2-trifluoromethyl-2H-1-benzopyran-3-carboxylic acid;
n4) 8-phenyl-2-trifluoromethyl-2H-1-benzopyran-3-carboxylic acid;
n5) 7,8-dimethyl-2-trifluoromethyl-2H-1-benzopyran-3-carboxylic acid;
n6) 6,8-bis(dimethylethyl)-2-trifluoromethyl-2H-1-benzopyran-3-carboxylic acid;
n7) 7-(1-methylethyl)-2-trifluoromethyl-2H-1-benzopyran-3-carboxylic acid;
n8) 7-phenyl-2-trifluoromethyl-2H-1-benzopyran-3-carboxylic acid;
n9) 6-chloro-7-ethyl-2-trifluoromethyl-2H-1-benzopyran-3-carboxylic acid;
n10) 6-chloro-8-ethyl-2-trifluoromethyl-2H-1-benzopyran-3-carboxylic acid;
o1) 6-chloro-7-phenyl-2-trifluoromethyl-2H-1-benzopyran-3-carboxylic acid;
o2) 6,7-dichloro-2-trifluoromethyl-2H-1-benzopyran-3-carboxylic acid;
o3) 6,8-dichloro-2-trifluoromethyl-2H-1-benzopyran-3-carboxylic acid;
o4) 2-trifluoromethyl-3H-naphtho[2,1-b]pyran-3-carboxylic acid;
o5) 6-chloro-8-methyl-2-trifluoromethyl-2H-1-benzopyran-3-carboxylic acid;
o6) 8-chloro-6-methyl-2-trifluoromethyl-2H-1-benzopyran-3-carboxylic acid;
o7) 8-chloro-6-methoxy-2-trifluoromethyl-2H-1-benzopyran-3-carboxylic acid;
o8) 6-bromo-8-chloro-2-trifluoromethyl-2H-1-benzopyran-3-carboxylic acid;
o9) 8-bromo-6-fluoro-2-trifluoromethyl-2H-1-benzopyran-3-carboxylic acid;
o10) 8-bromo-6-methyl-2-trifluoromethyl-2H-1-benzopyran-3-carboxylic acid;
p1) 8-bromo-5-fluoro-2-trifluoromethyl-2H-1-benzopyran-3-carboxylic acid;
p2) 6-chloro-8-fluoro-2-trifluoromethyl-2H-1-benzopyran-3-carboxylic acid;
p3) 6-bromo-8-methoxy-2-trifluoromethyl-2H-1-benzopyran-3-carboxylic acid;
p4) 6-[[(phenylmethyl)amino]sulfonyl]-2-trifluoromethyl-2H-1-benzopyran-3-carboxylic acid;
p5) 6-[(dimethylamino)sulfonyl]-2-trifluoromethyl-2H-1-benzopyran-3-carboxylic acid;
p6) 6-[(methylamino)sulfonyl]-2-trifluoromethyl-2H-1-benzopyran-3-carboxylic acid;
p7) 6-[(4-morpholino)sulfonyl]-2-trifluoromethyl-2H-1-benzopyran-3-carboxylic acid;
p8) 6-[(1,1-dimethylethyl)aminosulfonyl]-2-trifluoromethyl-2H-1-benzopyran-3-carboxylic acid;
p9) 6-[(2-methylpropyl)aminosulfonyl]-2-trifluoromethyl-2H-1-benzopyran-3-carboxylic acid;
p10) 6-methylsulfonyl-2-trifluoromethyl-2H-1-benzopyran-3-carboxylic acid;

q1) 8-chloro-6-[[(phenylmethyl)amino]sulfonyl]-2-trifluoromethyl-2H-1-benzopyran-3-carboxylic acid;
q2) 6-phenylacetyl-2-trifluoromethyl-2H-1-benzopyran-3-carboxylic acid;
q3) 6,8-dibromo-2-trifluoromethyl-2H-1-benzopyran-3-carboxylic acid;
q4) 8-chloro-5,6-dimethyl-2-trifluoromethyl-2H-1-benzopyran-3-carboxylic acid;
q5) 6,8-dichloro-(S)-2-trifluoromethyl-2H-1-benzopyran-3-carboxylic acid;
q6) 6-benzylsulfonyl-2-trifluoromethyl-2H-1-benzopyran-3-carboxylic acid;
q7) 6-[[N-(2-furylmethyl)amino]sulfonyl]-2-trifluoromethyl-2H-1-benzopyran-3-carboxylic acid;
q8) 6-[[N-(2-phenylethyl)amino]sulfonyl]-2-trifluoromethyl-2H-1-benzopyran-3-carboxylic acid;
q9) 6-iodo-2-trifluoromethyl-2H-1-benzopyran-3-carboxylic acid;
q10) 7-(1,1-dimethylethyl)-2-pentafluoroethyl-2H-1-benzopyran-3-carboxylic acid;
r1) 5,5-dimethyl-3-(3-fluorophenyl)-4-(4-methyl-sulphonyl-2(5H)-fluranone;
r2) 6-chloro-2-trifluoromethyl-2H-1-benzothiopyran-3-carboxylic acid;
r3) 4-[5-(4-chlorophenyl)-3-(trifluoromethyl)-1H-pyrazol-1-yl]benzenesulfonamide;
r4) 4-[5-(4-methylphenyl)-3-(trifluoromethyl)-1H-pyrazol-1-yl]benzenesulfonamide;
r5) 4-[5-(3-fluoro-4-methoxyphenyl)-3-(difluoromethyl)-1H-pyrazol-1-yl]benzenesulfonamide;
r6) 3-[1-[4-(methylsulfonyl)phenyl]-4-trifluoromethyl-1H-imidazol-2-yl]pyridine;
r7) 2-methyl-5-[1-[4-(methylsulfonyl)phenyl]-4-trifluoromethyl-1H-imidazol-2-yl]pyridine;
r8) 4-[2-(5-methylpyridin-3-yl)-4-(trifluoromethyl)-1H-imidazol-1-yl]benzenesulfonamide;
r9) 4-[5-methyl-3-phenylisoxazol-4-yl]benzenesulfonamide;
r10) 4-[5-hydroxymethyl-3-phenylisoxazol-4-yl]benzenesulfonamide;
s1) [2-trifluoromethyl-5-(3,4-difluorophenyl)-4-oxazolyl]benzenesulfonamide;
s2) 4-[2-methyl-4-phenyl-5-oxazolyl]benzenesulfonamide; or
s3) 4-[5-(3-fluoro-4-methoxyphenyl-2-trifluoromethyl)-4-oxazolyl]benzenesulfonamide; or a pharmaceutically acceptable salt or prodrug thereof.

Cox-2 inhibitors that are useful in the methods and compositions of present invention can be supplied by any source as long as the Cox-2 inhibitor is pharmaceutically acceptable. Likewise, Cox-2 inhibitors that are useful in the compositions and methods of present invention can by synthesized, for example, according to the description in Example 1. Several Cox-2 inhibitors that are suitable for use with the compositions and methods of the present invention may be synthesized by the methods described in, for example, U.S. Pat. No. 5,466,823 (incorporated by reference) to Talley, et al. Cox-2 inhibitors can also be isolated and purified from natural sources. Cox-2 inhibitors should be of a quality and purity that is conventional in the trade for use in pharmaceutical products.

Preferred Cox-2 selective inhibitor compounds are those compounds selected from the group consisting of celecoxib, parecoxib, deracoxib, valdecoxib, etoricoxib, meloxicam, rofecoxib, lumiracoxib, RS 57067, T-614, BMS-347070 (Bristol Meyers Squibb, described in U.S. Pat. No. 6,180, 651; incorporated by reference), JTE-522 (Japan Tabacco), S-2474 (Shionogi), SVT-2016, CT-3 (Atlantic Pharmaceutical), ABT-963 (Abbott), SC-58125 (GD Searle), nimesulide, flosulide, NS-398 (Taisho Pharmaceutical), L-745337 (Merck), RWJ-63556, L-784512 (Merck), darbufelone (Pfizer), CS-502 (Sankyo), LAS-34475 (Almirall Prodesfarma), LAS-34555 (Almirall Prodesfarma), S-33516 (Servier), SD-8381 (Pharmacia, described in U.S. Pat. No. 6,034,256 (incorporated by reference)), MK-966 (Merck), L-783003 (Merck), T-614 (Toyama), D-1376 (Chiroscience), L-748731 (Merck), CGP-28238 (Novartis), BF-389 (Biofor/Scherer), GR-253035 (Glaxo Wellcome), prodrugs of any of them, and mixtures thereof.

More preferred is that the Cox-2 selective inhibitor is selected from the group consisting of celecoxib, parecoxib, deracoxib, valdecoxib, lumiracoxib, etoricoxib, rofecoxib, prodrugs of any of them, and mixtures thereof.

Even more preferred still is that the Cox-2 selective inhibitor is celecoxib.

Various classes of Cox-2 inhibitors useful in the present invention can be prepared as follows. Pyrazoles can be prepared by methods described in WO 95/15316 (incorporated by reference). Pyrazoles can further be prepared by methods described in WO 95/15315 (incorporated by reference). Pyrazoles can also be prepared by methods described in WO 96/03385 (incorporated by reference).

Thiophene analogs useful in the present invention can be prepared by methods described in WO 95/00501 (incorporated by reference). Preparation of thiophene analogs is also described in WO 94/15932 (incorporated by reference).

Oxazoles useful in the present invention can be prepared by the methods described in WO 95/00501 (incorporated by reference). Preparation of oxazoles is also described in WO 94/27980 (incorporated by reference).

Isoxazoles useful in the present invention can be prepared by the methods described in WO 96/25405 (incorporated by reference).

Imidazoles useful in the present invention can be prepared by the methods described in WO 96/03388 (incorporated by reference). Preparation of imidazoles is also described in WO 96/03387 (incorporated by reference).

Cyclopentene Cox-2 inhibitors useful in the present invention can be prepared by the methods described in U.S. Pat. No. 5,344,991 (incorporated by reference). Preparation of cyclopentene Cox-2 inhibitors is also described in WO 95/00501 (incorporated by reference).

Terphenyl compounds useful in the present invention can be prepared by the methods described in WO 96/16934 (incorporated by reference).

Thiazole compounds useful in the present invention can be prepared by the methods described in WO 96/03392 (incorporated by reference).

Pyridine compounds useful in the present invention can be prepared by the methods described in WO 96/03392 (incorporated by reference). Preparation of pyridine compounds is also described in WO 96/24585 (incorporated by reference).

Benzopyranopyrazolyl compounds useful in the present invention can be prepared by the methods described in WO 96/09304 (incorporated by reference).

Chromene compounds useful in the present invention can be prepared by the methods described in WO 98/47890 (incorporated by reference). Preparation of chromene compounds is also described in WO 00/23433 (incorporated by reference). Chromene compounds can further be prepared by the methods described in U.S. Pat. No. 6,077,850 (incorporated by reference). Preparation of chromene compounds is further described in U.S. Pat. No. 6,034,256 (incorporated by reference).

Arylpyridazinones useful in the present invention can be prepared by the methods described in WO 00/24719 (incorporated by reference). Preparation of arylpyridazinones is also described in WO 99/10332 (incorporated by reference). Arylpyridazinones can further be prepared by the methods described in WO 99/10331 (incorporated by reference).

5-Alkyl-2-arylaminophenylacetic acids and derivatives useful in the present invention can be prepared by the methods described in WO 99/11605 (incorporated by reference).

Diarylmethylidenefuran derivative Cox-2 selective inhibitors useful in the present invention can be prepared by the methods described in U.S. Pat. No. 6,180,651 (incorporated by reference).

The celecoxib used in the compositions and methods of the present invention can be prepared in the manner set forth in U.S. Pat. No. 5,466,823 (incorporated by reference).

The valdecoxib used in the compositions and methods of the present invention can be prepared in the manner set forth in U.S. Pat. No. 5,633,272 (incorporated by reference).

The parecoxib used in the compositions and methods of the present invention can be prepared in the manner set forth in U.S. Pat. No. 5,932,598 (incorporated by reference).

The rofecoxib used in the compositions and methods of the present invention can be prepared in the manner set forth in U.S. Pat. No. 5,474,995 (incorporated by reference).

The deracoxib used in the compositions and methods of the present invention can be prepared in the manner set forth in U.S. Pat. No. 5,521,207 (incorporated by reference).

The etoricoxib used in the compositions and methods of the present invention can be prepared in the manner set forth in WO 98/03484 (incorporated by reference).

The meloxicam used in the compositions and methods of the present invention can be prepared in the manner set forth in U.S. Pat. No. 4,233,299 (incorporated by reference).

The compound 4-(4-cyclohexyl-2-methyloxazol-5-yl)-2-fluorobenzenesulfonamide used in the compositions and methods of the present invention can be prepared in the manner set forth in U.S. Pat. No. 5,994,381 (incorporated by reference).

The compound 2-(3,4-difluorophenyl)-4-(3-hydroxy-3-methylbutoxy)-5-[4-(methylsulfonyl)phenyl]-3(2H)-pyridazinone used in the compositions and methods of the present invention can be prepared in the manner set forth in WO 00/24719 (incorporated by reference).

The compound 2-(3,5-difluorophenyl)-3-[4-(methylsulfonyl)phenyl]-2-cyclopenten-1-one used in the compositions and methods of the present invention can be prepared in the manner set forth in EP 0863134.

The compound 2-[(2-chloro-6-fluorophenyl)amino]-5-methyl-benzeneacetic acid used in the compositions and methods of the present invention can be prepared in the manner set forth in WO 99/11605 (incorporated by reference).

The compound N-[2-(cyclohexyloxy)-4-nitrophenyl]methanesulfonamide used in the compositions and methods of the present invention can be prepared in the manner set forth in U.S. Pat. No. 4,885,367 (incorporated by reference).

The compound (3Z)-3-[(4-chlorophenyl)[4-(methylsulfonyl)phenyl]methylene]dihydro-2(3H)-furanone used in the compositions and methods of the present invention can be prepared in the manner set forth in U.S. Pat. No. 6,180,651 (incorporated by reference).

Cytosolic Phospholipases A2 (cPLA2) Inhibitors

In certain embodiments, the PGE2 inhibitor is an inhibitor of cytosolic phospholipases A2 (cPLA2), such as, merely to illustrate, arachidonyl trifluoromethyl ketone,

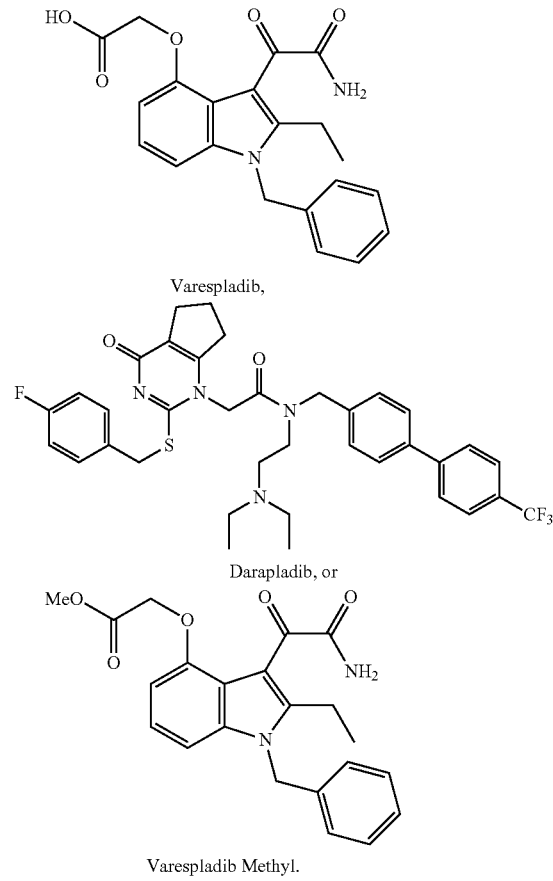

Varespladib,

Darapladib, or

Varespladib Methyl.

B. Other Exemplary Combinations

The subject immuno-DASH inhibitors, with or without PGE2 inhibitors, can be used as part of a therapy that can further include administering an inhibitor of immune checkpoint molecule or an activator of a costimulatory molecule, or a combination thereof. Exemplary inhibitors of immune checkpoints include inhibitors of one or more of PD-1, CTLA-4, TIM-3, LAG-3, CEACAM, VISTA, BTLA, TIGIT, LAIR1, CD160, 2B4, NLRP1, NLRP3, STING or TGFR beta. Exemplary activators of costimulatory molecules include agonists of one or more of OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand. Exemplary inhibitor of immune checkpoints and exemplary activators of costimulatory molecules can be found in PCT Publication WO 2016054555, which is incorporated by reference herein.

Exemplary types of chemotherapy drugs with which the subject immuno-DASH inhibitors can be used in combination therapies include: DNA-alkylating drugs (such as cyclophosphamide, ifosfamide, cisplatin, carboplatin, dacarbazine), antimetabolites (5-fluorouracil, capecitabine, 6-mercaptopurine, methotrexate, gemcitabine, cytarabine, fludarabine), mitotic inhibitors (such as paclitaxel, docetaxel, vinblastine, vincristine), anticancer antibiotics (such as daunorubicin, doxorubicin, epirubicin, idarubicin, mitoxantrone), topoisomerase I and/or II inhibitors (such as topotecan, irinotecan, etoposide, teniposide), and hormone therapy (such as tamoxifen, flutamide)

In some embodiments, the chemotherapeutic agent is selected from the group consisting of vemurafenib, GDC-0879, PLX-4720, 5-fluorouracil, aldesleukin, aminopterin, asparaginase, bleomycin sulfate, capecitabine, carboplatin, chlorambucil, cisplatin, cladribine, clofarabine, cyclophosphamide, cytarabine, dacarbazine, dactinomycin, daunorubicin hydrochloride, decitabine, docetaxel, doxorubicin, doxorubicin hydrochloride, epirubicin hydrochloride, etoposide, etoposide phosphate, floxuridine, fludarabine, fluorouracil, gemcitabine, gemcitabine hydrochloride, hydroxyurea, idarubicin hydrochloride, ifosfamide, interferons, interferon-α2a, interferon-α2b, interferon-αn3, interferon-α1b, interleukins, iproplatin, irinotecan, lobaplatin, mechlorethamine hydrochloride, melphalan, mercatopurine, methotrexate, methotrexate sodium, mitomycin, mitoxantrone, nedaplatin, ormiplatin, oxaliplatin, paclitaxel, pemetrexed, pegaspargase, pentostatin, prednisone, profimer sodium, procabazine hydrochloride, raltitrexed, satraplatin, taxol, taxotere, teniposide, thioguanine, topotecan hydrochloride, triplatin tetranitrate (BBR3464), tetraplatin, vinblastine sulfate, vincristine sulfate and vinorelbine tartrate.

Recent evidence indicates that certain anticancer drugs, such as anthracyclines, induce an immunogenic type of apoptosis that stimulates the engulfment of apoptotic bodies by dendritic cells (DCs) and the activation of cytotoxic CD8+ T cells through cross-priming. In some embodiments, the chemotherapeutic agent is an agent that induces immunogenic cell death, e.g., antigenic apoptosis, of tumor cells. For instance, the effects of the chemotherapeutic agent can include increasing the cell surface expression of calreticulin and/or heat shock protein 70 (HSP70). Exemplary chemotherapeutic agents of this kind include anthracyclines such as doxorubicin.

In a preferred embodiment, the invention is directed to the combination of immuno-DASH inhibitor, or a pharmaceutically acceptable salt thereof, with an antitumor platinum coordination complex in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer, brain cancer and lymphoma. This chemotherapeutic group includes, but is not limited to cisplatin, oxaliplatin, carboplatin, triplatin tetranitrate (BBR3464), satraplatin, tetraplatin, ormiplatin, iproplatin, nedaplatin and lobaplatin. Particularly preferred is the combination of immuno-DASH inhibitor, or a pharmaceutically acceptable salt thereof, with cisplatin, oxaliplatin, carboplatin, triplatin tetranitrate, satraplatin, tetraplatin, ormiplatin, iproplatin, nedaplatin and lobaplatin, and even more preferred is the combination with cisplatin and oxaliplatin in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer and brain cancer. In another embodiment, the invention is directed to the combination of immuno-DASH inhibitor, or a pharmaceutically acceptable salt thereof, with an antimetabolite in the treatment of cancer, and more particularly in the treatment of a cancer selected from lung cancer, sarcoma, malignant melanoma, bladder carcinoma, prostate cancer, pancreas carcinoma, gastric carcinoma, ovarian cancer, hepatoma, breast cancer, colorectal cancer, kidney cancer, esophageal cancer, brain cancer, anal cancer, leukaemia and lymphoma. This chemotherapeutic group includes, but is not limited to 5-fluorouracil, gemcitabine, cytarabine, capecitabine, decitabine, floxuridine, fludarabine, aminopterin, methotrexate, pemetrexed, raltitrexed, cladribine, clofarabine, mercaptopurine, pentostatin, and thioguanine. Particularly preferred is the combination of immuno-DASH inhibitor, or a pharmaceutically acceptable salt thereof, with 5-fluorouracil, gemcitabine, cytarabine, capecitabine, decitabine, floxuridine, fludarabine, aminopterin, methotrexate, pemetrexed, raltitrexed, cladribine, clofarabine, mercaptopurine, pentostatin, and thioguanine, and even more preferred is the combination with 5-fluorouracil, gemcitabine, cytarabine and methotrexate in the treatment of cancer, and more particularly in the treatment of a cancer selected from lung cancer, sarcoma, malignant melanoma, prostate cancer, pancreas carcinoma, gastric carcinoma, ovarian cancer, hepatoma, breast cancer, colorectal cancer, kidney cancer, brain cancer, leukemia and lymphoma.

In another embodiment, the invention is directed to the combination of immuno-DASH inhibitor, or a pharmaceutically acceptable salt thereof, with a mitotic inhibitor in the treatment of cancer, and more particularly in the treatment of a cancer selected from lung cancer, sarcoma, prostate cancer, gastric carcinoma, ovarian cancer, hepatoma, breast cancer, colorectal cancer, kidney cancer, brain cancer, leukemia, and lymphoma. This chemotherapeutic group includes, but is not limited to paclitaxel, docetaxel, vinblastine, vincristine, vindesine, and vinorelbine. Particularly preferred is the combination of immuno-DASH inhibitor, or a pharmaceutically acceptable salt thereof, with paclitaxel, docetaxel, vinblastine, vincristine, vindesine, and vinorelbine, and even more preferred is the combination with paclitaxel, docetaxel, vincristine and vinorelbine in the treatment of cancer, and more particularly in the treatment of a cancer selected from lung cancer, sarcoma, prostate cancer, gastric carcinoma, ovarian cancer, hepatoma, breast cancer, colorectal cancer, kidney cancer and brain cancer.

In another embodiment, the invention is directed to the combination of immuno-DASH inhibitor, or a pharmaceutically acceptable salt thereof, with an anticancer antibiotic in the treatment of cancer, and more particularly in the treatment of lung cancer, sarcoma, malignant melanoma, bladder carcinoma, prostate cancer, pancreas carcinoma, thyroid cancer, gastric carcinoma, ovarian cancer, hepatoma, breast cancer, colorectal cancer, kidney cancer, neuroblastoma, brain cancer, anal cancer, testicular cancer, leukemia, multiple myeloma and lymphoma. This chemotherapeutic group includes, but is not limited to daunorubicin, doxorubicin, epirubicin, idarubicin, mitoxantrone, pixantrone, valrubicin, mitomycin C, bleomycin, actinomycin A and mithramycin. Particularly preferred is the combination of immuno-DASH inhibitor, or a pharmaceutically acceptable salt thereof, with daunorubicin, doxorubicin, epirubicin, idarubicin, mitoxantrone, pixantrone, valrubicin, mitomycin C, bleomycin, actinomycin D and mithramycin, and even more preferred is the combination with daunorubicin, doxorubicin, mitomycin C and actinomycin D in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, brain cancer, leukemia and lymphoma.

In another embodiment, the invention is directed to the combination of immuno-DASH inhibitor, or a pharmaceutically acceptable salt thereof, with a topoisomerase I and/or II inhibitor in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, neuroblastoma, brain cancer, cervical cancer, testicular cancer, leukemia and lymphoma. This chemotherapeutic group includes, but is not limited to topotecan, SN-38, irinotecan, camptothecin, rubitecan, etoposide, amsacrine and teniposide. Particularly preferred is the combination of PM00104, or a pharmaceutically acceptable salt thereof, with topotecan, SN-38, irinotecan, camptothecin, rubitecan, etoposide, amsacrine and teniposide, and even more preferred is the combination with topotecan, irinotecan and etoposide in the treatment of cancer, and more particularly in the treatment of lung cancer, sarcoma, malignant melanoma, prostate cancer, pancreas carcinoma, gastric carcinoma, ovarian cancer, hepatoma, breast cancer, colorectal cancer, kidney cancer, and brain cancer.

In another embodiment, the invention is directed to the combination of immuno-DASH inhibitor, or a pharmaceutically acceptable salt thereof, with a proteosome inhibitor in the treatment of cancer, and more particularly in the treatment of lung cancer, prostate cancer, pancreas carcinoma, gastric carcinoma, hepatoma, colorectal cancer, brain cancer, multiple myeloma and lymphoma. This chemotherapeutic group includes, but is not limited to bortezomib, disulfiram, epigallocatechin gallate, and salinosporamide A. Particularly preferred is the combination of immuno-DASH inhibitor, or a pharmaceutically acceptable salt thereof, with bortezomib, disulfiram, epigallocatechin gallate, and salinosporamide A, and even more preferred is the combination with bortezomib in the treatment of cancer, and more particularly in the treatment of lung cancer, prostate cancer, pancreas carcinoma, gastric carcinoma, hepatoma, colorectal cancer and brain cancer.

In another embodiment, the invention is directed to the combination of immuno-DASH inhibitor, or a pharmaceutically acceptable salt thereof, with a histone deacetylase inhibitor in the treatment of cancer, and more particularly in the treatment of lung cancer, sarcoma, prostate cancer, pancreas carcinoma, gastric carcinoma, ovarian cancer, breast cancer, colorectal cancer, kidney cancer, brain cancer and lymphoma. This chemotherapeutic group includes, but is not limited to romidepsin, panobinostat, vorinostat, mocetinostat, belinostat, entinostat, resminostat, PCI-24781, AR-42, CUDC-101, and valproic acid. Particularly preferred is the combination of immuno-DASH inhibitor, or a pharmaceutically acceptable salt thereof, with romidepsin, panobinostat, vorinostat, mocetinostat, belinostat, entinostat, resminostat, PCI-24781, AR-42, CUDC-101, and valproic acid, and even more preferred is the combination with vorinostat in the treatment of cancer, and more particularly in the treatment of lung cancer, sarcoma, prostate cancer, pancreas carcinoma, gastric carcinoma, ovarian cancer, breast cancer, colorectal cancer, kidney cancer and brain cancer.

In another embodiment, the invention is directed to the combination of immuno-DASH inhibitor, or a pharmaceutically acceptable salt thereof, with a nitrogen mustard alkylating agent in the treatment of cancer, and more particularly in the treatment of lung cancer, sarcoma, bladder carcinoma, gastric carcinoma, ovarian cancer, hepatoma, breast cancer, colorectal cancer, kidney cancer, leukemia, multiple myeloma and lymphoma. This chemotherapeutic group includes, but is not limited to melphalan, ifosfamide, chlorambucil, cyclophosphamide, mechlorethamine, uramustine, estramustine and bendamustine. Particularly preferred is the combination of immuno-DASH inhibitor, or a pharmaceutically acceptable salt thereof, with melphalan, ifosfamide, chlorambucil, cyclophosphamide, mechlorethamine, uramustine, estramustine and bendamustine, and even more preferred is the combination with cyclophosphamide in the treatment of cancer, and more particularly in the treatment of lung cancer, sarcoma, gastric carcinoma, ovarian cancer, hepatoma, breast cancer, colorectal cancer and kidney cancer. In another embodiment, the invention is directed to the combination of immuno-DASH inhibitor, or a pharmaceutically acceptable salt thereof, with a nitrosourea alkylating agent in the treatment of cancer, and more particularly in the treatment of lung cancer, ovarian cancer, breast cancer, brain cancer, multiple myeloma and lymphoma. This chemotherapeutic group includes, but is not limited to lomustine, semustine, carmustine, fotemustine and streptozotocin. Particularly preferred is the combination of immuno-DASH inhibitor, or a pharmaceutically acceptable salt thereof, with lomustine, semustine, carmustine, fotemustine and streptozotocin, and even more preferred is the combination with carmustine in the treatment of cancer, and more particularly in the treatment of lung cancer, ovarian cancer and breast cancer.

In another embodiment, the invention is directed to the combination of immuno-DASH inhibitor, or a pharmaceutically acceptable salt thereof, with a nonclassical alkylating agent in the treatment of cancer, and more particularly in the treatment of lung cancer, sarcoma, malignant melanoma, pancreas carcinoma, gastric carcinoma, ovarian cancer, breast cancer, colorectal cancer, kidney cancer, brain cancer, leukemia and lymphoma. This chemotherapeutic group includes, but is not limited to procarbazine, dacarbazine, temozolomide and altretamine. Particularly preferred is the combination of immuno-DASH inhibitor, or a pharmaceutically acceptable salt thereof, with procarbazine, dacarbazine, temozolomide and altretamine, and even more preferred is the combination with dacarbazine and tezolomide in the treatment of lung cancer, sarcoma, malignant melanoma, gastric carcinoma, ovarian cancer, breast cancer, colorectal cancer, kidney cancer and brain cancer. In another embodiment, the invention is directed to the combination of immuno-DASH inhibitor, or a pharmaceutically acceptable salt thereof, with an estrogen antagonist in the treatment of cancer, and more particularly in the treatment of breast cancer. This chemotherapeutic group includes, but is not limited to toremifene, fulvestrant, tamoxifen and nafoxidine. Particularly preferred is the combination of immuno-DASH inhibitor, or a pharmaceutically acceptable salt thereof, with toremifene, fulvestrant, tamoxifen and nafoxidine, and even more preferred is the combination with tamoxifen in the treatment of breast cancer.

In another embodiment, the invention is directed to the combination of immuno-DASH inhibitor, or a pharmaceutically acceptable salt thereof, with an androgen antagonist in the treatment of cancer, and more particularly in the treatment of prostate cancer. This chemotherapeutic group includes, but is not limited to bicalutamide, flutamide, MDV3100 and nilutamide. Particularly preferred is the combination of immuno-DASH inhibitor, or a pharmaceutically acceptable salt thereof, with bicalutamide, flutamide, MDV3100 and nilutamide, and even more preferred is the combination with flutamide in the treatment of prostate cancer.

In another embodiment, the invention is directed to the combination of immuno-DASH inhibitor, or a pharmaceutically acceptable salt thereof, with a mTOR inhibitor in the treatment of cancer, and more particularly in the treatment of lung cancer, sarcoma, malignant melanoma, prostate cancer, pancreas carcinoma, gastric carcinoma, ovarian cancer, breast cancer, colorectal cancer, kidney cancer and brain cancer. This chemotherapeutic group includes, but is not limited to sirolimus, temsirolimus, everolimus, ridaforolimus, KU-0063794 and WYE-354. Particularly preferred is the combination of immuno-DASH inhibitor, or a pharmaceutically acceptable salt thereof, with sirolimus, temsirolimus, everolimus, ridaforolimus, KU-0063794 and WYE-354, and even more preferred is the combination with temsirolimus in the treatment of lung cancer, sarcoma, malignant melanoma, prostate cancer, pancreas carcinoma, gastric carcinoma, ovarian cancer, breast cancer, colorectal cancer and brain cancer.

In another embodiment, the invention is directed to the combination of immuno-DASH inhibitor, or a pharmaceutically acceptable salt thereof, with a tyrosine kinase inhibitor in the treatment of cancer, and more particularly in the treatment of a cancer selected from lung cancer, sarcoma, prostate cancer, pancreas carcinoma, gastric carcinoma, ovarian cancer, hepatoma, breast cancer, colorectal cancer, kidney cancer and brain cancer. This chemotherapeutic group includes, but is not limited to erlotinib, sorafenib, axitinib, bosutinib, cediranib, crizotinib, dasatinib, gefitinib, imatinib, canertinib, lapatinib, lestaurtinib, neratinib, nilotinib, semaxanib, sunitinib, vatalanib and vandetanib. Particularly preferred is the combination of immuno-DASH inhibitor, or a pharmaceutically acceptable salt thereof, with erlotinib, sorafenib, axitinib, bosutinib, cediranib, crizotinib, dasatinib, gefitinib, imatinib, canertinib, lapatinib, lestaurtinib, neratinib, nilotinib, semaxanib, sunitinib, vatalanib and vandetanib, and even more preferred is the combination with erlotinib in the treatment of cancer, and more particularly in the treatment of a cancer selected from lung cancer, sarcoma, prostate cancer, pancreas carcinoma, gastric carcinoma, ovarian cancer, hepatoma, breast cancer, colorectal cancer, kidney cancer and brain cancer.

Another aspect of the present invention relates to any one of the foregoing methods, further comprising administering to the patient a MAP kinase pathway inhibitor or a WNT pathway inhibitor.

In some embodiments, the MAP kinase pathway inhibitor is selected from the group consisting of a BRAF inhibitor, a MEK inhibitor, a PI3K inhibitor and a c-KIT inhibitor.

In some embodiments, the BRAF inhibitor is selected from the group consisting of GDC-0879, PLX-4720, sorafenib tosylate, dabrafenib and LGX818.

In some embodiments, the MEK inhibitor is selected from the group consisting of GSK1120212, selumetinib and MEK162.

In some embodiments, the WNT pathway inhibitor is a β-catenin inhibitor or a frizzled inhibitor.

In some embodiments, the β-catenin inhibitor is selected from the group consisting of niclosamide, XAV-939, FH 535 and ICG 001.

Another aspect of the present invention relates to any one of the foregoing methods, further comprising administering to the patient a cancer vaccine. In some embodiments, the cancer vaccine is a dendritic cell vaccine.

Another aspect of the present invention relates to any one of the foregoing methods, further comprising administering to the patient an adoptive cell transfer.

In some embodiments, the adoptive cell transfer is a CAR-T cell therapy.

Another aspect of the present invention relates to any one of the foregoing methods, further comprising administering to the patient an antibody therapy.

Another aspect of the present invention relates to any one of the foregoing methods, wherein administration of the immuno-DASH-inhibitor enhances antibody-dependent cell-mediated cytotoxicity of the antibody therapy.

In some embodiment, the antibody therapy is selected from the group consisting of trastuzamab, cetuximab, bevacizumab, and rituximab.

A. Exemplary PD-1 Antagonists

The PD-1 gene is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Daeron, M (1997) Immunol Today 18:286-91). Two ligands for PD-1 have been identified, PD-L1 and PD-L2, that have been shown to downregulate T cell activation upon binding to PD-1 (Freeman et al. (2000) J Exp Med 192: 1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members. PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170: 1257-66).

In certain embodiments, PD-1 antagonists of the invention include agents that bind to ligands of PD-1 and interfere with, reduce, or inhibit the binding of one or more ligands to the PD-1 receptor, or bind directly to the PD-1 receptor, without engaging in signal transduction through the PD-1 receptor. In one embodiment, the PD-1 antagonist binds directly to PD-1 and blocks PD-1 inhibitory signal transduction. In another embodiment the PD-1 antagonist binds to one or more ligands of PD-1 (e.g., PD-L1 and PD-L2) and reduces or inhibits the ligand(s) from triggering inhibitory signal transduction through the PD-1. In one embodiment, the PD-1 antagonist binds directly to PD-L1, inhibiting or preventing PD-L1 from binding to PD-1, thereby blocking PD-1 inhibitory signal transduction.

PD-1 antagonists used in the methods and compositions of the present invention include PD-1 binding scaffold proteins and include, but are not limited to, PD-ligands, antibodies and multivalent agents. In a particular embodiment, the antagonist is a fusion protein, such as AMP-224. In another embodiment, the antagonist is an anti-PD-1 antibody ("PD-1 antibody"). Anti-human-PD-1 antibodies (or VH and/or VL domains derived therefrom) suitable for use in the invention can be generated using methods well known in the art. Alternatively, art recognized anti-PD-1 antibodies can be used. For example, antibodies MK-3475 or CT-011 can be used. Additionally, monoclonal antibodies 5C4, 17D8, 2D3, 4H1, 4A11, 7D3, and 5F4, described in WO 2006/121168, the teachings of which are hereby incorporated by reference, can be used. Antibodies that compete with any of these art-recognized antibodies for binding to PD-1 also can be used.

In another embodiment, the PD-1 antagonist is an anti-PD-L1 antibody. Anti-human-PD-L1 antibodies (or VH and/ or VL domains derived therefrom) suitable for use in the invention can be generated using methods well known in the art. Alternatively, art recognized anti-PD-L1 antibodies can be used. For example, MEDI4736 (also known as Anti-B7-H1) or MPDL3280A (also known as RG7446) can be used. Additionally, monoclonal antibodies 12A4, 3G10, 10A5, 5F8, 10H10, 1B12, 7H1, 11E6, 12B7, and 13G4 described in WO 2007/005874 and U.S. Pat. No. 7,943,743, the teachings of which are hereby incorporated by reference, can be used. Antibodies that compete with any of these art-recognized antibodies for binding to PD-L1 also can be used.

An exemplary anti-PD-L1 antibody is 12A4 (WO 2007/005874 and U.S. Pat. No. 7,943,743; both are incorporated by reference). In one embodiment, the antibody comprises the heavy and light chain CDRs or VRs of 12A4. Accordingly, in one embodiment, the antibody comprises the CDR1, CDR2, and CDR3 domains of the VH region of 12A4 having the sequence shown in SEQ ID NO: 1 and the CDR1, CDR2 and CDR3 domains of the VL region of 12A4 having the sequence shown in SEQ ID NO: 3. In another embodiment, the antibody comprises the heavy chain CDR1, CDR2 and CDR3 domains having the sequences set forth in SEQ ID NOs: 5, 6, and 7, respectively, and the light chain CDR1, CDR2 and CDR3 domains having the sequences set forth in SEQ ID NOs: 8, 9, and 10, respectively. In another embodiment, the antibody comprises VH and/or VL regions having the amino acid sequences set forth in SEQ ID NO: 1 and/or SEQ ID NO: 3, respectively. In another embodiment, the antibody comprises the heavy chain variable (VH) and/or light chain variable (VL) regions encoded by the nucleic acid sequences set forth in SEQ ID NO: 2 and/or SEQ ID NO: 4, respectively. In another embodiment, the antibody competes for binding with, and/or binds to the same epitope on PD-L1 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO: 1 or SEQ ID NO: 3).

Anti-PD-1 or anti-PD-L1 antibodies may bind to PD-1 or PD-L1, respectively, with a KD of $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M or less.

In one embodiment, the PD-1 inhibitor is an anti-PD-1 antibody chosen from Nivolumab, Pembrolizumab or Pidilizumab. A preferred PD-1 inhibitor is Nivolumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO 2006/121168; both are incorporated by reference. In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) New England Journal of Medicine 369 (2): 134-44, WO2009/114335, and U.S. Pat. No. 8,354,509.

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO 2009/101611; incorporated by reference. Other anti-PD1 antibodies are disclosed in U.S. Pat. No. 8,609,089, US 2010/028330, and/or US 2012/0114649; all are incorporated by reference. Other anti-PD1 antibodies include AMP 514 (Amplimmune).

In some embodiments, the PD-1 inhibitor is an immunoadhesin {e.g., an immunoadhesin comprising an extracellular or PD-1 binding portion of PD-L1 or PD-L2 fused to a constant region {e.g., an Fc region of an immunoglobulin sequence). In some embodiments, the PD-1 inhibitor is AMP-224. In some embodiments, the PD-L1 inhibitor is anti-PD-L1 antibody. In some embodiments, the anti-PD-L1 inhibitor is chosen from YW243.55.S70, MPDL3280A, MEDI-4736, MSB-0010718C, or MDX-1105.

In one embodiment, the PD-L1 inhibitor is MDX-1105. MDX-1105, also known as BMS-936559, is an anti-PD-L1 antibody described in WO 2007/005874; incorporated by reference. In one embodiment, the PD-L1 inhibitor is YW243.55.S70. The YW243.55.S70 antibody is an anti-PD-L1 described in WO 2010/077634 (heavy and light chain variable region sequences shown in SEQ ID Nos. 11 and 12, respectively); incorporated by reference.

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 2012/0039906; both are incorporated by reference. In other embodiments, the PD-L2 inhibitor is AMP-224. AMP-224 is a PD-L2 Fc fusion soluble receptor that blocks the interaction between PD1 and B7-H1 (B7-DCIg; Amplimmune; e.g., disclosed in WO 2010/027827 and WO 2011/066342; both are incorporated by reference).

In certain embodiments, the PD-1 pathway inhibitor is a small molecule antagonist of PD-1 pathway signaling. Such small molecule antagonists include those agents that bind to one or more of PD-1, PD-1L and/or PD-1L2 and inhibits the interaction of PD-1 with PD-1L1 and/or PD-1L2.

Exemplary small molecule antagonist of PD-1 pathway signaling can be found in, inter alia, published US applications 2014/0294898 and 2014/0199334, and published PCT Applications WO 2013/132317 and WO 2012/168944, each of which is incorporated by reference herein.

Merely to illustrate, the subject combination therapy can be practiced with small molecule antagonist selected from the group consisting of

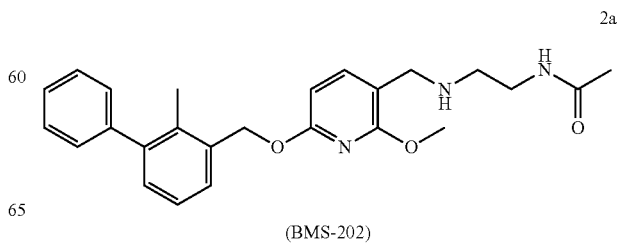

(BMS-202)

2a

-continued

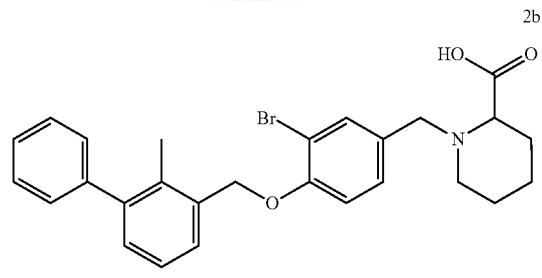

(BMS-8)

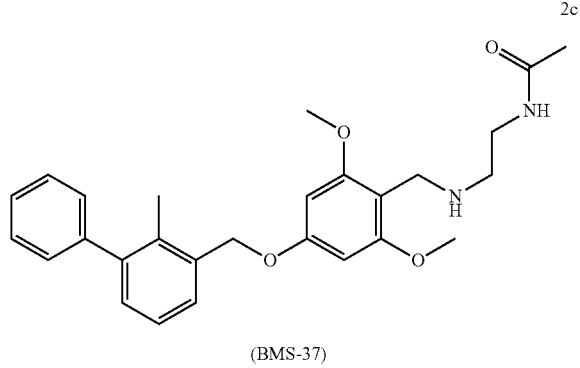

(BMS-37)

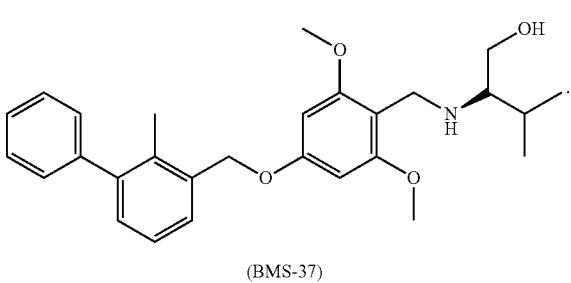

(BMS-37)

In other embodiments, the small molecule antagonist is represented in the general formula ("Ser-Thr-Asn-Ser" disclosed as SEQ ID NO: 13)

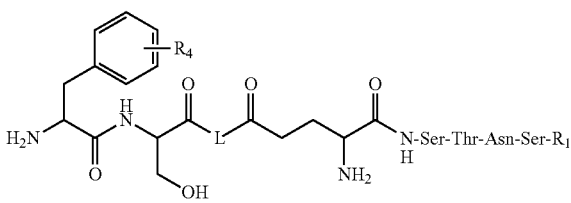

wherein,
$R_j$ is free C-terminal or amidated C-terminal of Ser;
L is a linker selected from —NH(CH$_2$)$_n$NH— or —NH(CH$_2$CH$_2$O)$_n$NH—;
$R_4$ is selected from hydrogen, amino(C$_1$-C$_{20}$)alkyl, —NHCOCH$_3$ or —NHCONH$_2$;

or a retro analogue or a pharmaceutically acceptable stereoisomer or a pharmaceutically acceptable salt thereof.

In still other embodiments, the small molecule antagonist is represented in the general formula ("Ser-Asn-Thr-Ser" disclosed as SEQ ID NO: 14)

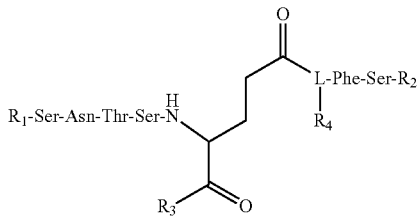

wherein,
$R_1$ is N-terminal of Ser; or (C$_1$-C$_{20}$)acyl substituted with either hydroxyl group or amino group of Ser;
L is a linker selected from —NH(CH$_2$)$_n$NH—, —NH(CH$_2$)$_n$CH(NH$_2$)CO—, —OOC(CH$_2$)$_m$COO—, —NH(CH$_2$)$_n$CO—, —NH(CH$_2$CH$_2$O)$_n$NH—, —NH(CH$_2$CH$_2$O)$_n$CO— or —CO(CH$_2$CH$_2$O)$_n$CO—;
$R_2$ is free C-terminal, amidated C-terminal or N-terminal of Am$_2$; or Y—R$_5$;
Y is an optional linker selected from —OOC(CH$_2$)$_m$COO—, —CO(CH$_2$)$_n$NH—, —CO(CH$_2$CH$_2$O)$_n$NH— or —COCH$_2$(OCH$_2$CH$_2$)$_n$NH—;
$R_5$ is an albumin binding moiety such as maleimido propionic acid;
$R_3$ is OH or NH$_2$;
$R_4$ is a substituent on phenyl group of Phe and is selected from hydrogen, amino(C$_1$-C$_{20}$)alkyl, —NHCOCH$_3$ or —NHCONH$_2$;
n is an integer having values selected from 2 to 10, both inclusive;
m is an integer having values selected from 0 to 8, both inclusive; and
one of the peptide bond (—CONH—) of Ser-Asn, Asn-Thr or Thr-Ser may be replaced with a modified peptide bond of

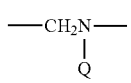

wherein Q is hydrogen, —CO(C$_1$-C$_{20}$)alkyl or —COO(C$_1$-C$_{20}$)alkyl group; wherein one or more or all amino acids may be in the D-configuration;

or a retro analogue or a pharmaceutically acceptable stereoisomer or a pharmaceutically acceptable salt thereof.

For instance, the small molecule antagonist can be selected from the group consisting of ("Ser-Asn-Thr-Ser" disclosed as SEQ ID NO: 14)

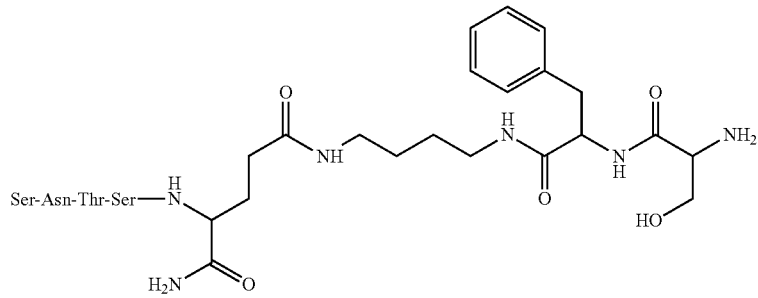
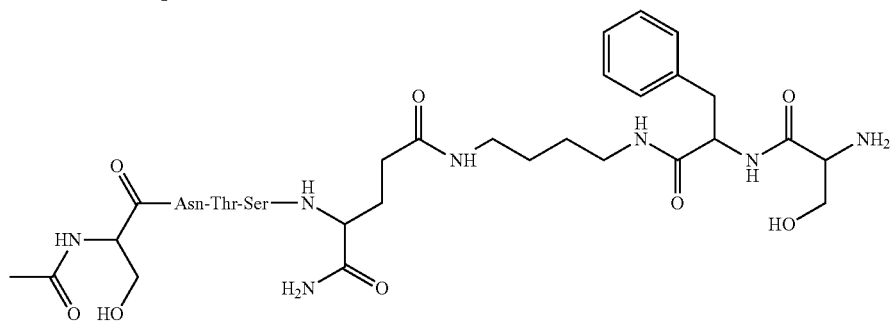
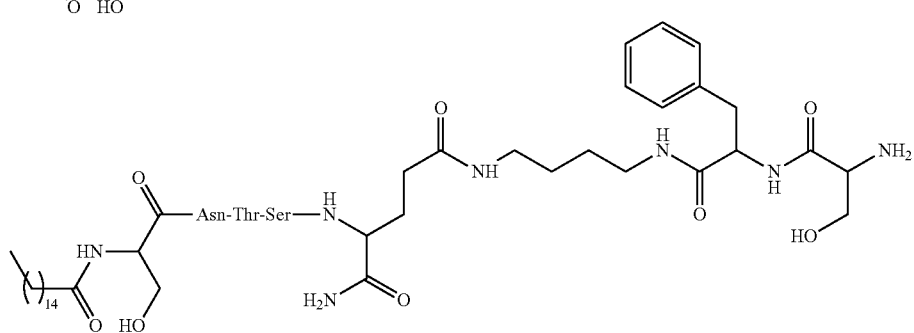
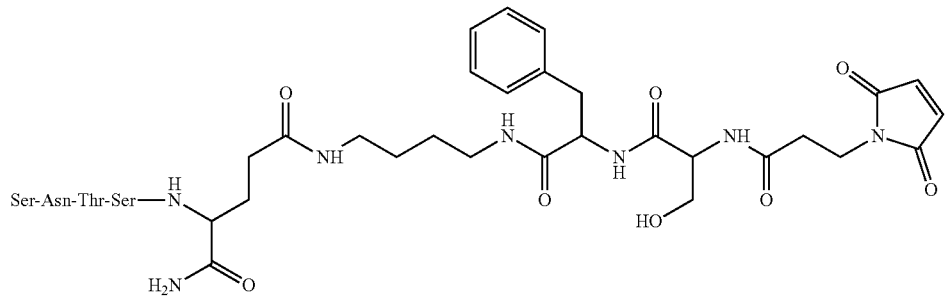
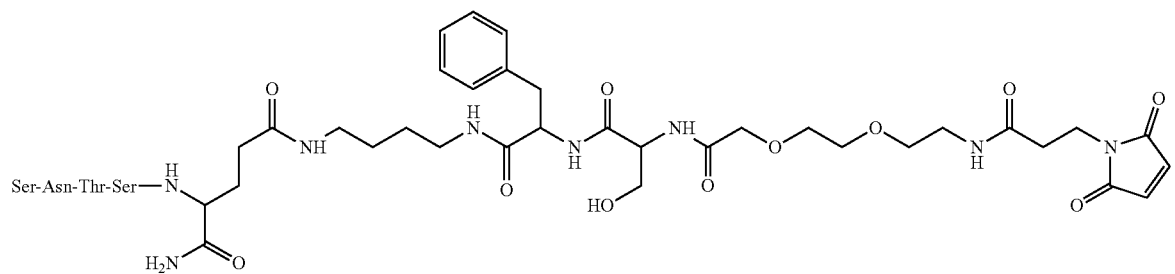
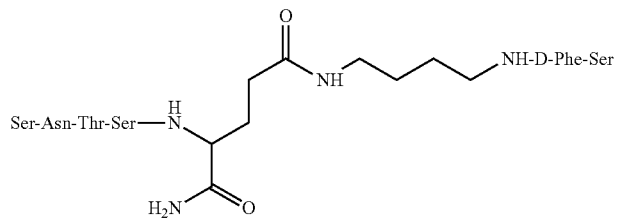

-continued
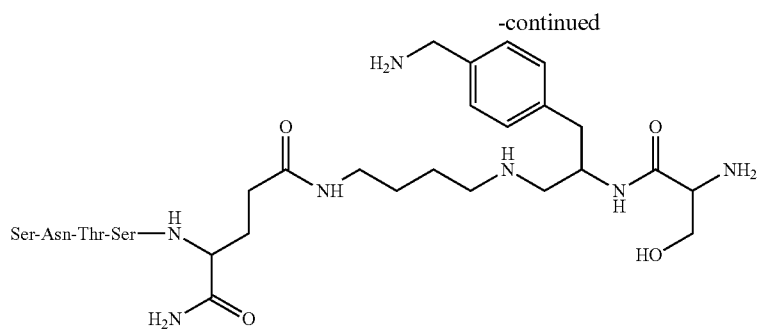
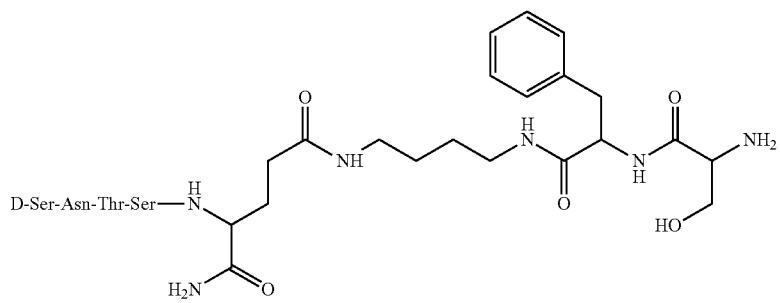
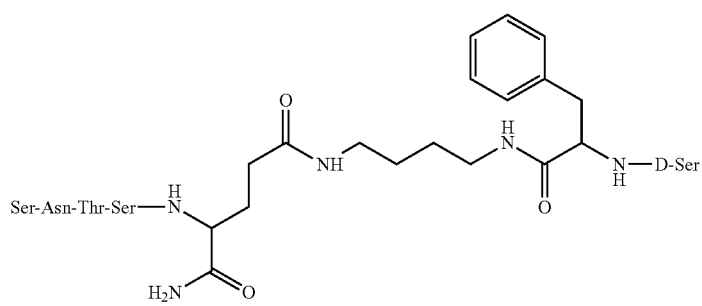
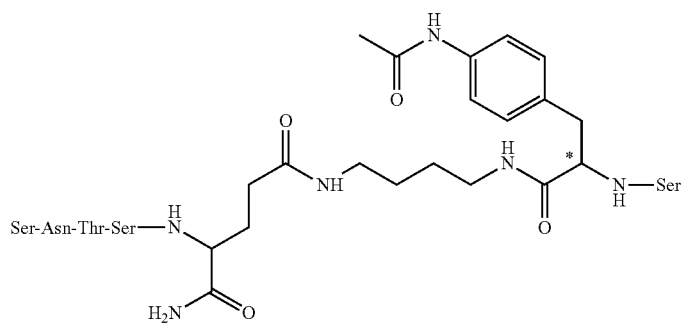
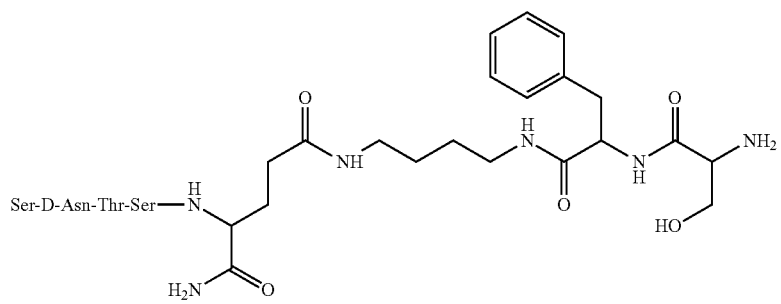

-continued
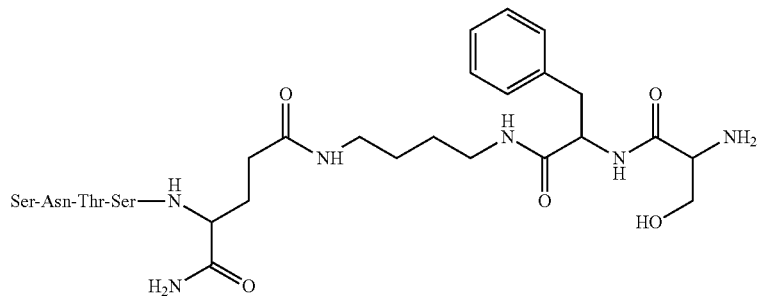
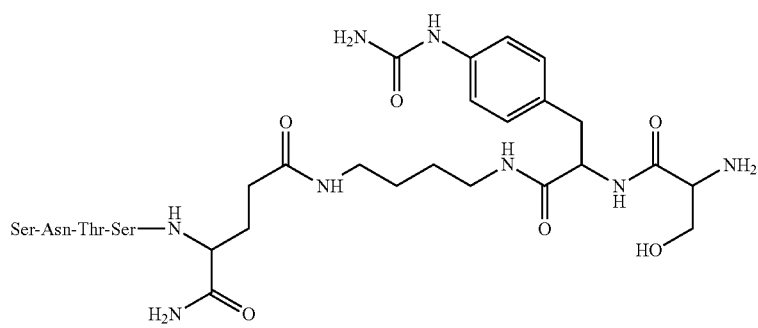
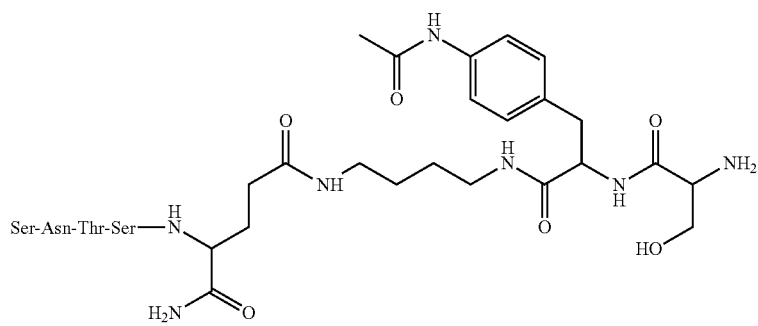
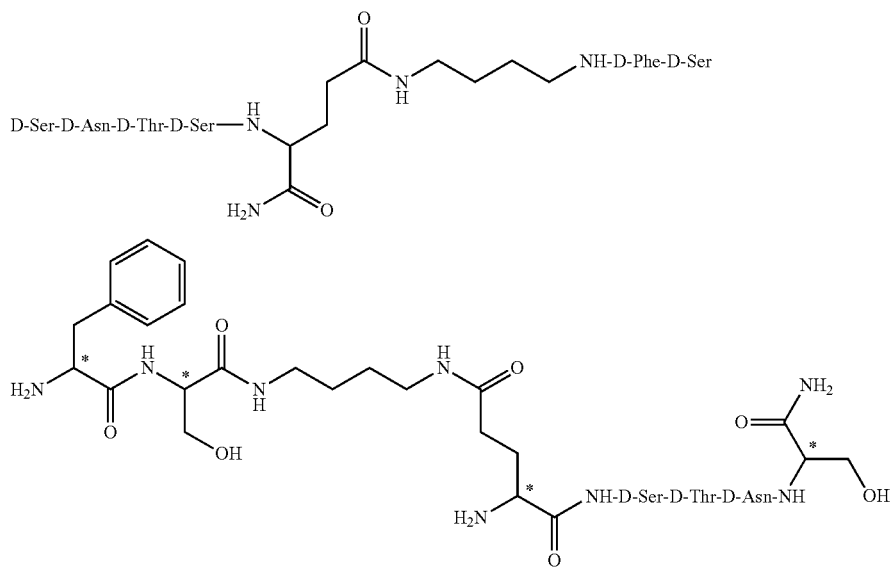

-continued
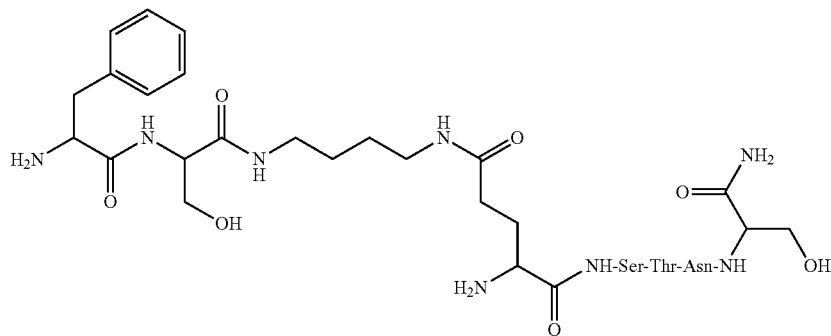
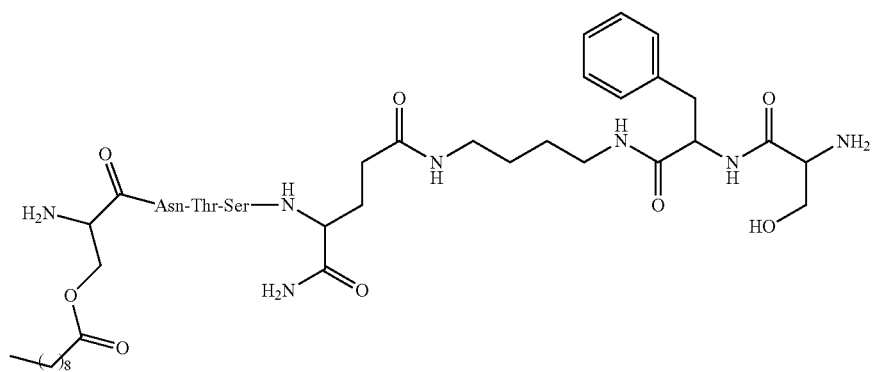
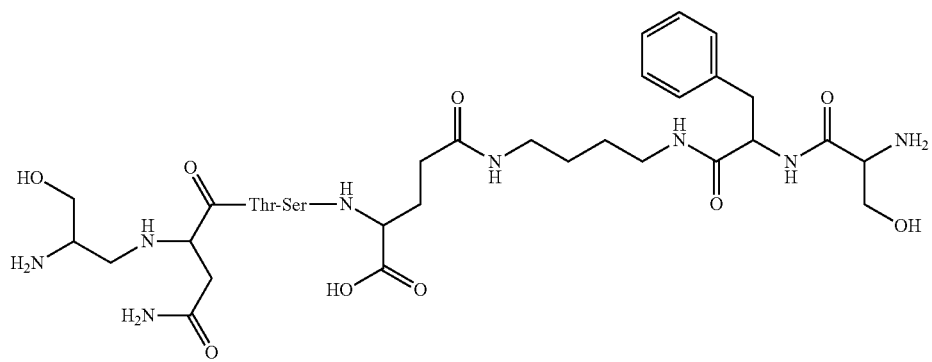
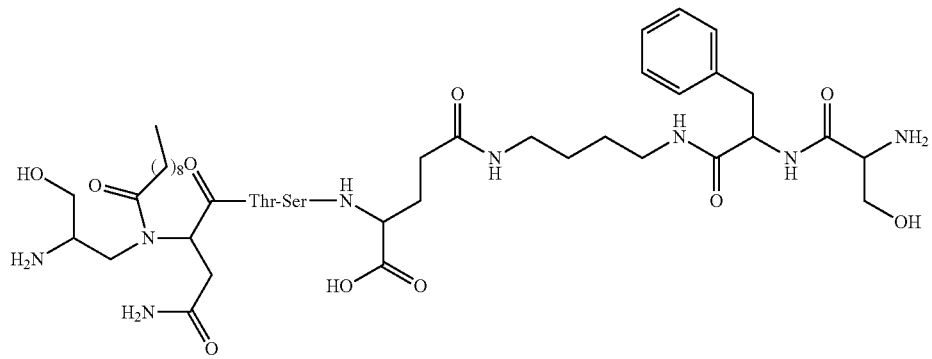

-continued
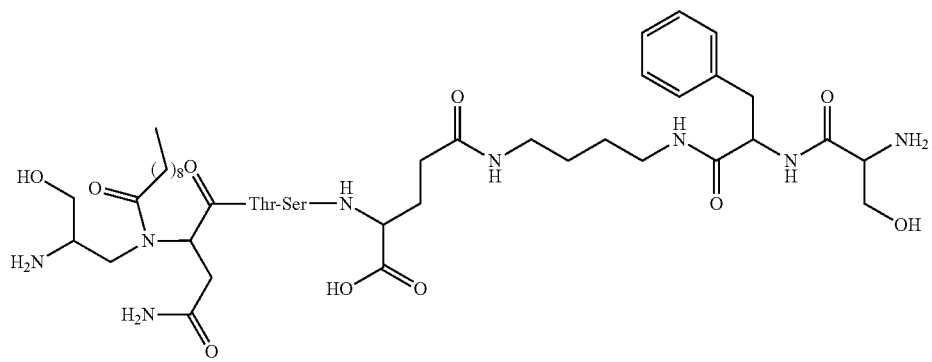
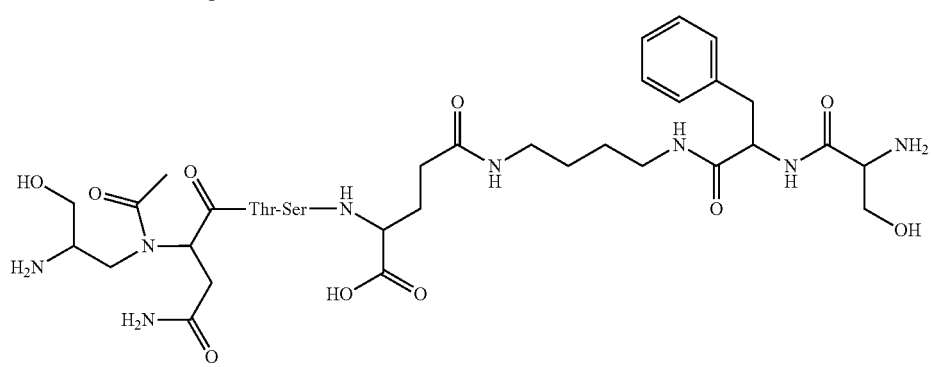
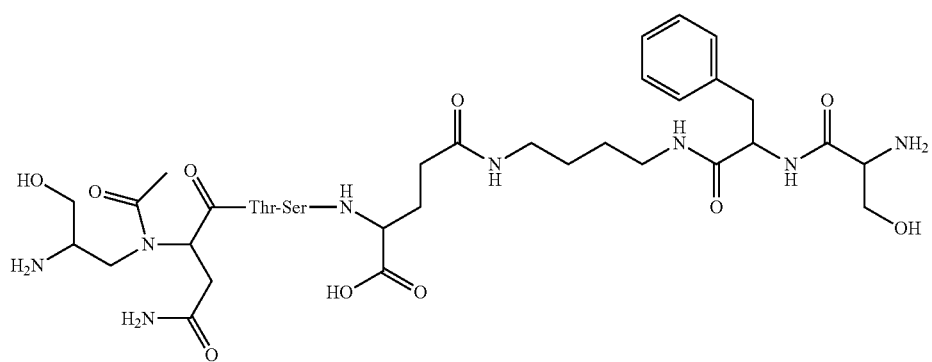
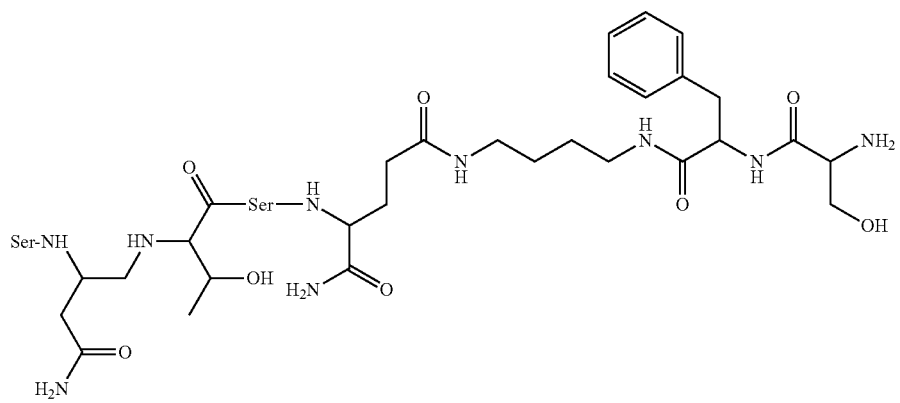

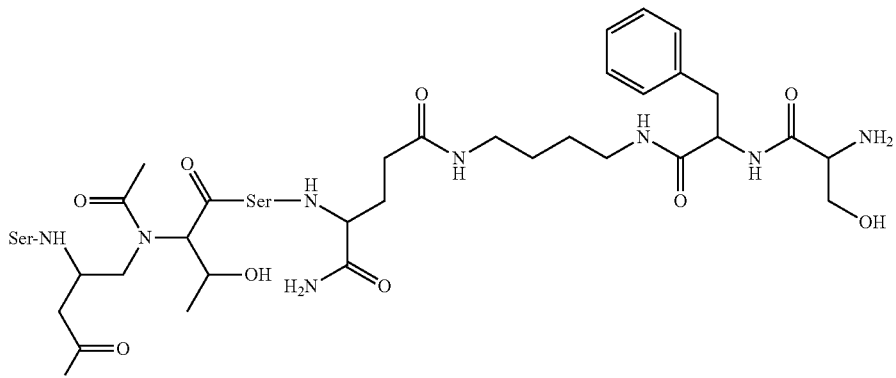
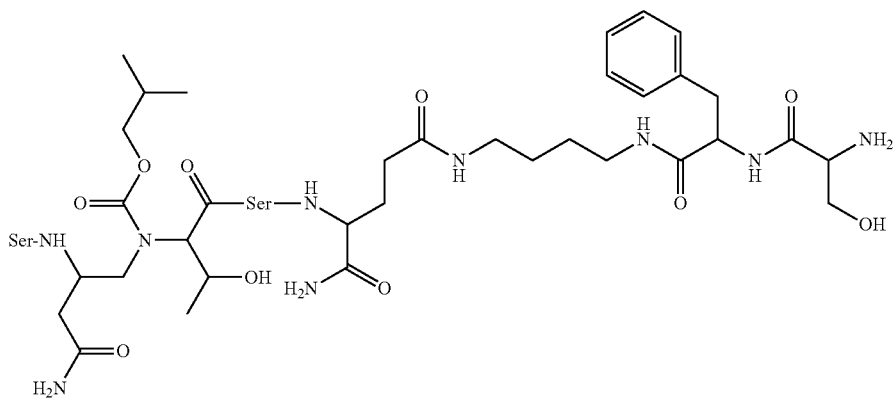
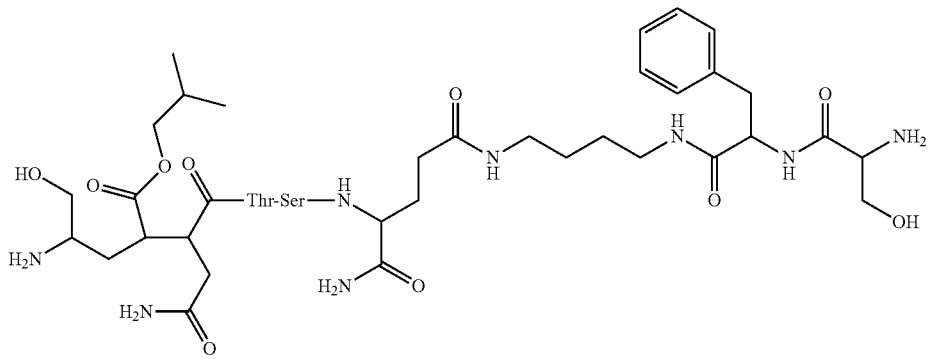
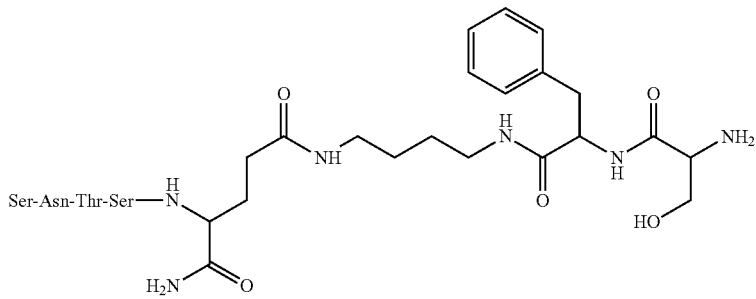
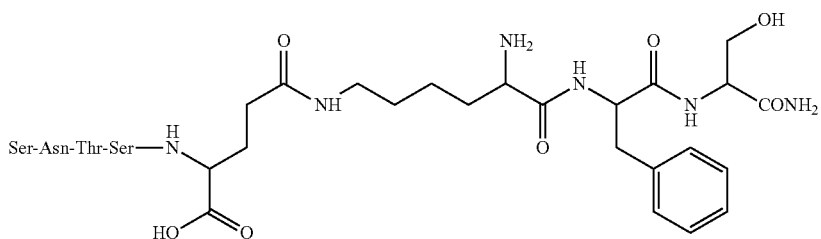

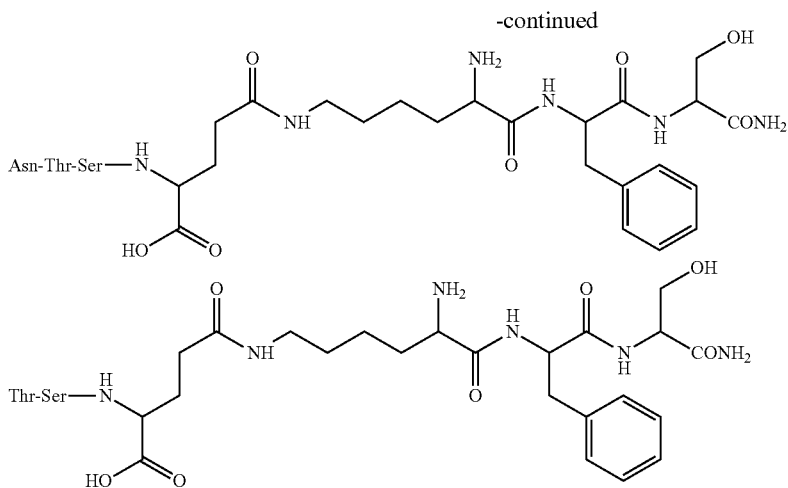

B. Exemplary CTLA-4 Antagonists

In certain embodiments, a combination described herein includes a CTLA-4 inhibitor. Exemplary anti-CTLA-4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9).

Information regarding tremelimumab (or antigen-binding fragments thereof) for use in the methods provided herein can be found in U.S. Pat. No. 6,682,736 (where it is referred to as 11.2.1), the disclosure of which is incorporated herein by reference in its entirety. Tremelimumab (also known as CP-675,206, CP-675, CP-675206, and ticilimumab) is a human IgG2 monoclonal antibody that is highly selective for CTLA-4 and blocks binding of CTLA-4 to CD80 (B7.1) and CD86 (B7.2). It has been shown to result in immune activation in vitro and some patients treated with tremelimumab have shown tumor regression.

Tremelimumab for use in the methods provided herein comprises a heavy chain and a light chain or a heavy chain variable region and a light chain variable region. In a specific aspect, tremelimumab or an antigen-binding fragment thereof for use in the methods provided herein comprises a light chain variable region comprising the amino acid sequences shown herein above and a heavy chain variable region comprising the amino acid sequence shown herein above. In a specific aspect, tremelimumab or an antigen-binding fragment thereof for use in the methods provided herein comprises a heavy chain variable region and a light chain variable region, wherein the heavy chain variable region comprises the Kabat-defined CDR1, CDR2, and CDR3 sequences shown herein above, and wherein the light chain variable region comprises the Kabat-defined CDR1, CDR2, and CDR3 sequences shown herein above. Those of ordinary skill in the art would easily be able to identify Chothia-defined, Abm-defined or other CDR definitions known to those of ordinary skill in the art. In a specific aspect, tremelimumab or an antigen-binding fragment thereof for use in the methods provided herein comprises the variable heavy chain and variable light chain CDR sequences of the antibody as disclosed in U.S. Pat. No. 6,682,736, which is herein incorporated by reference in its entirety.

The present invention also contemplates utilizing small molecule inhibitors of CTLA-4, such as described by Huxley et al. 2004 Cell Chemical Biology 11:1651-1658, which includes compounds of the formula:

| Compound | W | Z | X | R |
|---|---|---|---|---|
| 1 | F | H | CH | OH |
| 2 | F | H | CH | NHCH$_2$CH$_2$CH$_2$NMe$_2$ |
| 3 | H | H | N | |
| 4 | F | H | N | |
| 5 | F | H | N | |
| 6 | F | F | N | |

Other small molecule CTLA-4 antagonists include

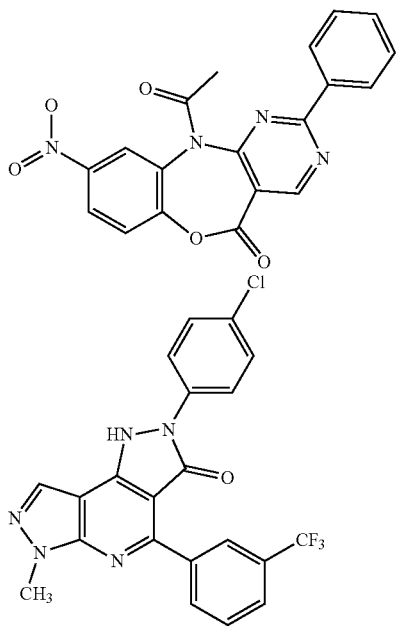

In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

Other exemplary anti-CTLA-4 antibodies are disclosed, e.g., in U.S. Pat. No. 5,811,097 (incorporated by reference).

In one embodiment, the inhibitor is a soluble ligand (e.g., a CTLA-4-Ig), or an antibody or antibody fragment that binds to PD-L1, PD-L2 or CTLA-4. For example, the anti-PD-1 antibody molecule can be administered in combination with an anti-CTLA-4 antibody, e.g., ipilimumab, for example, to treat a cancer (e.g., a cancer chosen from: a melanoma, e.g., a metastatic melanoma; a lung cancer, e.g., a non-small cell lung carcinoma; or a prostate cancer).

V. Pharmaceutical Compositions

In certain embodiments, the present invention relates to pharmaceutical compositions comprising a crystalline compound or salt of a compound of formula (I) and one or more pharmaceutically acceptable excipients.

Exemplary pharmaceutically acceptable excipients are presented herein, and include, for example binders, disintegrating agents, lubricants, corrigents, solubilizing agents, suspension aids, emulsifying agents, coating agents, cyclodextrins, and/or buffers. Although the dosage could vary depending on the symptoms, age and body weight of the patient, the nature and severity of the disorder to be treated or prevented, the route of administration and the form of the drug, in general, a daily dosage of from 0.01 to 3000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

In certain embodiments, the individual to which the composition is administered is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is sterile and pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop, through ophthalmic mucous membrane administration or penetration of the corneal epithelium.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the compounds. These salts can be prepared in situ during the final isolation and purification of the compounds, or by separately reacting a purified compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. Preparation of the crystalline salts is detailed in the Examples, below (See, for example, Berge et al. (1977) "Pharmaceutical Salts", J. Pharm. Sci. 66: 1-19.).

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Other representative salts include the copper and iron salts. Representative organic amines useful for the formation of base addition salts include ethylamine, diethylamine, ethylenediamine, ethanolamine, diethanolamine, piperazine, and the like (see, for example, Berge et al., supra).

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually or buccally); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. Compositions or compounds may also be administered as a bolus, electuary or paste.

To prepare solid dosage forms for oral administration capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the compositions of the present invention can also include adjuvants such as wetting agents, lubricants, emulsifying and suspending agents such as sodium lauryl sulfate and magnesium stearate, or sweetening, flavoring, coloring, perfuming, preservative, or antioxidant agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, vaginal rings for sustained-release (e.g., polymeric vaginal rings) creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compounds described herein can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. Ophthalmic routes of administration include local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, intravitreal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, metacresol, benzoic acid and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous, intravitreal or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

These compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compounds, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of metabolism or excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect or the maximally tolerated dose. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, the invention relates to any one of the aforementioned methods, wherein the compound is administered to the mammal chronically. In certain embodiments, chronic administration or chronic dosing takes place over a period of time. In certain embodiments, the period of time is greater than about 2 weeks, greater than about 3 weeks, greater than about 4 weeks, greater than about 5 weeks, greater than about 6 weeks, greater than about 7 weeks, greater than about 8 weeks, greater than about 9 weeks, or greater than about 10 weeks. In certain embodiments, a chronic dose is about 0.1 mg/kg/day, about 0.2 mg/kg/day, about 0.3 mg/kg/day, about 0.4 mg/kg/day, about 0.5 mg/kg/day, about 0.6 mg/kg/day, about 0.7 mg/kg/day, about 0.8 mg/kg/day, about 0.9 mg/kg/day, about 1 mg/kg/day, about 1.5 mg/kg/day, about 2 mg/kg/day, about 2.5 mg/kg/day, about 3 mg/kg/day, about 3.5 mg/kg/day, about 4 mg/kg/day, about 4.5 mg/kg/day, or about 5 mg/kg/day over a period of time. In certain embodiments, a chronic dose is about 0.5 µmole/kg/day, about 1 µmole/kg/day, about 1.5 µmole/kg/day, about 2 µmole/kg/day, about 2.5 µmole/kg/day, about 3 µmole/kg/day, about 3.5 µmole/kg/day, about 4 µmole/kg/day, about 4.5 µmole/kg/day, about 5 µmole/kg/day, about 5.5 mole/kg/day, about 6 µmole/kg/day, about 6.5 µmole/kg/day, about 7 µmole/kg/day, about 7.5 mole/kg/day, about 8 µmole/kg/day, about 8.5 µmole/kg/day, about 9 µmole/kg/day, about 9.5 µmole/kg/day, about 10 µmole/kg/day, about 11 µmole/kg/day, about 12 µmole/kg/day, about 13 mole/kg/day, about 14 µmole/kg/day, or about 15 µmole/kg/day over a period of time.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn, Cu, Fe or other metal salts.

The pharmaceutically acceptable acid addition salts can also exist as various solvates, such as with water, methanol, ethanol, dimethylformamide, dichloromethane, acetonitrile, acetone, ethyl acetate, cyclopentyl methyl ether and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Example 1. Synthetic Scheme

Synthesis of the compounds of the invention may involve a coupling reaction using a coupling reagent, such as HATU, etc, followed by de-protection when necessary, using, for example a reagent such as $BCl_3$ or $HCl-PhB(OH)_2$ method when necessary. Some of the target compounds were purified by RP-HPLC using Varian semi-preparative system with a Discovery C18 569226-U RP-HPLC column. The mobile phase was typically made by mixing water (0.1% TFA) with acetonitrile (0.08% TFA) in gradient concentration. The compound code, structure and characterization are shown in Table 1.

Scheme 1. General synthetic method

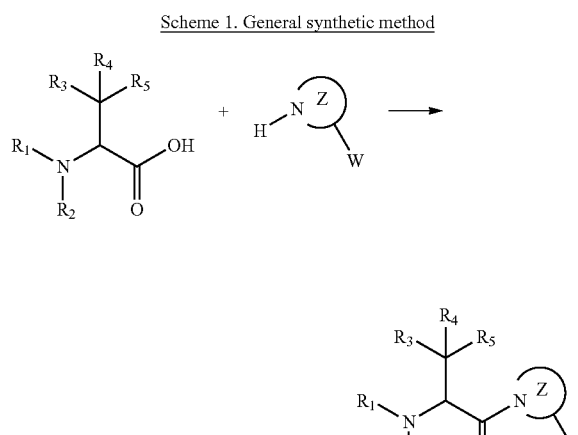

Exampled synthetic procedures of Gly(1-Adamantyl)-boro-Pro (ARI-5544 or 3102A-2C)

Scheme 2. Synthetic method for ARI-5544[a]

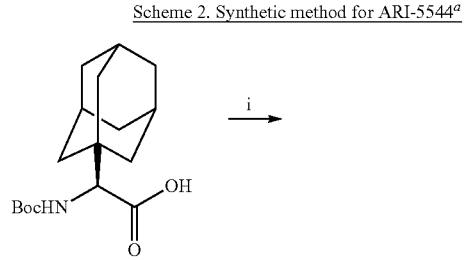

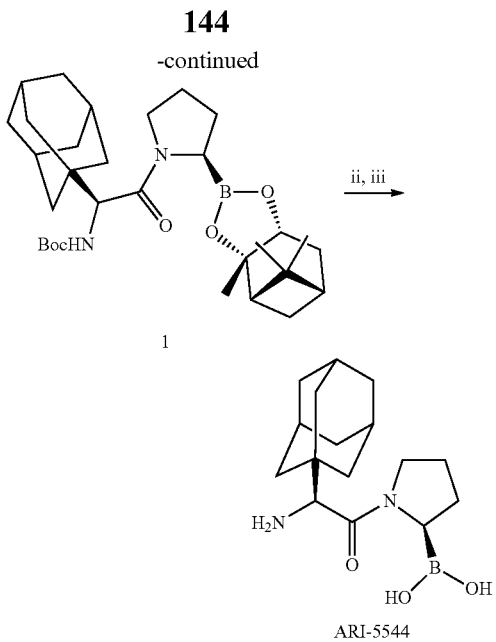

[a]Reagents and conditions: i. L-boroPro-pn, HATU, DIEA, DMF, 0° C. to r.t., 93%; ii. 4N HCl (g) in dioxane, 0° C. to r.t.; iii. PhB(OH)$_2$, MTBE-H$_2$O, 67% over two steps.

Synthesis of Gly(1-adamantyl)-boroPro (ARI-5544). A solution of 4 N HCl (g) in dioxane (5 mL, 20 mmol) was added to Compound 1 (0.86 g, 1.6 mmol) under dry ice/acetone cooling and then was allowed to stir for 3 hrs at room temperature. The reaction mixture was concentrated under reduced pressure and then co-evaporated with ethyl ether (3×15 mL) to afford (+)-pinandiol protected ARI-5544) which was dissolved with a pre-cooled 0.08 N HCl (10 mL). Then, tert-Butyl methyl ether (MTBE) (10 mL) and phenylboronic acid (0.22 g, 1.7 mmol) were added. The mixture was stirred at room temperature for 3 hours and the aqueous phase was separated. The MTBE layer was extracted with 0.08 N HCl (5 mL) and the combined water extractions were washed with ether (3×10 ml). Concentrated the aqueous phase on rotovap (<30° C.) and the crude product was purified by preparative HPLC (eluents: solvent A, 0.1% TFA in water; solvent B, 0.08% TFA in acetonitrile). Collected the desired fractions and concentrated to approximately 10 mL and freeze dry to give Compound ARI-5544 as a TFA salt (0.45 g, 67% over two steps). $^1$H NMR (D$_2$O): δ 1.60-1.75 (m, 14H), 1.85-2.15 (m, 6H), 3.07 (dd, J=11.1, 6.9 Hz, 1H), 3.46-3.52 (m, 1H), 3.76 (t, J=9.4 Hz, 1H), 3.91 (s, 1H). MS (ESI+) for C$_{16}$H$_{27}$BN$_2$O$_3$ m/z (rel intensity): 577.5 ([2×(M−H2O)+H]+, 76), 307.4 2 ([M+H]+, 100), 289.4 ([M−H2O+H]+, 24).

Exampled Synthetic Procedures of 3102C

Scheme 3. Synthetic method for 3102C[a]

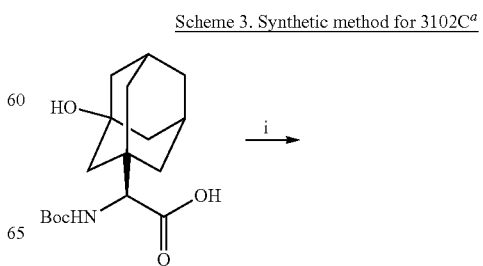

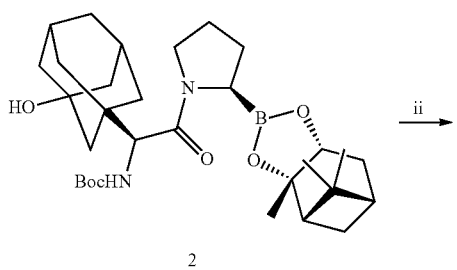

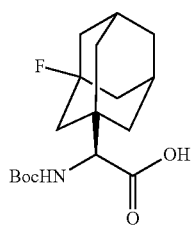

2
Chemical Formula:
C₁₇H₂₆FNO₄
Exact Mass: 327.18

5870
Chemical Formula:
C₁₆H₂₆BFN₂O₃
Exact Mass: 324.20

3102C

*a* Reagents and conditions: i. L-boroPro-pn, HATU, DIEA, DMF, 0° C. to r.t., 90%; ii. BCl₃ in CH₂Cl₂, -78° C. to r.t., 55%.

Synthesis of 3102C. Starting from N-Boc-L-3-hydroxy-1-Adamantyl-Glycine with the similar coupling reaction described above for the preparation of 1, compound 2 was prepared. This product (0.28 g, 0.5 mmol) was dissolved in dry dichloromethane (5.0 mL) and cooled to −78° C. while BCl₃ (1 M in dichloromethane, 5.0 mL) was added dropwise. The mixture was stirred at −78° C. for 1 hr, brought to room temperature and then concentrated in vacuo. The residue was partitioned between ether (5 mL) and water (5 mL). The aqueous layer was washed twice with more ether (2×5 mL), concentrated in vacuo and further purified by semipreparative RP-HPLC to give 3102C as a TFA salt (0.13 g, 55%).

Synthesis of 5870. Synthetic Scheme: i. DAST; ii. LiOH; iii. L-boroPro-pn, HATU, DIEA; iv. BCl3.

Synthesis of 5871. Synthetic Scheme: i. MeI, K2CO3, DMF; ii.4 eq. DAST and high temperature; iii. LiOH; iv. L-boroPro-pn, HATU, DIEA; v. HCl then PhB(OH)2.

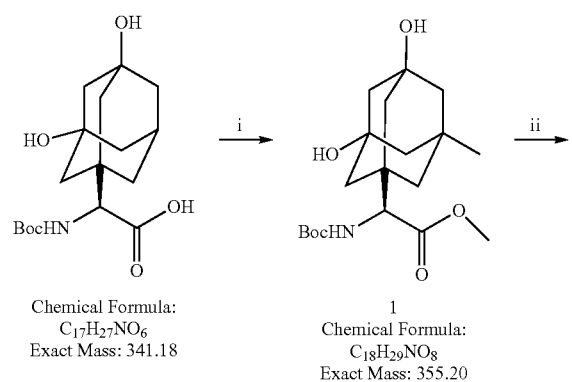

Chemical Formula:
C₁₇H₂₇NO₆
Exact Mass: 341.18

1
Chemical Formula:
C₁₈H₂₉NO₈
Exact Mass: 355.20

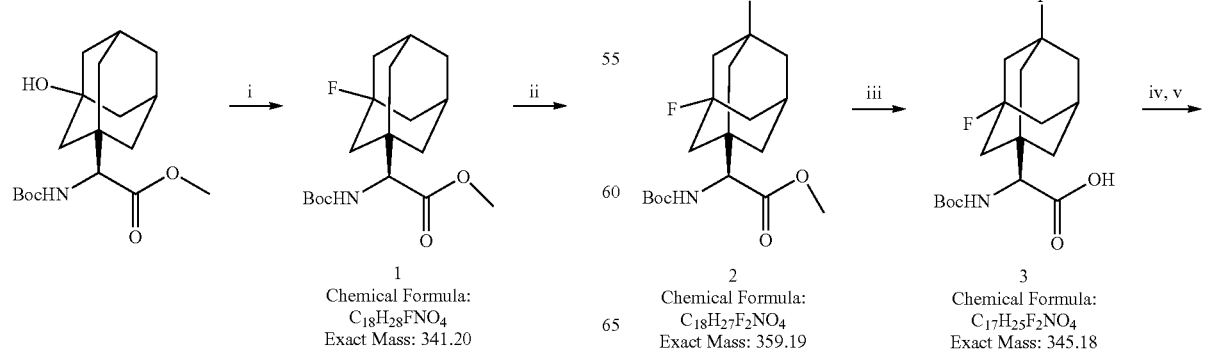

1
Chemical Formula:
C₁₈H₂₈FNO₄
Exact Mass: 341.20

2
Chemical Formula:
C₁₈H₂₇F₂NO₄
Exact Mass: 359.19

3
Chemical Formula:
C₁₇H₂₅F₂NO₄
Exact Mass: 345.18

-continued

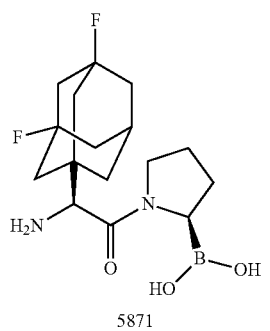

5871
Chemical Formula:
$C_{16}H_{25}BF_2N_2O_4$
Exact Mass: 342.19

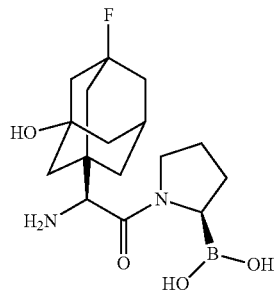

5874
Chemical Formula: $C_{18}H_{26}BFN_2O_4$
Exact Mass: 340.20

Synthesis of 5873. Synthetic Scheme: i.L-boroPro-pn, HATU, DIEA; ii. BCl3

Synthesis of Gly(3-hydroxyl-5,7,-dimethyl-adamantyl)-boroPro. Synthetic Scheme: i. MeI, K2CO3; ii. TrisylN3, KHMDS; iii. H2/Pd—C, Boc2O; iv. KOH; v. KMnO4; vi. L-boroPro-pn, HATU, DIEA; vii. HCl then PhB(OH)2.

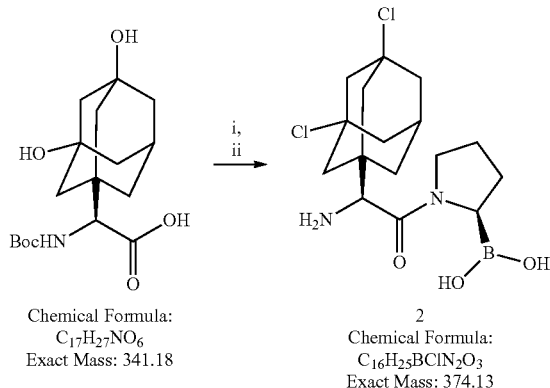 [SMILES: CC(C)(C)OC(=O)N[C@H](C(=O)O)C12CC3CC(O)(CC(O)(C3)C1)C2 ; N[C@H](C(=O)N1CCC[C@H]1B(O)O)C12CC3CC(Cl)(CC(Cl)(C3)C1)C2]

Chemical Formula:
$C_{17}H_{27}NO_6$
Exact Mass: 341.18

2
Chemical Formula:
$C_{16}H_{25}BClN_2O_3$
Exact Mass: 374.13

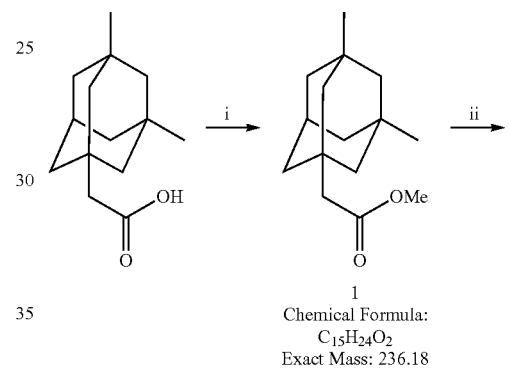

1
Chemical Formula:
$C_{15}H_{24}O_2$
Exact Mass: 236.18

2
Chemical Formula:
$C_{15}H_{23}N_3O_2$
Exact Mass: 277.18

3
Chemical Formula:
$C_{19}H_{31}NO_4$
Exact Mass: 377.23

Synthesis of 5874. Synthetic Scheme: i. 1eq. DAST at low temperature; ii. LiOH; iii. L-boroPro-pn, HATU, DIEA; iv. HCl then PhB(OH)$_2$.

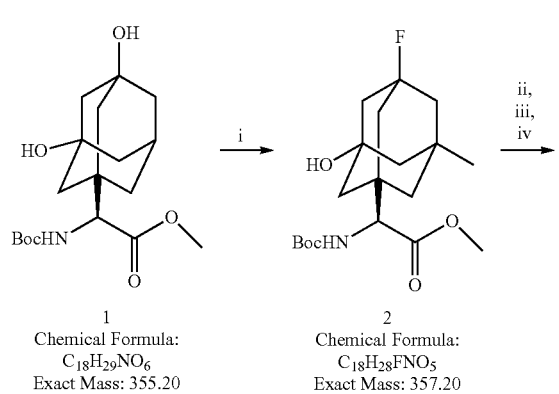

1
Chemical Formula:
$C_{18}H_{29}NO_6$
Exact Mass: 355.20

2
Chemical Formula:
$C_{18}H_{28}FNO_5$
Exact Mass: 357.20

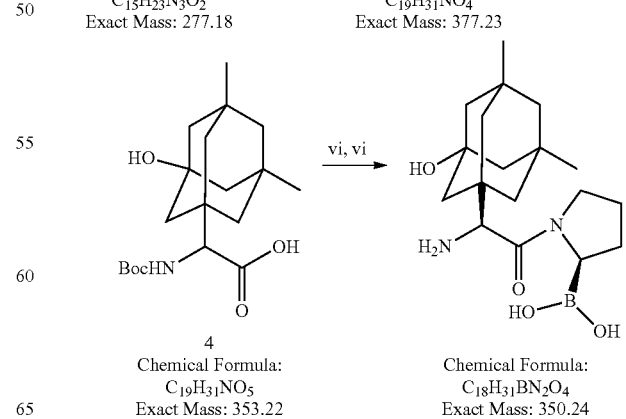

4
Chemical Formula:
$C_{19}H_{31}NO_5$
Exact Mass: 353.22

Chemical Formula:
$C_{18}H_{31}BN_2O_4$
Exact Mass: 350.24

149

Synthesis of 5879. Synthetic Scheme: i. DAST; ii. LiOH; iii. L-boroPro-pn, HATU, DIEA; iv. BCl3.

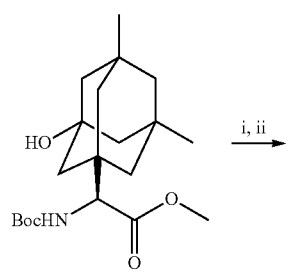

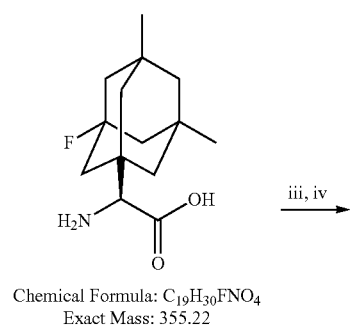

Chemical Formula: C₁₉H₃₀FNO₄
Exact Mass: 355.22

150

-continued

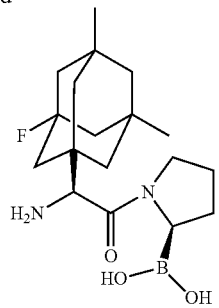

Chemical Formula: C₁₈H₃₀BFN₂O₃
Exact Mass: 352.23

Synthesis of 5880. Synthetic Scheme: i. L-boroPro-pn, HATU, DIEA; ii. BCl3.

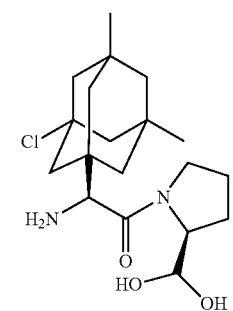

Chemical Formula: C₁₈H₃₀BClN₂O₃
Exact Mass: 368.20

Synthesis of 6067. Synthetic Scheme: i. Oxidation; ii. DAST; iii. H2/Pd—C; iv. L-boroPro-pn, HATU, DIEA; v. HCl; vi. PhB(OH)2.

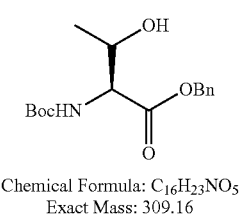

Chemical Formula: C₁₆H₂₃NO₅
Exact Mass: 309.16

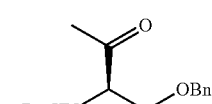

1
Chemical Formula: C₁₆H₂₁NO₅
Exact Mass: 307.14

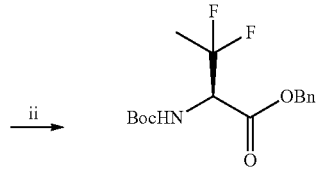

2
Chemical Formula: C₁₆H₂₁F₂NO₄
Exact Mass: 329.14

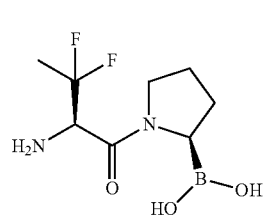

6067
Chemical Formula: C₈H₁₅BF₂N₂O₃
Exact Mass: 236.11

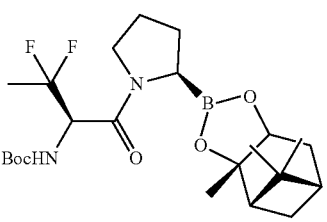

4
Chemical Formula: C₂₃H₃₇BF₂N₂O₅
Exact Mass: 470.28

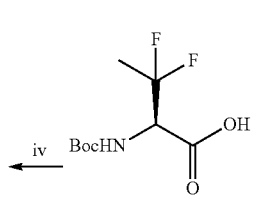

3
Chemical Formula: C₉H₁₅F₂NO₄
Exact Mass: 239.10

TABLE 1

*Compounds code, structures, and chemical characterization*

| Compound | Structure | Characterization |
|---|---|---|
| ARI-5544 (3102A-2C) | 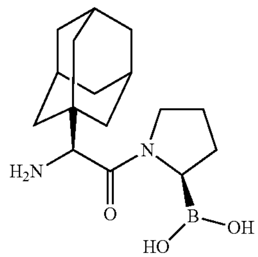 [SMILES: N[C@H](C(=O)N1CCC[C@H]1B(O)O)C12CC3CC(CC(C3)C1)C2] | $^1$H NMR (D$_2$O): δ 1.60-1.75 (m, 13H), 1.85-2.15 (m, 6H), 3.07 (dd, J = 11.1, 6.9 Hz, 1H), 3.46-3.52 (m, 1H), 3.76 (t, J = 9.4 Hz, 1H), 3.91 (s, 1H). MS (ESI+) for C$_{16}$H$_{27}$BN$_2$O$_3$ m/z (rel intensity): 577.5 ([2 × (M − H$_2$O) + H]$^+$, 76), 307.4 ([M + H]$^+$, 100), 289.4 ([M − H$_2$O + H]$^+$, 24). |
| 3102A-2D | 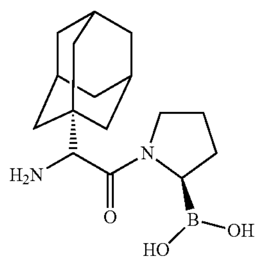 | $^1$H NMR (D$_2$O): δ 1.56-1.75 (m, 13H), 1.95-2.10 (m, 6H), 3.05-3.10 (m, 1H), 3.50-3.60 (m, 1H), 3.65-3.75 (m, 1H), 3.89 (s, 1H). MS (ESI+) for C$_{16}$H$_{27}$BN$_2$O$_3$ m/z (rel intensity): 577.1 ([2 × (M − H$_2$O) + H]$^+$, 65), 289.1 ([M − H$_2$O + H]$^+$, 100). |
| 3102A | 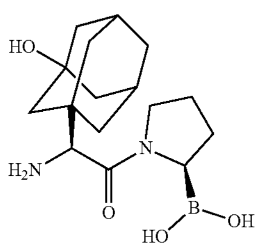 [SMILES: N[C@H](C(=O)N1CCC[C@H]1B(O)O)C12CC3CC(CC(O)(C3)C1)C2] | $^1$H NMR (D$_2$O): δ 1.43-1.80 (m, 13H), 1.83-1.92 (m, 1H), 2.08-2.16 (m, 2H), 2.27 (s, 2H), 3.08 (dd, J = 11.2, 6.9 Hz, 1H), 3.44-3.56 (m, 1H), 3.76 (t, J = 8.5 Hz, 1H), 4.03 (s, 1H). MS (ESI+) for C$_{16}$H$_{27}$BN$_2$O$_4$ m/z (rel intensity): 609.4 ([2 × (M − H$_2$O) + H]$^+$, 15), 323.2 ([M + H]$^+$, 50), 305.2 ([M − H$_2$O + H]$^+$, 100). |
| 3102A-2B | 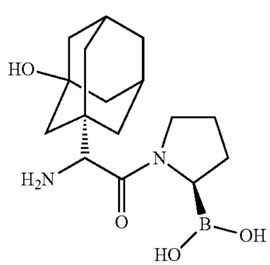 | $^1$H NMR (D$_2$O): δ 1.30-1.80 (m, 13 H), 1.85-2.10 (m, 3H), 2.24 (s, 2H), 3.04-3.08 (m, 1H), 3.50-3.60 (m, 1H), 3.65-3.75 (m, 1H), 4.02 (s, 1H). MS (ESI+) for C$_{16}$H$_{27}$BN$_2$O$_4$ m/z (rel intensity): 609.3 ([2 × (M − H$_2$O) + H]$^+$, 21), 323.2 ([M + H]$^+$, 7), 305.1 ([M − H$_2$O + H]$^+$, 100). |
| 3102C | 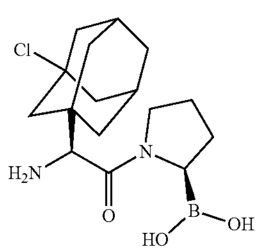 [SMILES: N[C@H](C(=O)N1CCC[C@H]1B(O)O)C12CC3CC(CC(Cl)(C3)C1)C2] | $^1$H NMR (D$_2$O): δ 1.54-1.80 (m, 7H), 1.85-1.95 (m, 1H), 2.00-2.21 (m, 8H), 2.27 (s, 2H), 3.09 (dd, J = 11.2, 7.0 Hz, 1H), 3.40-3.55 (m, 1H), 3.77 (t, J = 7.7 Hz, 1H), 4.03 (s, 1H). MS (ESI+) for C$_{16}$H$_{26}$BClN$_2$O$_3$ m/z (rel intensity): 341.2 ([M + H]$^+$, 50), 323.3 ([M − H$_2$O + H]$^+$, 100). |
| 8596-1 | 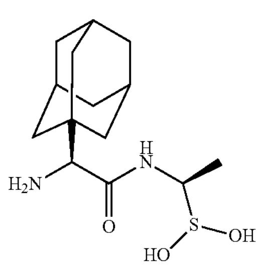 | $^1$H NMR (D$_2$O) δ 1.18 (d, J = 7.4 Hz, 3H), 1.61-1.76 (m, 12H), 2.04 (s, 3H), 2.88 (q, J = 7.3 Hz, 1H), 3.57 (s, 1H). MS (ESI+) for C$_{14}$H$_{25}$BN$_2$O$_3$, m/z (rel intensity): 525.4 ([2 × (M − H$_2$O) + H]$^+$, 20), 263.2 ([M − H$_2$O + H]$^+$, 100). |

TABLE 1-continued

Compounds code, structures, and chemical characterization

| Compound | Structure | Characterization |
|---|---|---|
| 4268 | 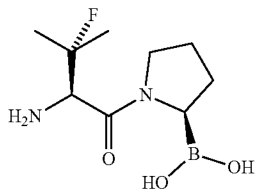 | $^1$H NMR (D$_2$O): δ 1.29-2.09 (m, 10H), 3.05-3.15 (m, 1H), 3.45-3.60 (m, 1H), 3.70-3.80 (m, 1H), 4.49 (d, J = 11.5 Hz, 1H). MS (ESI+) for C$_9$H$_{18}$BFN$_2$O$_3$ m/z (rel intensity): 429.1 ([2 × (M − H$_2$O) + H]$^+$, 100), 214.9 ([M − H$_2$O + H]$^+$, 80). |
| 4175CH | 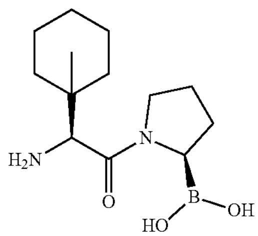 | $^1$H NMR (D$_2$O): δ 1.09 (s, 3H), 1.40-1.75 (m, 11H), 1.80-1.95 (m, 1H), 2.00-2.15 (m, 2H), 3.06 (dd, J = 11.5, 7.0 Hz, 1H), 3.47-3.56 (m, 1H), 3.76-3.82 (m, 1H), 4.04 (s, 1H). MS (ESI+) for C$_{13}$H$_{25}$BN$_2$O$_3$ m/z (rel intensity): 501.5 ([2 × (M − H$_2$O) + H]$^+$, 100), 269.3 ([M − H$_2$O + H]$^+$, 50). |
| 4175CP | 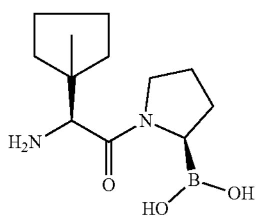 | $^1$H NMR (D$_2$O): δ 0.95 (s, 3H), 1.30-1.80 (m, 10H), 1.95-2.05 (m, 2H), 2.95-3.05 (m, 1H), 3.35-3.70 (m, 2H), 4.08 (s, 1H). MS (ESI+) for C$_{12}$H$_{23}$BN$_2$O$_3$ m/z (rel intensity): 473.2 ([2 × (M − H$_2$O) + H]$^+$, 34), 237.1 ([M − H$_2$O + H]$^+$, 100). |
| 4175CP-DL | 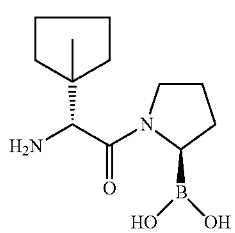 | $^1$H NMR (D$_2$O): δ 0.97 (s, 3H), 1.30-1.60 (m, 9H), 1.90-2.00 (m, 3H), 2.95-3.05 (m, 1H), 3.30-3.60 (m, 2H), 4.06 (s, 1H). MS (ESI+) for C$_{12}$H$_{23}$BN$_2$O$_3$ m/z (rel intensity): 473.2 ([2 × (M − H$_2$O) + H]$^+$, 66), 237.1 ([M − H$_2$O + H]$^+$, 100). |
| 4949-1 | 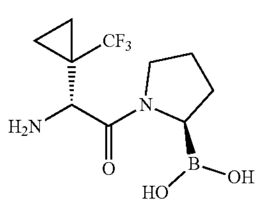 [SMILES: N[C@@H](C(=O)N1CCC[C@H]1B(O)O)C1(C(F)(F)F)CC1] | $^1$H NMR (D$_2$O): δ 0.76-0.84 (m, 1H), 1.15-1.25 (m, 1H), 1.36-1.45 (m, 2H), 1.75-1.81 (m, 1H), 1.98-2.18 (m, 3H), 3.12 (t, J = 8.3 Hz, 1H), 3.50-3.70 (m, 2H). MS (ESI+) for C$_{10}$H$_{16}$BF$_3$N$_2$O$_3$ m/z (rel intensity): 525.2 ([2 × (M − H$_2$O) + H]$^+$, 56), 263.1 ([M − H$_2$O + H]$^+$, 100). |
| 4949-2 | 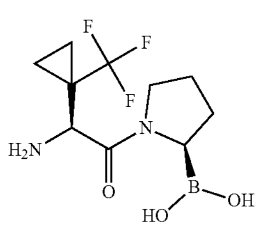 [SMILES: N[C@H](C(=O)N1CCC[C@H]1B(O)O)C1(C(F)(F)F)CC1] | $^1$H NMR (D$_2$O): δ 1.15-1.23 (m, 1H), 1.36 (s, 3H), 1.68-2.03 (m, 2H), 2.12-2.15 (m, 2H), 3.13 (t, J = 9.3 Hz, 1H), 3.47-3.56 (m, 1H), 3.72-3.78 (m, 1H), 4.86 (s, 1H). MS (ESI+) for C$_{10}$H$_{16}$BF$_3$N$_2$O$_3$ m/z (rel intensity): 525.2 ([2 × (M − H$_2$O) + H]$^+$, 50), 281.1 ([M + H]$^+$, 100), 263.1 ([M − H$_2$O + H]$^+$, 26). |
| 4367 | 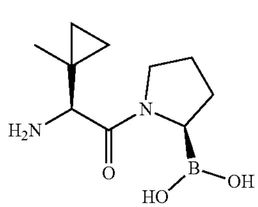 [SMILES: CC1([C@H](N)C(=O)N2CCC[C@H]2B(O)O)CC1] | $^1$H NMR (D$_2$O): δ 0.50-0.95 (m, 4H), 1.05 (s, 3H), 1.65-1.75 (m, 1H), 1.80-1.95 (m, 1H), 2.00-2.10 (m, 2H), 3.00-3.10 (m, 1H), 3.40-3.55 (m, 1H), 3.60-3.70 (m, 2H), 3.81 (s, 1H). MS (ESI+) for C$_{10}$H$_{19}$BN$_2$O$_3$ m/z (rel intensity): 417.2 ([2 × (M − H$_2$O) + H]$^+$, 87), 227.1 ([M + H]$^+$, 45), 209.0 ([M − H$_2$O + H]$^+$, 89). |

TABLE 1-continued

Compounds code, structures, and chemical characterization

| Compound | Structure | Characterization |
|---|---|---|
| 4367DL | 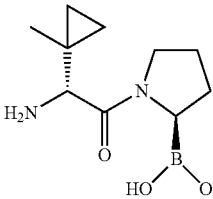 | $^{1}$H NMR (D$_2$O): δ 0.35-0.65 (m, 3H), 0.70-0.85 (m, 1H), 0.99 (s, 1H), 1.09 (s, 3H), 1.65-1.75 (m, 1H), 1.80-2.10 (m, 3H), 3.00-3.10 (m, 1H), 3.40-3.55 (m, 1H), 3.60-3.75 (m, 1H), 4.01 (s, 1H). MS (ESI+) for C$_{10}$H$_{19}$BN$_2$O$_3$ m/z (rel intensity): 417.2 ([2 × (M − H$_2$O) + H]$^+$, 70), 209.0 ([M − H$_2$O + H]$^+$, 100). |
| 5349 | 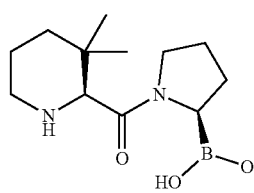 | $^{1}$H NMR (D$_2$O): δ 0.60-1.20 (m, 8H), 1.60-2.15 (m, 6H), 3.00-3.11 (m, 2H), 3.40-3.55 (m, 2H), 3.75-3.85 (m, 1H), 4.05-4.30 (m, 1H). MS (ESI+) for C$_{12}$H$_{23}$BN$_2$O$_3$ m/z (rel. intensity): 255.2 ([M + H]$^+$, 100). |
| 5362 | 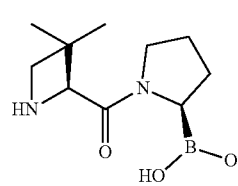 | $^{1}$H NMR (D$_2$O): δ 0.90-1.52 (m, 6H), 1.70-1.80 (m, 1H), 1.90-2.15 (m, 3H), 3.07-3.14 (m, 1H), 3.27-3.31 (m, 1H), 3.50-3.72 (m, 2H), 3.90-3.95 (m, 1H), 5.32 (s, 1H). MS (ESI+) for C$_{10}$H$_{19}$BN$_2$O$_3$ m/z (rel intensity): 227.2 ([M + H]$^+$, 100). |
| 5363 | 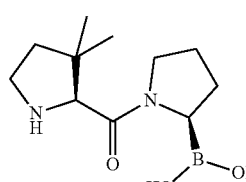 | $^{1}$H NMR (D$_2$O): δ 1.05-1.10 (m, 3H), 1.25-1.35 (m, 3H), 1.70-2.15 (m, 6H), 3.10 (dd, J = 11.0, 6.9 Hz, 1H), 3.43-3.80 (m, 4H), 4.29 (s, 1H). MS (ESI+) for C$_{11}$H$_{21}$BN$_2$O$_3$ m/z (rel intensity): 241.2 ([M + H]$^+$, 100). |

Example 2. Exemplary DASH-Inhibitors

Figure 15:
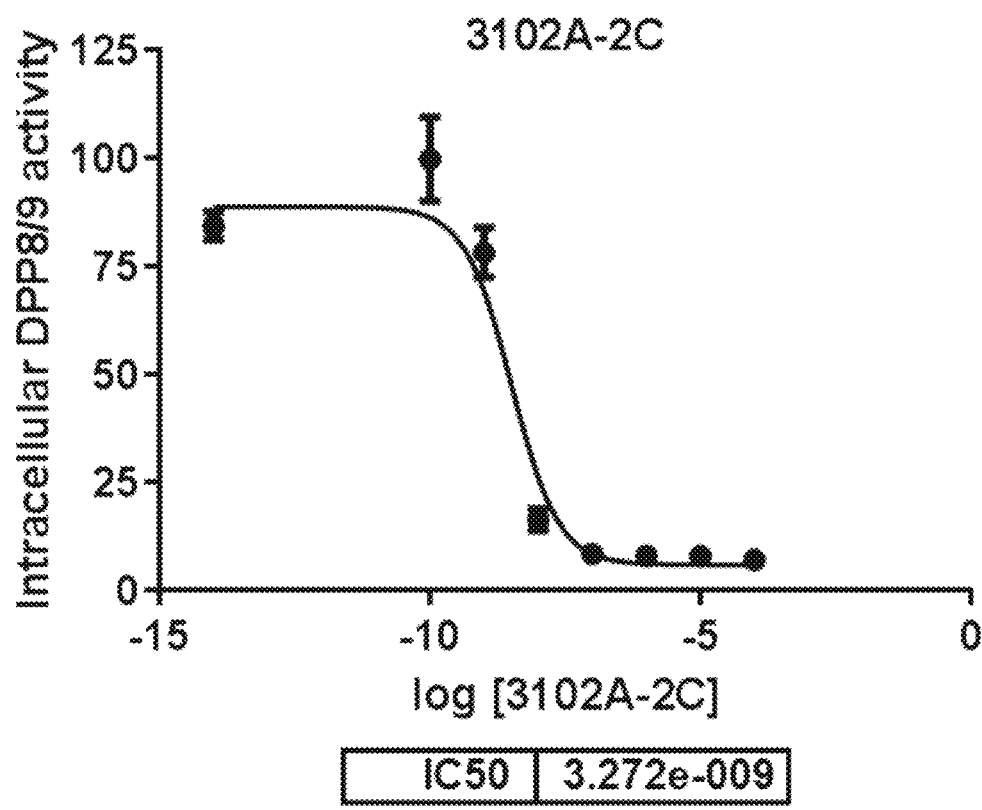
FIG. 15 depicts an intracellular DPP8/9 inhibition assay for ARI-5544 (f/k/a 3102A-2C) in 293T cells.

The following table provides, in columns 3-7, the inhibitory IC50's as determined for cell-free preparations of DPP8, DPP9, DPP4, DPP2, FAP (fibroblast activating protein) and PREP. These IC50 values (in nM) were determined following the protocol set forth in Example 4 below. See also FIGS. 11 and 15. Where calculated, the table also provides the intracellular IC50 ("IIC50") for inhibition of DPP8 and DPP9 in whole cells, according to the protocol described in Example 3 below. In certain instances, the table also provides the IC50 for inducing pyroptosis of macrophages in cell culture.

| Cmpd ID | Structure | DPP8 | DPP9 | DPP4 | DPP2 | FAP | PREP | IIC50 DPP8/9 | Pyroptosis |
|---|---|---|---|---|---|---|---|---|---|
| 5544 | 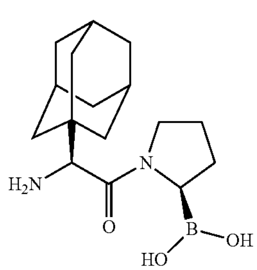 [SMILES: N[C@H](C(=O)N1CCC[C@H]1B(O)O)C12CC3CC(CC(C3)C1)C2] | 7.8 | 6.1 | 6.4 | 27 | 31 | 42 | 4.7 | 1.7 |

-continued

| Cmpd ID | Structure | DPP8 | DPP9 | DPP4 | DPP2 | FAP | PREP | IIC50 DPP8/9 | Pyroptosis |
|---|---|---|---|---|---|---|---|---|---|
| 3102C | 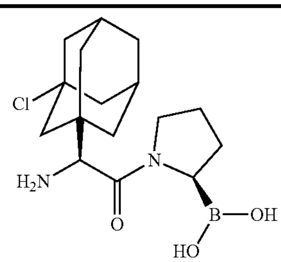 | 5 | 4 | 6 | 21 | 20 | 15 | 2.7 | NA |
| 4175CH | 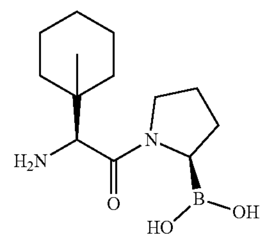 | 5.4 | 2.7 | 2.8 | 54 | 76 | 34 | 5.8 | 6.0 |
| 4175CP | 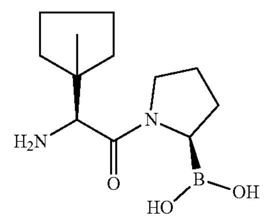 | 5.3 | 5.6 | 2.9 | 9.2 | 88 | 68 | 27 | 33 |
| 4268 | 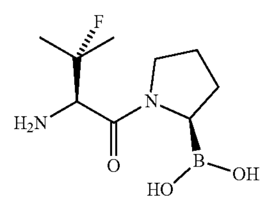 | 10 | 14 | 12 | 68 | 75 | 23 | 27 | 87 |
| 5362 | 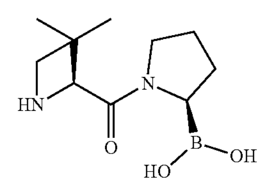 | 4.5 | 2.4 | 0.5 | 67 | 58 | 1200 | 110 | NA |
| 4949 | 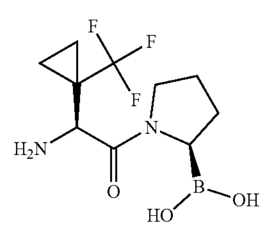 [SMILES: N[C@H](C(=O)N1CCC[C@H]1B(O)O)C1(C(F)(F)F)CC1] | 24 | 19 | 22 | 39 | 1200 | 58 | NA | 1900 |
| 3102A | 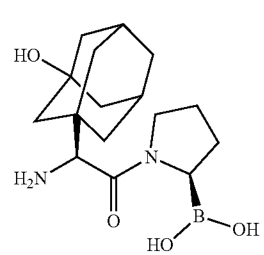 [SMILES: N[C@H](C(=O)N1CCC[C@H]1B(O)O)C12CC3CC(CC(O)(C3)C1)C2] | 10 | 7 | 7.2 | 81 | 9 | 49 | 1200 | NA |

| Cmpd ID | Structure | DPP8 | DPP9 | DPP4 | DPP2 | FAP | PREP | IC50 DPP8/9 | Pyroptosis |
|---|---|---|---|---|---|---|---|---|---|
| 5320 | 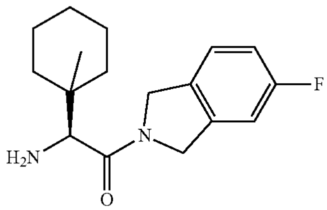 | 1.9 | 7.9 | 2070 | 53,940 | >100,000 | 89,450 | 280 | NA |
| 5349 | 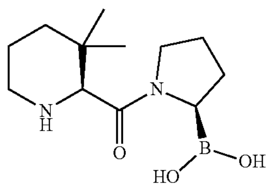 [SMILES: CC1(C)CCCN[C@@H]1C(=O)N1CCC[C@H]1B(O)O] | 250 | 3100 | 92 | 610 | 14,000 | 730 | NA | NA |
| 5363 | 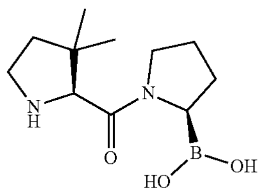 [SMILES: CC1(C)CCN[C@@H]1C(=O)N1CCC[C@H]1B(O)O] | 5.5 | 5.2 | 1.4 | 110 | 32 | 1400 | 270 | NA |
| 4367 | 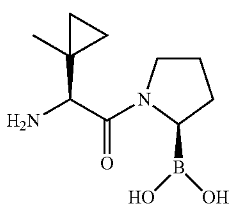 [SMILES: CC1([C@H](N)C(=O)N2CCC[C@H]2B(O)O)CC1] | 5.6 | 1.5 | 1.4 | 34 | 350 | 200 | 55 | NA |
| 5870 | 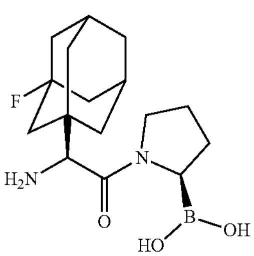 [SMILES: N[C@H](C(=O)N1CCC[C@H]1B(O)O)C12CC3CC(CC(C3)C1)C2] | 9.7 | 8.4 | 9.3 | 58 | 33 | | 9.1 | |

Example 3. Protocol for Determining the Intracellular IC$_{50}$ Against DPP Activity in 293T Cells Since 293T cells express low levels of endogenous DPP8/9 but not DPP IV, DPP II, or FAP, this allows for assessment of intracellular DPP8/9 inhibition without interference from other background DPP activity. (Danilova, O. et al. (2007) Bioorg. Med. Chem. Lett. 17, 507-510; Wang, X. M. et al. (2005) Hepatology 42, 935-945) This information allows for assessment of cell penetrability of the compounds.

Materials 293T cells (ATCC, Cat. No. CRL-11268)

RPMI 1640 cell culture media without phenol red (VWR, Cat. No. 45000-410) supplemented with 2 mM L-glutamine (VWR, Cat. No. 45000-676), 10 mM HEPES (VWR, Cat. No. 45000-690), 1 mM sodium pyruvate (VWR, Cat. No. 45000-710), 4500 mg/L glucose (VWR, Cat. No. 45001-116), 1× penicillin-streptomycin (VWR, Cat. No. 45000-652)

Inhibitor or prodrug

4000× substrate solution (100 mM Ala-Pro-AFC (Bachem, Cat. No. I-1680) in DMSO)

96-well black clear-bottom plates (BD Biosciences, Cat. No. 353948)

Instrumentation

Plate shaker

Molecular Devices SpectraMax® M2e microplate reader

Protocol

Assay Setup

Trypsinize and spin down cells from a 75 cm2 or larger flask, wash with PBS and resuspend in RPMI 1640. Count the cells in the resulting suspension and adjust the volume such that it has 100,000 cells per 75 μL. Add 100 μL of RPMI 1640 alone to rows A-C of column 1 in a 96-well black clear-bottomed plate. Add 75 µL of the cell suspension to the remaining wells in columns 2-10. Equilibrate the plates at 37° C. overnight.

Sample Preparation

1. To prepare the compound for the assay, dissolve it in either DMSO or, if cyclization is suspected, in pH 2.0 water (0.01 N HCl) to a final concentration of 100 mM. For pH 2.0 stocks, incubate at room temperature for a minimum of four hours and up to overnight. From this, prepare a 4 mM stock in RPMI 1640. If the inhibitor is insoluble at this concentration, dilute the 100 mM stock 1:10 to 10 mM. Using this stock, prepare a 0.4 mM stock as described above. The pH of each diluted sample should be confirmed to be that of the cell culture medium (pH 7-8).

Figure 34:
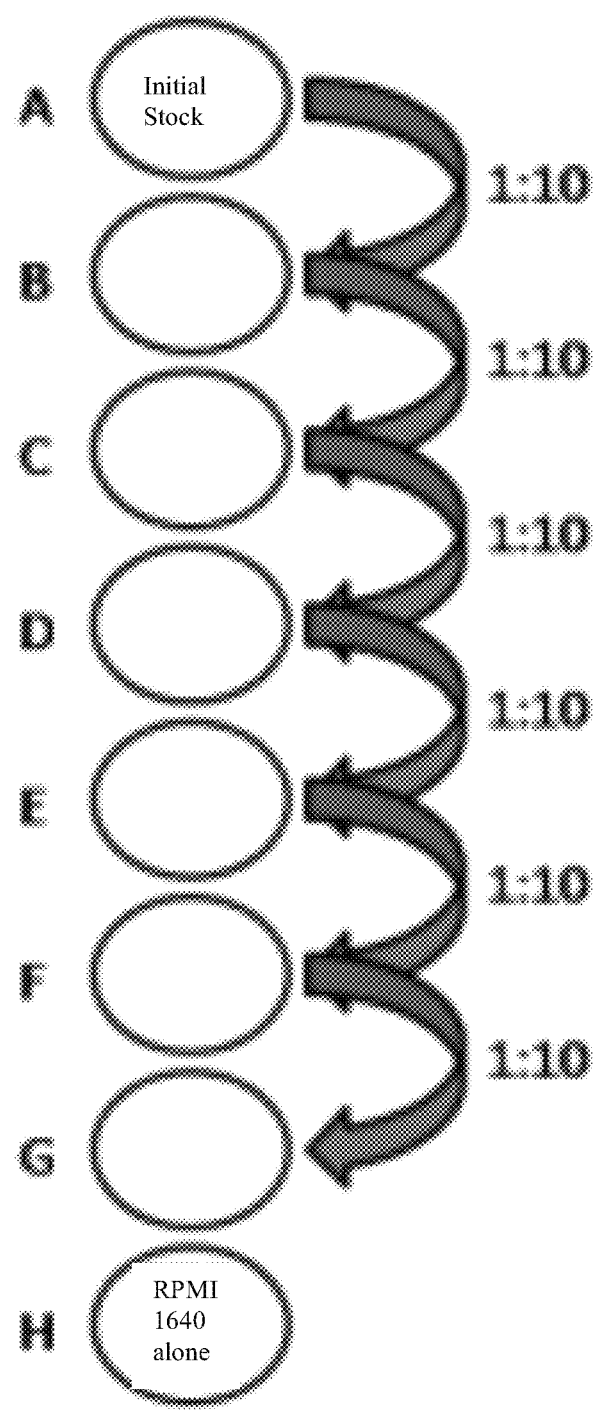
FIG. 34 shows the protocol set forth in example 3 for preparing serial dilutions to determine the intracellular $IC_{50}$ against DPP activity in 293T cells.

2. Prepare a dilution plate for the compounds prepared in step 3. To do so, add the 4 or 0.4 mM stocks prepared previously to row A of a 96-well plate. From this, perform 1:10 serial dilutions into RPMI 1640 down to row G as shown in FIG. 34. Row H should have RPMI 1640 cell culture medium alone.

3. Add 25 µL of the compound from the dilution plate prepared in step 4 to the assay plate in columns 2-10 where appropriate. Each sample should be tested in triplicate. Shake the plate briefly and allow it to incubate for two hours at 37° C.

4. During this time, the substrate should be prepared. To do so, dilute the 100 mM stock 1:400 into RPMI 1640 to its final working concentration of 250 µM. 5. After the incubation at 37° C. is complete, add 10 µL of the substrate prepared in step 5 to each well. Shake the plate briefly and allow it to incubate for 10 minutes at 37° C. Once complete, read the fluorescence at λex: 400, λem: 505.

Data Analysis

1. Import the fluorescence values directly into Prism as the y values. For the inhibitor concentrations, which are the x values, be sure to divide the concentrations in the dilution plate by 4 to account for their dilution in the assay. The x values must be converted into log values prior to their importation into Prism. The concentration for the no inhibitor wells (row H) should be entered as −14 (equal to 10-14 M).

2. Once the values have been entered, under "Analyze", choose "Nonlinear regression (curve fit)". At the subsequent prompt, choose "log(inhibitor) vs. response". This will calculate the IC50 values, which can be found in the "Results" section.

Example 4. Protocol for In Vitro Inhibition Assay for Dipeptidyl Peptidase IV, Dipeptidyl Peptidase 8. Dipeptidyl Peptidase 9, Dipeptidyl Peptidase II Fibroblast Activation Protein or Prolyl Oligopeptidase This assay may be used to determine the IC50 of various inhibitors against recombinant human dipeptidyl peptidase IV (DPPIV), dipeptidyl peptidase 8 (DPP8), dipeptidyl peptidase 9 (DPP9), dipeptidyl peptidase II, fibroblast activation protein (FAP) or prolyl oligopeptidase (PREP).

Materials
Enzymes
  Recombinant human DPPIV (R&D Systems, Cat. No. 1180-SE)
  Recombinant human DPP8 (Enzo Life Sciences, Cat. No. BML-SE527)
  Recombinant human DPP9 (R&D Systems, Cat. No. 5419-SE)
  Recombinant human DPPII (R&D Systems, Cat. No. 3438-SE)
  Recombinant human FAP (R&D Systems, Cat. No. 3715-SE)
  Recombinant human PREP (R&D Systems, Cat. No. 4308-SE)
Assay Buffers
  25 mM Tris, pH 8.0 (DPPIV and DPP9)
  50 mM Tris, pH 7.5 (DPP8)
  25 mM MES, pH 6.0 (DPPII)
  50 mM Tris, 140 mM NaCl, pH 7.5 (FAP)
  25 mM Tris, 0.25 M NaCl, pH 7.5 (PREP)
Substrates
  4000× substrate solution (100 mM Gly-Pro-AMC (VWR, Cat. No. 100042-646) in DMSO, DPPIV, DPP8 and DPP9)
  4000× substrate solution (100 mM Lys-Pro-AMC (Bachem, Cat. No. I-1745) in DMSO, DPPII)
  100× substrate solution (2.5 mM Z-Gly-Pro-AMC (VWR, Cat. No. I-1145.0050BA) in DMSO, FAP and PREP)
General Materials
  Compound
  96-well black clear-bottom plates (Costar, Cat. No. 3603)
Instrumentation
  Plate shaker
  Molecular Devices SpectraMax® M2e microplate reader Protocol 1. To prepare the compound for the assay, dissolve it in either DMSO or, if cyclization is suspected, in pH 2.0 water (0.01 N HCl) to a final concentration of 100 mM. For pH 2.0 stocks, incubate at room temperature for a minimum of four hours and up to overnight. From this, prepare a 1 mM stock at pH 7.4 in 50 mM Tris. If the inhibitor is insoluble at this concentration, dilute the 100 mM stock 1:10 to 10 mM. Using this stock, prepare a 0.1 mM stock as described above.

2. Prepare a dilution plate for the compound stocks to be tested. Add the 0.1 and/or 1 mM stocks prepared previously to row A of a 96-well plate. From this, perform 1:10 serial dilutions into the appropriate assay buffer down the columns as shown below:

3. Prepare 20× substrate solution by diluting the DMSO stocks into the appropriate assay buffer.

4. Dilute the enzymes into their appropriate assay buffers. The dilution factor is lot dependent and must be determined prior to performing the assay. The final enzyme concentrations should be 0.1, 0.8, 0.4, 0.2, 1.2, and 0.6 nM for DPPIV, 8, 9, II, FAP and PREP respectively. Add 180 µL to each well needed in columns 2-10. Column 1 should be prepared as shown below:

5. Add 20 µL of the compound of interest from the dilution plate prepared in step 2 to columns 2-10 of the assay plate where appropriate. Each sample should be tested in triplicate. Allow this to incubate for 10 minutes at room temperature, shaking the plate for the first two minutes.

6. Add 10 µL of 20× substrate prepared in step 3 to each well and allow this to incubate for 15 minutes at room temperature, shaking the plate for the first two minutes.

7. Read the fluorescence at λex: 380, λem: 460.

Data Analysis

1. Average the values for the blanks in wells A1, B1 and C1 and subtract this from the remaining wells. Import the resulting fluorescence values into Prism as the y values. For the compound concentrations, which are the x values, be sure to divide the concentrations in the dilution plate by 10.5 to account for their dilution in the assay plate. These must be converted into log values prior to their importation into Prism 2. Once the values have been entered, under "Analyze" and choose "Nonlinear regression (curve fit)". At the subsequent prompt, choose "log(inhibitor) vs. response". This will calculate the IC50 values, which can be found in the "Results" section.

Example 5. Assessment of Serum Cytokine Induction in Mice

Methodology:
Animals

For general screening purposes, approximately 8 week old male BALB/c mice are used, but others can be substituted if that particular strain is of interest, noting that their cytokine profiles may be different.

Materials
   Compound
   Vehicle
   pH 2.0 water (0.01 N HCl, oral)
   PBS (Mediatech, Cat. No. 21-030-CV, IP or SC)
   Cytokine Quantikine ELISA kit
   G-CSF (R&D Systems, Cat. No. MCS00)
   CXCL1 (R&D Systems, Cat. No. MKC00B)
   IL-18 (R&D Systems, Cat. No. 7625)
   IL-1β (R&D Systems, Cat. No. MLB00C)
   IFN-γ (R&D Systems, Cat. No. MIF00)
   IL-6 (R&D Systems, Cat. No. M6000B)
   Instrumentation
   Molecular Devices SpectraMax® $M2^e$ microplate reader Protocol
1. Mice (n=5) are allowed to acclimate for one week prior to dosing.
2. If mice are to be treated orally, they should be fasted for a minimum of two hours, up to overnight (not >15 hours).
3. Compounds of interest are prepared in either pH 2.0 water for oral (PO) or PBS for intraperitoneal (IP) or subcutaneous (SC) administration. IP and SC samples must also be sterilized via filtration through a 0.22 μm PVDF filter. The concentration should be prepared such that the appropriate dose is administered in a volume of 200 IL/animal.
4. For BALB/c mice, blood samples are collected via cardiac puncture at either three six hours post-Rx. Blood samples are collected in Eppendorf tubes and allowed to incubate for 30 minutes at room temperature before centrifugation at 14,000 rpm for 15 minutes at 4° C. for serum separation and collection.
5. Serum samples should be stored at −80° C. while awaiting analysis.
6. Cytokine levels are measured following the instructions supplied with the commercially available kits.

Results:
General Screen of Select Inhibitors for G-CSF Induction in BALB/c Mice

| Inhibitor | PID | Dose (μg/animal) | Route of Administration (200 μL/ animal) | Average [G-CSF] at 6 hrs (pg/mL) |
|---|---|---|---|---|
| Vehicle | N/A | N/A | PO | 550 |
|  |  |  | SC | 210 |
| FT-100 | 2054 | 20 | PO | 55000 |
|  |  |  | SC | 97000 |
| ARI-4175 | 4175 | 20 | PO | 19000 |
|  |  |  | SC | 65000 |
| ARI-5544 | 5544 | 5 | PO | 650 |
|  |  | 20 |  | 30000 |
|  |  |  | SC | 73000 |
| ARI-4175CH | 4175CH | 5 | PO | 1100 |
|  |  | 20 |  | 51000 |
|  |  |  | SC | 60000 |
| Arg-boroPro | 8205 | 20 | PO | 320 |
|  |  | 200 |  | 930 |
|  |  | 2000 |  | 3500 |
|  |  | 20 | SC | 160 |
|  |  | 200 |  | 670 |
|  |  | 2000 |  | 31000 |
| Glu-boroPro | 8120 | 20 | PO | 340 |
|  |  | 200 |  | 160 |
|  |  | 2000 |  | 2300 |
|  |  | 200 | SC | 210 |
|  |  | 2000 |  | 16000 |
| ARI-2243 | 2243 | 20 | PO | 330 |
|  |  | 50 | IP | 2100 |
|  |  | 100 |  | 2400 |
|  |  | 300 |  | 4400 |
| Sitagiptin | MKD431 | 1000 | PO | 340 |
|  |  | 200 | SC | 100 |
|  |  | 2000 |  | 950 |
| Org-boroPro | 1797 | 20 | PO | 20000 |
| threo-de-boroPro | 4316 | 20 | PO | 5000 |
| Deuterated PT-100 | 20540 | 20 | PO | 37000 |

Conclusion:

G-CSF has proven to serve as a representative cytokine for the overall response, so it is generally used for initial screening purposes.

Example 6. CT26 Efficacy Studies

Summary

The purpose of these experiments is to determine the efficacy of various small molecule inhibitors in combination with antibody checkpoint inhibitors in an immunocompetent mouse model. All animal studies are carried out under approved IACUC protocols. Data shown in FIGS. 12 and 13.

Description
Materials
   Female BALB/c mice, ideally 10-12 weeks old (n=10/group)
   CT26.WT cells (ATCC Cat. No. CRL-2638)
   RPMI 1640 cell culture media without phenol red (VWR, Cat. No. 45000-410) supplemented with 2 mM L-glutamine (VWR, Cat. No. 45000-676), 10 mM HEPES (VWR, Cat. No. 45000-690), 1 mM sodium pyruvate (VWR, Cat. No. 45000-710), 4500 mg/L glucose (VWR, Cat. No. 45001-116), 1× penicillin-streptomycin (VWR, Cat. No. 45000-652)
   Vehicle
   Oral (PO) dosing: pH 2.0 water (0.01 N HCl)
   Intraperitoneal (IP) dosing: sterile PBS
      Small molecule inhibitor
      Checkpoint antibodies
   α-PD-1 (clone RMP1-14, BioXCell Cat. No. BP0146)
   Rat IgG2a α-PD-1 isotype control (clone 2A3, BioXCell Cat. No. BP0089)
   α-CTLA-4 (clone 9D9, BioXCell Cat. No. BP0164)
   Mouse IgG2b α-CTLA-4 isotype control (clone MPC-11, BioXCell Cat. No. BP0086)

Protocol
1. Mice should be ordered and allowed to acclimate for a week prior to inoculation. Ideally, they should weigh approximately at least 18 g at the time of inoculation.
2. Mice are inoculated subcutaneously in the right flank with 5×105 CT26.WT cells per animal. This is carried out with 100 μL of a 5×10$^6$ cells/mL suspension prepared in RPMI 1640.
3. Dosing commencement timeline should be established prior to carrying out the experiment, as it may vary:
   a. ARI-5544 efficacy experiment commenced on day 2 following inoculation
   b. Efficacy of ARI-4175 alone experiment commenced when tumors averaged approximately 300 mm3
   c. ARI-4175 in combination with checkpoint inhibitors experiments commenced when tumors averaged approximately 50-100 mm3
4. Dosing schedules:
   a. Small molecule inhibitors (ARI-8205; IP, ARI-4175; PO), QD×5 (2 days off)
   b. Checkpoint antibodies and isotype controls, IP on days 3, 6 and 9 following commencement of ARI-4175 dosing
5. Experimental endpoints for individual animals were as follows:
   a. Poor body condition (severe lethargy, labored breathing, etc.)
   b. Body weight loss of >15% from the start of dosing
   c. Tumor measurement >14 mm in one direction
   d. Tumor ulceration measuring >5 mm in one direction
   e. Death
6. Tumors and other tissues may be collected at the conclusion of the study for further analysis, if needed

| CT26 Cell Viability Results | | |
|---|---|---|
| Inhibitor | PID | EC$_{50}$ (μM) |
| PT-100 | 2054 | >1000 |
| ARI-4175 | 4175 | >1000 |
| ARI-5544 | 5544 | >100 |
| ARI-4175CH | 4175CH | >1000 |
| Arg-boroPro | 8205 | >1000 |
| Glu-boroPro | 8120 | >1000 |
| ARI-2243 | 2243 | >1000 |
| Bortezomib | 4155 | 0.036 |

Example 7. MB49 Efficacy Studies

Data Shown in FIGS. 18, 19, 20, 21, 25, 26, 27, 28, 29, 30, 31 and 32
Materials
  Female C57BL/6 mice, 9-12 weeks old (n=10/group)
  MB49 cells (NIH)
  RPMI 1640 cell culture media without phenol red (VWR, Cat. No. 45000-410) supplemented with 2 mM L-glutamine (VWR, Cat. No. 45000-676), 10 mM HEPES (VWR, Cat. No. 45000-690), 1 mM sodium pyruvate (VWR, Cat. No. 45000-710), 4500 mg/L glucose (VWR, Cat. No. 45001-116), 1× penicillin-streptomycin (VWR, Cat. No. 45000-652)
  Vehicle (10% EtOH, 2% Tween 80, 2% Solutol HS-15, pH 2.0)
  DASH inhibitor
  Celecoxib (Cayman Chemicals, Cat. No. 10008672)
  Checkpoint antibodies
    α-PD-1 (clone RMP1-14, BioXCell Cat. No. BP0146)
    Rat IgG2a α-PD-1 isotype control (clone 2A3, BioXCell Cat. No. BP0089)

Figure 6:
FIG. 6 depicts the sensitivities of various cell lines to four individual ARI compounds.
Figure 6:
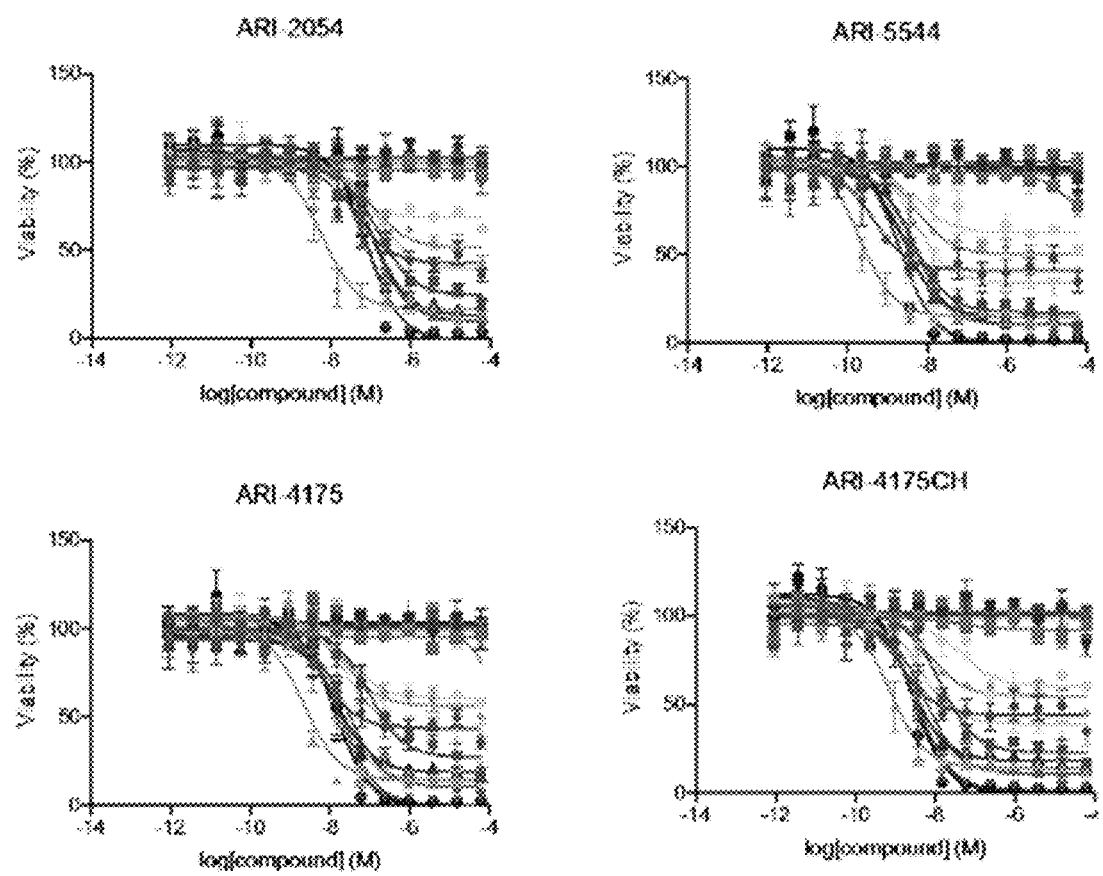

Protocol
1. Mice should be ordered and allowed to acclimate for a week prior to inoculation.
2. Mice were inoculated subcutaneously in the right flank with 1×10$^6$ MB49 cells per animal. This is carried out with 100 μL of a 1×10$^7$ cells/mL suspension prepared in RPMI 1640.
3. Dosing commenced three days following inoculation, which was day 4. Dosing specifics are provided below:
   a. DASH inhibitor; PO, QD×5 (2 days off)
   b. Celecoxib (CBX); 24 μg PO, BID×5 (2 days off)
      i. CBX was weighed out for each dosing period and fully dissolved in EtOH at a concentration higher than the final dose
      ii. The concentrated EtOH stock was diluted to its working concentration in vehicle prior to dosing
   c. Dose timing:
      i. DASH inhibitor and first CBX dose coadministered
      ii. Second CBX dose, 4 hrs post-initial dose
   d. α-PD-1 and isotype control antibodies; 200 μg IP on days 3, 6, 9 and 12 following commencement of DASH inhibitor and CBX dosing (days 7, 10, 13 and 16 following inoculation)
4. Body weight and tumor measurements were taken three days per week.
5. Experimental endpoints for individual animals were as follows:
   a. Poor body condition (severe lethargy, labored breathing, etc.)
   b. Body weight loss of >15% from the start of dosing
   c. Tumor measurement >20 mm in one direction
   d. Tumor ulceration measuring >5 mm in one direction
   e. Death Example 8. AML Cell Line IC$_{50}$ Values ARI-2054, ARI-5544, ARI-4175 and ARI-4175CH induce pyroptosis in AML cell lines. Here, we determine the sensitivity of AML cell lines to these compounds.
Methodology:
Cell Culture
  HT-1080, Jurkat, MCF7, THP-1, and U937 cells were purchased from ATCC. SET-2, RS4;11, and SKM-1 cells were purchased from DSMZ. HL-60, MV4;11, OCI-AML2, NB4, MOLM-13, NOMO-1, DAOY, HEL, IMR-5, K562, Kasumi-1, ONS-76, RDES-1, and TC-71 cells were a gift from Alex Kentsis and verified using STR genotyping (Genetica). HT-1080, DAOY, ONS-76, RDES-1, IMR-5 and TC-71 cells were grown in Dulbecco's modified Eagle's medium (DMEM) with 10% fetal bovine serum (FBS). MCF-7, Jurkat, THP-1, U937, HL-60, MV4;11, OCI-AML2, NB4, MOLM-13, NOMO-1, HEL, K562, SET-2, RS4;11, SKM-1 and Kasumi-1 were grown in RPMI-1640 medium with 10% FBS. All cells were grown at 37° C. in a 5% CO$_2$ incubator. Cell lines were tested for mycoplasma using the MycoAlert Mycoplasma Detection Kit (Lonza).
Drug Sensitivity
  Cells were plated (2000 cells/well) in white, 384-well clear bottom plates using an EL406 Microplate Washer/Dispenser (BioTek) in 25 μL final volume of media. Compounds were added using a pintool (CyBio) and cells were incubated for 48 h at 37° C. Assay plates were then removed from the incubator and allowed to equilibrate to room temperature on the bench top before addition of 10 μL of CellTiter-Glo reagent (Promega) according to the manufacturer's instructions. Assay plates were shaken on an orbital shaker for 2 minutes and incubated at room temperature on the bench top for 10 minutes. Luminescence was then read using a Cytation 5 Cell Imaging Multi-Mode Reader (BioTek). (FIG. 6)

| | | | IC$_{50}$ (nM) | | | |
|---|---|---|---|---|---|---|
| Cell line | Malignancy | FAB | ARI-2054 | ARI-5544 | ARI-4175 | ARI-4175CH |
| SET-2 | AML/MPN | | 6 | 0.2 | 2 | 1 |
| KG-1 | AML | M0 | 20 | 5 | 35 | 49 |
| SKM-1 | AML | M5 | 44 | 0.4 | 7 | 1 |
| MV4;11 | AML | M5 | 78 | 2 | 14 | 3 |
| OCI-AML3 | AML | M4 | 80 | 2 | 19 | 3 |
| NB4 | AML/APL | M3 | 100 | 3 | 14 | 3 |
| HL-60 | AML | M2 | 115 | 3 | 16 | 3 |
| MOLM-13 | AML | M5 | 120 | 5 | 28 | 6 |
| RS4;11 | AML/B-ALL | | 147 | 4 | 96 | 13 |
| NOMO-1 | AML | M5 | 160 | 5 | 30 | 4 |
| THP-1 | AML | M5 | 206 | 5 | 23 | 6 |
| DAOY | Medulloblastoma | | >60,000 | >60,000 | >60,000 | >60,000 |
| HEL | AML/Erythroleukemis | M6 | >60,000 | >60,000 | >60,000 | >60,000 |
| HT-1080 | Fibrosarcoma | | >60,000 | >60,000 | >60,000 | >60,000 |
| IMR-5 | Neuroblastoma | | >60,000 | >60,000 | >60,000 | >60,000 |
| Jurkat | T-ALL | | >60,000 | >60,000 | >60,000 | >60,000 |
| K562 | CML/Erythroleukemia | CML | >60,000 | >60,000 | >60,000 | >60,000 |
| Kasumi-1 | AML | M2 | >60,000 | >60,000 | >60,000 | >60,000 |
| MCF7 | Breast | | >60,000 | >60,000 | >60,000 | >60,000 |
| ONS-76 | Medulloblastoma | | >60,000 | >60,000 | >60,000 | >60,000 |
| RDES-1 | Ewing's sarcoma | | >60,000 | >60,000 | >60,000 | >60,000 |
| TC-71 | Ewing's sarcoma | | >60,000 | >60,000 | >60,000 | >60,000 |
| U937 | AML/histiocytic lymphoma | M5 | >60,000 | >60,000 | >60,000 | >60,000 |

Figure 7:
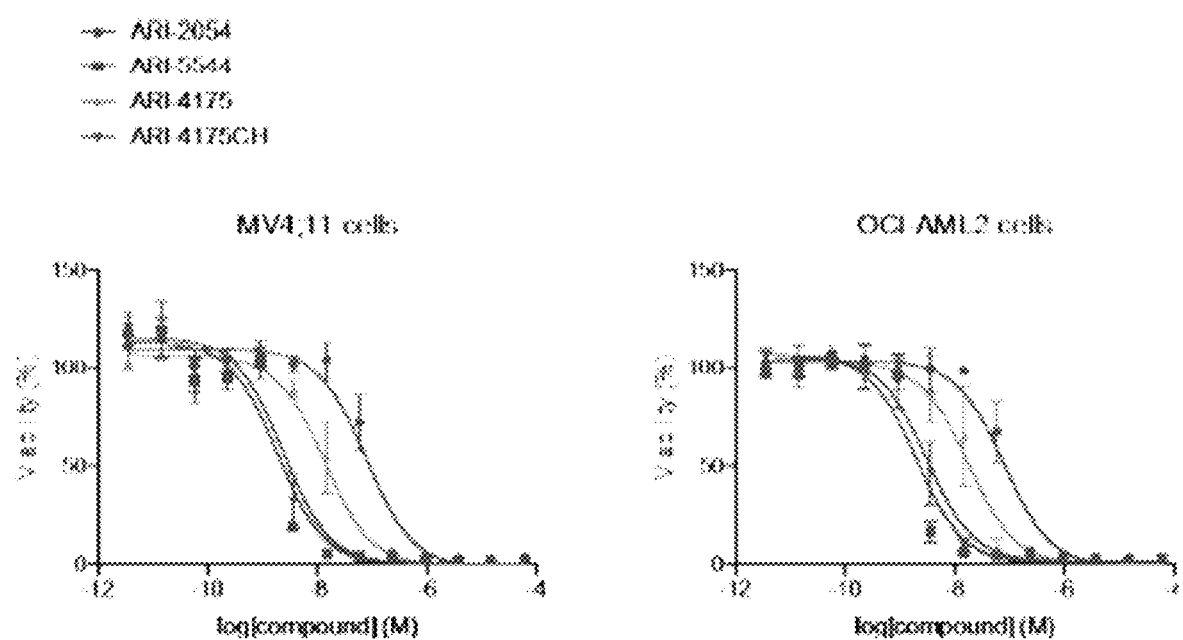
FIG. 7 depicts the activities of four individual ARI compounds against two cell lines, including ARI-5544 and ARI-4175CH (structures shown in Examples), ARI4175 (t-butylglycine-boroProline) and ARI-2054 (Valine-boro-Proline), against two human leukemia (AML) cell lines, illustrating that while the subject immuno-DASH inhibitors are not generally toxic in vitro at tumor concentrations equivalent to doses giving rise to tumor regressing/inhibition in vivo, those tumor cell lines arising from macrophage lineage are extremely sensitive to killing by immuno-DASH inhibitors.

Two-marker selection of cell line expression profiling (from the Cancer Cell Line Encyclopedia) reveals the expression of caspase-1 as a predictor of cell line sensitivity. The erythrocytic AML cell lines HEL and K562 do not express caspase-1. (FIG. 7)

Conclusions

The ARI compounds induce pyroptosis in 85% of non-erythrocytic AML cell lines. Kasumi-1 and U937 are the only AML cell lines that are resistant. Kasumi-1 does not express caspase-1 and therefore should not respond. Why U937 cells do not respond is currently unclear, but it should be noted that some consider these histiocytic lymphoma cells and not really monocytes. ARI-5544 and ARI-4175CH have low (single digit) nanomolar IC$_{50}$ values for all of these lines. ARI-2054 is significantly less potent, killing most of these AML cell lines with IC$_{50}$ values >100 nM.

Example 9. EnPlex IC$_{50}$ Values of ARI Compounds; In Vitro Inhibition of DPP4, 7, 8, 9 and FAP Methodology The EnPlex assay was performed as described previously (Bachovchin et al, *Nature Chemical Biology*, 2014). Compounds were assayed in triplicate.

Results

ARI-5544, ARI-4175CH, ARI-3102C, ARI-5836, and ARI-4175 are all highly potent inhibitors of DPP8/9 (IC$_{50}$s for DPP9<50 pM). These compounds have highly potent pyroptosis inducing activity in vitro (<10 nM). These compounds are all equally or more potent for DPP4, except for ARI-5836, which has a >10-fold preference for DPP9.

| | EnPlex IC$_{50}$ (pM) | | | | | Pyroptosis IC$_{50}$ (nM) | | |
|---|---|---|---|---|---|---|---|---|
| | | | | | | RAW 264.7 | MV4;11 | THP-1 |
| Compound | DPP4 | DPP7 | DPP8 | DPP9 | FAP | WT cells | Luc-Neo | sgGFP |
| ARI-5544 | 5 | 100,000 | 13 | 6 | >100,000 | 2 | <0.1 | 0.2 |
| ARI-4175CH | 5 | >100,000 | 16 | 12 | >100,000 | 6 | 0.2 | 0.9 |
| ARI-3102C | 6 | 7,000 | 89 | 3 | >100,000 | 3 | 1 | 7 |
| ARI-5836 | 447 | >100,000 | 190 | 40 | >100,000 | — | 1 | 2 |
| ARI-4175 | 4 | >100,000 | 8 | 3 | >100,000 | 14 | 8 | 7 |
| ARI-3102A | 17 | >100,000 | 9 | 168 | 484 | 173 | 571 | 376 |
| ARI-2107 | 79 | >100,000 | 47 | 67 | >100,000 | — | 165 | 65 |
| ARI-2054 | <0.3 | 333,600 | 51 | 332 | >100,000 | 98 | 60 | 168 |

Example 10. Oral PK profile of ARI-5544 and ARI-4175CH in mice Measuring of plasma drug concentrations following oral administration of ARI-5544 and ARI-4175CH in normal mice Methodology Mice:

BALB/c mice, male, Charles River Laboratories, 10 weeks of age.

Formulation:

Drugs dissolved in pH 2 water at 0.3 mg/mL. Administration of 10 mL/kg gives a dose of 3 mg/kg.

Treatment Groups:

3 mg/kg ARI-5544 by oral gavage, n=3, dose=3 mg/kg.
3 mg/kg ARI-4175CH by oral gavage, n=3, dose=3 mg/kg.

Samples:

1. Blood collected at 5, 10, 20, 30, 40, 60, 120 and 240 min post-dose from the tail vein into Li-heparin tubes.
2. Plasma prepared by centrifugation.
3. Drug concentrations measured by LCMS.

Figure 8:
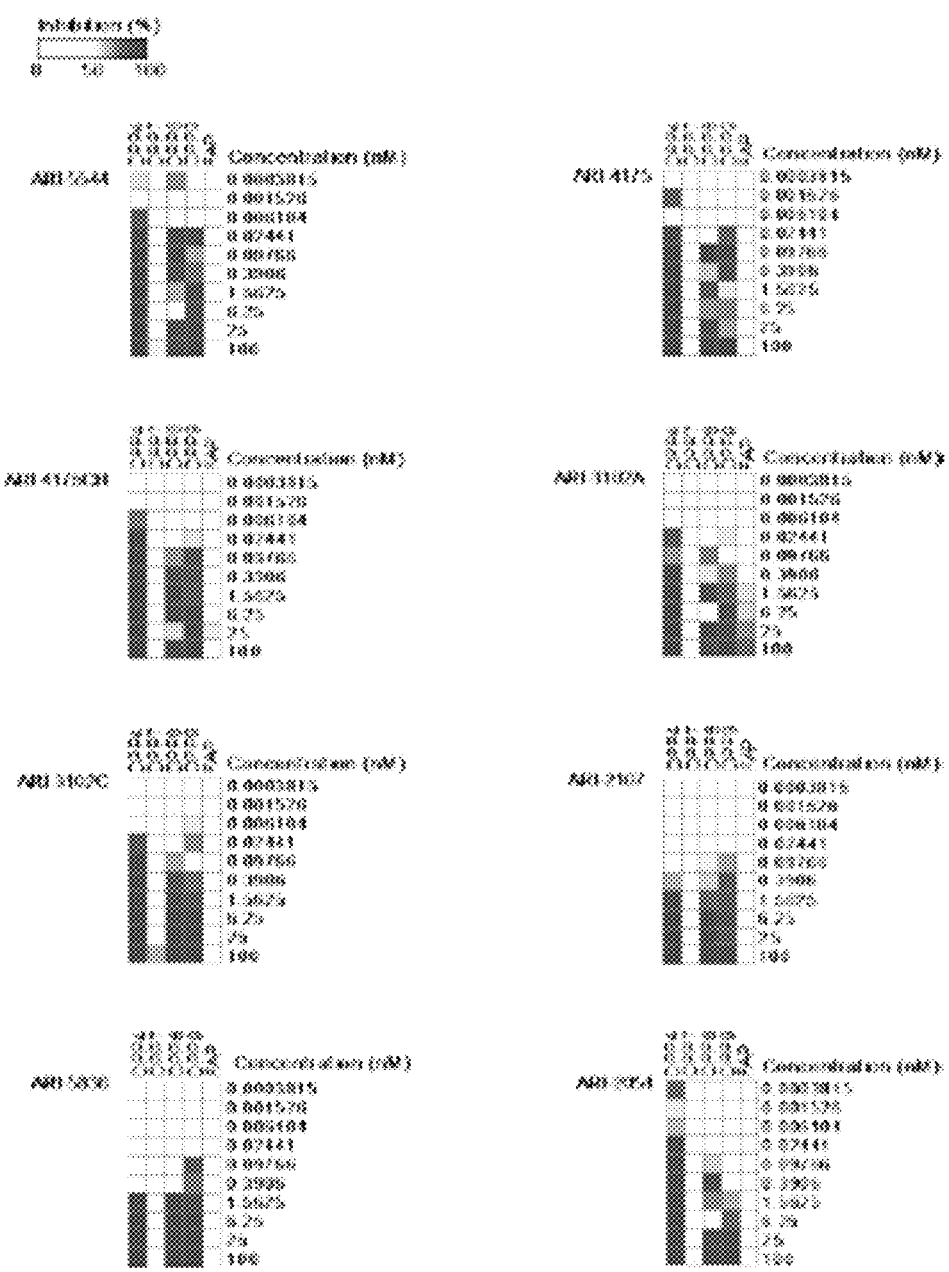
FIG. 8 depicts high potency, as measured by EnPlex, of ARI-5544, ARI-4175CH, ARI-3102C, ARI-5836, ARI-4175, ARI-3102A, ARI-2107, and ARI-2054 as inhibitors of DPP8/9 ($IC_{50}$s for DPP9 <50 pM).
Figure 9:
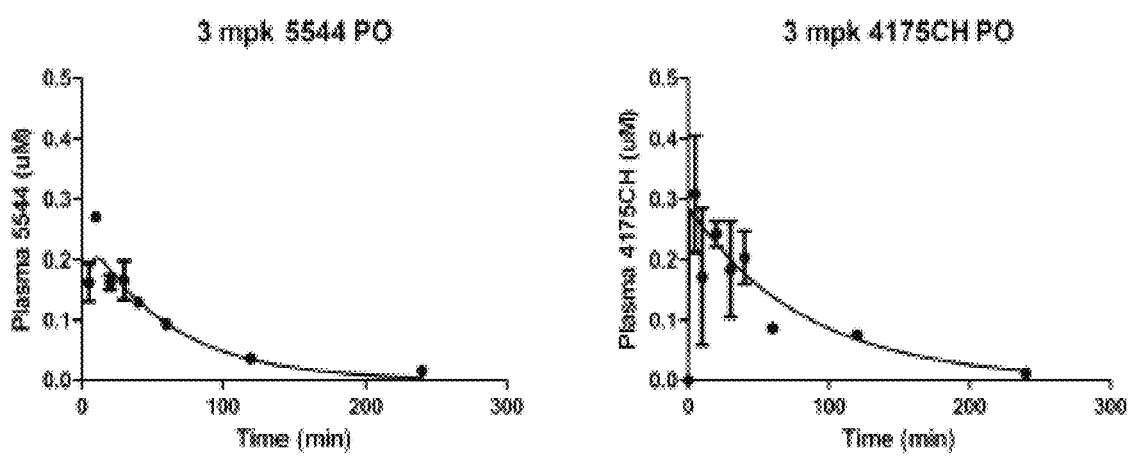
FIG. 9 depicts plasma concentrations of ARI-5544 and ARI-4175CH dosed PO at 3 mg/kg as a function of time.
Figure 10:
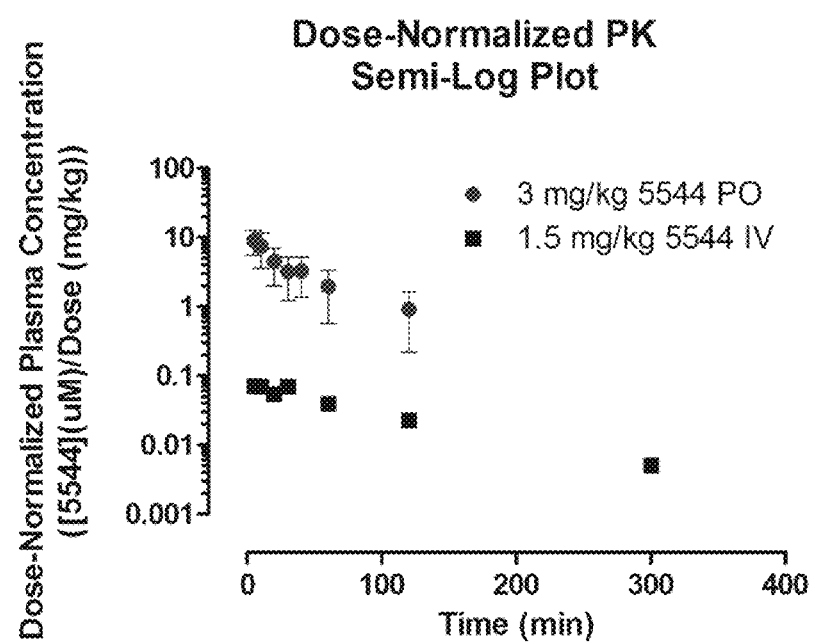
FIG. 10 shows the bioavailability of ARI-5544 as a function of route of administration and dose.

Results (See FIG. 8)

Plasma Drug Concentrations

| Time (min) | #1 | #2 | #3 |
|---|---|---|---|
| [5544] in Plasma (uM) | | | |
| 5 | 0.16 | 0.11 | 0.22 |
| 10 | NS | NS | 0.27 |
| 20 | 0.14 | 0.17 | 0.18 |
| 30 | 0.11 | 0.22 | 0.17 |
| 40 | 0.12 | 0.13 | 0.14 |
| 60 | 0.08 | 0.11 | 0.09 |
| 120 | 0.03 | 0.03 | 0.05 |
| 240 | 0.02 | 0.01 | 0.02 |
| [5544] in Plasma (uM) | | | |
| 5 | 0.28 | 0.23 | 0.42 |
| 10 | 0.25 | 0.09 | NS |
| 20 | 0.23 | 0.23 | 0.27 |
| 30 | 0.24 | 0.13 | NS |
| 40 | 0.17 | 0.25 | 0.19 |
| 60 | 0.00 | 0.09 | NS |
| 120 | 0.07 | 0.07 | 0.09 |
| 240 | 0.01 | 0.01 | NS |

NS: No Sample

Example 11. Enzymatic Assay

SID 53179: 3102A-2C rhDPP4 Inhibitory Activity
$IC_{50}$s pH 2=1.2 nM, pH 7.8=0.1 uM

| Enzyme | Type | Activity |
|---|---|---|
| DPP4 (pH 2) | $IC_{50}$ | 0.0012 μM |
| DPP4 (pH 7.8) | $IC_{50}$ | 0.1 μM |

SID 74561 In vitro DPP IV, DPP8, DPP9, DPPII, FAP and PREP inhibition assays

DPP IV $IC_{50}$=4.3 nM (pH 2.0), 460 nM (pH 7.4)
DPP8 $IC_{50}$=2.5 nM (pH 2.0), 1.4 uM (pH 7.4)
DPP9 $IC_{50}$=3.5 nM (pH 2.0), 1.5 uM (pH 7.4)
DPPII $IC_{50}$=21 nM (pH 2.0), 630 nM (pH 7.4)
FAP $IC_{50}$=66 nM (pH 2.0), 9.2 uM (pH 7.4)
PREP $IC_{50}$=62 nM (pH 2.0), 5.7 uM (pH 7.4)

| Enzyme | Type | Activity |
|---|---|---|
| DPPIV | $IC_{50}$ | 0.004 μM |
| DPP8 | $IC_{50}$ | 0.003 μM |
| DPP9 | $IC_{50}$ | 0.004 μM |
| DPPII | $IC_{50}$ | 0.021 μM |
| FAP | $IC_{50}$ | 0.066 μM |
| PREP | $IC_{50}$ | 0.062 μM |

Note: The compound was incubated at room temperature overnight at pH 2.0 or pH 7.4 prior to performing the assays SID 75066 Intracellular DPP8/9 Inhibition Assay with 293T Cells
$IIC_{50}$=3.3 nM

What is claimed is:

1. A compound represented by formula II, III, or IV, or a pharmaceutically acceptable salt thereof:

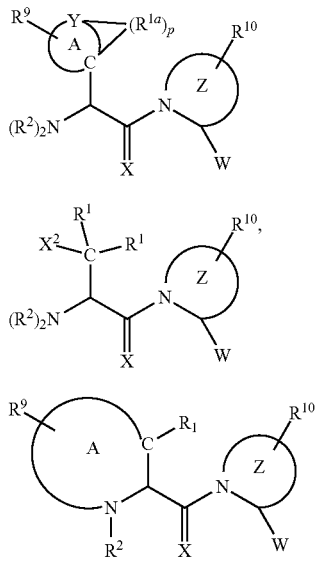

wherein
ring A, along with each occurrence of $R^{1a}$, represents a 7-12 membered polycyclic ring structure;

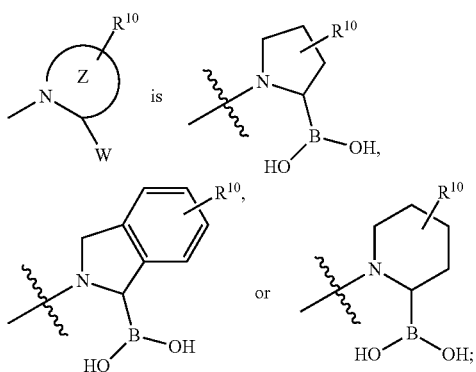

$R^1$ represents, for each occurrence, a hydrogen, a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —CF$_3$, —(CH$_2$)$_m$—R$^3$, —(CH$_2$)$_m$OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, or —(CH$_2$)$_n$—S—(CH$_2$)$_m$—R$^3$;

$R^{1a}$ represents a lower alkyl, —(CH$_2$)$_m$—, —(CH$_2$)$_m$—O—(CH$_2$)$_m$—; —(CH$_2$)$_m$—N—(CH$_2$)$_m$—; or —(CH$_2$)$_m$—S—(CH$_2$)$_m$—;

$R^2$ represents, for each occurrence, hydrogen, alkyl, alkynyl, —(CH$_2$)$_m$—R$^3$, —C(=O)-alkyl, —C(=O)-alkenyl, —C(=O)-alkynyl, or —C(=O)—(CH$_2$)$_m$—R$^3$;

$R^3$ represents, for each occurrence, hydrogen, or a substituted or unsubstituted alkyl, alkenyl, aryl, aralkyl, cycloalkyl, cycloalkenyl, or heterocycle;

$R^7$ represents hydrogen, a lower alkyl, an amine, or OR$^8$;

$R^8$ represents hydrogen, a substituted or unsubstituted alkyl, alkenyl, aryl, aralkyl, cycloalkyl, cycloalkenyl or heterocyclyl;

for formulae I and IV, $R^9$ represents one, two, or three substitutions to the ring A to which they are appended, each of which can independently be a halogen, a lower alkyl, a lower alkenyl, a lower alkynyl, a carboxyl, an ester, a formate, a ketone, a thioester, a thioacetate, a thioformate, an amino, an acylamino, an amido, a cyano, an isocyano, a thiocyanato, an isothiocyanato, a cyanato, a nitro, an azido, a sulfate, a sulfonate, a sulfonamido, lower alkyl-C(O)OH, —O-lower alkyl-C(O)OH, -guanidinyl; —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$^3$;

for formula II, $R^9$ is absent or represents one, two, or three substitutions to the ring A to which they are appended, each of which can independently be a halogen, a lower alkyl, a lower alkenyl, a lower alkynyl, a carboxyl, an ester, a formate, a ketone, a thioester, a thioacetate, a thioformate, an amino, an acylamino, an amido, a cyano, an isocyano, a thiocyanato, an isothiocyanato, a cyanato, a nitro, an azido, a sulfate, a sulfonate, a sulfonamido, lower alkyl-C(O)OH, —O-lower alkyl-C(O)OH, -guanidinyl; —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$^3$;

$R^{10}$ is absent or represents one, two, or three substitutions to the ring Z to which they are appended, each of which can independently be a halogen, a lower alkyl, a lower alkenyl, a lower alkynyl, a carboxyl, an ester, a formate, a ketone), a thioester, a thioacetate, a thioformate), an amino, an acylamino, an amido, a cyano, an isocyano, a thiocyanato, an isothiocyanato, a cyanato, a nitro, an azido, a sulfate, a sulfonate, a sulfonamido, lower alkyl-C(O)OH, —O-lower alkyl-C(O)OH, -guanidinyl; —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$^3$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$^3$;

X is O;
$X^2$ represents a halogen;
Y is C or N;
n is 0, 1, 2, or 3;
m is 0, 1, 2, or 3; and
p is 1, 2, or 3.

2. A compound selected from the group consisting of:

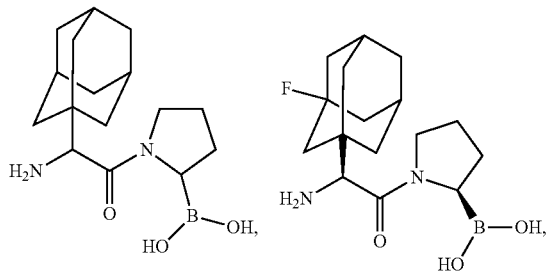

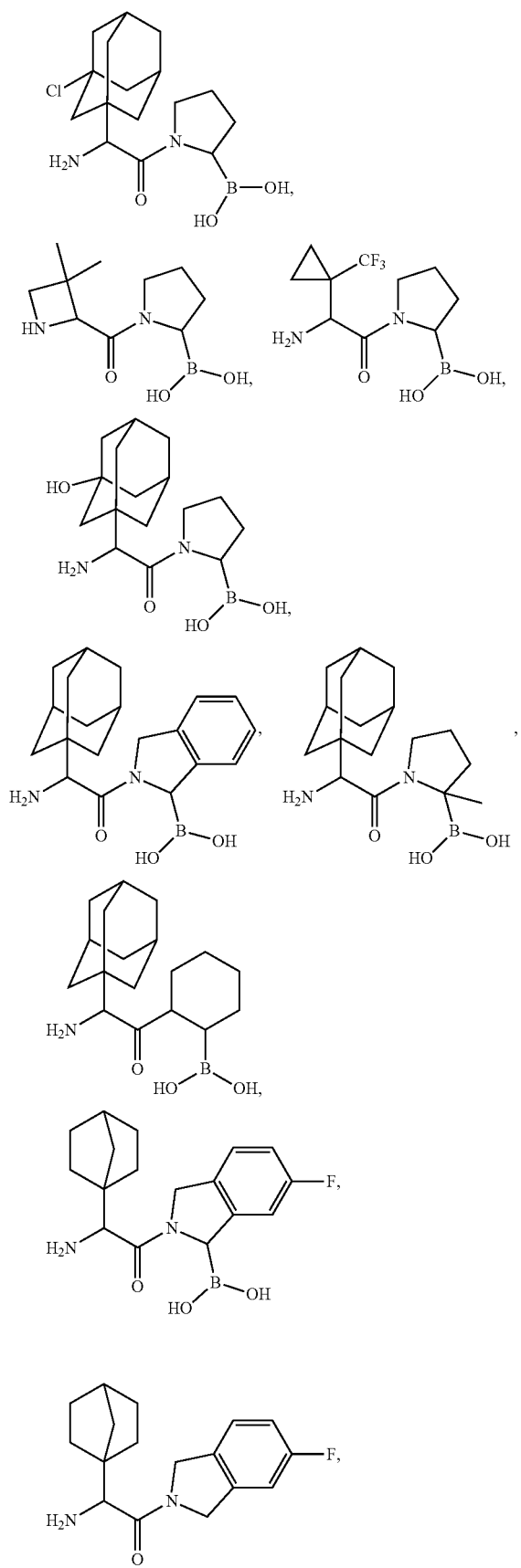
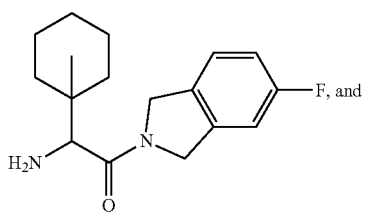
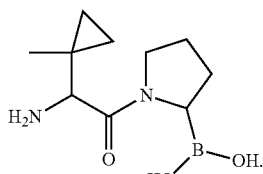
3. A compound selected from the group consisting of:
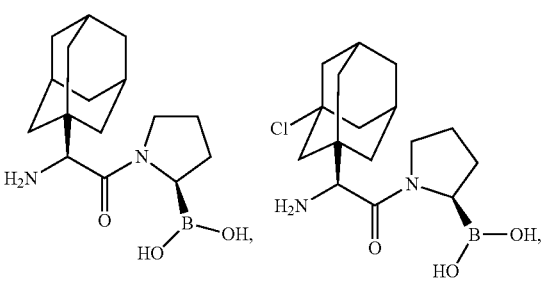
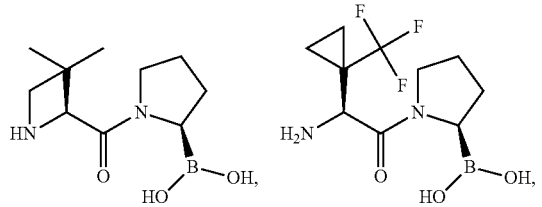
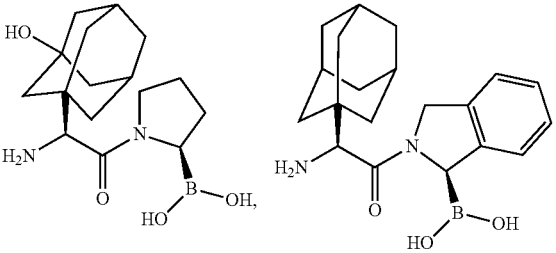
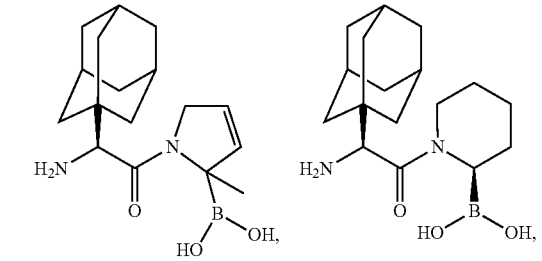

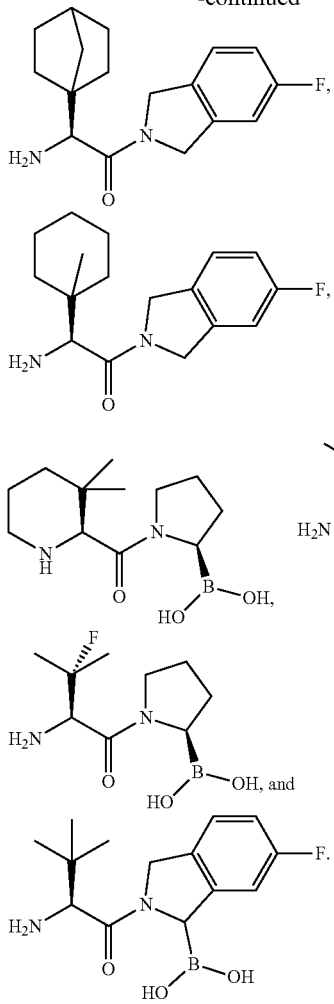

4. The compound of claim 2, wherein the compound is represented by:

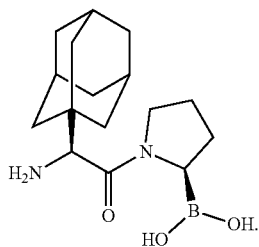

5. The compound of claim 3, wherein the compound is represented by:

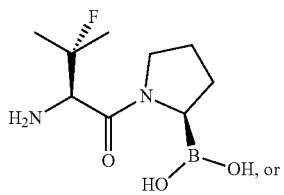

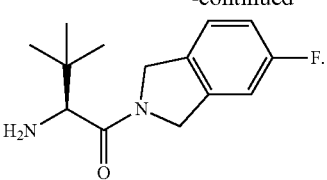

6. A pharmaceutical composition, comprising a compound of claim 1 and a pharmaceutically acceptable excipient.

7. A method for enhancing an immune response against a cancer, comprising:
  administering to a patient in need thereof a therapeutically effective amount of an immuno-DASH inhibitor of claim 1, thereby enhancing a cell-mediated immune response against the cancer,
  wherein:
  (a) at the therapeutically effective amount, the immuno-DASH inhibitor is characterized by a pharmacokinetic profile of being an inhibitor of DPP8, DPP9 and DPP4; and
  (b) the immuno-DASH inhibitor has: i) an in vivo $IC_{50}$ for DPP4 inhibition of less than 50 nM, and ii) an intracellular $IC_{50}$ for DPP8 and DPP9 inhibition less than 50 nM.

8. The compound of claim 3, wherein the compound is:

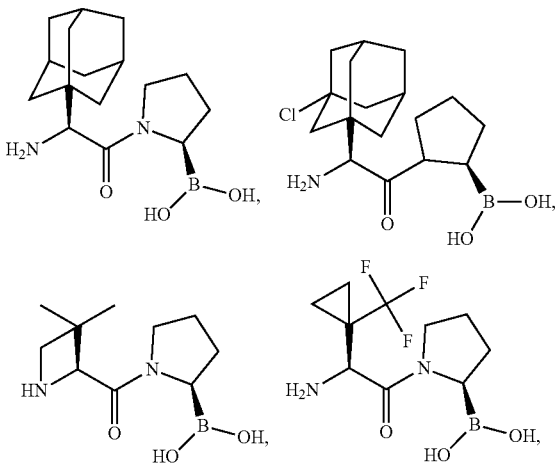

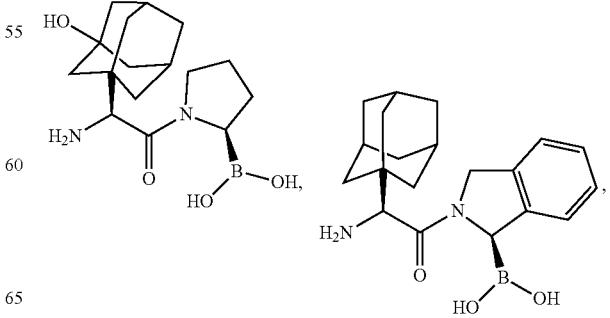

-continued

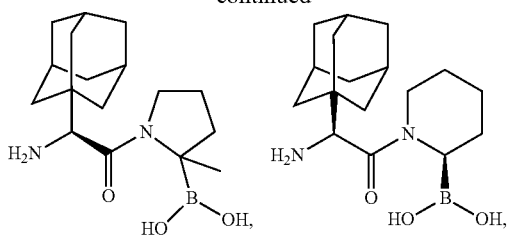

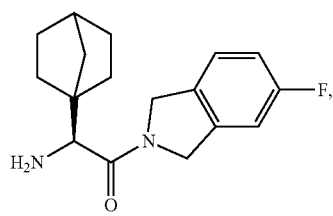

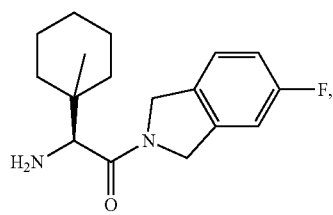

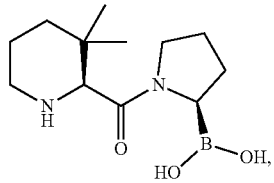

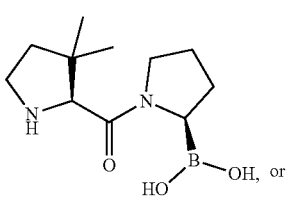

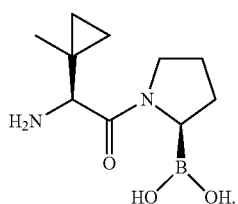

9. The compound of claim 2, wherein the compound is represented by:

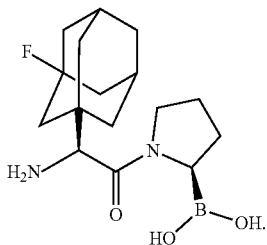

10. The method of claim 7, further comprising administering to the patient a PGE2 antagonist.

11. A method for treating a myeloproliferative disease, comprising:
 administering to a patient in need thereof a therapeutically effective amount of an immuno-DASH inhibitor of claim 1, thereby enhancing an immune response against the myeloproliferative disease,
 wherein:
 (a) at the therapeutically effective amount, the immuno-DASH inhibitor is characterized by a pharmacokinetic profile of being an inhibitor of DPP8, DPP9 and DPP4; and
 (b) the immuno-DASH inhibitor has: i) an in vivo $IC_{50}$ for DPP4 inhibition of less than 50 nM, and ii) an intracellular $IC_{50}$ for DPP8 and DPP9 inhibition less than 50 nM.

12. A method for treating a relapse of a cancer, comprising:
 administering to a patient in remission of a cancer a therapeutically effective amount of an immuno-DASH inhibitor of claim 1, thereby increasing G-CSF and CXCL1 cytokines in serum and enhance T-cell immunity against a cancer,
 wherein:
 (a) at the therapeutically effective amount, the immuno-DASH inhibitor is characterized by a pharmacokinetic profile of being an inhibitor DPP8, DPP9 and DPP4; and
 (b) the immuno-DASH inhibitor has: i) an in vivo IC50 for DPP4 inhibition of less than 50 nM, and ii) an intracellular IC50 for DPP8 and DPP9 inhibition less than 50 nM.

13. The method of claim 7, further comprising administering to the patient one or more chemotherapeutic agents or radiation therapy.

14. The method of claim 7, further comprising administering to the patient a cancer vaccine.

15. The method of claim 7, further comprising administering to the patient an adoptive cell transfer.

16. The method of claim 7, further comprising administering to the patient an antibody therapy.

17. The method of claim 7, further comprising administering to the patient at least one additional checkpoint inhibitor.

18. The method of claim 7, further comprising administering to the patient a MAP kinase pathway inhibitor or a WNT pathway inhibitor.

* * * * *

SEQUENCE LISTING

<160> NUMBER OF SEQ ID NOS: 14

<210> SEQ ID NO 1
<211> LENGTH: 117
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Gly Phe Ser Trp Val Arg Gln Ala Pro Gly Gln Gly Leu Glu Trp Met
            35                  40                  45

Gly Trp Ile Thr Ala Tyr Asn Gly Asn Thr Asn Tyr Ala Gln Lys Leu
        50                  55                  60

Gln Gly Arg Val Thr Met Thr Thr Asp Thr Ser Thr Ser Thr Val Tyr
65                  70                  75                  80

Met Glu Leu Arg Ser Leu Arg Ser Asp Asp Thr Ala Val Tyr Tyr Cys 85                  90                  95

Ala Arg Asp Tyr Phe Tyr Gly Met Asp Val Trp Gly Gln Gly Thr Thr
                100                 105                 110

Val Thr Val Ser Ser
        115

<210> SEQ ID NO 2
<211> LENGTH: 123
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Lys Ala His Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
                100                 105                 110

Trp Gly Gln Gly Thr Thr Val Thr Val Ser Ser
            115                 120

<210> SEQ ID NO 3
<211> LENGTH: 118
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Val His Trp Val Arg Gln Ala Pro Gly Gln Arg Leu Glu Trp Met
            35                  40                  45

Gly Trp Leu His Ala Asp Thr Gly Ile Thr Lys Phe Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Gln Leu Trp Phe Asp Tyr Trp Gly Gln Gly Thr
                100                 105                 110

Leu Val Thr Val Ser Ser
            115

<210> SEQ ID NO 4
<211> LENGTH: 120
<212> TYPE: PRT
<213> ORGANISM: Homo sapiens

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Val Ser Gly Ile Phe Ser Thr Tyr
                20                  25                  30

Ala Ile Asn Trp Val Arg Gln Ala Pro Gly Gln Gly Leu Glu Trp Met
            35                  40                  45

Gly Gly Ile Ile Pro Ile Phe Gly Thr Ala Asn His Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gln Gly Ile Ala Ala Ala Leu Phe Asp Tyr Trp Gly Gln
                100                 105                 110

Gly Thr Leu Val Thr Val Ser Ser
            115                 120

<210> SEQ ID NO 5
<211> LENGTH: 113
<212> TYPE: PRT
<213> ORGANISM: Homo sapiens

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Val Ser Gly Phe Thr Phe Asp Asp Tyr
                20                  25                  30

Val Val His Trp Val Arg Gln Ala Pro Gly Lys Gly Leu Glu Trp Val
            35                  40                  45

Ser Gly Ile Ser Gly Asn Ser Gly Asn Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Val Pro Phe Asp Tyr Trp Gly Gln Gly Thr Leu Val Thr Val Ser
                100                 105                 110

Ser

<210> SEQ ID NO 6
<211> LENGTH: 123
<212> TYPE: PRT
<213> ORGANISM: Homo sapiens

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Arg Ala His Tyr Ala Gln Lys Phe
        50                  55                  60

Gln Gly Arg Val Thr Ile Thr Ala Asp Glu Ser Thr Ser Thr Ala Tyr
65                  70                  75                  80

-continued

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 7
<211> LENGTH: 123
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Lys Tyr Asp Tyr Val Ser Gly Ser Pro Phe Gly Met Asp Val
            100                 105                 110

Trp Gly Gln Gly Thr Thr Val Thr Val Ser Ser
        115                 120

<210> SEQ ID NO 8
<211> LENGTH: 121
<212> TYPE: PRT
<213> ORGANISM: Homo sapiens

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Ser Ala Asn Tyr Ala Gln Lys Phe
    50                  55                  60

Gln Asp Arg Val Thr Ile Thr Ala Asp Glu Ser Thr Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Gly Trp Ser Arg Tyr Tyr Met Asp Val Trp Gly
            100                 105                 110

Gln Gly Thr Thr Val Thr Val Ser Ser
        115                 120

<210> SEQ ID NO 9
<211> LENGTH: 123
<212> TYPE: PRT
<213> ORGANISM: Homo sapiens

```
<400> SEQUENCE: 9

Gln Val Gln Leu Val Gln Ser Gly Ala Glu Val Lys Glu Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Ile Ala His Tyr Ala Gln Lys Phe
    50                  55                  60

Gln Gly Arg Val Thr Ile Thr Ala Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Lys Tyr Ser Tyr Val Ser Gly Ser Pro Phe Gly Met Asp Val
            100                 105                 110

Trp Gly Gln Gly Thr Thr Val Thr Val Ser Ser
        115                 120

<210> SEQ ID NO 10
<211> LENGTH: 121
<212> TYPE: PRT
<213> ORGANISM: Homo sapiens

<400> SEQUENCE: 10

Glu Val Gln Leu Val Glu Ser Gly Gly Gly Leu Val Gln Pro Gly Arg
1               5                   10                  15

Ser Leu Arg Leu Ser Cys Ala Ala Ser Gly Ile Thr Phe Asp Asp Tyr
            20                  25                  30

Gly Met His Trp Val Arg Gln Ala Pro Gly Lys Gly Leu Glu Trp Val
        35                  40                  45

Ser Gly Ile Ser Trp Asn Arg Gly Arg Ile Glu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Arg Phe Arg Tyr Phe Asp Trp Phe Leu Asp Tyr Trp Gly
            100                 105                 110

Gln Gly Thr Leu Val Thr Val Ser Ser
        115                 120

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Ser Phe Ser Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
```

```
                50                  55                  60
Lys Gly Arg Phe Val Phe Ser Leu Asp Thr Ser Val Ser Thr Ala Tyr
 65                  70                  75                  80

Leu Gln Ile Thr Ser Leu Thr Ala Glu Asp Thr Gly Met Tyr Phe Cys
                 85                  90                  95

Ala Lys Val Gly Tyr Asp Ala Leu Asp Tyr Trp Gly Gln Gly Thr Leu
                100                 105                 110

Val Thr Val Ser Ser
        115

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ser Glu Leu Lys Lys Pro Gly Ala
 1               5                  10                  15

Ser Val Lys Ile Ser Cys Lys Ala Ser Gly Tyr Thr Phe Thr Asn Tyr
                 20                  25                  30

Gly Met Asn Trp Val Arg Gln Ala Pro Gly Gln Gly Leu Gln Trp Met
                 35                  40                  45

Gly Trp Ile Asn Thr Asp Ser Gly Glu Ser Thr Tyr Ala Glu Glu Phe
         50                  55                  60

Lys Gly Arg Phe Val Phe Ser Leu Asp Thr Ser Val Ser Thr Ala Tyr
 65                  70                  75                  80

Leu Gln Ile Thr Ser Leu Thr Ala Glu Asp Thr Gly Met Tyr Phe Cys
                 85                  90                  95

Ala Lys Val Gly Tyr Asp Ala Leu Asp Tyr Trp Gly Gln Gly Thr Leu
                100                 105                 110

Val Thr Val Ser Ser
        115

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Thr Asn Ser
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Asn Thr Ser
 1
```